000000000000000000000000
US010647756B2

(12) United States Patent (10) Patent No.: US 10,647,756 B2
Finlay et al. (45) Date of Patent: May 12, 2020

(54) HUMANIZED ANTIBODIES

(71) Applicant: Pfizer Inc.

(72) Inventors: William James Jonathan Finlay, Dublin (IE); Lioudmila Tchistiakova, Stoneham, MA (US); Eric M. Bennett, Arlington, MA (US)

(73) Assignee: Pfizer Inc., New York, NY (US)

( * ) Notice: Subject to any disclaimer, the term of this patent is extended or adjusted under 35 U.S.C. 154(b) by 228 days.

(21) Appl. No.: 15/155,324

(22) Filed: May 16, 2016

(65) Prior Publication Data

US 2017/0073395 A1 Mar. 16, 2017

Related U.S. Application Data

(60) Provisional application No. 62/162,905, filed on May 18, 2015.

(51) Int. Cl.
*C40B 40/10* (2006.01)
*C07K 16/00* (2006.01)
*C07K 16/18* (2006.01)
*C07K 16/40* (2006.01)

(52) U.S. Cl.
CPC .............. *C07K 16/00* (2013.01); *C07K 16/18* (2013.01); *C07K 16/40* (2013.01); *C07K 2317/24* (2013.01); *C07K 2317/565* (2013.01); *C07K 2317/92* (2013.01); *C07K 2317/94* (2013.01); *C40B 40/10* (2013.01)

(58) Field of Classification Search
None
See application file for complete search history.

(56) References Cited

FOREIGN PATENT DOCUMENTS

WO 2004058184 7/2004

OTHER PUBLICATIONS

Almagro, "Identification of differences in the specificity-determining residues of antibodies that recognize antigens of different size: implications for the rational design of antibody repertoires." J. Mol. Recognition 2004; 17: pp. 132-143.
Finlay, W., "Exploiting Antibody Paratope Plasticity for Ultra-Humanization in rodents, rabbits and chickens." Meeting Presentation at PEGS, Europe, Nov. 2, 2015, 21 pages.
Finlay, W., "Simultaneous ultra-humanization, stabilization and essential paratope sampling of murine, avian and leporid IgGs, via Augmented Binary Substitution (ABS)." Meeting Presentation at PEGS, Lisbon, Nov. 3-7, 2014, 19 pages.
Finlay, W., "Simultaneous ultra-humanization, stabilization and essential paratope sampling of murine, avian and leporid IgGs, via Augmented Binary Substitution (ABS)" Meeting Presentation at PEGS, Abstract., 2014, 1 page.
Raghunathan et al., "Antigen-binding site anatomy and somatic mutations in antibodies that recognize different types of antigens.", J. Mol. Recognit. 2012; 25: pp. 103-113.

(Continued)

*Primary Examiner* — Christian C Boesen

(57) ABSTRACT

Disclosed herein are humanized antibodies in which human germline residues are introduces to the complementarity determining regions (CDRs) of a non-human donor antibody. Also described herein are libraries of antibody variable domains (e.g., phage-display libraries) and methods for screening for humanized antibodies.

14 Claims, 11 Drawing Sheets

Specification includes a Sequence Listing.

(56) References Cited

OTHER PUBLICATIONS

Ramirez-Benitez et al., "Analysis of Antibodies of Known Structure Suggests a Lack of Correspondence Between the Residues in Contact With the Antigen and Those Modified by Somatic Hypermutation." Proteins: Structure, Function, and Genetics, 2001; 45: pp. 199-206.

Townsend, S. et al., "Augmented Binary Substitution: Single-pass CDR germlining and stabilization of therapeutic antibodies." PNAS USA, PNAS, 2015; v112; No. 50: pp. 15354-15359.

Barbas et al: "In vitro evolution of a neutralizing human antibody to human immunodeficiency virus type 1 to enhance affinity and broaden strain cross-reactivity," Proc. Natl. Acad. Sci. USA, vol. 91, pp. 3809-3813, 1994.

Bird et al: "Single-Chain Antigen-Binding Proteins," Science, vol. 242, No. 4877, pp. 423-426, 1988.

Chothia et al: "Conformations of immunoglobulin hypervariable regions," Nature, vol. 342, pp. 877-883, 1989.

Holliger et al: "'Diabodies': Small bivalent and bispecific antibody fragments," Proc. Natl. Acad. Sci. USA, vol. 90, pp. 6444-6448, 1993.

Huston et al: "Protein engineering of antibody binding sites: Recovery of specific activity in an anti-digoxin single-chain Fv analogue produced in *Escherichia coli*," Proc. Natl. Acad. Sci. USA, vol. 85, pp. 5879-5883, 1988.

Jackson et al: "In vitro Antibody Maturation: Improvement of a High Affinity, Neutralizing Antibody Against IL-1β," Journal of Immunology, vol. 154, pp. 3310-3319, 1995.

Koren et al: "Clinical validation of the 'in silico' prediction of immunogenicity of a human recombinant therapeutic protein," Clinical Immunology, vol. 124, pp. 26-32, 2007.

Poljak et al: "Production and structure of diabodies," Structure, vol. 2, pp. 1121-1123, 1994.

Schier et al: "Identification of functional and structural amino-acid residues by parsimonious mutagenesis," Gene, vol. 169, pp. 147-155, 1996.

Ward et al: "Binding activities of a repertoire of single immunoglobulin variable domains secreted from *Escherichia coli*," Nature, vol. 341, pp. 544-546, 1989.

Wu et al: "Humanization of a Murine Monoclonal Antibody by Simultaneous Optimization of Framework and CDR Residues," Journal of Molecular Biology, vol. 294, pp. 151-162, 1999.

Wu et al: "Simultaneous Humanization and Affinity Optimization of Monoclonal Antibodies," Methods in Molecular Biology, vol. 207, pp. 197-212, 2003.

Yelton et al: "Affinity maturation of the BR96 anti-carcinoma antibody by codon-based mutagenesis," Journal of Immunology, vol. 155, pp. 1994-2004, 1995.

Zhang and Skolnick: "TM-align: a protein structure alignment algorithm based on the TM-score," Nucleic Acids Research, vol. 33, No. 7, pp. 2302-2309, 2005.

Jones et al: "Replacing the complementarity-determining regions in a human antibody with those from a mouse," Nature, vol. 321, pp. 522-525, 1986.

Lowman and Wells: "Monovalent phage display: A method for selecting variant proteins from random libraries," Methods: A Companion to Methods in Enzymology, vol. 3, No. 3, pp. 205-216, 1991.

Marks et al: "By-Passing Immunization: Building High Affinity Human Antibodies by Chain Shuffling," Bio/Technology, vol. 10, pp. 779-783, 1992.

Hawkins et al: "Selection of phage antibodies by binding affinity: Mimicking affinity maturation," Journal of Molecular Biology, vol. 226, No. 3, pp. 889-896, 1992.

Finlay et al "Affinity Maturation of a Humanized Rat Antibody for Anti-RAGE Therapy: Comprehensive Mutagenesis Reveals a High Level of Mutational Plasticity Both Inside and Outside the Complementarity-Determining Regions" JMB, vol. 388, pp. 541-558, 2009.

Rader ST al: "The Rabbit Antibody Repertoire as a Novel Source for the Generation of Therapeutic Human Antibodies" J. Bio. Chem., vol. 275, No. 18, pp. 13668-13676, 2000.

Shih et al: "An Ultra-specific Avian Antibody to Phosphorylated Tau Protein Reveals a Unique Mechanism for Phosphoepitope Recognition", J. Bio. Chem., vol. 287, No. 53, pp. 44425-44434, 2012.

Wells & Lowman "Rapid evolution of peptide and protein binding properties in vitro"; Curr. Opin. in Biotech., vol. 3, pp. 355-362, 1992.

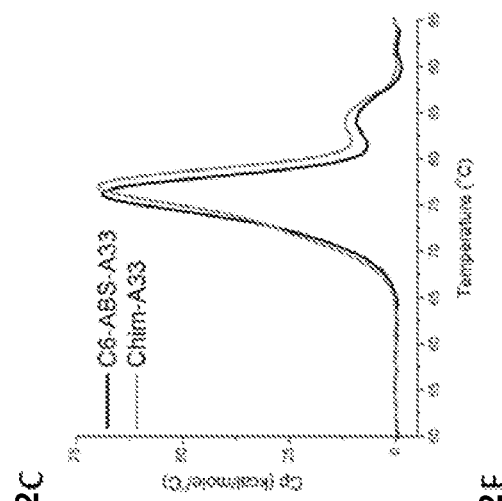
FIG. 2A
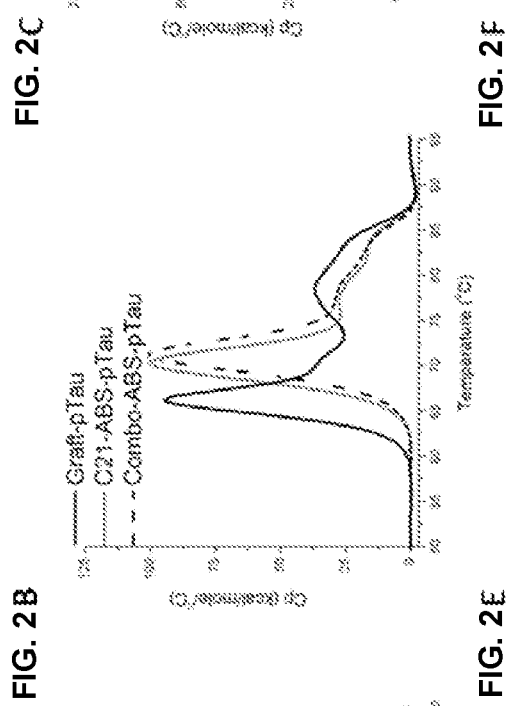
FIG. 2B
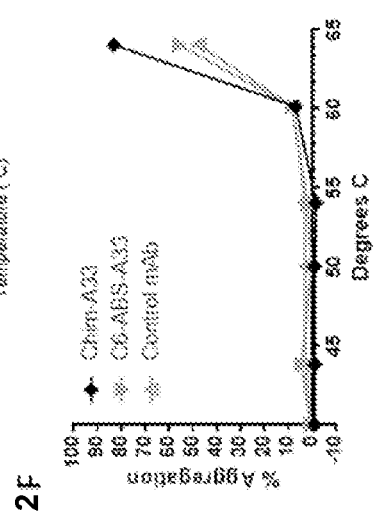
FIG. 2C
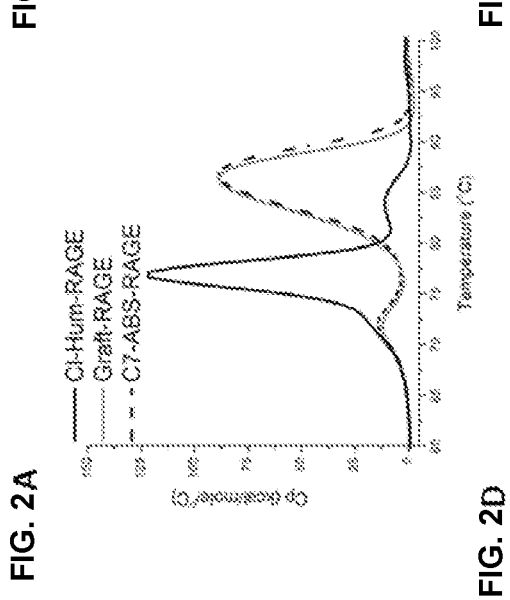
FIG. 2D
FIG. 2E
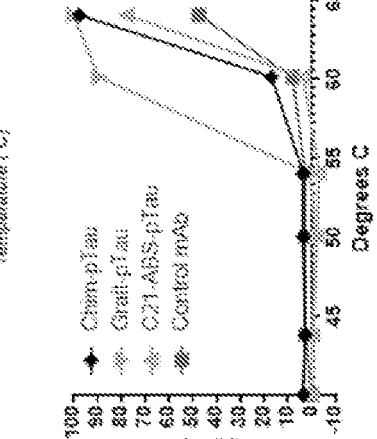
FIG. 2F From top to bottom, SEQ ID NOs: 12-29

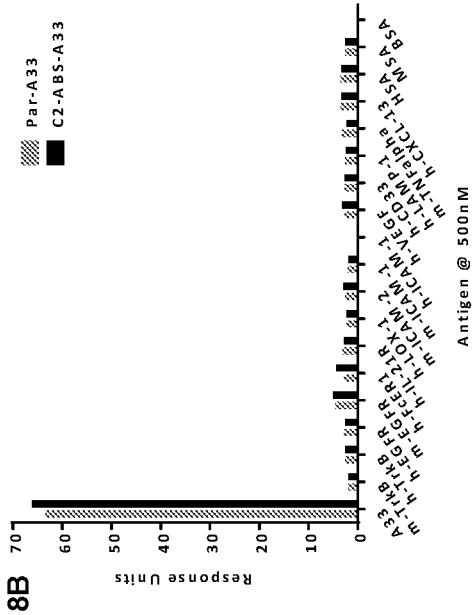
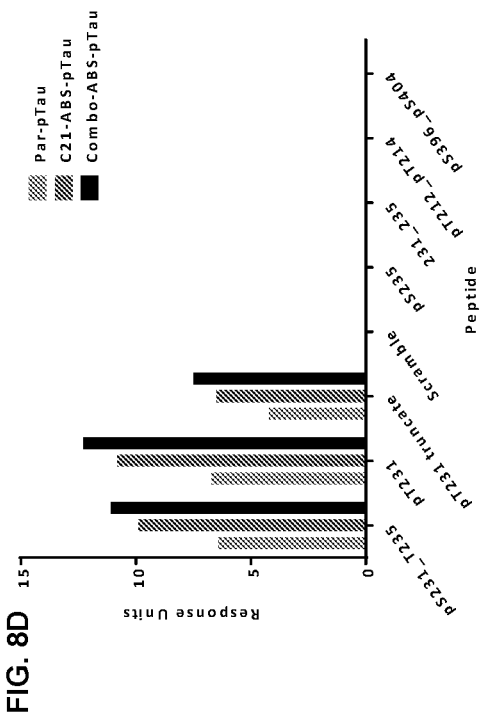
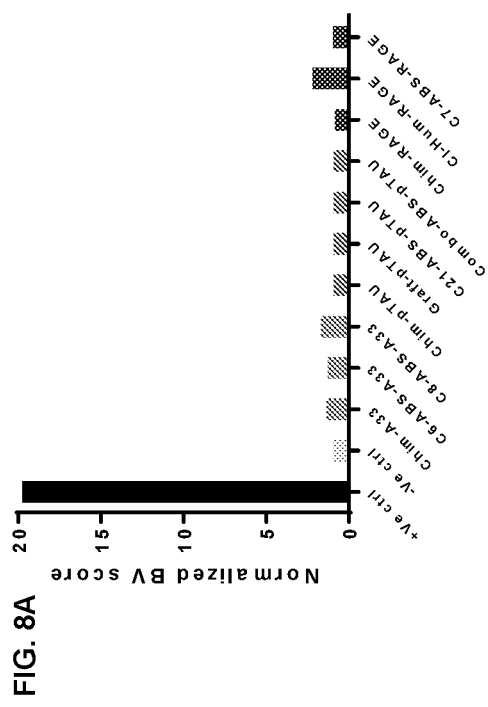
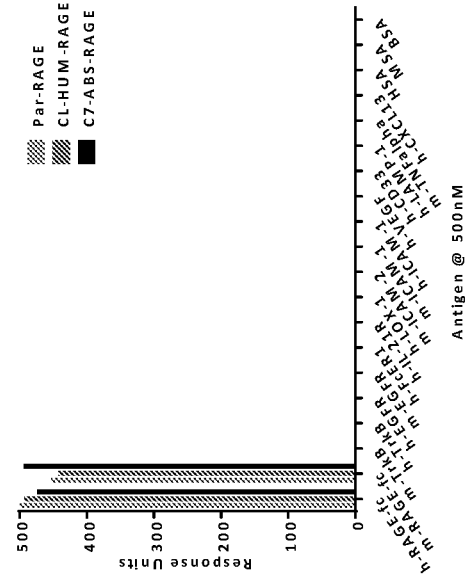

SEQUENCE LISTING

<160> NUMBER OF SEQ IDS NOS: 518

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Arg Ala Ser Gln Ser Ile Ser Ser Tyr Leu Asn
1               5                   10

```
<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Arg Ala Ser Gln Asp Val Gly Ile Tyr Val Asn
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

Ala Ala Ser Ser Leu Gln Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Construct

<400> SEQUENCE: 4

Arg Ala Thr Asn Leu Ala Asp
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Gln Gln Ser Tyr Ser Thr Pro Leu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Leu Glu Phe Asp Glu His Pro Leu Thr
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Phe Thr Phe Ser Ser Tyr Trp Met Ser
1               5                   10

<210> SEQ ID NO 8
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Gly Phe Thr Phe Asn Asn Tyr Trp Met Thr
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Synthetic Construct

<400> SEQUENCE: 9

Ala Asn Ile Lys Gln Asp Gly Ser Glu Lys Tyr Tyr Val Asp Ser Val
1               5                   10                  15

Lys Gly

<210> SEQ ID NO 10
<211> LENGTH: 18
<212> TYPE: PRT
<213> ORGANISM: Artificial Sequence
<220> FEATURE:
<223> OTHER INFORMATION: Synthetic Construct

<400> SEQUENCE: 10

Ala Ser Ile Asp Asn Ser Gly Asp Asn Thr Tyr Tyr Pro Asp Ser Val
1               5                   10                  15

Lys Asp

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gly Gly Asp Ile Thr Thr Gly Phe Asp Tyr
1               5                   10

<210> SEQ ID NO 12
<211> LENGTH: 105
<212> TYPE: PRT
<213> ORGANISM: Artificial Sequence
<220> FEATURE:
<223> OTHER INFORMATION: Synthetic Construct

<400> SEQUENCE: 12

Ser Ser Glu Leu Thr Gln Asp Pro Ala Val Ser Val Ala Leu Gly His
1               5                   10                  15

Thr Val Arg Ile Thr Cys Ser Gly Asp Asp Ser Tyr Tyr Gly Trp Tyr
                20                  25                  30

Gln Gln Lys Pro Gly Gln Ala Pro Val Thr Val Ile Tyr Gly Asn Asp
            35                  40                  45

Lys Arg Pro Ser Gly Ile Pro Asp Arg Phe Ser Gly Ser Ser Ser Gly
        50                  55                  60

Asn Thr Ala Ser Leu Thr Ile Thr Gly Ala Gln Ala Glu Asp Glu Ala
65                  70                  75                  80
```

Asp Tyr Tyr Cys Gly Ala Tyr Asp Ser Ser Gly Gly Gly Ile Phe
                85                  90                  95

Gly Gly Gly Thr Lys Leu Thr Val Leu
            100                 105

<210> SEQ ID NO 13
<211> LENGTH: 105
<212> TYPE: PRT
<213> ORGANISM: Artificial Sequence
<220> FEATURE:
<223> OTHER INFORMATION: Synthetic Construct

<400> SEQUENCE: 13

Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asp
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Ile Phe
                85                  90                  95

Gly Gly Gly Thr Lys Leu Thr Val Leu
            100                 105

<210> SEQ ID NO 14
<211> LENGTH: 105
<212> TYPE: PRT
<213> ORGANISM: Artificial Sequence
<220> FEATURE:
<223> OTHER INFORMATION: Synthetic Construct

<400> SEQUENCE: 14

Ser Ser Glu Leu Thr Gln Asp Pro Ala Val Ser Val Ala Leu Gly Gln
1               5                   10                  15

Thr Val Arg Ile Thr Cys Gln Gly Ser Asp Tyr Tyr Tyr Gly Trp Tyr
            20                  25                  30

Gln Gln Lys Pro Gly Gln Ala Pro Val Thr Val Ile Tyr Gly Asn Asp
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ser Tyr Asp Ser Ser Ala Gly His Gly Val Phe
                85                  90                  95

Gly Gly Gly Thr Lys Leu Thr Val Leu
            100                 105

<210> SEQ ID NO 15
<211> LENGTH: 105
<212> TYPE: PRT
<213> ORGANISM: Artificial Sequence
<220> FEATURE:
<223> OTHER INFORMATION: Synthetic Construct

<400> SEQUENCE: 15

Ser Ser Glu Leu Thr Gln Asp Pro Ala Val Ser Val Ala Leu Gly Gln

```
                1               5                   10                  15
            Thr Val Arg Ile Thr Cys Ser Gly Asp Asp Ser Tyr Tyr Gly Trp Tyr
                            20                  25                  30

Gln Gln Lys Pro Gly Gln Ala Pro Val Thr Val Ile Tyr Gly Asn Asn
                        35                  40                  45

Asn Arg Pro Ser Gly Ile Pro Asp Arg Phe Ser Gly Ser Ser Ser Gly
                    50                  55                  60

Asn Thr Ala Ser Leu Thr Ile Thr Gly Ala Gln Ala Glu Asp Glu Ala
            65                  70                  75                  80

Asp Tyr Tyr Cys Gly Ala Tyr Asp Gly Ser Gly Gly His Gly Val Phe
                            85                  90                  95

Gly Gly Gly Thr Lys Leu Thr Val Leu
                        100                 105

<210> SEQ ID NO 16
<211> LENGTH: 105
<212> TYPE: PRT
<213> ORGANISM: Artificial Sequence
<220> FEATURE:
<223> OTHER INFORMATION: Synthetic Construct

<400> SEQUENCE: 16

Ser Ser Glu Leu Thr Gln Asp Pro Ala Val Ser Val Ala Leu Gly Gln
            1               5                   10                  15

Thr Val Arg Ile Thr Cys Gln Gly Asp Ser Tyr Tyr Gly Trp Tyr
                            20                  25                  30

Gln Gln Lys Pro Gly Gln Ala Pro Val Thr Val Ile Tyr Gly Asn Asn
                        35                  40                  45

Asn Arg Pro Ser Gly Ile Pro Asp Arg Phe Ser Gly Ser Ser Ser Gly
                    50                  55                  60

Asn Thr Ala Ser Leu Thr Ile Thr Gly Ala Gln Ala Glu Asp Glu Ala
            65                  70                  75                  80

Asp Tyr Tyr Cys Gly Ala Tyr Asp Gly Ser Gly Gly His Gly Val Phe
                            85                  90                  95

Gly Gly Gly Thr Lys Leu Thr Val Leu
                        100                 105

<210> SEQ ID NO 17
<211> LENGTH: 105
<212> TYPE: PRT
<213> ORGANISM: Artificial Sequence
<220> FEATURE:
<223> OTHER INFORMATION: Synthetic Construct

<400> SEQUENCE: 17

Ser Ser Glu Leu Thr Gln Asp Pro Ala Val Ser Val Ala Leu Gly Gln
            1               5                   10                  15

Thr Val Arg Leu Thr Cys Gln Gly Asp Ser Tyr Tyr Gly Trp Tyr
                            20                  25                  30

Gln Gln Lys Pro Gly Gln Ala Pro Val Thr Val Ile Tyr Gly Asn Asn
                        35                  40                  45

Lys Arg Pro Ser Gly Ile Pro Asp Arg Phe Ser Gly Ser Ser Ser Gly
                    50                  55                  60

Asn Thr Ala Ser Leu Thr Ile Thr Gly Ala Gln Ala Glu Asp Glu Ala
            65                  70                  75                  80

Asp Tyr Tyr Cys Gly Ala Tyr Asp Ser Ser Gly Gly Gly Val Phe
                            85                  90                  95
```

```
Gly Gly Gly Thr Lys Leu Thr Val Leu
            100             105
```

<210> SEQ ID NO 18
<211> LENGTH: 105
<212> TYPE: PRT
<213> ORGANISM: Artificial Sequence
<220> FEATURE:
<223> OTHER INFORMATION: Synthetic Construct

<400> SEQUENCE: 18

```
Ser Ser Glu Leu Thr Gln Asp Pro Ala Val Ser Val Ala Leu Gly Gln
1               5                   10                  15

Thr Val Arg Ile Thr Cys Ser Gly Asp Ser Tyr Tyr Gly Trp Tyr
            20                  25                  30

Gln Gln Lys Pro Gly Gln Ala Pro Val Thr Val Ile Tyr Gly Asn Asp
            35                  40                  45

Lys Arg Pro Ser Gly Ile Pro Asp Arg Phe Ser Gly Ser Ser Ser Gly
        50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Gly Ser Gly Gly Gly Val Phe
                85                  90                  95

Gly Gly Gly Thr Lys Leu Thr Val Leu
            100             105
```

<210> SEQ ID NO 19
<211> LENGTH: 105
<212> TYPE: PRT
<213> ORGANISM: Artificial Sequence
<220> FEATURE:
<223> OTHER INFORMATION: Synthetic Construct

<400> SEQUENCE: 19

```
Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asp
            35                  40                  45

Asn Arg Pro Ser Gly Ile Pro Asp Arg Phe Ser Gly Ser Ser Ser Gly
        50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Ile Phe
                85                  90                  95

Gly Gly Gly Thr Lys Leu Thr Val Leu
            100             105
```

<210> SEQ ID NO 20
<211> LENGTH: 108
<212> TYPE: PRT
<213> ORGANISM: Homo sapiens

<400> SEQUENCE: 20

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30
```

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu
            100                 105

<210> SEQ ID NO 21
<211> LENGTH: 127
<212> TYPE: PRT
<213> ORGANISM: Artificial Sequence
<220> FEATURE:
<223> OTHER INFORMATION: Synthetic Construct

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Ser Trp Val Arg Gln Ala Pro Gly Lys Gly Leu Glu Trp Val
        35                  40                  45

Ala Gly Ile Thr Ser Arg Gly Gly Val Thr Gly Tyr Gly Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ala Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Met Trp Val Arg Gln Ala Pro Gly Lys Gly Leu Glu Trp Val
        35                  40                  45

Ser Gly Ile Thr Ser Arg Gly Gly Val Thr Gly Tyr Gly Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asn Ser Asp Gln Cys Gly Phe Pro Glu Ala Gly
            100                 105                 110

Cys Ile Asp Ala Trp Gly Gln Gly Thr Leu Val Thr Val Ser Ser
            115                 120                 125

<210> SEQ ID NO 23
<211> LENGTH: 127
<212> TYPE: PRT
<213> ORGANISM: Artificial Sequence
<220> FEATURE:
<223> OTHER INFORMATION: Synthetic Construct

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Ser Trp Val Arg Gln Ala Pro Gly Lys Gly Leu Glu Trp Val
        35                  40                  45

Ser Gly Ile Thr Gly Arg Gly Val Thr Gly Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Met Gly
            100                 105                 110

Cys Ile Asp Ala Trp Gly Gln Gly Thr Leu Val Thr Val Ser Ser
            115                 120                 125

<210> SEQ ID NO 24
<211> LENGTH: 127
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Met Trp Val Arg Gln Ala Pro Gly Lys Gly Leu Glu Trp Val
        35                  40                  45

Ala Gly Ile Thr Ser Arg Gly Val Thr Gly Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ala Asp Gln Cys Gly Phe Pro Glu Ala Gly
            100                 105                 110

Cys Ile Asp Ala Trp Gly Gln Gly Thr Leu Val Thr Val Ser Ser
            115                 120                 125

<210> SEQ ID NO 25
<211> LENGTH: 127
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Met Trp Val Arg Gln Ala Pro Gly Lys Gly Leu Glu Trp Val
        35                  40                  45

Ala Gly Ile Thr Ser Arg Gly Gly Val Thr Gly Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 26
<211> LENGTH: 127
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Met Trp Val Arg Gln Ala Pro Gly Lys Gly Leu Glu Trp Val
        35                  40                  45

Ser Gly Ile Thr Ser Arg Gly Gly Val Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 27
<211> LENGTH: 127
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Met Trp Val Arg Gln Ala Pro Gly Lys Gly Leu Glu Trp Val
        35                  40                  45

```
Ala Gly Ile Thr Ser Arg Gly Gly Val Thr Gly Tyr Gly Ser Ala Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ser Trp Gly Gln Gly Thr Leu Val Thr Val Ser Ser
            115                 120                 125

<210> SEQ ID NO 28
<211> LENGTH: 127
<212> TYPE: PRT
<213> ORGANISM: Artificial Sequence
<220> FEATURE:
<223> OTHER INFORMATION: Synthetic Construct

<400> SEQUENCE: 28

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Tyr
                20                  25                  30

Gln Met Met Trp Val Arg Gln Ala Pro Gly Lys Gly Leu Glu Trp Val
            35                  40                  45

Ala Gly Ile Thr Ser Arg Gly Gly Val Thr Gly Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
            115                 120                 125

<210> SEQ ID NO 29
<211> LENGTH: 98
<212> TYPE: PRT
<213> ORGANISM: Homo sapiens

<400> SEQUENCE: 29

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys
```

```
<210> SEQ ID NO 30
<211> LENGTH: 95
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 31
<211> LENGTH: 107
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ser Ser Met Ser Val Ser Leu Gly
1               5                   10                  15

Asp Thr Ile Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45

Tyr Arg Ala Thr Asn Leu Ala Asp Gly Val Pro Ser Arg Phe Ser Gly
50                  55                  60

Ser Arg Ser Gly Ser Ile Tyr Ser Leu Thr Ile Ser Ser Leu Glu Ser
65                  70                  75                  80

Glu Asp Val Ala Asp Tyr His Cys Leu Glu Phe Asp Glu His Pro Leu
                85                  90                  95

Thr Phe Gly Ser Gly Thr Lys Val Glu Ile Lys
            100                 105

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ile Tyr
            20                  25                  30

Val Asn Trp Tyr Gln Gln Lys Pro Gly Lys Ala Pro Lys Leu Leu Ile
        35                  40                  45

Tyr Arg Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Leu Glu Phe Asp Glu His Pro Leu
                    85                  90                  95

Thr Phe Gly Gly Gly Thr Lys Val Glu Ile Lys
                100                 105

<210> SEQ ID NO 33
<211> LENGTH: 107
<212> TYPE: PRT
<213> ORGANISM: Artificial Sequence
<220> FEATURE:
<223> OTHER INFORMATION: Synthetic Construct

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ile Tyr
                20                  25                  30

Val Asn Trp Phe Gln Gln Lys Pro Gly Lys Ala Pro Arg Arg Leu Ile
            35                  40                  45

Tyr Arg Ala Thr Asn Leu Ala Asp Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Glu Phe Asp Glu His Pro Leu
                    85                  90                  95

Thr Phe Gly Gly Gly Thr Lys Val Glu Ile Lys
                100                 105

<210> SEQ ID NO 34
<211> LENGTH: 107
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
                20                  25                  30

Leu Asn Trp Tyr Gln Gln Lys Pro Gly Lys Ala Pro Lys Leu Leu Ile
            35                  40                  45

Tyr Arg Ala Ser Ser Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Phe Asp Glu His Pro Leu
                    85                  90                  95

Thr Phe Gly Gly Gly Thr Lys Val Glu Ile Lys
                100                 105

<210> SEQ ID NO 35
<211> LENGTH: 98
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
```

-continued

```
                1               5                  10                  15
Ser Leu Arg Leu Ser Cys Ala Ala Ser Gly Phe Thr Phe Ser Ser Tyr
                    20                  25                  30
Trp Met Ser Trp Val Arg Gln Ala Pro Gly Lys Gly Leu Glu Trp Val
                    35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                    85                  90                  95
Ala Arg
```

<210> SEQ ID NO 36
<211> LENGTH: 119
<212> TYPE: PRT
<213> ORGANISM: Artificial Sequence
<220> FEATURE:
<223> OTHER INFORMATION: Synthetic Construct

<400> SEQUENCE: 36

```
Glu Val Gln Leu Val Glu Ser Gly Gly Gly Leu Val Gln Pro Gly Arg
1               5                   10                  15
Ser Leu Lys Leu Ser Cys Val Val Ser Gly Phe Thr Phe Asn Asn Tyr
                    20                  25                  30
Trp Met Thr Trp Ile Arg Gln Thr Pro Gly Lys Gly Leu Glu Trp Val
                    35                  40                  45
Ala Ser Ile Asn Asn Ser Gly Asp Asn Thr Tyr Tyr Pro Asp Ser Val
    50                  55                  60
Lys Asp Arg Phe Thr Ile Ser Arg Asp Asn Ala Lys Ser Thr Leu Tyr
65                  70                  75                  80
Leu Gln Met Asn Ser Leu Arg Ser Glu Asp Thr Ala Thr Tyr Tyr Cys
                    85                  90                  95
Thr Arg Gly Gly Asp Ile Thr Thr Gly Phe Asp Tyr Trp Gly Gln Gly
                    100                 105                 110
Val Met Val Thr Val Ser Ser
        115
```

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct

<400> SEQUENCE: 37

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Asn Tyr
                    20                  25                  30
Trp Met Thr Trp Val Arg Gln Ala Pro Gly Lys Gly Leu Glu Trp Val
                    35                  40                  45
Ala Ser Ile Asp Asn Ser Gly Asp Asn Thr Tyr Tyr Pro Asp Ser Val
    50                  55                  60
Lys Asp Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
```

-continued

```
                85                  90                  95

Ala Arg Gly Gly Asp Ile Thr Thr Gly Phe Asp Tyr Trp Gly Gln Gly
            100                 105                 110

Thr Leu Val Thr Val Ser Ser
        115

<210> SEQ ID NO 38
<211> LENGTH: 119
<212> TYPE: PRT
<213> ORGANISM: Artificial Sequence
<220> FEATURE:
<223> OTHER INFORMATION: Synthetic Construct

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Ile Asp Asn Ser Gly Asp Asn Thr Tyr Tyr Pro Asp Ser Val
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ile Thr Thr Gly Phe Asp Tyr Trp Gly Gln Gly
            100                 105                 110

Thr Leu Val Thr Val Ser Ser
        115

<210> SEQ ID NO 39
<211> LENGTH: 119
<212> TYPE: PRT
<213> ORGANISM: Artificial Sequence
<220> FEATURE:
<223> OTHER INFORMATION: Synthetic Construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Ser Ile Asp Gln Asp Gly Ser Asn Lys Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ile Thr Thr Gly Leu Asp Tyr Trp Gly Gln Gly
            100                 105                 110

Thr Leu Val Thr Val Ser Ser
        115

<210> SEQ ID NO 40
<211> LENGTH: 96
```

```
<212> TYPE: PRT
<213> ORGANISM: Homo sapiens

<400> SEQUENCE: 40

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 41
<211> LENGTH: 104
<212> TYPE: PRT
<213> ORGANISM: Artificial Sequence
<220> FEATURE:
<223> OTHER INFORMATION: Synthetic Construct

<400> SEQUENCE: 41

Ala Leu Thr Gln Pro Thr Ser Val Ser Ala Asn Leu Gly Gly Ser Val
1               5                   10                  15

Glu Ile Thr Cys Ser Gly Ser Asp Tyr Asp Tyr Gly Trp Tyr Gln Gln
            20                  25                  30

Lys Ala Pro Gly Ser Ala Pro Val Thr Val Ile Tyr Trp Asn Asp Lys
        35                  40                  45

Arg Pro Ser Asp Ile Pro Ser Arg Phe Ser Gly Ser Thr Ser Gly Ser
    50                  55                  60

Thr Ser Thr Leu Thr Ile Thr Gly Val Gln Ala Glu Asp Glu Ala Val
65                  70                  75                  80

Tyr Tyr Cys Gly Ala Tyr Asp Gly Ser Ala Gly Gly Ile Phe Gly
                85                  90                  95

Ala Gly Thr Thr Leu Thr Val Leu
            100

<210> SEQ ID NO 42
<211> LENGTH: 105
<212> TYPE: PRT
<213> ORGANISM: Artificial Sequence
<220> FEATURE:
<223> OTHER INFORMATION: Synthetic Construct

<400> SEQUENCE: 42

Ser Ser Glu Leu Thr Gln Asp Pro Ala Val Ser Val Ala Leu Gly Gln
1               5                   10                  15

Thr Val Arg Ile Thr Cys Ser Gly Ser Asp Tyr Asp Tyr Gly Trp Tyr
            20                  25                  30

Gln Gln Lys Pro Gly Gln Ala Pro Val Leu Val Ile Tyr Trp Asn Asp
        35                  40                  45

Lys Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80
```

```
Asp Tyr Tyr Cys Gly Ala Tyr Asp Gly Ser Ala Gly Gly Ile Phe
                85                  90                  95

Gly Gly Gly Thr Lys Leu Thr Val Leu
            100             105

<210> SEQ ID NO 43
<211> LENGTH: 105
<212> TYPE: PRT
<213> ORGANISM: Artificial Sequence
<220> FEATURE:
<223> OTHER INFORMATION: Synthetic Construct

<400> SEQUENCE: 43

Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asp
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Ile Phe
                85                  90                  95

Gly Gly Gly Thr Lys Leu Thr Val Leu
            100             105

<210> SEQ ID NO 44
<211> LENGTH: 105
<212> TYPE: PRT
<213> ORGANISM: Artificial Sequence
<220> FEATURE:
<223> OTHER INFORMATION: Synthetic Construct

<400> SEQUENCE: 44

Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asn
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ser Tyr Asp Ser Ser Gly His Gly Val Phe
                85                  90                  95

Gly Gly Gly Thr Lys Leu Thr Val Leu
            100             105

<210> SEQ ID NO 45
<211> LENGTH: 98
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
50                       55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Lys

<210> SEQ ID NO 46
<211> LENGTH: 127
<212> TYPE: PRT
<213> ORGANISM: Artificial Sequence
<220> FEATURE:
<223> OTHER INFORMATION: Synthetic Construct

<400> SEQUENCE: 46

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Leu Ser Ser Tyr
         20                  25                  30

Gln Met Met Trp Val Arg Gln Ala Pro Gly Lys Gly Leu Glu Trp Val
         35                  40                  45

Ala Gly Ile Thr Ser Arg Gly Val Thr Gly Tyr Gly Ser Ala Val
50                       55                  60

Lys Gly Arg Ala Thr Ile Ser Arg Asp Asn Gly Gln Ser Thr Val Arg
65                   70                  75                  80

Leu Gln Leu Asn Asn Leu Arg Ala Glu Asp Thr Gly Thr Tyr Tyr Cys
                 85                  90                  95

Ala Lys Pro Ala Leu Asp Ser Asp Gln Cys Gly Phe Pro Glu Ala Gly
            100                 105                 110

Cys Ile Asp Ala Trp Gly His Gly Thr Glu Val Ile Val Ser Ser
            115                 120                 125

<210> SEQ ID NO 47
<211> LENGTH: 127
<212> TYPE: PRT
<213> ORGANISM: Artificial Sequence
<220> FEATURE:
<223> OTHER INFORMATION: Synthetic Construct

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
         20                  25                  30

Gln Met Met Trp Val Arg Gln Ala Pro Gly Lys Gly Leu Glu Trp Val
         35                  40                  45

Ser Gly Ile Thr Ser Arg Gly Gly Val Thr Gly Tyr Gly Ser Ala Val
50                       55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 48
<211> LENGTH: 127
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Gln Met Met Trp Val Arg Gln Ala Pro Gly Lys Gly Leu Glu Trp Val
        35                  40                  45

Ala Gly Ile Thr Gly Arg Gly Gly Val Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 49
<211> LENGTH: 127
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Ser Trp Val Arg Gln Ala Pro Gly Lys Gly Leu Glu Trp Val
        35                  40                  45

Ala Gly Ile Thr Gly Arg Gly Gly Val Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Met Gly
            100                 105                 110

Cys Ile Asp Ala Trp Gly Gln Gly Thr Leu Val Thr Val Ser Ser
        115                 120                 125

<210> SEQ ID NO 50
<211> LENGTH: 109
<212> TYPE: PRT
<213> ORGANISM: Artificial Sequence
<220> FEATURE:
<223> OTHER INFORMATION: Synthetic Construct

<400> SEQUENCE: 50

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Phe Leu Phe Asn Gly
            20                  25                  30

Val Ser Trp Tyr Gln Gln Lys Pro Gly Lys Pro Pro Lys Phe Leu Ile
        35                  40                  45

Ser Gly Ala Ser Asn Leu Glu Ser Gly Val Pro Pro Arg Phe Ser Gly
    50                  55                  60

Ser Gly Ser Gly Thr Asp Tyr Thr Leu Thr Ile Gly Val Gln Ala
65                  70                  75                  80

Glu Asp Val Ala Thr Tyr Tyr Cys Leu Gly Gly Tyr Ser Gly Ser Ser
                85                  90                  95

Gly Leu Thr Phe Gly Ala Gly Thr Asn Val Glu Ile Lys
            100                 105

<210> SEQ ID NO 51
<211> LENGTH: 109
<212> TYPE: PRT
<213> ORGANISM: Artificial Sequence
<220> FEATURE:
<223> OTHER INFORMATION: Synthetic Construct

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Phe Leu Phe Asn Gly
            20                  25                  30

Val Ser Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Gly Tyr Ser Gly Ser Ser
                85                  90                  95

Gly Leu Thr Phe Gly Gly Gly Thr Lys Val Glu Ile Lys
            100                 105

<210> SEQ ID NO 52
<211> LENGTH: 109
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Leu Phe Asn Gly
            20                  25                  30

Val Ser Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Gly Tyr Ser Gly Ser Thr
                 85                  90                  95

Gly Leu Thr Phe Gly Gly Gly Thr Lys Val Glu Ile Lys
            100                 105

<210> SEQ ID NO 53
<211> LENGTH: 124
<212> TYPE: PRT
<213> ORGANISM: Artificial Sequence
<220> FEATURE:
<223> OTHER INFORMATION: Synthetic Construct

<400> SEQUENCE: 53

Gln Glu Gln Leu Met Glu Ser Gly Gly Gly Leu Val Thr Leu Gly Gly
1               5                   10                  15

Ser Leu Lys Leu Ser Cys Lys Ala Ser Gly Ile Asp Phe Ser His Tyr
            20                  25                  30

Gly Ile Ser Trp Val Arg Gln Ala Pro Gly Lys Gly Leu Glu Trp Ile
        35                  40                  45

Ala Tyr Ile Tyr Pro Asn Tyr Gly Ser Val Asp Tyr Ala Ser Trp Val
    50                  55                  60

Asn Gly Arg Phe Thr Ile Ser Leu Asp Asn Ala Gln Asn Thr Val Phe
65                  70                  75                  80

Leu Gln Met Ile Ser Leu Thr Ala Ala Asp Thr Ala Thr Tyr Phe Cys
                85                  90                  95

Ala Arg Asp Arg Gly Tyr Tyr Ser Gly Arg Gly Thr Arg Leu Asp
            100                 105                 110

Leu Trp Gly Gln Gly Thr Leu Val Thr Ile Ser Ser
        115                 120

<210> SEQ ID NO 54
<211> LENGTH: 124
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Val Asp Tyr Ala Ser Trp Val
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Tyr Tyr Ser Gly Arg Gly Thr Arg Leu Asp
            100                 105                 110

Leu Trp Gly Gln Gly Thr Leu Val Thr Val Ser Ser
        115                 120

<210> SEQ ID NO 55
```

```
<211> LENGTH: 124
<212> TYPE: PRT
<213> ORGANISM: Artificial Sequence
<220> FEATURE:
<223> OTHER INFORMATION: Synthetic Construct

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Ser Tyr Gly Ser Thr Asp Tyr Ala Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Ala Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 56
<211> LENGTH: 98
<212> TYPE: PRT
<213> ORGANISM: Homo sapiens

<400> SEQUENCE: 56

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 57
<211> LENGTH: 98
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60
```

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 58
<211> LENGTH: 98
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 59
<211> LENGTH: 98
<212> TYPE: PRT
<213> ORGANISM: Homo sapiens

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 60
<211> LENGTH: 98
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
 50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 61
<211> LENGTH: 98
<212> TYPE: PRT
<213> ORGANISM: Homo sapiens

<400> SEQUENCE: 61

Gln Val Gln Leu Val Gln Ser Trp Ala Glu Val Arg Lys Ser Gly Ala
1               5                   10                  15

Ser Val Lys Val Ser Cys Ser Phe Ser Gly Phe Thr Ile Thr Ser Tyr
                20                  25                  30

Gly Ile His Trp Val Gln Ser Pro Gly Gln Gly Leu Glu Trp Met
        35                  40                  45

Gly Trp Ile Asn Pro Gly Asn Gly Ser Pro Tyr Ala Lys Lys Phe
 50                  55                  60

Gln Gly Arg Phe Thr Met Thr Arg Asp Met Ser Thr Thr Ala Tyr
65                  70                  75                  80

Thr Asp Leu Ser Ser Leu Thr Ser Glu Asp Met Ala Val Tyr Tyr
                85                  90                  95

Ala Arg

<210> SEQ ID NO 62
<211> LENGTH: 98
<212> TYPE: PRT
<213> ORGANISM: Homo sapiens

<400> SEQUENCE: 62

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
                20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
 50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 63
<211> LENGTH: 98
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala

```
                1               5                  10                  15
            Ser Val Lys Val Ser Cys Lys Ala Ser Gly Tyr Thr Phe Thr Ser Tyr
                            20                  25                  30

Tyr Met His Trp Val Arg Gln Ala Pro Gly Gln Gly Leu Glu Trp Met
                    35                  40                  45

Gly Ile Ile Asn Pro Ser Gly Ser Thr Ser Tyr Ala Gln Lys Phe
                50                  55                  60

Gln Gly Arg Val Thr Met Thr Arg Asp Thr Ser Thr Ser Thr Val Tyr
             65                  70                  75                  80

Met Glu Leu Ser Ser Leu Arg Ser Glu Asp Thr Ala Val Tyr Tyr Cys
                            85                  90                  95

Ala Arg

<210> SEQ ID NO 64
<211> LENGTH: 98
<212> TYPE: PRT
<213> ORGANISM: Homo sapiens

<400> SEQUENCE: 64

Gln Met Gln Leu Val Gln Ser Gly Pro Glu Val Lys Lys Pro Gly Thr
             1               5                  10                  15

Ser Val Lys Val Ser Cys Lys Ala Ser Gly Phe Thr Phe Thr Ser Ser
                            20                  25                  30

Ala Val Gln Trp Val Arg Gln Ala Arg Gly Gln Arg Leu Glu Trp Ile
                    35                  40                  45

Gly Trp Ile Val Gly Ser Gly Asn Thr Asn Tyr Ala Gln Lys Phe
                50                  55                  60

Gln Glu Arg Val Thr Ile Thr Arg Asp Met Ser Thr Ser Thr Ala Tyr
             65                  70                  75                  80

Met Glu Leu Ser Ser Leu Arg Ser Glu Asp Thr Ala Val Tyr Tyr Cys
                            85                  90                  95

Ala Ala

<210> SEQ ID NO 65
<211> LENGTH: 98
<212> TYPE: PRT
<213> ORGANISM: Homo sapiens

<400> SEQUENCE: 65

Gln Val Gln Leu Gly Gln Ser Glu Ala Glu Val Lys Lys Pro Gly Ala
             1               5                  10                  15

Ser Val Lys Val Ser Cys Lys Ala Ser Gly Tyr Thr Phe Thr Cys Cys
                            20                  25                  30

Ser Leu His Trp Leu Gln Gln Ala Pro Gly Gln Gly Leu Glu Arg Met
                    35                  40                  45

Arg Trp Ile Thr Leu Tyr Asn Gly Asn Thr Asn Tyr Ala Lys Lys Phe
                50                  55                  60

Gln Gly Arg Val Thr Ile Thr Arg Asp Met Ser Leu Arg Thr Ala Tyr
             65                  70                  75                  80

Ile Glu Leu Ser Ser Leu Arg Ser Glu Asp Ser Ala Val Tyr Tyr Trp
                            85                  90                  95

Ala Arg

<210> SEQ ID NO 66
<211> LENGTH: 98
<212> TYPE: PRT
```

<213> ORGANISM: Homo sapiens

<400> SEQUENCE: 66

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 67
<211> LENGTH: 98
<212> TYPE: PRT
<213> ORGANISM: Homo sapiens

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 68
<211> LENGTH: 98
<212> TYPE: PRT
<213> ORGANISM: Homo sapiens

<400> SEQUENCE: 68

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 69
<211> LENGTH: 95
<212> TYPE: PRT
<213> ORGANISM: Homo sapiens
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid

<400> SEQUENCE: 69

Gln Val Gln Leu Leu Gln Pro Gly Val Gln Val Lys Lys Pro Gly Ser
1               5                   10                  15

Ser Val Lys Val Ser Cys Ala Ser Arg Tyr Thr Phe Thr Lys Tyr Phe
            20                  25                  30

Thr Arg Trp Val Gln Ser Pro Gly Gln Gly His Xaa Trp Met Gly Ile
        35                  40                  45

Asn Pro Tyr Asn Asp Asn Thr His Tyr Ala Gln Thr Phe Trp Gly Arg
    50                  55                  60

Val Thr Ile Thr Ser Asp Arg Ser Met Ser Thr Ala Tyr Met Glu Leu
65                  70                  75                  80

Ser Xaa Leu Arg Ser Glu Asp Met Val Val Tyr Tyr Cys Val Arg
                85                  90                  95

<210> SEQ ID NO 70
<211> LENGTH: 100
<212> TYPE: PRT
<213> ORGANISM: Homo sapiens

<400> SEQUENCE: 70

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 71
<211> LENGTH: 98
<212> TYPE: PRT
<213> ORGANISM: Homo sapiens

<400> SEQUENCE: 71

Gln Val Thr Leu Lys Glu Ser Gly Pro Ala Leu Val Lys Pro Thr Gln
1               5                   10                  15

Thr Leu Met Leu Thr Cys Thr Phe Ser Gly Phe Ser Leu Ser Thr Ser
            20                  25                  30

Gly Met Gly Val Gly Ile Cys Gln Pro Ser Ala Lys Ala Leu Glu Trp

```
                35                  40                  45
Leu Ala His Ile Tyr Asn Asp Asn Lys Tyr Tyr Ser Pro Ser Leu Lys
 50                  55                  60

Ser Arg Leu Ile Ile Ser Lys Asp Thr Ser Lys Asn Glu Val Val Leu
 65                  70                  75                  80

Thr Val Ile Asn Met Asp Ile Val Asp Thr Ala Thr His Tyr Cys Ala
                 85                  90                  95

Arg Arg
```

<210> SEQ ID NO 72
<211> LENGTH: 100
<212> TYPE: PRT
<213> ORGANISM: Homo sapiens

<400> SEQUENCE: 72

```
Gln Val Thr Leu Lys Glu Ser Gly Pro Val Leu Val Lys Pro Thr Glu
 1               5                  10                  15

Thr Leu Thr Leu Thr Cys Thr Val Ser Gly Phe Ser Leu Ser Asn Ala
                 20                  25                  30

Arg Met Gly Val Ser Trp Ile Arg Gln Pro Pro Gly Lys Ala Leu Glu
                 35                  40                  45

Trp Leu Ala His Ile Phe Ser Asn Asp Glu Lys Ser Tyr Ser Thr Ser
 50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100
```

<210> SEQ ID NO 73
<211> LENGTH: 100
<212> TYPE: PRT
<213> ORGANISM: Homo sapiens

<400> SEQUENCE: 73

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Met Cys Val Ser Trp Ile Arg Gln Pro Pro Gly Lys Ala Leu Glu
                 35                  40                  45

Trp Leu Ala Leu Ile Asp Trp Asp Asp Asp Lys Tyr Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100
```

<210> SEQ ID NO 74
<211> LENGTH: 98
<212> TYPE: PRT
<213> ORGANISM: Homo sapiens

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 75
<211> LENGTH: 99
<212> TYPE: PRT
<213> ORGANISM: Homo sapiens

<400> SEQUENCE: 75

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp

<210> SEQ ID NO 76
<211> LENGTH: 98
<212> TYPE: PRT
<213> ORGANISM: Homo sapiens

<400> SEQUENCE: 76

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 77
<211> LENGTH: 97

```
<212> TYPE: PRT
<213> ORGANISM: Homo sapiens

<400> SEQUENCE: 77
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Asp | Met | His | Trp | Val | Arg | Gln | Ala | Thr | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Ala | Ile | Gly | Thr | Ala | Gly | Asp | Thr | Tyr | Tyr | Pro | Gly | Ser | Val | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Glu | Asn | Ala | Lys | Asn | Ser | Leu | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Gly | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

Arg

```
<210> SEQ ID NO 78
<211> LENGTH: 100
<212> TYPE: PRT
<213> ORGANISM: Homo sapiens

<400> SEQUENCE: 78
```

| Glu | Val | Gln | Leu | Val | Glu | Ser | Gly | Gly | Gly | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Arg | Ile | Lys | Ser | Lys | Thr | Asp | Gly | Gly | Thr | Thr | Asp | Tyr | Ala | Ala |
|---|---|---|---|---|---|---|---|---|---|---|---|---|---|---|---|
| | 50 | | | | | 55 | | | | | 60 | | | | |

| Pro | Val | Lys | Gly | Arg | Phe | Thr | Ile | Ser | Arg | Asp | Asp | Ser | Lys | Asn | Thr |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Lys | Thr | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr |
|---|---|---|---|
| | | | 100 |

```
<210> SEQ ID NO 79
<211> LENGTH: 98
<212> TYPE: PRT
<213> ORGANISM: Homo sapiens

<400> SEQUENCE: 79
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Asn | Ser |
|---|---|---|---|---|---|---|---|---|---|---|---|---|---|---|---|
| | | | 20 | | | | | 25 | | | | | 30 | | |

| Asp | Met | Asn | Trp | Ala | Arg | Lys | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Gly | Val | Ser | Trp | Asn | Gly | Ser | Arg | Thr | His | Tyr | Val | Asp | Ser | Val |
|---|---|---|---|---|---|---|---|---|---|---|---|---|---|---|---|
| | 50 | | | | | 55 | | | | | 60 | | | | |

| Lys | Arg | Arg | Phe | Ile | Ile | Ser | Arg | Asp | Asn | Ser | Arg | Asn | Ser | Leu | Tyr |
|---|---|---|---|---|---|---|---|---|---|---|---|---|---|---|---|
| 65 | | | | | 70 | | | | | 75 | | | | | 80 |

| Leu | Gln | Lys | Asn | Arg | Arg | Arg | Ala | Glu | Asp | Met | Ala | Val | Tyr | Tyr | Cys |
|---|---|---|---|---|---|---|---|---|---|---|---|---|---|---|---|
| | | | | 85 | | | | | 90 | | | | | 95 | |

Val Arg

<210> SEQ ID NO 80
<211> LENGTH: 98
<212> TYPE: PRT
<213> ORGANISM: Homo sapiens

<400> SEQUENCE: 80

```
Thr Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Phe Leu Tyr
65                  70                  75                  80

Gln Gln Met Asn Ser Leu Arg Pro Glu Asp Met Ala Val Tyr Tyr Cys
                85                  90                  95

Val Arg
```

<210> SEQ ID NO 81
<211> LENGTH: 98
<212> TYPE: PRT
<213> ORGANISM: Homo sapiens

<400> SEQUENCE: 81

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg
```

<210> SEQ ID NO 82
<211> LENGTH: 98
<212> TYPE: PRT
<213> ORGANISM: Homo sapiens

<400> SEQUENCE: 82

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60
```

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg

<210> SEQ ID NO 83
<211> LENGTH: 99
<212> TYPE: PRT
<213> ORGANISM: Homo sapiens

<400> SEQUENCE: 83

Glu Val His Leu Val Glu Ser Gly Gly Ala Leu Val Gln Pro Gly Gly
1               5                   10                  15

Ser Leu Arg Leu Ser Cys Ala Ala Ser Gly Phe Thr Phe Ser Tyr Tyr
            20                  25                  30

Tyr Met Ser Gly Val Arg Gln Ala Pro Gly Lys Gly Leu Glu Trp Val
        35                  40                  45

Gly Phe Ile Arg Asn Lys Ala Asn Gly Gly Thr Thr Glu Thr Thr Ser
    50                  55                  60

Val Lys Gly Arg Phe Thr Ile Ser Arg Asp Asp Ser Lys Ser Ile Thr
65                  70                  75                  80

Tyr Leu Gln Met Lys Ser Leu Lys Thr Glu Asp Thr Ala Val Tyr Tyr
            85                  90                  95

Cys Ser Arg

<210> SEQ ID NO 84
<211> LENGTH: 98
<212> TYPE: PRT
<213> ORGANISM: Homo sapiens

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys

<210> SEQ ID NO 85
<211> LENGTH: 98
<212> TYPE: PRT
<213> ORGANISM: Homo sapiens

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val

```
              35                  40                  45
Ser Ala Ile Ser Gly Ser Gly Gly Ser Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
             85                   90                  95
Ala Lys

<210> SEQ ID NO 86
<211> LENGTH: 96
<212> TYPE: PRT
<213> ORGANISM: Homo sapiens

<400> SEQUENCE: 86

Glu Met Gln Leu Val Glu Ser Gly Gly Gly Leu Gln Lys Pro Ala Trp
 1               5                  10                  15
Ser Pro Arg Leu Ser Cys Ala Ala Ser Gln Phe Thr Phe Ser Ser Tyr
             20                  25                  30
Tyr Met Asn Cys Val Arg Gln Ala Pro Gly Asn Gly Leu Glu Leu Val
             35                  40                  45
Gln Val Asn Pro Asn Gly Gly Ser Thr Tyr Leu Ile Asp Ser Gly Lys
     50                  55                  60
Asp Arg Phe Asn Thr Ser Arg Asp Asn Ala Lys Asn Thr Leu His Leu
 65                  70                  75                  80
Gln Met Asn Ser Leu Lys Thr Glu Asp Thr Ala Leu Tyr Cys Thr Arg
             85                  90                  95

<210> SEQ ID NO 87
<211> LENGTH: 96
<212> TYPE: PRT
<213> ORGANISM: Homo sapiens

<400> SEQUENCE: 87

Glu Val Glu Leu Ile Glu Pro Thr Glu Asp Leu Arg Gln Pro Gly Lys
 1               5                  10                  15
Phe Leu Arg Leu Ser Cys Val Ala Ser Arg Phe Ala Phe Ser Ser Phe
             20                  25                  30
Met Ser Pro Val His Gln Ser Ala Gly Lys Gly Leu Glu Val Ile Asp
             35                  40                  45
Ile Lys Asp Asp Gly Ser Gln Ile His His Ala Asp Ser Val Lys Gly
     50                  55                  60
Arg Phe Ser Ile Ser Lys Asp Asn Ala Lys Asn Ser Leu Tyr Leu Gln
 65                  70                  75                  80
Met Asn Ser Gln Arg Thr Glu Asp Met Ala Val Tyr Gly Cys Thr Gly
             85                  90                  95

<210> SEQ ID NO 88
<211> LENGTH: 95
<212> TYPE: PRT
<213> ORGANISM: Homo sapiens

<400> SEQUENCE: 88

Glu Val Gln Leu Val Glu Ser Gly Asp Pro Arg Gln Pro Gly Gly
 1               5                  10                  15
Ser Leu Arg Leu Ser Cys Ala Asp Ser Gly Leu Thr Phe Ser Ser Tyr
             20                  25                  30
```

```
Arg Asn Ser Val Ser Gln Ala Pro Gly Lys Gly Leu Glu Val Val Asp
            35                  40                  45
Ile Gln Cys Asp Gly Ser Gln Ile Cys Tyr Ala Ser Leu Lys Ser Lys
 50                      55                  60
Phe Thr Ile Ser Lys Glu Asn Ala Lys Asn Ser Leu Tyr Leu Leu Met
 65                  70                  75                  80
Asn Ser Leu Arg Ala Ala Gly Thr Ala Val Cys Tyr Cys Met Gly
                85                  90                  95
```

<210> SEQ ID NO 89
<211> LENGTH: 98
<212> TYPE: PRT
<213> ORGANISM: Homo sapiens

<400> SEQUENCE: 89

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
 50                      55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg
```

<210> SEQ ID NO 90
<211> LENGTH: 98
<212> TYPE: PRT
<213> ORGANISM: Homo sapiens

<400> SEQUENCE: 90

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
            35                  40                  45
Ala Val Ile Ser Tyr Asp Gly Ser Asn Lys Tyr Tyr Ala Asp Ser Val
 50                      55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg
```

<210> SEQ ID NO 91
<211> LENGTH: 96
<212> TYPE: PRT
<213> ORGANISM: Homo sapiens

<400> SEQUENCE: 91

```
Glu Val Glu Leu Ile Glu Ser Ile Glu Asp Leu Arg Gln Pro Gly Lys
 1               5                  10                  15
```

```
Phe Leu Arg Leu Ser Cys Val Ala Ser Arg Phe Ala Phe Ser Ser Phe
            20                  25                  30

Met Ser Arg Val His Gln Ser Pro Gly Lys Gly Leu Glu Val Ile Asp
            35                  40                  45

Ile Lys Asp Asp Gly Ser Gln Ile His His Ala Asp Ser Val Lys Gly
50                      55                  60

Arg Phe Ser Ile Ser Lys Asp Asn Ala Lys Asn Ser Leu Tyr Leu Gln
65                  70                  75                  80

Met Asn Thr Gln Arg Ala Glu Asp Val Ala Val Tyr Gly Tyr Thr Gly
                85                  90                  95
```

<210> SEQ ID NO 92
<211> LENGTH: 96
<212> TYPE: PRT
<213> ORGANISM: Homo sapiens

<400> SEQUENCE: 92

```
Glu Val Gln Leu Val Glu Ser Gly Glu Asp Pro Arg Gln Pro Gly Gly
1               5                   10                  15

Ser Leu Arg Leu Ser Cys Ala Asp Ser Gly Leu Thr Phe Ser Ser Tyr
            20                  25                  30

Met Ser Ser Val Ser Gln Ala Pro Gly Lys Gly Leu Glu Val Val Asp
            35                  40                  45

Ile Gln Cys Asp Gly Ser Gln Ile Cys Tyr Ala Gln Ser Val Lys Ser
50                      55                  60

Lys Phe Thr Ile Ser Lys Glu Asn Ala Lys Asn Ser Leu Tyr Leu Gln
65                  70                  75                  80

Met Asn Ser Leu Arg Ala Glu Gly Thr Ala Val Cys Tyr Cys Met Gly
                85                  90                  95
```

<210> SEQ ID NO 93
<211> LENGTH: 98
<212> TYPE: PRT
<213> ORGANISM: Homo sapiens

<400> SEQUENCE: 93

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 94
<211> LENGTH: 98
<212> TYPE: PRT
<213> ORGANISM: Homo sapiens

<400> SEQUENCE: 94

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
 50                  55                  60

Lys Gly Arg Phe Ile Ile Ser Arg Asp Asn Ser Arg Asn Thr Leu Tyr
 65                  70                  75                  80

Leu Gln Thr Asn Ser Leu Arg Ala Glu Asp Thr Ala Val Tyr Tyr Cys
                85                  90                  95

Val Arg
```

<210> SEQ ID NO 95
<211> LENGTH: 96
<212> TYPE: PRT
<213> ORGANISM: Homo sapiens

<400> SEQUENCE: 95

```
Glu Val Gln Leu Val Glu Ser Arg Gly Val Leu Val Gln Pro Gly Gly
 1               5                  10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
 50                  55                  60

Arg Phe Thr Ile Ser Arg Asp Asn Ser Lys Asn Thr Leu His Leu Gln
 65                  70                  75                  80

Met Asn Ser Leu Arg Ala Glu Asp Thr Ala Val Tyr Tyr Cys Lys Lys
                85                  90                  95
```

<210> SEQ ID NO 96
<211> LENGTH: 97
<212> TYPE: PRT
<213> ORGANISM: Homo sapiens

<400> SEQUENCE: 96

```
Glu Val Gln Leu Val Glu Ser Gly Gly Gly Leu Val Gln Pro Arg Gly
 1               5                  10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
 50                  55                  60

Arg Phe Thr Ile Ser Arg Asp Asn Ser Lys Asn Thr Leu Tyr Leu Gln
 65                  70                  75                  80

Met Asn Asn Leu Arg Ala Glu Gly Thr Ala Ala Tyr Tyr Cys Ala Arg
                85                  90                  95

Tyr
```

<210> SEQ ID NO 97
<211> LENGTH: 99
<212> TYPE: PRT
<213> ORGANISM: Homo sapiens

<400> SEQUENCE: 97

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp
```

<210> SEQ ID NO 98
<211> LENGTH: 99
<212> TYPE: PRT
<213> ORGANISM: Homo sapiens

<400> SEQUENCE: 98

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Leu Ile Ser Trp Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp
```

<210> SEQ ID NO 99
<211> LENGTH: 97
<212> TYPE: PRT
<213> ORGANISM: Homo sapiens

<400> SEQUENCE: 99

```
Glu Asp Gln Leu Val Glu Ser Gly Gly Gly Leu Val Gln Pro Gly Gly
1               5                   10                  15

Ser Leu Arg Pro Ser Cys Ala Ala Ser Gly Phe Ala Phe Ser Ser Tyr
            20                  25                  30

Ala Leu His Trp Val Arg Arg Ala Pro Gly Lys Gly Leu Glu Trp Val
            35                  40                  45

Ser Ala Ile Gly Thr Gly Gly Asp Thr Tyr Tyr Ala Asp Ser Val Met
        50                  55                  60

Gly Arg Phe Thr Ile Ser Arg Asp Asn Ala Lys Lys Ser Leu Tyr Leu
65                  70                  75                  80

His Met Asn Ser Leu Ile Ala Glu Asp Met Ala Val Tyr Tyr Cys Ala
                85                  90                  95

Arg
```

<210> SEQ ID NO 100

```
<211> LENGTH: 98
<212> TYPE: PRT
<213> ORGANISM: Homo sapiens

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 101
<211> LENGTH: 100
<212> TYPE: PRT
<213> ORGANISM: Homo sapiens

<400> SEQUENCE: 101

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Thr Ala
50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 102
<211> LENGTH: 97
<212> TYPE: PRT
<213> ORGANISM: Homo sapiens

<400> SEQUENCE: 102

Glu Val Gln Leu Val Glu Ser Gly Gly Leu Val Gln Pro Gly Gly Ser
1               5                   10                  15

Leu Arg Leu Ser Cys Ala Ala Ser Gly Phe Thr Phe Ser Ser Ser Trp
            20                  25                  30

Met His Trp Val Cys Gln Ala Pro Glu Lys Gly Leu Glu Trp Val Ala
        35                  40                  45

Asp Ile Lys Cys Asp Gly Ser Glu Lys Tyr Tyr Val Asp Ser Val Lys
50                  55                  60

Gly Arg Leu Thr Ile Ser Arg Asp Asn Ala Lys Asn Ser Leu Tyr Leu
65                  70                  75                  80

Gln Val Asn Ser Leu Arg Ala Glu Asp Met Thr Val Tyr Tyr Cys Val
```

-continued

```
                    85                  90                  95

Arg

<210> SEQ ID NO 103
<211> LENGTH: 97
<212> TYPE: PRT
<213> ORGANISM: Homo sapiens

<400> SEQUENCE: 103

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 104
<211> LENGTH: 93
<212> TYPE: PRT
<213> ORGANISM: Homo sapiens

<400> SEQUENCE: 104

Glu Val Gln Leu Val Glu Ser Glu Glu Asn Gln Arg Gln Leu Gly Gly
1               5                   10                  15

Ser Leu Arg Leu Ser Cys Ala Asp Ser Gly Leu Thr Phe Ser Ser Tyr
            20                  25                  30

Met Ser Ser Asp Ser Gln Ala Pro Gly Lys Gly Leu Glu Val Val Asp
        35                  40                  45

Ile Asp Arg Ser Gln Leu Cys Tyr Ala Gln Ser Val Lys Ser Arg Phe
    50                  55                  60

Thr Ile Ser Lys Glu Asn Ala Lys Asn Ser Leu Cys Leu Gln Met Asn
65                  70                  75                  80

Ser Leu Arg Ala Glu Gly Thr Ala Val Tyr Tyr Cys Met
                85                  90

<210> SEQ ID NO 105
<211> LENGTH: 97
<212> TYPE: PRT
<213> ORGANISM: Homo sapiens

<400> SEQUENCE: 105

Glu Val Gln Leu Val Glu Ser Gly Glu Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met His Trp Val Arg Gln Ala Pro Arg Lys Gly Leu Trp Val Ser
        35                  40                  45

Val Ile Ser Thr Ser Gly Asp Thr Val Leu Tyr Thr Asp Ser Val Lys
    50                  55                  60

Gly Arg Phe Thr Ile Ser Arg Asp Asn Ala Gln Asn Ser Leu Ser Leu
```

```
            65                  70                  75                  80
Gln Met Asn Ser Leu Arg Ala Glu Gly Thr Val Val Tyr Tyr Cys Val
                    85                  90                  95
Lys

<210> SEQ ID NO 106
<211> LENGTH: 97
<212> TYPE: PRT
<213> ORGANISM: Homo sapiens

<400> SEQUENCE: 106

Glu Val Glu Leu Ile Glu Ser Ile Gly Leu Arg Gln Leu Gly Lys
1               5                   10                  15

Phe Leu Arg Leu Ser Cys Val Ala Ser Gly Phe Thr Phe Ser Ser Tyr
                20                  25                  30

Met Ser Trp Val Asn Glu Thr Leu Gly Lys Gly Leu Glu Gly Val Ile
            35                  40                  45

Asp Val Lys Tyr Asp Gly Ser Gln Ile Tyr His Ala Asp Ser Val Lys
        50                  55                  60

Gly Arg Phe Thr Ile Ser Lys Asp Asn Ala Lys Asn Ser Pro Tyr Leu
65                  70                  75                  80

Gln Thr Asn Ser Leu Arg Ala Glu Asp Met Thr Met His Gly Cys Thr
                85                  90                  95

Gly

<210> SEQ ID NO 107
<211> LENGTH: 98
<212> TYPE: PRT
<213> ORGANISM: Homo sapiens

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Tyr Val
            35                  40                  45

Ser Ala Ile Ser Ser Asn Gly Gly Ser Thr Tyr Tyr Ala Asn Ser Val
        50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 108
<211> LENGTH: 97
<212> TYPE: PRT
<213> ORGANISM: Homo sapiens

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45
```

```
Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 109
<211> LENGTH: 97
<212> TYPE: PRT
<213> ORGANISM: Homo sapiens

<400> SEQUENCE: 109

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Tyr Met Asn Trp Val Arg Gln Ala Pro Gly Lys Gly Leu Glu Trp Val
             35                  40                  45

Ser Ser Ile Ser Ser Ser Ser Thr Ile Tyr Tyr Ala Asp Ser Val Lys
        50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Arg

<210> SEQ ID NO 110
<211> LENGTH: 99
<212> TYPE: PRT
<213> ORGANISM: Homo sapiens

<400> SEQUENCE: 110

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Val Arg Gln Ala Pro Gly Lys Gly Leu Glu Trp Val
             35                  40                  45

Gly Phe Ile Arg Asn Lys Ala Asn Gly Gly Thr Thr Glu Tyr Thr Ser
        50                  55                  60

Val Lys Gly Arg Phe Thr Ile Ser Arg Asp Asp Ser Lys Ser Ile Thr
 65                  70                  75                  80

Tyr Leu Gln Met Asn Ser Leu Arg Ala Glu Asp Thr Ala Val Tyr Tyr
                 85                  90                  95

Cys Ala Arg

<210> SEQ ID NO 111
<211> LENGTH: 100
<212> TYPE: PRT
<213> ORGANISM: Homo sapiens

<400> SEQUENCE: 111

Glu Val Gln Leu Val Glu Ser Gly Gly Gly Leu Val Gln Pro Gly Gly
 1               5                  10                  15
```

```
Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 112
<211> LENGTH: 100
<212> TYPE: PRT
<213> ORGANISM: Homo sapiens

<400> SEQUENCE: 112

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 113
<211> LENGTH: 98
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 114
<211> LENGTH: 98
<212> TYPE: PRT
```

<213> ORGANISM: Homo sapiens

<400> SEQUENCE: 114

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 115
<211> LENGTH: 98
<212> TYPE: PRT
<213> ORGANISM: Homo sapiens

<400> SEQUENCE: 115

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 116
<211> LENGTH: 98
<212> TYPE: PRT
<213> ORGANISM: Homo sapiens

<400> SEQUENCE: 116

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

```
<210> SEQ ID NO 117
<211> LENGTH: 99
<212> TYPE: PRT
<213> ORGANISM: Homo sapiens

<400> SEQUENCE: 117

Gln Leu Gln Leu Gln Glu Ser Gly Ser Gly Leu Val Lys Pro Ser Gln
1               5                   10                  15

Thr Leu Ser Leu Thr Cys Ala Val Ser Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
    50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 118
<211> LENGTH: 99
<212> TYPE: PRT
<213> ORGANISM: Homo sapiens

<400> SEQUENCE: 118

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 119
<211> LENGTH: 99
<212> TYPE: PRT
<213> ORGANISM: Homo sapiens

<400> SEQUENCE: 119

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Leu Val Thr Ile Ser Val Asp Thr Ser Lys Asn Gln Phe
65                  70                  75                  80
```

```
Ser Leu Lys Leu Ser Ser Val Thr Ala Ala Asp Thr Ala Val Tyr Tyr
                 85                  90                  95

Cys Ala Arg

<210> SEQ ID NO 120
<211> LENGTH: 97
<212> TYPE: PRT
<213> ORGANISM: Homo sapiens

<400> SEQUENCE: 120

Gln Val Gln Leu Gln Gln Trp Gly Ala Gly Leu Leu Lys Pro Ser Glu
1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 121
<211> LENGTH: 98
<212> TYPE: PRT
<213> ORGANISM: Homo sapiens

<400> SEQUENCE: 121

Gln Val Gln Leu Gln Glu Ser Gly Pro Gly Leu Val Lys Pro Ser Glu
1               5                  10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ser Thr Tyr Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 122
<211> LENGTH: 99
<212> TYPE: PRT
<213> ORGANISM: Homo sapiens

<400> SEQUENCE: 122

Gln Leu Gln Leu Gln Glu Ser Gly Pro Gly Leu Val Lys Pro Ser Glu
1               5                  10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45
```

-continued

```
Trp Ile Gly Ser Ile Tyr Tyr Ser Gly Ser Thr Tyr Tyr Asn Pro Ser
    50                  55                  60
Leu Lys Ser Arg Val Thr Ile Ser Val Asp Thr Ser Lys Asn Gln Phe
65                  70                  75                  80
Ser Leu Lys Leu Ser Ser Val Thr Ala Ala Asp Thr Ala Val Tyr Tyr
                85                  90                  95
Cys Ala Arg

<210> SEQ ID NO 123
<211> LENGTH: 97
<212> TYPE: PRT
<213> ORGANISM: Homo sapiens

<400> SEQUENCE: 123

Gln Val Gln Leu Gln Glu Ser Gly Pro Gly Leu Val Lys Pro Ser Glu
1               5                   10                  15
Thr Leu Ser Leu Ile Cys Ala Val Ser Gly Asp Ser Ile Ser Ser Gly
                20                  25                  30
Asn Trp Ile Trp Val Arg Gln Pro Pro Gly Lys Gly Leu Glu Trp Ile
            35                  40                  45
Gly Glu Ile His His Ser Gly Ser Thr Tyr Tyr Asn Pro Ser Leu Lys
    50                  55                  60
Ser Arg Ile Thr Met Ser Val Asp Thr Ser Lys Asn Gln Phe Tyr Leu
65                  70                  75                  80
Lys Leu Ser Ser Val Thr Ala Ala Asp Thr Ala Val Tyr Tyr Cys Ala
                85                  90                  95
Arg

<210> SEQ ID NO 124
<211> LENGTH: 97
<212> TYPE: PRT
<213> ORGANISM: Homo sapiens

<400> SEQUENCE: 124

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
                20                  25                  30
Tyr Trp Ser Trp Ile Arg Gln Pro Pro Gly Lys Gly Leu Glu Trp Ile
            35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg

<210> SEQ ID NO 125
<211> LENGTH: 99
<212> TYPE: PRT
<213> ORGANISM: Homo sapiens

<400> SEQUENCE: 125

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser Ser Gly
```

```
                    20                  25                  30
Ser Tyr Tyr Trp Ser Trp Ile Arg Gln Pro Gly Lys Gly Leu Glu
                35                  40                  45

Trp Ile Gly Tyr Ile Tyr Tyr Ser Gly Ser Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 126
<211> LENGTH: 98
<212> TYPE: PRT
<213> ORGANISM: Homo sapiens

<400> SEQUENCE: 126

Glu Val Gln Leu Val Gln Ser Gly Ala Glu Val Lys Lys Pro Gly Glu
 1                5                  10                  15

Ser Leu Arg Ile Ser Cys Lys Gly Ser Gly Tyr Ser Phe Thr Ser Tyr
                 20                  25                  30

Trp Ile Ser Trp Val Arg Gln Met Pro Gly Lys Gly Leu Glu Trp Met
                35                  40                  45

Gly Arg Ile Asp Pro Ser Asp Ser Tyr Thr Asn Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 127
<211> LENGTH: 98
<212> TYPE: PRT
<213> ORGANISM: Homo sapiens

<400> SEQUENCE: 127

Glu Val Gln Leu Val Gln Ser Gly Ala Glu Val Lys Lys Pro Gly Glu
 1                5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
                35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 128
<211> LENGTH: 98
<212> TYPE: PRT
<213> ORGANISM: Homo sapiens

<400> SEQUENCE: 128
```

```
Glu Val Gln Leu Leu Gln Ser Ala Ala Glu Val Lys Arg Pro Gly Glu
1               5                   10                  15

Ser Leu Arg Ile Ser Cys Lys Thr Ser Gly Tyr Ser Phe Thr Ser Tyr
                20                  25                  30

Trp Ile His Trp Val Arg Gln Met Pro Gly Lys Glu Leu Glu Trp Met
            35                  40                  45

Gly Ser Ile Tyr Pro Gly Asn Ser Asp Thr Arg Tyr Ser Pro Ser Phe
        50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Ala Ala Met Tyr Tyr Cys
                85                  90                  95

Val Arg
```

<210> SEQ ID NO 129
<211> LENGTH: 101
<212> TYPE: PRT
<213> ORGANISM: Homo sapiens

<400> SEQUENCE: 129

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
                35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100
```

<210> SEQ ID NO 130
<211> LENGTH: 98
<212> TYPE: PRT
<213> ORGANISM: Homo sapiens

<400> SEQUENCE: 130

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg
```

```
<210> SEQ ID NO 131
<211> LENGTH: 94
<212> TYPE: PRT
<213> ORGANISM: Homo sapiens

<400> SEQUENCE: 131

Leu Gln Leu Val Gln Ser Gly Pro Glu Val Lys Lys Pro Gly Ala Ser
1               5                   10                  15

Val Lys Val Ser Tyr Lys Ser Ser Gly Tyr Thr Phe Thr Ile Tyr Gly
                20                  25                  30

Met Asn Trp Val Thr Pro Gly Gln Gly Phe Glu Trp Met Trp Ile Ile
            35                  40                  45

Thr Tyr Thr Gly Asn Pro Thr Tyr Thr His Gly Phe Thr Gly Trp Phe
    50                  55                  60

Val Phe Ser Met Asp Thr Ser Val Ser Thr Ala Cys Leu Gln Ile Ser
65                  70                  75                  80

Ser Leu Lys Ala Glu Asp Thr Ala Glu Tyr Tyr Cys Ala Lys
                85                  90

<210> SEQ ID NO 132
<211> LENGTH: 98
<212> TYPE: PRT
<213> ORGANISM: Homo sapiens

<400> SEQUENCE: 132

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Thr Tyr
                20                  25                  30

Gly Met Asn Trp Val Pro Gln Ala Pro Gly Gln Gly Leu Glu Trp Met
            35                  40                  45

Gly Trp Phe Asn Thr Tyr Thr Gly Asn Pro Thr Tyr Ala Gln Gly Phe
    50                  55                  60

Thr Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg

<210> SEQ ID NO 133
<211> LENGTH: 95
<212> TYPE: PRT
<213> ORGANISM: Homo sapiens

<400> SEQUENCE: 133

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95
```

<210> SEQ ID NO 134
<211> LENGTH: 95
<212> TYPE: PRT
<213> ORGANISM: Homo sapiens

<400> SEQUENCE: 134

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro
                85                  90                  95
```

<210> SEQ ID NO 135
<211> LENGTH: 95
<212> TYPE: PRT
<213> ORGANISM: Homo sapiens

<400> SEQUENCE: 135

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Tyr Pro
                85                  90                  95
```

<210> SEQ ID NO 136
<211> LENGTH: 95
<212> TYPE: PRT
<213> ORGANISM: Homo sapiens

<400> SEQUENCE: 136

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95
```

```
<210> SEQ ID NO 137
<211> LENGTH: 95
<212> TYPE: PRT
<213> ORGANISM: Homo sapiens

<400> SEQUENCE: 137

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 138
<211> LENGTH: 94
<212> TYPE: PRT
<213> ORGANISM: Homo sapiens

<400> SEQUENCE: 138

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Tyr Gln Gln Lys Pro Gly Lys Ala Pro Lys Leu Leu Ile Tyr
        35                  40                  45

Asp Ala Ser Ser Leu Glu Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Phe Asn Asn Tyr Pro
                85                  90

<210> SEQ ID NO 139
<211> LENGTH: 95
<212> TYPE: PRT
<213> ORGANISM: Homo sapiens

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 140
```

```
<211> LENGTH: 95
<212> TYPE: PRT
<213> ORGANISM: Homo sapiens

<400> SEQUENCE: 140

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro
                85                  90                  95

<210> SEQ ID NO 141
<211> LENGTH: 95
<212> TYPE: PRT
<213> ORGANISM: Homo sapiens

<400> SEQUENCE: 141

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Asn Tyr
            20                  25                  30
Leu Ala Trp Tyr Gln Gln Lys Pro Gly Lys Val Pro Lys Leu Leu Ile
        35                  40                  45
Tyr Ala Ala Ser Thr Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Lys Tyr Asn Ser Ala Pro
                85                  90                  95

<210> SEQ ID NO 142
<211> LENGTH: 95
<212> TYPE: PRT
<213> ORGANISM: Homo sapiens

<400> SEQUENCE: 142

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Pro
                85                  90                  95

<210> SEQ ID NO 143
<211> LENGTH: 95
```

<212> TYPE: PRT
<213> ORGANISM: Homo sapiens

<400> SEQUENCE: 143

```
Asp Ile Gln Leu Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro
                85                  90                  95
```

<210> SEQ ID NO 144
<211> LENGTH: 95
<212> TYPE: PRT
<213> ORGANISM: Homo sapiens

<400> SEQUENCE: 144

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

<210> SEQ ID NO 145
<211> LENGTH: 95
<212> TYPE: PRT
<213> ORGANISM: Homo sapiens

<400> SEQUENCE: 145

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Ser
            20                  25                  30

Leu Ala Trp Tyr Gln Gln Lys Pro Gly Lys Ala Pro Lys Leu Leu Leu
        35                  40                  45

Tyr Ala Ala Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 146
<211> LENGTH: 95
<212> TYPE: PRT

<213> ORGANISM: Homo sapiens

<400> SEQUENCE: 146

Val Ile Trp Met Thr Gln Ser Pro Ser Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Cys Leu Gln Ser
65              70                  75                  80

Glu Asp Phe Ala Thr Tyr Tyr Cys Gln Gln Tyr Tyr Ser Phe Pro
                85                  90                  95

<210> SEQ ID NO 147
<211> LENGTH: 95
<212> TYPE: PRT
<213> ORGANISM: Homo sapiens

<400> SEQUENCE: 147

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ala Asn Ser Phe Pro
                85                  90                  95

<210> SEQ ID NO 148
<211> LENGTH: 95
<212> TYPE: PRT
<213> ORGANISM: Homo sapiens

<400> SEQUENCE: 148

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Phe Asn Asn Tyr Pro
                85                  90                  95

<210> SEQ ID NO 149
<211> LENGTH: 95
<212> TYPE: PRT
<213> ORGANISM: Homo sapiens

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 150
<211> LENGTH: 95
<212> TYPE: PRT
<213> ORGANISM: Homo sapiens

<400> SEQUENCE: 150

Asn Ile Gln Met Thr Gln Ser Pro Ser Ala Met Ser Ala Ser Val Gly
1               5                   10                  15

Asp Arg Val Thr Ile Thr Cys Arg Ala Arg Gln Gly Ile Ser Asn Tyr
            20                  25                  30

Leu Ala Trp Phe Gln Gln Lys Pro Gly Lys Val Pro Lys His Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 151
<211> LENGTH: 95
<212> TYPE: PRT
<213> ORGANISM: Homo sapiens

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 152
<211> LENGTH: 95
<212> TYPE: PRT
<213> ORGANISM: Homo sapiens

<400> SEQUENCE: 152

Asp Ile Gln Leu Thr Gln Ser Pro Ser Leu Ser Ala Ser Val Gly
1               5                   10                  15

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
                35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Gly Gln Arg Thr Tyr Asn Ala Pro
                85                  90                  95

<210> SEQ ID NO 153
<211> LENGTH: 95
<212> TYPE: PRT
<213> ORGANISM: Homo sapiens

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 154
<211> LENGTH: 95
<212> TYPE: PRT
<213> ORGANISM: Homo sapiens

<400> SEQUENCE: 154

Asp Ile Gln Met Ile Gln Ser Pro Ser Phe Leu Ser Ala Ser Val Gly
1               5                   10                  15

Asp Arg Val Ser Ile Ile Cys Trp Ala Ser Glu Gly Ile Ser Ser Asn
            20                  25                  30

Leu Ala Trp Tyr Leu Gln Lys Pro Gly Lys Ser Pro Lys Leu Phe Leu
                35                  40                  45

Tyr Asp Ala Lys Asp Leu His Pro Gly Val Ser Ser Arg Phe Ser Gly
    50                  55                  60

Arg Gly Ser Gly Thr Asp Phe Thr Leu Thr Ile Ile Ser Leu Lys Pro
65                  70                  75                  80

Glu Asp Phe Ala Ala Tyr Tyr Cys Lys Gln Asp Phe Ser Tyr Pro
                85                  90                  95

<210> SEQ ID NO 155
<211> LENGTH: 95
<212> TYPE: PRT
<213> ORGANISM: Homo sapiens

<400> SEQUENCE: 155

```
Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Tyr Ser Thr Pro
                85                  90                  95
```

<210> SEQ ID NO 156
<211> LENGTH: 100
<212> TYPE: PRT
<213> ORGANISM: Homo sapiens

<400> SEQUENCE: 156

```
Asp Ile Val Met Thr Gln His Leu Leu Ser Leu Pro Ile Pro Leu Gly
1               5                   10                  15

Glu Pro Ala Ser Ile Ser Cys Arg Ser Ser Gln Ser Leu Leu His Ser
            20                  25                  30

Asp Gly Asn Thr Tyr Leu Asp Trp Tyr Leu Gln Lys Pro Gly Gln Ser
        35                  40                  45

Pro Gln Leu Leu Ile Tyr Thr Ile Ser Asn Lys Phe Tyr Gly Val Pro
50                  55                  60

Asn Lys Phe Ser Gly Ser Arg Ser Gly Thr Gly Phe Thr Leu Lys Phe
65                  70                  75                  80

Ser Lys Val Glu Ala Glu Asp Val Gly Val Tyr Cys Cys Glu Gln Gly
                85                  90                  95

Leu Gln Gly Pro
            100
```

<210> SEQ ID NO 157
<211> LENGTH: 100
<212> TYPE: PRT
<213> ORGANISM: Homo sapiens

<400> SEQUENCE: 157

```
Asp Ile Val Met Thr Gln Thr Pro Pro Ser Leu Pro Val Asn Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Arg Val Ser Asn His Leu Ser Gly Val Pro
50                  55                  60

Asp Arg Phe Ser Gly Ser Gly Ser Gly Ser Asp Phe Thr Leu Lys Ile
65                  70                  75                  80

Ser Trp Val Glu Ala Glu Asp Val Gly Val Tyr Tyr Cys Met Gln Ala
                85                  90                  95

Thr Gln Phe Pro
            100
```

<210> SEQ ID NO 158

<211> LENGTH: 100
<212> TYPE: PRT
<213> ORGANISM: Homo sapiens

<400> SEQUENCE: 158

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 159
<211> LENGTH: 100
<212> TYPE: PRT
<213> ORGANISM: Homo sapiens

<400> SEQUENCE: 159

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 160
<211> LENGTH: 99
<212> TYPE: PRT
<213> ORGANISM: Homo sapiens

<400> SEQUENCE: 160

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Met Gln Gly Ile
                85                  90                  95

His Leu Pro

<210> SEQ ID NO 161
<211> LENGTH: 100
<212> TYPE: PRT
<213> ORGANISM: Homo sapiens

<400> SEQUENCE: 161

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 162
<211> LENGTH: 101
<212> TYPE: PRT
<213> ORGANISM: Homo sapiens

<400> SEQUENCE: 162

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 163
<211> LENGTH: 100
<212> TYPE: PRT
<213> ORGANISM: Homo sapiens

<400> SEQUENCE: 163

Asp Ile Val Met Thr Gln Thr Pro Ser Leu Pro Val Asn Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu His Trp Tyr Pro Gln Lys Pro Gly Gln Ser
        35                  40                  45
```

```
Pro Gln Leu Leu Ile Tyr Arg Val Ser Ser Arg Phe Ser Gly Val Pro
        50                  55                  60

Asp Arg Phe Ser Gly Ser Gly Ser Gly Ser Asp Phe Thr Leu Lys Ile
65                  70                  75                  80

Ser Trp Val Glu Ala Glu Asp Val Gly Val Tyr Tyr Cys Met Gln Ala
                85                  90                  95

Thr Gln Phe Pro
            100

<210> SEQ ID NO 164
<211> LENGTH: 100
<212> TYPE: PRT
<213> ORGANISM: Homo sapiens

<400> SEQUENCE: 164

Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Val Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro
            100

<210> SEQ ID NO 165
<211> LENGTH: 100
<212> TYPE: PRT
<213> ORGANISM: Homo sapiens

<400> SEQUENCE: 165

Glu Ile Val Met Thr Gln Thr Pro Leu Ser Leu Ser Ile Thr Pro Gly
1               5                   10                  15

Glu Gln Ala Ser Ile Ser Cys Arg Ser Ser Gln Ser Leu Leu His Ser
            20                  25                  30

Asp Gly Tyr Thr Tyr Leu Tyr Trp Phe Leu Gln Lys Ala Arg Pro Val
        35                  40                  45

Ser Thr Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Asp
                85                  90                  95

Ala Gln Asp Pro
            100

<210> SEQ ID NO 166
<211> LENGTH: 100
<212> TYPE: PRT
<213> ORGANISM: Homo sapiens

<400> SEQUENCE: 166
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 167
<211> LENGTH: 100
<212> TYPE: PRT
<213> ORGANISM: Homo sapiens

<400> SEQUENCE: 167

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100
```

<210> SEQ ID NO 168
<211> LENGTH: 100
<212> TYPE: PRT
<213> ORGANISM: Homo sapiens

<400> SEQUENCE: 168

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100
```

<210> SEQ ID NO 169
<211> LENGTH: 101
<212> TYPE: PRT
<213> ORGANISM: Homo sapiens

<400> SEQUENCE: 169

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 170
<211> LENGTH: 96
<212> TYPE: PRT
<213> ORGANISM: Homo sapiens

<400> SEQUENCE: 170

Glu Ile Val Met Thr Gln Ser Pro Pro Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Thr Trp Tyr Gln Gln Lys Pro Gly Gln Ala Pro Arg Leu Leu
        35                  40                  45

Ile Tyr Gly Ala Ser Thr Arg Ala Thr Ser Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp His Asn Leu Pro
                85                  90                  95

<210> SEQ ID NO 171
<211> LENGTH: 95
<212> TYPE: PRT
<213> ORGANISM: Homo sapiens

<400> SEQUENCE: 171

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

85                  90                  95

<210> SEQ ID NO 172
<211> LENGTH: 95
<212> TYPE: PRT
<213> ORGANISM: Homo sapiens

<400> SEQUENCE: 172

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 173
<211> LENGTH: 96
<212> TYPE: PRT
<213> ORGANISM: Homo sapiens

<400> SEQUENCE: 173

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 174
<211> LENGTH: 89
<212> TYPE: PRT
<213> ORGANISM: Homo sapiens

<400> SEQUENCE: 174

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln
                85

<210> SEQ ID NO 175
<211> LENGTH: 89
<212> TYPE: PRT
<213> ORGANISM: Homo sapiens

<400> SEQUENCE: 175

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln
                85

<210> SEQ ID NO 176
<211> LENGTH: 90
<212> TYPE: PRT
<213> ORGANISM: Homo sapiens

<400> SEQUENCE: 176

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Arg Leu Gln
65                  70                  75                  80

Ser Glu Asp Phe Ala Val Tyr Tyr Cys Gln
                85                  90

<210> SEQ ID NO 177
<211> LENGTH: 95
<212> TYPE: PRT
<213> ORGANISM: Homo sapiens

<400> SEQUENCE: 177

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 178
<211> LENGTH: 96
<212> TYPE: PRT
<213> ORGANISM: Homo sapiens

<400> SEQUENCE: 178

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Arg Ser Asn Trp His
                85                  90                  95

<210> SEQ ID NO 179
<211> LENGTH: 96
<212> TYPE: PRT
<213> ORGANISM: Homo sapiens

<400> SEQUENCE: 179

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 180
<211> LENGTH: 95
<212> TYPE: PRT
<213> ORGANISM: Homo sapiens

<400> SEQUENCE: 180

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

```
<210> SEQ ID NO 181
<211> LENGTH: 95
<212> TYPE: PRT
<213> ORGANISM: Homo sapiens

<400> SEQUENCE: 181

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 182
<211> LENGTH: 96
<212> TYPE: PRT
<213> ORGANISM: Homo sapiens

<400> SEQUENCE: 182

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 183
<211> LENGTH: 101
<212> TYPE: PRT
<213> ORGANISM: Homo sapiens

<400> SEQUENCE: 183

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
                100
```

<210> SEQ ID NO 184
<211> LENGTH: 95
<212> TYPE: PRT
<213> ORGANISM: Homo sapiens

<400> SEQUENCE: 184

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 185
<211> LENGTH: 95
<212> TYPE: PRT
<213> ORGANISM: Homo sapiens

<400> SEQUENCE: 185

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 186
<211> LENGTH: 95
<212> TYPE: PRT
<213> ORGANISM: Homo sapiens

<400> SEQUENCE: 186

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 187
<211> LENGTH: 95
<212> TYPE: PRT
<213> ORGANISM: Homo sapiens

<400> SEQUENCE: 187

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95

<210> SEQ ID NO 188
<211> LENGTH: 99
<212> TYPE: PRT
<213> ORGANISM: Homo sapiens

<400> SEQUENCE: 188

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
            20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Leu Gln Ser Lys
                85                  90                  95

Asn Phe Pro

<210> SEQ ID NO 189
<211> LENGTH: 98
<212> TYPE: PRT
<213> ORGANISM: Homo sapiens

<400> SEQUENCE: 189

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly

<210> SEQ ID NO 190
<211> LENGTH: 99
<212> TYPE: PRT
<213> ORGANISM: Homo sapiens

<400> SEQUENCE: 190

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 191
<211> LENGTH: 98
<212> TYPE: PRT
<213> ORGANISM: Homo sapiens

<400> SEQUENCE: 191

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Met Gly Asn Tyr
            20                  25                  30

Ala Val Ser Trp Tyr Gln Gln Leu Pro Gly Thr Ala Pro Lys Leu Leu
            35                  40                  45

Ile Tyr Glu Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Trp
65                  70                  75                  80

Pro Glu Asp Glu Ala Asp Tyr Tyr Cys Leu Ala Trp Asp Thr Ser Pro
                85                  90                  95

Arg Ala

<210> SEQ ID NO 192
<211> LENGTH: 98
<212> TYPE: PRT
<213> ORGANISM: Homo sapiens

<400> SEQUENCE: 192

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

```
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly

<210> SEQ ID NO 193
<211> LENGTH: 98
<212> TYPE: PRT
<213> ORGANISM: Homo sapiens

<400> SEQUENCE: 193

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Tyr Val Tyr Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly

<210> SEQ ID NO 194
<211> LENGTH: 99
<212> TYPE: PRT
<213> ORGANISM: Homo sapiens

<400> SEQUENCE: 194

Gln Ser Val Leu Thr Gln Pro Pro Ser Val Ser Gly Ala Pro Gly Gln
 1               5                  10                  15

Arg Val Thr Ile Ser Cys Thr Gly Ser Ser Asn Ile Gly Ala Gly
             20                  25                  30

Tyr Val Val His Trp Tyr Gln Gln Leu Pro Gly Thr Ala Pro Lys Leu
             35                  40                  45

Leu Ile Tyr Gly Asn Ser Asn Arg Pro Ser Gly Val Pro Asp Gln Phe
 50                  55                  60

Ser Gly Ser Lys Ser Gly Thr Ser Ala Ser Leu Ala Ile Thr Gly Leu
 65                  70                  75                  80

Gln Ser Glu Asp Glu Ala Asp Tyr Tyr Cys Lys Ala Trp Asp Asn Ser
                 85                  90                  95

Leu Asn Ala

<210> SEQ ID NO 195
<211> LENGTH: 98
<212> TYPE: PRT
<213> ORGANISM: Homo sapiens

<400> SEQUENCE: 195

Gln Ser Val Leu Thr Gln Pro Pro Ser Val Ser Ala Ala Pro Gly Gln
 1               5                  10                  15

Lys Val Thr Ile Ser Cys Ser Gly Ser Ser Asn Ile Gly Asn Asn
             20                  25                  30

Tyr Val Ser Trp Tyr Gln Gln Leu Pro Gly Thr Ala Pro Lys Leu Leu
```

```
                35                   40                  45
Ile Tyr Asp Asn Asn Lys Arg Pro Ser Gly Ile Pro Asp Arg Phe Ser
        50                   55                  60
Gly Ser Lys Ser Gly Thr Ser Ala Thr Leu Gly Ile Thr Gly Leu Gln
65                  70                   75                  80
Thr Gly Asp Glu Ala Asp Tyr Tyr Cys Gly Thr Trp Asp Ser Ser Leu
                85                   90                  95
Ser Ala
```

<210> SEQ ID NO 196
<211> LENGTH: 97
<212> TYPE: PRT
<213> ORGANISM: Homo sapiens

<400> SEQUENCE: 196

```
Gln Ser Val Leu Thr Gln Pro Pro Ser Val Ser Trp Ala Thr Arg Gln
1               5                   10                  15
Arg Leu Thr Val Ser Cys Thr Gly Ser Ser Ser Asn Thr Gly Thr Gly
                20                  25                  30
Tyr Asn Val Asn Cys Trp Gln Leu Pro Arg Thr Asp Pro Lys Leu Leu
                35                  40                  45
Arg His Gly Asp Lys Asn Trp Ala Ser Trp Val Ser Asp Gln Phe Ser
        50                  55                  60
Gly Ser Lys Ser Gly Ser Leu Ala Ser Leu Gly Thr Thr Gly Leu Trp
65                  70                  75                  80
Ala Glu Asp Lys Thr Asp Tyr His Cys Gln Ser Arg Asp Ile Cys Val
                85                  90                  95
Leu
```

<210> SEQ ID NO 197
<211> LENGTH: 97
<212> TYPE: PRT
<213> ORGANISM: Homo sapiens

<400> SEQUENCE: 197

```
Gln Ser Ala Leu Ile Gln Pro Pro Ser Val Ser Gly Ser Pro Gly Gln
1               5                   10                  15
Ser Val Thr Ile Ser Cys Thr Gly Thr Ser Ser Asp Val Gly Ser Tyr
                20                  25                  30
Asp Tyr Val Ser Trp Tyr Gln Gln His Pro Gly Thr Val Pro Lys Pro
                35                  40                  45
Met Ile Tyr Asn Val Asn Thr Gln Pro Ser Gly Val Pro Asp Arg Phe
        50                  55                  60
Ser Gly Ser Lys Ser Gly Asn Thr Ala Ser Met Thr Ile Ser Gly Leu
65                  70                  75                  80
Gln Ala Glu Asp Glu Ala Asp Tyr Cys Cys Ser Tyr Thr Ser Ser Ala
                85                  90                  95
Thr
```

<210> SEQ ID NO 198
<211> LENGTH: 99
<212> TYPE: PRT
<213> ORGANISM: Homo sapiens

<400> SEQUENCE: 198

```
Gln Ser Ala Leu Thr Gln Pro Pro Ser Ala Ser Gly Ser Pro Gly Gln
1               5                   10                  15
```

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                    85                  90                  95

Asn Asn Phe

<210> SEQ ID NO 199
<211> LENGTH: 99
<212> TYPE: PRT
<213> ORGANISM: Homo sapiens

<400> SEQUENCE: 199

Gln Ser Ala Leu Thr Gln Pro Arg Ser Val Ser Gly Ser Pro Gly Gln
 1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                    85                  90                  95

Tyr Thr Phe

<210> SEQ ID NO 200
<211> LENGTH: 99
<212> TYPE: PRT
<213> ORGANISM: Homo sapiens

<400> SEQUENCE: 200

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                    85                  90                  95

Ser Thr Leu

<210> SEQ ID NO 201
<211> LENGTH: 99
<212> TYPE: PRT
<213> ORGANISM: Homo sapiens

<400> SEQUENCE: 201

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Leu Tyr Thr Ser Ser
                85                  90                  95

Ser Thr Phe

<210> SEQ ID NO 202
<211> LENGTH: 99
<212> TYPE: PRT
<213> ORGANISM: Homo sapiens

<400> SEQUENCE: 202

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu

<210> SEQ ID NO 203
<211> LENGTH: 99
<212> TYPE: PRT
<213> ORGANISM: Homo sapiens

<400> SEQUENCE: 203

Gln Ser Ala Leu Thr Gln Pro Pro Phe Val Ser Gly Ala Pro Gly Gln
1               5                   10                  15

Ser Val Thr Ile Ser Cys Thr Gly Thr Ser Ser Asp Val Gly Asp Tyr
            20                  25                  30

Asp His Val Phe Trp Tyr Gln Lys Arg Leu Ser Thr Thr Ser Arg Leu
        35                  40                  45

Leu Ile Tyr Asn Val Asn Thr Arg Pro Ser Gly Ile Ser Asp Leu Phe
50                  55                  60

Ser Gly Ser Lys Ser Gly Asn Met Ala Ser Leu Thr Ile Ser Gly Leu
65                  70                  75                  80

Lys Ser Glu Val Glu Ala Asn Tyr His Cys Ser Leu Tyr Ser Ser Ser
                85                  90                  95

Tyr Thr Phe

<210> SEQ ID NO 204
<211> LENGTH: 97
<212> TYPE: PRT
<213> ORGANISM: Homo sapiens

<400> SEQUENCE: 204

Gln Ser Val Leu Thr Gln Pro Arg Ser Val Ser Arg Ser Pro Gly Gln
1               5                   10                  15

Val Thr Ile Phe Cys Thr Gly Thr Ser Ser Asp Ile Gly Gly Tyr Asp
            20                  25                  30

Leu Val Ser Trp Cys Gln His Pro Gly Lys Ala Pro Lys Leu Met Ile
        35                  40                  45

Tyr Asp Val Ala Asn Trp Pro Ser Gly Ala Pro Gly Cys Phe Ser Gly
    50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys Ser Ser Tyr Ala Gly Ser Tyr Asn
                85                  90                  95

Phe

<210> SEQ ID NO 205
<211> LENGTH: 97
<212> TYPE: PRT
<213> ORGANISM: Homo sapiens

<400> SEQUENCE: 205

Gln Ser Val Leu Thr Gln Pro Arg Ser Val Ser Arg Ser Pro Gly Gln
1               5                   10                  15

Val Thr Ile Phe Cys Thr Gly Thr Ser Ser Asp Ile Gly Gly Tyr Asp
            20                  25                  30

Leu Val Ser Trp Cys Gln His Pro Gly Lys Ala Pro Lys Leu Met Ile
        35                  40                  45

Tyr Asp Val Gly Asn Trp Pro Ser Gly Ala Pro Gly Cys Phe Ser Gly
    50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys Ser Ser Tyr Ala Gly Ser Tyr Asn
                85                  90                  95

Phe

<210> SEQ ID NO 206
<211> LENGTH: 95
<212> TYPE: PRT
<213> ORGANISM: Homo sapiens

<400> SEQUENCE: 206

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

```
Asp Glu Ala Asp Tyr Tyr Cys Gln Ala Trp Asp Ser Ser Thr Ala
                85                  90                  95

<210> SEQ ID NO 207
<211> LENGTH: 95
<212> TYPE: PRT
<213> ORGANISM: Homo sapiens

<400> SEQUENCE: 207

Ser Tyr Glu Leu Thr Gln Pro Leu Ser Val Ser Val Ala Leu Gly Gln
1               5                   10                  15

Thr Ala Arg Ile Thr Cys Gly Gly Asn Asn Ile Gly Ser Lys Asn Val
            20                  25                  30

His Trp Tyr Gln Gln Lys Pro Gly Gln Ala Pro Val Leu Val Ile Tyr
        35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95

<210> SEQ ID NO 208
<211> LENGTH: 96
<212> TYPE: PRT
<213> ORGANISM: Homo sapiens

<400> SEQUENCE: 208

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

<210> SEQ ID NO 209
<211> LENGTH: 96
<212> TYPE: PRT
<213> ORGANISM: Homo sapiens

<400> SEQUENCE: 209

Ser Tyr Glu Leu Thr Gln Pro His Ser Val Ser Val Ala Thr Ala Gln
1               5                   10                  15

Met Ala Arg Ile Thr Cys Gly Gly Asn Asn Ile Gly Ser Lys Ala Val
            20                  25                  30

His Trp Tyr Gln Gln Lys Pro Gly Gln Asp Pro Val Leu Val Ile Tyr
        35                  40                  45

Ser Asp Ser Asn Arg Pro Ser Gly Ile Pro Glu Arg Phe Ser Gly Ser
    50                  55                  60

Asn Pro Gly Asn Thr Thr Thr Leu Thr Ile Ser Arg Ile Glu Ala Gly
65                  70                  75                  80

Asp Glu Ala Asp Tyr Tyr Cys Gln Val Trp Asp Ser Ser Ser Asp His
```

<210> SEQ ID NO 210
<211> LENGTH: 93
<212> TYPE: PRT
<213> ORGANISM: Homo sapiens

<400> SEQUENCE: 210

Ser Tyr Glu Leu Thr Gln Pro Pro Ala Val Ser Val Ser Pro Gly Gln
1               5                   10                  15

Thr Ala Arg Ile Ser Cys Ser Gly Asp Val Leu Arg Asp Asn Tyr Ala
            20                  25                  30

Asp Trp Tyr Pro Gln Lys Pro Gly Gln Ala Pro Val Leu Val Ile Tyr
        35                  40                  45

Lys Asp Gly Glu Arg Pro Ser Gly Ile Pro Glu Arg Phe Ser Gly Ser
    50                  55                  60

Thr Ser Gly Asn Thr Thr Ala Leu Thr Ile Ser Arg Val Leu Thr Lys
65                  70                  75                  80

Gly Gly Ala Asp Tyr Tyr Cys Phe Ser Gly Asp Asn Asn
                85                  90

<210> SEQ ID NO 211
<211> LENGTH: 96
<212> TYPE: PRT
<213> ORGANISM: Homo sapiens

<400> SEQUENCE: 211

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
            20                  25                  30

Tyr Trp Tyr Gln Gln Lys Pro Gly Gln Phe Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Ile Val Thr Leu Thr Ile Ser Gly Val Gln Ala Glu
65                  70                  75                  80

Asp Glu Ala Asp Tyr Tyr Cys Leu Ser Ala Asp Ser Ser Gly Thr Tyr
                85                  90                  95

<210> SEQ ID NO 212
<211> LENGTH: 96
<212> TYPE: PRT
<213> ORGANISM: Homo sapiens

<400> SEQUENCE: 212

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 213
<211> LENGTH: 96
<212> TYPE: PRT
<213> ORGANISM: Homo sapiens

<400> SEQUENCE: 213

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

<210> SEQ ID NO 214
<211> LENGTH: 94
<212> TYPE: PRT
<213> ORGANISM: Homo sapiens

<400> SEQUENCE: 214

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
                85                  90

<210> SEQ ID NO 215
<211> LENGTH: 96
<212> TYPE: PRT
<213> ORGANISM: Homo sapiens

<400> SEQUENCE: 215

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

```
<210> SEQ ID NO 216
<211> LENGTH: 94
<212> TYPE: PRT
<213> ORGANISM: Homo sapiens

<400> SEQUENCE: 216

Ser Tyr Glu Leu Thr Gln Pro Ser Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn
                85                  90

<210> SEQ ID NO 217
<211> LENGTH: 94
<212> TYPE: PRT
<213> ORGANISM: Homo sapiens

<400> SEQUENCE: 217

Ser Ser Glu Leu Ser Gln Glu Pro Ala Val Ser Val Ala Leu Gly Thr
1               5                   10                  15

Ala Arg Ile Thr Cys Gln Gly Asp Ser Ile Glu Asp Ser Val Val Asn
            20                  25                  30

Trp Tyr Lys Gln Lys Pro Ser Gln Ala Pro Gly Leu Val Ile Leu Asn
        35                  40                  45

Ser Val Gln Ser Ser Gly Ile Pro Lys Lys Phe Ser Gly Ser Ser Ser
    50                  55                  60

Gly Asn Met Ala Thr Leu Thr Ile Thr Gly Ile Gln Val Glu Asp Lys
65                  70                  75                  80

Ala Asp Tyr Tyr Cys Gln Ser Trp Asp Ser Ser Arg Thr His
                85                  90

<210> SEQ ID NO 218
<211> LENGTH: 94
<212> TYPE: PRT
<213> ORGANISM: Homo sapiens

<400> SEQUENCE: 218

Ser Ser Gly Pro Thr Gln Val Pro Ala Val Ser Val Ala Leu Gly Gln
1               5                   10                  15

Met Ala Arg Ile Thr Cys Gln Gly Asp Ser Met Glu Gly Ser Tyr Glu
            20                  25                  30

His Trp Tyr Gln Gln Lys Pro Gly Gln Ala Pro Val Leu Val Ile Tyr
        35                  40                  45

Asp Ser Ser Asp Arg Pro Ser Arg Ile Pro Glu Arg Phe Ser Gly Ser
    50                  55                  60

Lys Ser Gly Asn Thr Thr Thr Leu Thr Ile Thr Gly Ala Gln Ala Glu
65                  70                  75                  80

Asp Glu Ala Asp Tyr Tyr Tyr Gln Leu Ile Asp Asn His Ala
                85                  90
```

<210> SEQ ID NO 219
<211> LENGTH: 103
<212> TYPE: PRT
<213> ORGANISM: Homo sapiens

<400> SEQUENCE: 219

Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
        35                  40                  45

Lys Val Lys Ser Asp Gly Ser His Ser Lys Gly Asp Gly Ile Pro Asp
    50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 220
<211> LENGTH: 99
<212> TYPE: PRT
<213> ORGANISM: Homo sapiens

<400> SEQUENCE: 220

Gln Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Ser Tyr Ile
            20                  25                  30

Ile Ala Trp His Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Ser Gly Ser Ser Ser Gly Ala Asp Arg Tyr Leu Thr Ile Ser
65                  70                  75                  80

Asn Leu Gln Leu Glu Asp Glu Ala Asp Tyr Tyr Cys Glu Thr Trp Asp
                85                  90                  95

Ser Asn Thr

<210> SEQ ID NO 221
<211> LENGTH: 99
<212> TYPE: PRT
<213> ORGANISM: Homo sapiens

<400> SEQUENCE: 221

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
        35                  40                  45

Lys Leu Asn Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

```
Ser Leu Gln Ser Glu Asp Glu Ala Asp Tyr Tyr Cys Gln Thr Trp Gly
                85                  90                  95

Thr Gly Ile

<210> SEQ ID NO 222
<211> LENGTH: 104
<212> TYPE: PRT
<213> ORGANISM: Homo sapiens

<400> SEQUENCE: 222

Gln Pro Val Leu Thr Gln Pro Ser Ser Ala Ser Pro Gly Glu
1               5                   10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Arg Tyr
            35                  40                  45

Leu Leu Tyr Tyr Tyr Ser Asp Ser Asp Lys Gly Gln Gly Ser Gly Val
        50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 223
<211> LENGTH: 104
<212> TYPE: PRT
<213> ORGANISM: Homo sapiens

<400> SEQUENCE: 223

Gln Pro Val Leu Thr Gln Pro Thr Ser Leu Ser Ala Ser Pro Gly Ala
1               5                   10                  15

Ser Ala Arg Phe Thr Cys Thr Leu Arg Ser Gly Ile Asn Val Gly Thr
                20                  25                  30

Tyr Arg Ile Tyr Trp Tyr Gln Gln Lys Pro Gly Ser Leu Pro Arg Tyr
            35                  40                  45

Leu Leu Arg Tyr Lys Ser Asp Ser Asp Lys Gln Gln Gly Ser Gly Val
        50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Ser
            100

<210> SEQ ID NO 224
<211> LENGTH: 104
<212> TYPE: PRT
<213> ORGANISM: Homo sapiens

<400> SEQUENCE: 224

Gln Ala Val Leu Thr Gln Pro Ser Leu Ser Ala Ser Pro Gly Ala
1               5                   10                  15

Ser Ala Ser Leu Thr Cys Thr Leu Arg Ser Gly Ile Asn Val Gly Thr
                20                  25                  30

Tyr Arg Ile Tyr Trp Tyr Gln Gln Lys Pro Gly Ser Pro Pro Gln Tyr
            35                  40                  45
```

```
Leu Leu Arg Tyr Lys Ser Asp Ser Asp Lys Gln Gln Gly Ser Gly Val
        50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100
```

<210> SEQ ID NO 225
<211> LENGTH: 104
<212> TYPE: PRT
<213> ORGANISM: Homo sapiens

<400> SEQUENCE: 225

```
Gln Pro Val Leu Thr Gln Pro Thr Ser Leu Ser Ala Ser Pro Gly Ala
 1               5                  10                  15

Ser Ala Arg Leu Thr Cys Thr Leu Arg Ser Gly Ile Asn Leu Gly Ser
                20                  25                  30

Tyr Arg Ile Phe Trp Tyr Gln Gln Lys Pro Glu Ser Pro Pro Arg Tyr
            35                  40                  45

Leu Leu Ser Tyr Tyr Ser Asp Ser Ser Lys His Gln Gly Ser Gly Val
        50                  55                  60

Pro Ser Arg Phe Ser Gly Ser Lys Asp Ala Ser Ser Asn Ala Gly Ile
 65                  70                  75                  80

Leu Val Ile Ser Gly Leu Gln Ser Glu Asp Glu Ala Asp Tyr Tyr Cys
                85                  90                  95

Met Ile Trp His Ser Ser Ala Ser
            100
```

<210> SEQ ID NO 226
<211> LENGTH: 105
<212> TYPE: PRT
<213> ORGANISM: Homo sapiens

<400> SEQUENCE: 226

```
Gln Pro Val Leu Thr Gln Pro Ser Ser His Ser Ala Ser Ser Gly Ala
 1               5                  10                  15

Ser Val Arg Leu Thr Cys Met Leu Ser Ser Gly Phe Ser Val Gly Asp
                20                  25                  30

Phe Trp Ile Arg Trp Tyr Gln Gln Lys Pro Gly Asn Pro Pro Arg Tyr
            35                  40                  45

Leu Leu Tyr Tyr His Ser Asp Ser Asn Lys Gly Gln Gly Ser Gly Val
        50                  55                  60

Pro Ser Arg Phe Ser Gly Ser Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                85                  90                  95

Gly Thr Trp His Ser Asn Ser Lys Thr
            100                 105
```

<210> SEQ ID NO 227
<211> LENGTH: 98
<212> TYPE: PRT
<213> ORGANISM: Homo sapiens

<400> SEQUENCE: 227

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn
```

<210> SEQ ID NO 228
<211> LENGTH: 98
<212> TYPE: PRT
<213> ORGANISM: Homo sapiens

<400> SEQUENCE: 228

```
Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Phe Gln Gln Lys Pro Gly Gln Ala Pro Arg Ala
        35                  40                  45

Leu Ile Tyr Ser Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Tyr Tyr Gly Gly
                85                  90                  95

Ala Gln
```

<210> SEQ ID NO 229
<211> LENGTH: 98
<212> TYPE: PRT
<213> ORGANISM: Homo sapiens

<400> SEQUENCE: 229

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg
```

<210> SEQ ID NO 230
<211> LENGTH: 98

-continued

```
<212> TYPE: PRT
<213> ORGANISM: Homo sapiens

<400> SEQUENCE: 230

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile

<210> SEQ ID NO 231
<211> LENGTH: 104
<212> TYPE: PRT
<213> ORGANISM: Homo sapiens

<400> SEQUENCE: 231

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
            20                  25                  30

Val Asp Trp Tyr Gln Gln Arg Pro Gly Lys Gly Pro Arg Phe Val Met
        35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val
                100

<210> SEQ ID NO 232
<211> LENGTH: 98
<212> TYPE: PRT
<213> ORGANISM: Homo sapiens

<400> SEQUENCE: 232

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95
```

Ser Ala

<210> SEQ ID NO 233
<211> LENGTH: 104
<212> TYPE: PRT
<213> ORGANISM: Homo sapiens

<400> SEQUENCE: 233

Arg Pro Val Leu Thr Gln Pro Pro Ser Leu Ser Ala Ser Pro Gly Ala
1               5                   10                  15

Thr Ala Arg Leu Pro Cys Thr Leu Ser Ser Asp Leu Ser Val Gly Gly
            20                  25                  30

Lys Asn Met Phe Trp Tyr Gln Gln Lys Pro Gly Ser Ser Pro Arg Leu
        35                  40                  45

Phe Leu Tyr His Tyr Ser Asp Ser Asp Lys Gln Leu Gly Pro Gly Val
    50                  55                  60

Pro Ser Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
                85                  90                  95

Gln Val Tyr Glu Ser Ser Ala Asn
            100

<210> SEQ ID NO 234
<211> LENGTH: 98
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (35)..(35)
<223> OTHER INFORMATION: Xaa can be any naturally occurring amino acid

<400> SEQUENCE: 234

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Xaa Trp Val Arg Gln Ala Pro Gly Lys Gly Leu Glu Trp Val
        35                  40                  45

Gly Trp Ile Ser Pro Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 235
<211> LENGTH: 103
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid

<400> SEQUENCE: 235

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Xaa Trp Ser Trp Val Arg Gln Ala Pro Gly Lys Gly Leu Glu
        35                  40                  45

Trp Val Gly Trp Ile Ser Pro Lys Ala Asn Gly Gly Ser Thr Tyr Tyr
    50                  55                  60

Ala Asp Ser Val Lys Gly Arg Phe Thr Ile Ser Arg Asp Asn Ser Lys
65                  70                  75                  80

Asn Thr Leu Tyr Leu Gln Met Asn Ser Leu Arg Ala Glu Asp Thr Ala
                85                  90                  95

Val Tyr Tyr Cys Ala Arg Xaa
            100

<210> SEQ ID NO 236
<211> LENGTH: 98
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Xaa Xaa His Trp Val Arg Gln Ala Pro Gly Gln Gly Leu Glu Trp Met
        35                  40                  45

Gly Trp Ile Asn Pro Xaa Asn Gly Asn Thr Asn Tyr Ala Gln Lys Phe
    50                  55                  60

Gln Gly Arg Val Thr Ile Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 237
<211> LENGTH: 100
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid

```
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid

<400> SEQUENCE: 237
```

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Xaa Trp Ile Arg Gln Pro Pro Gly Lys Ala Leu Glu
        35                  40                  45

Trp Leu Ala Xaa Ile Tyr Trp Asn Asp Asp Lys Tyr Tyr Ser Xaa Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Xaa
            100

```
<210> SEQ ID NO 238
<211> LENGTH: 99
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid

<400> SEQUENCE: 238
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Ser Asp Gly Xaa Ser Thr Tyr Tyr Ala Asp Ser Val
50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Xaa

```
<210> SEQ ID NO 239
<211> LENGTH: 101
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (58)..(58)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 239
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Ala | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Val | Ile | Ser | Ser | Lys | Ala | Asp | Gly | Xaa | Ser | Thr | Tyr | Tyr | Ala | Asp |
|---|---|---|---|---|---|---|---|---|---|---|---|---|---|---|---|
| 50 | | | | | 55 | | | | | 60 | | | | | |

| Ser | Val | Lys | Gly | Arg | Phe | Thr | Ile | Ser | Arg | Asp | Asn | Ser | Lys | Asn | Ser |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Ser | Leu | Arg | Ala | Glu | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Ala | Arg | Xaa |
|---|---|---|---|---|
| | | | | 100 |

```
<210> SEQ ID NO 240
<211> LENGTH: 98
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(33)
<223> OTHER INFORMATION: Xaa can be any naturally occurring amino acid

<400> SEQUENCE: 240
```

| Gln | Val | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Ala | Val | Ser | Gly | Gly | Ser | Ile | Ser | Ser | Gly |
|---|---|---|---|---|---|---|---|---|---|---|---|---|---|---|---|
| | | | 20 | | | | | 25 | | | | | 30 | | |

| Xaa | Tyr | Tyr | Trp | Trp | Ile | Arg | Gln | Pro | Pro | Gly | Lys | Gly | Leu | Glu | Trp |
|---|---|---|---|---|---|---|---|---|---|---|---|---|---|---|---|
| | | 35 | | | | | 40 | | | | | 45 | | | |

| Ile | Gly | Tyr | Ile | Tyr | Tyr | Ser | Gly | Ser | Thr | Tyr | Tyr | Asn | Pro | Ser | Leu |
|---|---|---|---|---|---|---|---|---|---|---|---|---|---|---|---|
| | | 50 | | | | | 55 | | | | | 60 | | | |

| Lys | Ser | Arg | Val | Thr | Ile | Ser | Val | Asp | Thr | Ser | Lys | Asn | Gln | Phe | Ser |
|---|---|---|---|---|---|---|---|---|---|---|---|---|---|---|---|
| 65 | | | | | 70 | | | | | 75 | | | | | 80 |

| Leu | Lys | Leu | Ser | Ser | Val | Thr | Ala | Ala | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg |
|---|---|

```
<210> SEQ ID NO 241
<211> LENGTH: 99
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(33)
<223> OTHER INFORMATION: Xaa can be any naturally occurring amino acid

<400> SEQUENCE: 241
```

| Gln | Val | Gln | Leu | Gln | Glu | Ser | Gly | Pro | Gly | Leu | Val | Lys | Pro | Ser | Glu |
|---|---|---|---|---|---|---|---|---|---|---|---|---|---|---|---|

```
            1               5                  10                 15
        Thr Leu Ser Leu Thr Cys Ala Val Ser Gly Gly Ser Ile Ser Ser Gly
                        20                  25                  30

Xaa Tyr Tyr Trp Ser Trp Ile Arg Gln Pro Pro Gly Lys Gly Leu Glu
                    35                  40                  45

Trp Ile Gly Tyr Ile Tyr Tyr Ser Gly Ser Thr Tyr Tyr Asn Pro Ser
                50                  55                  60

Leu Lys Ser Arg Val Thr Ile Ser Val Asp Thr Ser Lys Asn Gln Phe
        65                  70                  75                  80

Ser Leu Lys Leu Ser Ser Val Thr Ala Ala Asp Thr Ala Val Tyr Tyr
                        85                  90                  95

Cys Ala Arg

<210> SEQ ID NO 242
<211> LENGTH: 98
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 242

Glu Val Gln Leu Val Gln Ser Gly Ala Glu Val Lys Lys Pro Gly Glu
        1               5                   10                  15

Ser Leu Arg Ile Ser Cys Lys Gly Ser Gly Tyr Ser Phe Thr Ser Tyr
                        20                  25                  30

Trp Ile Xaa Trp Val Arg Gln Met Pro Gly Lys Gly Leu Glu Trp Met
                    35                  40                  45

Gly Xaa Ile Tyr Pro Gly Asp Ser Asp Thr Arg Tyr Ser Pro Ser Phe
                50                  55                  60

Gln Gly His Val Thr Ile Ser Ala Asp Lys Ser Ile Ser Thr Ala Tyr
        65                  70                  75                  80

Leu Gln Trp Ser Ser Leu Lys Ala Ser Asp Thr Ala Met Tyr Tyr Cys
                        85                  90                  95

Ala Arg

<210> SEQ ID NO 243
<211> LENGTH: 101
<212> TYPE: PRT
<213> ORGANISM: Artificial Sequence
<220> FEATURE:
<223> OTHER INFORMATION: Synthetic Construct

<400> SEQUENCE: 243

Gln Val Gln Leu Gln Gln Ser Gly Pro Gly Leu Val Lys Pro Ser Gln
        1               5                   10                  15

Thr Leu Ser Leu Thr Cys Ala Ile Ser Gly Asp Ser Val Ser Ser Asn
                        20                  25                  30

Ser Ala Ala Trp Asn Trp Ile Arg Gln Ser Pro Ser Arg Gly Leu Glu
                    35                  40                  45

Trp Leu Gly Arg Thr Tyr Tyr Arg Ser Lys Trp Tyr Asn Asp Tyr Ala
                50                  55                  60
```

```
Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg
            100

<210> SEQ ID NO 244
<211> LENGTH: 98
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid

<400> SEQUENCE: 244

Gln Val Gln Leu Val Gln Ser Gly Xaa Glu Xaa Lys Xaa Pro Gly Ala
 1                5                  10                  15

Ser Val Lys Val Ser Cys Lys Ala Ser Gly Tyr Xaa Phe Thr Xaa Tyr
```

```
            20                  25                  30
Xaa Met Asn Trp Val Xaa Gln Ala Pro Gly Gln Gly Leu Glu Trp Met
            35                  40                  45

Gly Trp Xaa Asn Thr Xaa Thr Gly Asn Pro Thr Tyr Ala Gln Gly Phe
        50                  55                  60

Thr Gly Arg Phe Val Phe Ser Xaa Asp Thr Ser Xaa Ser Thr Ala Tyr
65                  70                  75                  80

Leu Gln Ile Xaa Ser Leu Lys Ala Glu Asp Xaa Ala Xaa Tyr Tyr Cys
                85                  90                  95

Ala Arg

<210> SEQ ID NO 245
<211> LENGTH: 88
<212> TYPE: PRT
<213> ORGANISM: Artificial Sequence
<220> FEATURE:
<223> OTHER INFORMATION: Synthetic Construct

<400> SEQUENCE: 245

Gln Ser Val Leu Thr Gln Pro Pro Ser Val Ser Val Ser Pro Gly Gln
1               5                   10                  15

Ser Val Thr Ile Thr Cys Thr Gly Ser Ser Ser Gly Ser Tyr Tyr
            20                  25                  30

Val Ser Trp Tyr Gln Gln Lys Pro Gly Gln Ala Pro Lys Leu Leu Ile
            35                  40                  45

Tyr Glu Asp Ser Asn Arg Pro Ser Gly Val Pro Asp Arg Phe Ser Gly
        50                  55                  60

Ser Lys Ser Gly Asn Thr Ala Ser Leu Thr Ile Ser Gly Leu Gln Ala
65                  70                  75                  80

Glu Asp Glu Ala Asp Tyr Tyr Cys
                85

<210> SEQ ID NO 246
<211> LENGTH: 97
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 246

Gln Ser Val Leu Thr Gln Pro Pro Ser Val Ser Val Ser Pro Gly Gln
1               5                   10                  15

Ser Val Thr Ile Thr Cys Thr Gly Ser Ser Ser Asp Val Gly Gly Ser
            20                  25                  30

Tyr Tyr Val Ser Trp Tyr Gln Gln Lys Pro Gly Gln Ala Pro Lys Leu
            35                  40                  45

Leu Ile Tyr Glu Asp Ser Asn Arg Xaa Lys Xaa Gln Lys Pro Ser Gly
        50                  55                  60

Val Pro Asp Arg Phe Ser Gly Ser Lys Asp Ala Ser Gly Asn Thr Ala
65                  70                  75                  80

Ser Leu Thr Ile Ser Gly Leu Gln Ala Glu Asp Glu Ala Asp Tyr Tyr
                85                  90                  95
```

Cys

<210> SEQ ID NO 247
<211> LENGTH: 89
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid

<400> SEQUENCE: 247

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn Asn
            20                  25                  30

Xaa Val Xaa Trp Tyr Gln Gln Leu Pro Gly Thr Ala Pro Lys Leu Leu
        35                  40                  45

Ile Tyr Gly Asn Asn Xaa Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys
                85

<210> SEQ ID NO 248
<211> LENGTH: 90
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 248

Gln Ser Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn
            20                  25                  30

Asn Xaa Val Xaa Trp Tyr Gln Gln Leu Pro Gly Thr Ala Pro Lys Leu
        35                  40                  45

Leu Ile Tyr Gly Asn Asn Xaa Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

```
Gln Ser Glu Asp Glu Ala Asp Tyr Tyr Cys
                85                  90
```

<210> SEQ ID NO 249
<211> LENGTH: 90
<212> TYPE: PRT
<213> ORGANISM: Artificial Sequence
<220> FEATURE:
<223> OTHER INFORMATION: Synthetic Construct

<400> SEQUENCE: 249

```
Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys
                85                  90
```

<210> SEQ ID NO 250
<211> LENGTH: 87
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 250

```
Ser Tyr Glu Leu Thr Gln Pro Pro Ser Val Ser Val Ser Pro Gly Gln
1               5                   10                  15

Thr Ala Arg Ile Thr Cys Ser Gly Asp Xaa Leu Gly Xaa Lys Tyr Ala
                20                  25                  30

His Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser
        50                  55                  60

Ser Ser Gly Asn Thr Ala Thr Leu Thr Ile Ser Gly Xaa Gln Ala Glu
65                  70                  75                  80

Asp Glu Ala Asp Tyr Tyr Cys
                85
```

<210> SEQ ID NO 251
<211> LENGTH: 87
<212> TYPE: PRT
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 251

Ser Tyr Glu Leu Thr Gln Pro Pro Ser Val Ser Val Ser Pro Gly Gln
1               5                   10                  15

Thr Ala Arg Ile Thr Cys Ser Gly Asp Xaa Leu Gly Xaa Lys Tyr Ala
            20                  25                  30

His Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Asn Thr Ala Thr Leu Thr Ile Ser Gly Xaa Gln Ala Glu
65                  70                  75                  80

Asp Glu Ala Asp Tyr Tyr Cys
                85

<210> SEQ ID NO 252
<211> LENGTH: 92
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid

<400> SEQUENCE: 252

Gln Pro Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Xaa
            20                  25                  30

Ile Ala Trp His Gln Gln Pro Gly Lys Xaa Pro Arg Tyr Leu Met
        35                  40                  45

Lys Leu Xaa Ser Asp Gly Ser His Ser Lys Gly Asp Gly Ile Pro Asp
    50                  55                  60

Arg Phe Ser Gly Ser Ser Gly Ala Asp Arg Tyr Leu Thr Ile Ser
65                  70                  75                  80

Asn Leu Gln Ser Glu Asp Glu Ala Asp Tyr Tyr Cys
                85                  90

<210> SEQ ID NO 253
<211> LENGTH: 92
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid

<400> SEQUENCE: 253

Gln Pro Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Xaa
            20                  25                  30

Ile Ala Trp His Gln Gln Pro Gly Lys Xaa Pro Arg Tyr Leu Met
        35                  40                  45

Lys Leu Xaa Ser Asp Gly Ser His Ser Lys Gly Asp Gly Ile Pro Asp
    50                  55                  60

Arg Phe Ser Gly Ser Ser Ser Gly Ala Asp Arg Tyr Leu Thr Ile Ser
65                  70                  75                  80

Asn Leu Gln Ser Glu Asp Glu Ala Asp Tyr Tyr Cys
                85                  90

<210> SEQ ID NO 254
<211> LENGTH: 96
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 254

Gln Pro Val Leu Thr Gln Pro Thr Ser Leu Ser Ala Ser Pro Gly Ala
1               5                   10                  15

Ser Ala Arg Leu Thr Cys Thr Leu Arg Ser Gly Ile Asn Val Gly Xaa
            20                  25                  30

Tyr Arg Ile Tyr Trp Tyr Gln Gln Lys Pro Gly Ser Pro Pro Arg Tyr
        35                  40                  45

Leu Leu Xaa Tyr Xaa Ser Asp Ser Asp Lys Xaa Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95
```

```
<210> SEQ ID NO 255
<211> LENGTH: 96
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 255

Gln Pro Val Leu Thr Gln Pro Thr Ser Leu Ser Ala Ser Pro Gly Ala
1               5                   10                  15

Ser Ala Arg Leu Thr Cys Thr Leu Arg Ser Gly Ile Asn Val Gly Xaa
            20                  25                  30

Tyr Arg Ile Tyr Trp Tyr Gln Gln Lys Pro Gly Ser Pro Pro Arg Tyr
        35                  40                  45

Leu Leu Xaa Tyr Xaa Ser Asp Ser Asp Lys Xaa Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

<210> SEQ ID NO 256
<211> LENGTH: 91
<212> TYPE: PRT
<213> ORGANISM: Artificial Sequence
<220> FEATURE:
<223> OTHER INFORMATION: Synthetic Construct

<400> SEQUENCE: 256

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys
                85                  90

<210> SEQ ID NO 257
<211> LENGTH: 90
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 257

Gln Xaa Val Val Thr Gln Glu Pro Ser Leu Thr Val Ser Pro Gly Gly
1               5                   10                  15

Thr Val Thr Leu Thr Cys Xaa Ser Ser Thr Gly Ala Val Thr Ser Gly
            20                  25                  30

Xaa Tyr Pro Xaa Trp Phe Gln Gln Lys Pro Gly Gln Ala Pro Arg Xaa
        35                  40                  45

Leu Ile Tyr Xaa Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Xaa
65                  70                  75                  80

Gln Pro Glu Asp Glu Ala Glu Tyr Tyr Cys
                85                  90

<210> SEQ ID NO 258
<211> LENGTH: 90
<212> TYPE: PRT
<213> ORGANISM: Artificial Sequence
<220> FEATURE:
<223> OTHER INFORMATION: Synthetic Construct

<400> SEQUENCE: 258

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys
                85                  90

<210> SEQ ID NO 259
<211> LENGTH: 93
```

```
<212> TYPE: PRT
<213> ORGANISM: Artificial Sequence
<220> FEATURE:
<223> OTHER INFORMATION: Synthetic Construct

<400> SEQUENCE: 259

Gln Pro Val Leu Thr Gln Pro Pro Ser Ala Ser Ala Ser Leu Gly Ala
1               5                   10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
    50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys
                85                  90

<210> SEQ ID NO 260
<211> LENGTH: 89
<212> TYPE: PRT
<213> ORGANISM: Artificial Sequence
<220> FEATURE:
<223> OTHER INFORMATION: Synthetic Construct

<400> SEQUENCE: 260

Gln Ala Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
                20                  25                  30

Gly Ala Ala Trp Leu Gln Gln His Gln Gly His Pro Pro Lys Leu Leu
            35                  40                  45

Ser Tyr Arg Asn Asn Asn Arg Pro Ser Gly Ile Ser Glu Arg Leu Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys
                85

<210> SEQ ID NO 261
<211> LENGTH: 96
<212> TYPE: PRT
<213> ORGANISM: Artificial Sequence
<220> FEATURE:
<223> OTHER INFORMATION: Synthetic Construct

<400> SEQUENCE: 261

Arg Pro Val Leu Thr Gln Pro Pro Ser Leu Ser Ala Ser Pro Gly Ala
1               5                   10                  15

Thr Ala Arg Leu Pro Cys Thr Leu Ser Ser Asp Leu Ser Val Gly Gly
                20                  25                  30

Lys Asn Met Phe Trp Tyr Gln Gln Lys Pro Gly Ser Ser Pro Arg Leu
            35                  40                  45

Phe Leu Tyr His Tyr Ser Asp Ser Asp Lys Gln Leu Gly Pro Gly Val
    50                  55                  60

Pro Ser Arg Val Ser Gly Ser Lys Glu Thr Ser Ser Asn Thr Ala Phe
65                  70                  75                  80

Leu Leu Ile Ser Gly Leu Gln Pro Glu Asp Glu Ala Asp Tyr Tyr Cys
```

```
<210> SEQ ID NO 262
<211> LENGTH: 88
<212> TYPE: PRT
<213> ORGANISM: Artificial Sequence
<220> FEATURE:
<223> OTHER INFORMATION: Synthetic Construct

<400> SEQUENCE: 262

Asp Ile Val Met Thr Gln Ser Pro Ser Ser Leu Ser Ala Ser Pro Gly
1               5                   10                  15

Glu Arg Ala Thr Ile Ser Cys Arg Ala Ser Gln Gly Ile Ser Ser Tyr
            20                  25                  30

Leu Ala Trp Tyr Gln Gln Lys Pro Gly Gln Ala Pro Lys Leu Leu Ile
        35                  40                  45

Tyr Ala Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys
                85

<210> SEQ ID NO 263
<211> LENGTH: 94
<212> TYPE: PRT
<213> ORGANISM: Artificial Sequence
<220> FEATURE:
<223> OTHER INFORMATION: Synthetic Construct

<400> SEQUENCE: 263

Asp Ile Val Met Thr Gln Ser Pro Ser Ser Leu Ser Ala Ser Pro Gly
1               5                   10                  15

Glu Arg Ala Thr Ile Ser Cys Arg Ala Ser Gln Ser Leu Leu His Ser
            20                  25                  30

Asp Gly Ile Ser Ser Tyr Leu Ala Trp Tyr Gln Gln Lys Pro Gly Gln
        35                  40                  45

Ala Pro Lys Leu Leu Ile Tyr Ala Ala Ser Ser Arg Ala Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Val Tyr Tyr Cys
                85                  90

<210> SEQ ID NO 264
<211> LENGTH: 88
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (31)..(31)
<223> OTHER INFORMATION: Xaa can be any naturally occurring amino acid

<400> SEQUENCE: 264

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Xaa Tyr
            20                  25                  30

Leu Ala Trp Tyr Gln Gln Lys Pro Gly Lys Ala Pro Lys Leu Leu Ile
```

```
                35                  40                  45
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 265
<211> LENGTH: 88
<212> TYPE: PRT
<213> ORGANISM: Artificial Sequence
<220> FEATURE:
<223> OTHER INFORMATION: Synthetic Construct

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 266
<211> LENGTH: 93
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 266

Asp Ile Val Met Thr Gln Thr Pro Leu Ser Leu Pro Val Thr Xaa Gly
1               5                   10                  15

Glu Pro Ala Ser Ile Ser Cys Arg Ser Ser Gln Ser Leu Leu His Ser
                20                  25                  30

Asp Gly Asn Thr Tyr Leu Asp Trp Tyr Leu Gln Lys Pro Gly Gln Ser
                35                  40                  45

Pro Gln Leu Leu Ile Tyr Xaa Xaa Ser Asn Arg Xaa Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys
                85                  90
```

```
<210> SEQ ID NO 267
<211> LENGTH: 94
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 267

Asp Ile Val Met Thr Gln Thr Pro Leu Ser Leu Pro Val Thr Xaa Gly
1               5                   10                  15

Glu Pro Ala Ser Ile Ser Cys Arg Ser Ser Gln Ser Leu Leu His Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Xaa Xaa Ser Asn Arg Xaa Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys
                85                  90

<210> SEQ ID NO 268
<211> LENGTH: 93
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 268

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Xaa Thr Tyr Leu Xaa Trp Tyr Leu Gln Lys Pro Gly Gln Ser
        35                  40                  45

Pro Gln Leu Leu Ile Tyr Xaa Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys
                85                  90
```

<210> SEQ ID NO 269
<211> LENGTH: 94
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid

<400> SEQUENCE: 269

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Asp Gly Xaa Thr Tyr Leu Xaa Trp Tyr Leu Gln Lys Pro Gly Gln
        35                  40                  45

Ser Pro Gln Leu Leu Ile Tyr Xaa Val Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys
                85                  90

<210> SEQ ID NO 270
<211> LENGTH: 89
<212> TYPE: PRT
<213> ORGANISM: Artificial Sequence
<220> FEATURE:
<223> OTHER INFORMATION: Synthetic Construct

<400> SEQUENCE: 270

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys
                85

<210> SEQ ID NO 271
<211> LENGTH: 89
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)

<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 271

Glu Ile Val Xaa Thr Gln Ser Pro Ala Thr Leu Ser Leu Ser Pro Gly
 1               5                  10                  15

Glu Arg Ala Thr Leu Ser Cys Arg Ala Ser Gln Ser Val Xaa Ser Ser
            20                  25                  30

Tyr Leu Ala Trp Tyr Gln Gln Lys Pro Gly Gln Ala Pro Arg Leu Leu
        35                  40                  45

Ile Tyr Xaa Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Xaa
65                  70                  75                  80

Pro Glu Asp Phe Ala Val Tyr Tyr Cys
                85

<210> SEQ ID NO 272
<211> LENGTH: 94
<212> TYPE: PRT
<213> ORGANISM: Artificial Sequence
<220> FEATURE:
<223> OTHER INFORMATION: Synthetic Construct

<400> SEQUENCE: 272

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys
                85                  90

<210> SEQ ID NO 273
<211> LENGTH: 88
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature

```
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 273

Xaa Ile Val Leu Thr Gln Ser Pro Xaa Phe Xaa Ser Val Thr Pro Xaa
1               5                   10                  15

Glu Lys Val Thr Ile Thr Cys Arg Ala Ser Xaa Ser Ile Gly Xaa Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys
                85

<210> SEQ ID NO 274
<211> LENGTH: 92
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 274

Xaa Ile Val Leu Thr Gln Ser Pro Xaa Phe Xaa Ser Val Thr Pro Xaa
1               5                   10                  15

Glu Lys Val Thr Ile Thr Cys Arg Ala Ser Xaa Ser Val Ser Phe Ser
                20                  25                  30

Ile Gly Xaa Ser Leu His Trp Tyr Gln Gln Lys Pro Asp Gln Ser Pro
            35                  40                  45

Lys Leu Leu Ile Lys Tyr Ala Ser Gln Ser Phe Ser Gly Val Pro Ser
```

```
                50              55              60
Arg Phe Ser Gly Ser Gly Ser Gly Thr Asp Phe Thr Leu Thr Ile Asn
 65                  70                  75                  80

Ser Leu Glu Ala Glu Asp Ala Ala Thr Tyr Tyr Cys
                 85                  90
```

<210> SEQ ID NO 275
<211> LENGTH: 88
<212> TYPE: PRT
<213> ORGANISM: Artificial Sequence
<220> FEATURE:
<223> OTHER INFORMATION: Synthetic Construct

<400> SEQUENCE: 275

```
Glu Ile Val Leu Thr Gln Ser Pro Asp Phe Gln Ser Val Thr Pro Lys
 1               5                   10                  15

Glu Lys Val Thr Ile Thr Cys Arg Ala Ser Gln Ser Ile Gly Ser Ser
                 20                  25                  30

Leu His Trp Tyr Gln Lys Pro Asp Gln Ser Pro Lys Leu Leu Ile
             35                  40                  45

Lys Tyr Ala Ser Gln Ser Phe Ser Gly Val Pro Ser Arg Phe Ser Gly
         50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys
                 85
```

<210> SEQ ID NO 276
<211> LENGTH: 88
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid

```
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid

<400> SEQUENCE: 276

Xaa Xaa Val Xaa Thr Gln Ser Pro Xaa Phe Xaa Ser Val Thr Pro Xaa
1               5                   10                  15

Glu Lys Val Thr Ile Thr Cys Xaa Ala Ser Xaa Xaa Ile Gly Xaa Xaa
                20                  25                  30

Leu Xaa Trp Tyr Gln Gln Lys Pro Asp Gln Xaa Pro Lys Leu Leu Ile
        35                  40                  45

Lys Tyr Ala Ser Gln Ser Xaa Ser Gly Val Pro Ser Arg Phe Ser Gly
50                  55                  60

Ser Gly Ser Gly Thr Asp Phe Thr Xaa Thr Ile Xaa Ser Leu Glu Ala
65                  70                  75                  80

Glu Asp Ala Ala Thr Tyr Tyr Cys
                85

<210> SEQ ID NO 277
<211> LENGTH: 92
<212> TYPE: PRT
<213> ORGANISM: Artificial Sequence
<220> FEATURE:
<223> OTHER INFORMATION: Synthetic Construct

<400> SEQUENCE: 277

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Ser Phe Leu
                20                  25                  30

Gly Ile Asn Leu Ile His Trp Tyr Gln Gln Lys Pro Gly Gln Pro Pro
        35                  40                  45

Lys Leu Leu Ile Tyr Gln Ala Ser Asn Lys Asp Thr Gly Val Pro Ala
50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys
                85                  90

<210> SEQ ID NO 278
<211> LENGTH: 11
<212> TYPE: PRT
<213> ORGANISM: Artificial Sequence
<220> FEATURE:
<223> OTHER INFORMATION: Synthetic Construct

<400> SEQUENCE: 278

Arg Ala Ser Gln Ser Ile Ser Ser Tyr Leu Asn
1               5                   10
```

```
<210> SEQ ID NO 279
<211> LENGTH: 11
<212> TYPE: PRT
<213> ORGANISM: Artificial Sequence
<220> FEATURE:
<223> OTHER INFORMATION: Synthetic Construct

<400> SEQUENCE: 279

Arg Ala Ser Gln Asp Val Gly Ile Tyr Val Asn
1               5                   10

<210> SEQ ID NO 280
<211> LENGTH: 11
<212> TYPE: PRT
<213> ORGANISM: Artificial Sequence
<220> FEATURE:
<223> OTHER INFORMATION: Synthetic Construct

<400> SEQUENCE: 280

Arg Ala Ser Gln Asp Val Gly Ile Tyr Val Asn
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Synthetic Construct

<400> SEQUENCE: 281

Arg Ala Ser Gln Ser Ile Gly Ser Tyr Leu Asn
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Synthetic Construct

<400> SEQUENCE: 282

Arg Ala Ser Gln Ser Ile Ser Ser Tyr Leu Asn
1               5                   10

<210> SEQ ID NO 283
<211> LENGTH: 11
<212> TYPE: PRT
<213> ORGANISM: Artificial Sequence
<220> FEATURE:
<223> OTHER INFORMATION: Synthetic Construct

<400> SEQUENCE: 283

Leu Ala Ser Glu Phe Leu Phe Asn Gly Val Ser
1               5                   10

<210> SEQ ID NO 284
<211> LENGTH: 11
<212> TYPE: PRT
<213> ORGANISM: Artificial Sequence
<220> FEATURE:
<223> OTHER INFORMATION: Synthetic Construct

<400> SEQUENCE: 284

Leu Ala Ser Glu Phe Leu Phe Asn Gly Val Ser
1               5                   10

<210> SEQ ID NO 285
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 285

Arg Ala Ser Gln Phe Leu Phe Asn Gly Val Ser
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Synthetic Construct

<400> SEQUENCE: 286

Gln Gly Asp Ser Leu Arg Ser Tyr Tyr Ala Ser
1               5                   10

<210> SEQ ID NO 287
<211> LENGTH: 8
<212> TYPE: PRT
<213> ORGANISM: Artificial Sequence
<220> FEATURE:
<223> OTHER INFORMATION: Synthetic Construct

<400> SEQUENCE: 287

Ser Gly Ser Asp Tyr Asp Tyr Gly
1               5

<210> SEQ ID NO 288
<211> LENGTH: 8
<212> TYPE: PRT
<213> ORGANISM: Artificial Sequence
<220> FEATURE:
<223> OTHER INFORMATION: Synthetic Construct

<400> SEQUENCE: 288

Ser Gly Ser Asp Tyr Asp Tyr Gly
1               5

<210> SEQ ID NO 289
<211> LENGTH: 8
<212> TYPE: PRT
<213> ORGANISM: Artificial Sequence
<220> FEATURE:
<223> OTHER INFORMATION: Synthetic Construct

<400> SEQUENCE: 289

Gln Gly Asp Asp Ser Tyr Tyr Gly
1               5

<210> SEQ ID NO 290
<211> LENGTH: 8
<212> TYPE: PRT
<213> ORGANISM: Artificial Sequence
<220> FEATURE:
<223> OTHER INFORMATION: Synthetic Construct

<400> SEQUENCE: 290

Gln Gly Asp Asp Ser Tyr Tyr Gly
1               5

<210> SEQ ID NO 291
<211> LENGTH: 7
```

<212> TYPE: PRT
<213> ORGANISM: Artificial Sequence
<220> FEATURE:
<223> OTHER INFORMATION: Synthetic Construct

<400> SEQUENCE: 291

Ala Ala Ser Ser Leu Gln Ser
1               5

<210> SEQ ID NO 292
<211> LENGTH: 7
<212> TYPE: PRT
<213> ORGANISM: Artificial Sequence
<220> FEATURE:
<223> OTHER INFORMATION: Synthetic Construct

<400> SEQUENCE: 292

Arg Ala Thr Asn Leu Ala Asp
1               5

<210> SEQ ID NO 293
<211> LENGTH: 7
<212> TYPE: PRT
<213> ORGANISM: Artificial Sequence
<220> FEATURE:
<223> OTHER INFORMATION: Synthetic Construct

<400> SEQUENCE: 293

Arg Ala Thr Asn Leu Ala Asp
1               5

<210> SEQ ID NO 294
<211> LENGTH: 7
<212> TYPE: PRT
<213> ORGANISM: Artificial Sequence
<220> FEATURE:
<223> OTHER INFORMATION: Synthetic Construct

<400> SEQUENCE: 294

Arg Ala Ser Ser Leu Ala Ser
1               5

<210> SEQ ID NO 295
<211> LENGTH: 7
<212> TYPE: PRT
<213> ORGANISM: Artificial Sequence
<220> FEATURE:
<223> OTHER INFORMATION: Synthetic Construct

<400> SEQUENCE: 295

Ala Ala Ser Ser Leu Gln Ser
1               5

<210> SEQ ID NO 296
<211> LENGTH: 7
<212> TYPE: PRT
<213> ORGANISM: Artificial Sequence
<220> FEATURE:
<223> OTHER INFORMATION: Synthetic Construct

<400> SEQUENCE: 296

Gly Ala Ser Asn Leu Glu Ser
1               5

<210> SEQ ID NO 297
<211> LENGTH: 7
<212> TYPE: PRT

```
<213> ORGANISM: Artificial Sequence
<220> FEATURE:
<223> OTHER INFORMATION: Synthetic Construct

<400> SEQUENCE: 297

Gly Ala Ser Asn Leu Glu Ser
1               5

<210> SEQ ID NO 298
<211> LENGTH: 7
<212> TYPE: PRT
<213> ORGANISM: Artificial Sequence
<220> FEATURE:
<223> OTHER INFORMATION: Synthetic Construct

<400> SEQUENCE: 298

Ala Ala Ser Asn Leu Glu Ser
1               5

<210> SEQ ID NO 299
<211> LENGTH: 7
<212> TYPE: PRT
<213> ORGANISM: Artificial Sequence
<220> FEATURE:
<223> OTHER INFORMATION: Synthetic Construct

<400> SEQUENCE: 299

Gly Lys Asn Asn Arg Pro Ser
1               5

<210> SEQ ID NO 300
<211> LENGTH: 7
<212> TYPE: PRT
<213> ORGANISM: Artificial Sequence
<220> FEATURE:
<223> OTHER INFORMATION: Synthetic Construct

<400> SEQUENCE: 300

Trp Asn Asp Lys Arg Pro Ser
1               5

<210> SEQ ID NO 301
<211> LENGTH: 7
<212> TYPE: PRT
<213> ORGANISM: Artificial Sequence
<220> FEATURE:
<223> OTHER INFORMATION: Synthetic Construct

<400> SEQUENCE: 301

Trp Asn Asp Lys Arg Pro Ser
1               5

<210> SEQ ID NO 302
<211> LENGTH: 7
<212> TYPE: PRT
<213> ORGANISM: Artificial Sequence
<220> FEATURE:
<223> OTHER INFORMATION: Synthetic Construct

<400> SEQUENCE: 302

Gly Asn Asp Asn Arg Pro Ser
1               5

<210> SEQ ID NO 303
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 303

Gly Asn Asn Asn Arg Pro Ser
1               5

<210> SEQ ID NO 304
<211> LENGTH: 9
<212> TYPE: PRT
<213> ORGANISM: Artificial Sequence
<220> FEATURE:
<223> OTHER INFORMATION: Synthetic Construct

<400> SEQUENCE: 304

Gln Gln Ser Tyr Ser Thr Pro Leu Thr
1               5

<210> SEQ ID NO 305
<211> LENGTH: 9
<212> TYPE: PRT
<213> ORGANISM: Artificial Sequence
<220> FEATURE:
<223> OTHER INFORMATION: Synthetic Construct

<400> SEQUENCE: 305

Leu Glu Phe Asp Glu His Pro Leu Thr
1               5

<210> SEQ ID NO 306
<211> LENGTH: 9
<212> TYPE: PRT
<213> ORGANISM: Artificial Sequence
<220> FEATURE:
<223> OTHER INFORMATION: Synthetic Construct

<400> SEQUENCE: 306

Leu Glu Phe Asp Glu His Pro Leu Thr
1               5

<210> SEQ ID NO 307
<211> LENGTH: 9
<212> TYPE: PRT
<213> ORGANISM: Artificial Sequence
<220> FEATURE:
<223> OTHER INFORMATION: Synthetic Construct

<400> SEQUENCE: 307

Leu Glu Phe Asp Glu His Pro Leu Thr
1               5

<210> SEQ ID NO 308
<211> LENGTH: 9
<212> TYPE: PRT
<213> ORGANISM: Artificial Sequence
<220> FEATURE:
<223> OTHER INFORMATION: Synthetic Construct

<400> SEQUENCE: 308

Gln Gln Ser Tyr Ser Thr Pro Leu Thr
1               5

<210> SEQ ID NO 309
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 309

Leu Gly Gly Tyr Ser Gly Ser Ser Gly Leu Thr
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthetic Construct

<400> SEQUENCE: 310

Leu Gly Gly Tyr Ser Gly Ser Ser Gly Leu Thr
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Synthetic Construct

<400> SEQUENCE: 311

Gln Gly Gly Tyr Ser Gly Ser Thr Gly Leu Thr
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Synthetic Construct

<400> SEQUENCE: 312

Asn Ser Arg Asp Ser Ser Gly Asn His Val Val
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic Construct

<400> SEQUENCE: 313

Gly Ala Tyr Asp Gly Ser Ala Gly Gly Gly Ile
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic Construct

<400> SEQUENCE: 314

Gly Ala Tyr Asp Gly Ser Ala Gly Gly Gly Ile
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Synthetic Construct

<400> SEQUENCE: 315

Gly Ala Tyr Asp Ser Ser Gly Gly Gly Ile
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Synthetic Construct

<400> SEQUENCE: 316

Gly Ser Tyr Asp Ser Ser Gly Gly His Gly Val
1               5                   10

<210> SEQ ID NO 317
<211> LENGTH: 10
<212> TYPE: PRT
<213> ORGANISM: Artificial Sequence
<220> FEATURE:
<223> OTHER INFORMATION: Synthetic Construct

<400> SEQUENCE: 317

Gly Phe Thr Phe Ser Ser Tyr Trp Met Ser
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Synthetic Construct

<400> SEQUENCE: 318

Gly Phe Thr Phe Ser Asn Tyr Trp Met Thr
1               5                   10

<210> SEQ ID NO 319
<211> LENGTH: 10
<212> TYPE: PRT
<213> ORGANISM: Artificial Sequence
<220> FEATURE:
<223> OTHER INFORMATION: Synthetic Construct

<400> SEQUENCE: 319

Gly Phe Thr Phe Ser Asn Tyr Trp Met Thr
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Synthetic Construct

<400> SEQUENCE: 320

Gly Phe Thr Phe Ser Ser Tyr Trp Met Ser
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 321

Gly Phe Thr Phe Ser Ser Tyr Ala Met Ser
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Synthetic Construct

<400> SEQUENCE: 322

Gly Ile Asp Phe Ser His Tyr Gly Ile Ser
1               5                   10

<210> SEQ ID NO 323
<211> LENGTH: 10
<212> TYPE: PRT
<213> ORGANISM: Artificial Sequence
<220> FEATURE:
<223> OTHER INFORMATION: Synthetic Construct

<400> SEQUENCE: 323

Gly Ile Asp Phe Ser His Tyr Gly Ile Ser
1               5                   10

<210> SEQ ID NO 324
<211> LENGTH: 10
<212> TYPE: PRT
<213> ORGANISM: Artificial Sequence
<220> FEATURE:
<223> OTHER INFORMATION: Synthetic Construct

<400> SEQUENCE: 324

Gly Phe Thr Phe Ser His Tyr Gly Ile Ser
1               5                   10

<210> SEQ ID NO 325
<211> LENGTH: 10
<212> TYPE: PRT
<213> ORGANISM: Artificial Sequence
<220> FEATURE:
<223> OTHER INFORMATION: Synthetic Construct

<400> SEQUENCE: 325

Gly Phe Thr Phe Ser Ser Tyr Ala Met Ser
1               5                   10

<210> SEQ ID NO 326
<211> LENGTH: 10
<212> TYPE: PRT
<213> ORGANISM: Artificial Sequence
<220> FEATURE:
<223> OTHER INFORMATION: Synthetic Construct

<400> SEQUENCE: 326

Gly Phe Thr Leu Ser Ser Tyr Gln Met Met
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Synthetic Construct

<400> SEQUENCE: 327
```

Gly Phe Thr Leu Ser Ser Tyr Gln Met Met
1               5                   10

<210> SEQ ID NO 328
<211> LENGTH: 10
<212> TYPE: PRT
<213> ORGANISM: Artificial Sequence
<220> FEATURE:
<223> OTHER INFORMATION: Synthetic Construct

<400> SEQUENCE: 328

Gly Phe Thr Leu Ser Ser Tyr Gln Met Met
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Synthetic Construct

<400> SEQUENCE: 329

Gly Phe Thr Phe Ser Ser Tyr Gln Met Ser
1               5                   10

<210> SEQ ID NO 330
<211> LENGTH: 18
<212> TYPE: PRT
<213> ORGANISM: Artificial Sequence
<220> FEATURE:
<223> OTHER INFORMATION: Synthetic Construct

<400> SEQUENCE: 330

Ala Asn Ile Lys Gln Asp Gly Ser Glu Lys Tyr Tyr Val Asp Ser Val
1               5                   10                  15

Lys Gly

<210> SEQ ID NO 331
<211> LENGTH: 18
<212> TYPE: PRT
<213> ORGANISM: Artificial Sequence
<220> FEATURE:
<223> OTHER INFORMATION: Synthetic Construct

<400> SEQUENCE: 331

Ala Ser Ile Asp Asn Ser Gly Asp Asn Thr Tyr Tyr Pro Asp Ser Val
1               5                   10                  15

Lys Asp

<210> SEQ ID NO 332
<211> LENGTH: 18
<212> TYPE: PRT
<213> ORGANISM: Artificial Sequence
<220> FEATURE:
<223> OTHER INFORMATION: Synthetic Construct

<400> SEQUENCE: 332

Ala Ser Ile Asp Asn Ser Gly Asp Asn Thr Tyr Tyr Pro Asp Ser Val
1               5                   10                  15

Lys Asp

<210> SEQ ID NO 333
<211> LENGTH: 18
<212> TYPE: PRT

```
<213> ORGANISM: Artificial Sequence
<220> FEATURE:
<223> OTHER INFORMATION: Synthetic Construct

<400> SEQUENCE: 333

Ala Ser Ile Asp Gln Asp Gly Ser Asn Lys Tyr Tyr Pro Asp Ser Val
1               5                   10                  15

Lys Gly

<210> SEQ ID NO 334
<211> LENGTH: 18
<212> TYPE: PRT
<213> ORGANISM: Artificial Sequence
<220> FEATURE:
<223> OTHER INFORMATION: Synthetic Construct

<400> SEQUENCE: 334

Ser Ala Ile Ser Gly Ser Gly Gly Ser Thr Tyr Tyr Ala Asp Ser Val
1               5                   10                  15

Lys Gly

<210> SEQ ID NO 335
<211> LENGTH: 18
<212> TYPE: PRT
<213> ORGANISM: Artificial Sequence
<220> FEATURE:
<223> OTHER INFORMATION: Synthetic Construct

<400> SEQUENCE: 335

Ala Tyr Ile Tyr Pro Asn Tyr Gly Ser Val Asp Tyr Ala Ser Trp Val
1               5                   10                  15

Asn Gly

<210> SEQ ID NO 336
<211> LENGTH: 18
<212> TYPE: PRT
<213> ORGANISM: Artificial Sequence
<220> FEATURE:
<223> OTHER INFORMATION: Synthetic Construct

<400> SEQUENCE: 336

Ser Tyr Ile Tyr Pro Asn Tyr Gly Ser Val Asp Tyr Ala Ser Trp Val
1               5                   10                  15

Asn Gly

<210> SEQ ID NO 337
<211> LENGTH: 18
<212> TYPE: PRT
<213> ORGANISM: Artificial Sequence
<220> FEATURE:
<223> OTHER INFORMATION: Synthetic Construct

<400> SEQUENCE: 337

Ser Tyr Ile Tyr Pro Ser Tyr Gly Ser Thr Asp Tyr Ala Ser Ser Val
1               5                   10                  15

Lys Gly

<210> SEQ ID NO 338
<211> LENGTH: 18
<212> TYPE: PRT
<213> ORGANISM: Artificial Sequence
<220> FEATURE:
<223> OTHER INFORMATION: Synthetic Construct
```

```
<400> SEQUENCE: 338

Ser Ala Ile Ser Gly Ser Gly Gly Ser Thr Tyr Tyr Ala Asp Ser Val
1               5                   10                  15

Lys Gly

<210> SEQ ID NO 339
<211> LENGTH: 18
<212> TYPE: PRT
<213> ORGANISM: Artificial Sequence
<220> FEATURE:
<223> OTHER INFORMATION: Synthetic Construct

<400> SEQUENCE: 339

Ala Gly Ile Thr Ser Arg Gly Gly Val Thr Gly Tyr Gly Ser Ala Val
1               5                   10                  15

Lys Gly

<210> SEQ ID NO 340
<211> LENGTH: 18
<212> TYPE: PRT
<213> ORGANISM: Artificial Sequence
<220> FEATURE:
<223> OTHER INFORMATION: Synthetic Construct

<400> SEQUENCE: 340

Ala Gly Ile Thr Ser Arg Gly Gly Val Thr Gly Tyr Gly Ser Ala Val
1               5                   10                  15

Lys Gly

<210> SEQ ID NO 341
<211> LENGTH: 18
<212> TYPE: PRT
<213> ORGANISM: Artificial Sequence
<220> FEATURE:
<223> OTHER INFORMATION: Synthetic Construct

<400> SEQUENCE: 341

Ala Gly Ile Thr Gly Arg Gly Gly Val Thr Gly Tyr Ala Asp Ser Val
1               5                   10                  15

Lys Gly

<210> SEQ ID NO 342
<211> LENGTH: 18
<212> TYPE: PRT
<213> ORGANISM: Artificial Sequence
<220> FEATURE:
<223> OTHER INFORMATION: Synthetic Construct

<400> SEQUENCE: 342

Ser Gly Ile Thr Gly Arg Gly Gly Val Thr Gly Tyr Ala Asp Ser Val
1               5                   10                  15

Lys Gly

<210> SEQ ID NO 343
<211> LENGTH: 10
<212> TYPE: PRT
<213> ORGANISM: Artificial Sequence
<220> FEATURE:
<223> OTHER INFORMATION: Synthetic Construct

<400> SEQUENCE: 343

Gly Gly Asp Ile Thr Thr Gly Phe Asp Tyr
1               5                   10
```

<210> SEQ ID NO 344
<211> LENGTH: 10
<212> TYPE: PRT
<213> ORGANISM: Artificial Sequence
<220> FEATURE:
<223> OTHER INFORMATION: Synthetic Construct

<400> SEQUENCE: 344

Gly Gly Asp Ile Thr Thr Gly Phe Asp Tyr
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Synthetic Construct

<400> SEQUENCE: 345

Gly Gly Asp Ile Thr Thr Gly Leu Asp Tyr
1               5                   10

<210> SEQ ID NO 346
<211> LENGTH: 15
<212> TYPE: PRT
<213> ORGANISM: Artificial Sequence
<220> FEATURE:
<223> OTHER INFORMATION: Synthetic Construct

<400> SEQUENCE: 346

Asp Arg Gly Tyr Tyr Ser Gly Ser Arg Gly Thr Arg Leu Asp Leu
1               5                   10                  15

<210> SEQ ID NO 347
<211> LENGTH: 15
<212> TYPE: PRT
<213> ORGANISM: Artificial Sequence
<220> FEATURE:
<223> OTHER INFORMATION: Synthetic Construct

<400> SEQUENCE: 347

Asp Arg Gly Tyr Tyr Ser Gly Ser Arg Gly Thr Arg Leu Asp Leu
1               5                   10                  15

<210> SEQ ID NO 348
<211> LENGTH: 15
<212> TYPE: PRT
<213> ORGANISM: Artificial Sequence
<220> FEATURE:
<223> OTHER INFORMATION: Synthetic Construct

<400> SEQUENCE: 348

Asp Arg Gly Tyr Tyr Ser Gly Ser Arg Gly Thr Arg Leu Asp Leu
1               5                   10                  15

<210> SEQ ID NO 349
<211> LENGTH: 18
<212> TYPE: PRT
<213> ORGANISM: Artificial Sequence
<220> FEATURE:
<223> OTHER INFORMATION: Synthetic Construct

<400> SEQUENCE: 349

Pro Ala Leu Asp Ser Asp Gln Cys Gly Phe Pro Glu Ala Gly Cys Ile
1               5                   10                  15

```
<210> SEQ ID NO 350
<211> LENGTH: 18
<212> TYPE: PRT
<213> ORGANISM: Artificial Sequence
<220> FEATURE:
<223> OTHER INFORMATION: Synthetic Construct

<400> SEQUENCE: 350

Pro Ala Leu Asp Ser Asp Gln Cys Gly Phe Pro Glu Ala Gly Cys Ile
1               5                   10                  15

Asp Ala

<210> SEQ ID NO 351
<211> LENGTH: 18
<212> TYPE: PRT
<213> ORGANISM: Artificial Sequence
<220> FEATURE:
<223> OTHER INFORMATION: Synthetic Construct

<400> SEQUENCE: 351

Pro Ala Leu Asp Ser Asp Gln Cys Gly Phe Pro Glu Ala Gly Cys Ile
1               5                   10                  15

Asp Ala

<210> SEQ ID NO 352
<211> LENGTH: 18
<212> TYPE: PRT
<213> ORGANISM: Artificial Sequence
<220> FEATURE:
<223> OTHER INFORMATION: Synthetic Construct

<400> SEQUENCE: 352

Pro Ala Leu Asp Ser Asp Gln Cys Gly Phe Pro Glu Met Gly Cys Ile
1               5                   10                  15

Asp Ala

<210> SEQ ID NO 353
<211> LENGTH: 109
<212> TYPE: PRT
<213> ORGANISM: Artificial Sequence
<220> FEATURE:
<223> OTHER INFORMATION: Synthetic Construct

<400> SEQUENCE: 353

Glu Leu Val Met Thr Gln Thr Pro Pro Ser Leu Ser Ala Ser Val Gly
1               5                   10                  15

Glu Thr Val Arg Ile Arg Cys Leu Ala Ser Glu Phe Leu Phe Asn Gly
                20                  25                  30

Val Ser Trp Tyr Gln Gln Lys Pro Gly Lys Pro Pro Lys Phe Leu Ile
            35                  40                  45

Ser Gly Ala Ser Asn Leu Glu Ser Gly Val Pro Pro Arg Phe Ser Gly
        50                  55                  60

Ser Gly Ser Gly Thr Asp Tyr Thr Leu Thr Ile Gly Gly Val Gln Ala
65                  70                  75                  80

Glu Asp Val Ala Thr Tyr Tyr Cys Leu Gly Gly Tyr Ser Gly Ser Ser
                85                  90                  95

Gly Leu Thr Phe Gly Ala Gly Thr Asn Val Glu Ile Lys
            100                 105
```

-continued

```
<210> SEQ ID NO 354
<211> LENGTH: 107
<212> TYPE: PRT
<213> ORGANISM: Homo sapiens

<400> SEQUENCE: 354

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 355
<211> LENGTH: 109
<212> TYPE: PRT
<213> ORGANISM: Artificial Sequence
<220> FEATURE:
<223> OTHER INFORMATION: Synthetic Construct

<400> SEQUENCE: 355

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Val Ser Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Tyr Ser Gly Ser Thr
                85                  90                  95

Gly Leu Thr Phe Gly Gly Gly Thr Lys Val Glu Ile Lys
            100                 105

<210> SEQ ID NO 356
<211> LENGTH: 109
<212> TYPE: PRT
<213> ORGANISM: Artificial Sequence
<220> FEATURE:
<223> OTHER INFORMATION: Synthetic Construct

<400> SEQUENCE: 356

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Phe Leu Phe Asn Gly
            20                  25                  30

Val Ser Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Gly Tyr Ser Gly Ser Ser
                    85                  90                  95

Gly Leu Thr Phe Gly Gly Gly Thr Lys Val Glu Ile Lys
                100                 105

<210> SEQ ID NO 357
<211> LENGTH: 109
<212> TYPE: PRT
<213> ORGANISM: Artificial Sequence
<220> FEATURE:
<223> OTHER INFORMATION: Synthetic Construct

<400> SEQUENCE: 357

Asp Ile Gln Met Thr Gln Ser Pro Ser Ser Leu Ser Ala Ser Val Gly
 1               5                  10                  15

Asp Arg Val Thr Ile Thr Cys Arg Ala Ser Glu Ser Leu Ser Ser Tyr
                20                  25                  30

Leu Ser Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gly Gly Tyr Ser Gly Ser Ser
                    85                  90                  95

Gly Leu Thr Phe Gly Gly Gly Thr Lys Val Glu Ile Lys
                100                 105

<210> SEQ ID NO 358
<211> LENGTH: 109
<212> TYPE: PRT
<213> ORGANISM: Artificial Sequence
<220> FEATURE:
<223> OTHER INFORMATION: Synthetic Construct

<400> SEQUENCE: 358

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Phe Leu Phe Asn Gly
                20                  25                  30

Leu Ser Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Gly Tyr Ser Gly Ser Thr
                    85                  90                  95

Gly Leu Thr Phe Gly Gly Gly Thr Lys Val Glu Ile Lys
                100                 105

<210> SEQ ID NO 359
<211> LENGTH: 109
<212> TYPE: PRT
<213> ORGANISM: Artificial Sequence
<220> FEATURE:
```

<223> OTHER INFORMATION: Synthetic Construct

<400> SEQUENCE: 359

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Leu Phe Asn Gly
            20                  25                  30

Val Ser Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Gly Tyr Ser Gly Ser Thr
                85                  90                  95

Gly Leu Thr Phe Gly Gly Gly Thr Lys Val Glu Ile Lys
            100                 105

<210> SEQ ID NO 360
<211> LENGTH: 109
<212> TYPE: PRT
<213> ORGANISM: Artificial Sequence
<220> FEATURE:
<223> OTHER INFORMATION: Synthetic Construct

<400> SEQUENCE: 360

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Phe Leu Phe Asn Gly
            20                  25                  30

Val Ser Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Gly Tyr Ser Gly Ser Ser
                85                  90                  95

Gly Leu Thr Phe Gly Gly Gly Thr Lys Val Glu Ile Lys
            100                 105

<210> SEQ ID NO 361
<211> LENGTH: 109
<212> TYPE: PRT
<213> ORGANISM: Artificial Sequence
<220> FEATURE:
<223> OTHER INFORMATION: Synthetic Construct

<400> SEQUENCE: 361

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Leu Phe Asn Gly
            20                  25                  30

Val Ser Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gly Gly Tyr Ser Gly Ser Ser
                    85                  90                  95

Gly Leu Thr Phe Gly Gly Gly Thr Lys Val Glu Ile Lys
                100                 105
```

<210> SEQ ID NO 362
<211> LENGTH: 109
<212> TYPE: PRT
<213> ORGANISM: Artificial Sequence
<220> FEATURE:
<223> OTHER INFORMATION: Synthetic Construct

<400> SEQUENCE: 362

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Phe Leu Phe Asn Val
            20                  25                  30

Leu Val Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Gly Tyr Ser Gly Ser Thr
                85                  90                  95

Gly Leu Thr Phe Gly Gly Gly Thr Lys Val Glu Ile Lys
                100                 105
```

<210> SEQ ID NO 363
<211> LENGTH: 109
<212> TYPE: PRT
<213> ORGANISM: Artificial Sequence
<220> FEATURE:
<223> OTHER INFORMATION: Synthetic Construct

<400> SEQUENCE: 363

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Phe Leu Phe Asn Gly
            20                  25                  30

Val Ser Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Gly Tyr Ser Gly Ser Ser
                85                  90                  95

Gly Leu Thr Phe Gly Gly Gly Thr Lys Val Glu Ile Lys
                100                 105
```

<210> SEQ ID NO 364
<211> LENGTH: 109
<212> TYPE: PRT
<213> ORGANISM: Artificial Sequence
<220> FEATURE:
<223> OTHER INFORMATION: Synthetic Construct

<400> SEQUENCE: 364

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Phe Leu Phe Asn Gly
            20                  25                  30

Val Ser Trp Tyr Gln Lys Pro Gly Lys Ala Pro Lys Leu Leu Ile
            35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Ser Gly Ser Ser
                85                  90                  95

Gly Leu Thr Phe Gly Gly Gly Thr Lys Val Glu Ile Lys
            100                 105
```

<210> SEQ ID NO 365
<211> LENGTH: 124
<212> TYPE: PRT
<213> ORGANISM: Artificial Sequence
<220> FEATURE:
<223> OTHER INFORMATION: Synthetic Construct

<400> SEQUENCE: 365

```
Gln Glu Gln Leu Met Glu Ser Gly Gly Gly Leu Val Thr Leu Gly Gly
1               5                   10                  15

Ser Leu Lys Leu Ser Cys Lys Ala Ser Gly Ile Asp Phe Ser His Tyr
            20                  25                  30

Gly Ile Ser Trp Val Arg Gln Ala Pro Gly Lys Gly Leu Glu Trp Ile
        35                  40                  45

Ala Tyr Ile Tyr Pro Asn Tyr Gly Ser Val Asp Tyr Ala Ser Trp Val
    50                  55                  60

Asn Gly Arg Phe Thr Ile Ser Leu Asp Asn Ala Gln Asn Thr Val Phe
65                  70                  75                  80

Leu Gln Met Ile Ser Leu Thr Ala Ala Asp Thr Ala Thr Tyr Phe Cys
                85                  90                  95

Ala Arg Asp Arg Gly Tyr Tyr Ser Gly Ser Arg Gly Thr Arg Leu Asp
            100                 105                 110

Leu Trp Gly Gln Gly Thr Leu Val Thr Ile Ser Ser
        115                 120
```

<210> SEQ ID NO 366
<211> LENGTH: 109
<212> TYPE: PRT
<213> ORGANISM: Homo sapiens

<400> SEQUENCE: 366

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Trp Gly Gln Gly Thr Leu Val Thr Val Ser Ser
        100                 105

<210> SEQ ID NO 367
<211> LENGTH: 124
<212> TYPE: PRT
<213> ORGANISM: Artificial Sequence
<220> FEATURE:
<223> OTHER INFORMATION: Synthetic Construct

<400> SEQUENCE: 367

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Pro Asn Gly Gly Ser Val Tyr Tyr Ala Asp Ser Val
        50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Tyr Tyr Thr Gly Ser Arg Gly Thr Arg Leu Ala
            100                 105                 110

Leu Trp Gly Gln Gly Thr Leu Val Thr Val Ser Ser
        115                 120

<210> SEQ ID NO 368
<211> LENGTH: 124
<212> TYPE: PRT
<213> ORGANISM: Artificial Sequence
<220> FEATURE:
<223> OTHER INFORMATION: Synthetic Construct

<400> SEQUENCE: 368

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
                20                  25                  30

Gly Ile Ser Trp Val Arg Gln Ala Pro Gly Lys Gly Leu Glu Trp Val
            35                  40                  45

Ser Tyr Ile Tyr Pro Asn Tyr Gly Ser Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gln Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 369
<211> LENGTH: 124
<212> TYPE: PRT
<213> ORGANISM: Artificial Sequence
<220> FEATURE:
<223> OTHER INFORMATION: Synthetic Construct

<400> SEQUENCE: 369

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Ile Ser Trp Val Arg Gln Ala Pro Gly Lys Gly Leu Glu Trp Val
        35                  40                  45

Ser Tyr Ile Tyr Gly Asn Gly Gly Ser Val Asp Tyr Ala Ser Trp Val
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Tyr Tyr Ser Val Ser Arg Gly Thr Arg Leu Asp
            100                 105                 110

Leu Trp Gly Gln Gly Thr Leu Val Thr Val Ser Ser
        115                 120

<210> SEQ ID NO 370
<211> LENGTH: 124
<212> TYPE: PRT
<213> ORGANISM: Artificial Sequence
<220> FEATURE:
<223> OTHER INFORMATION: Synthetic Construct

<400> SEQUENCE: 370

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Ser Tyr Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 371
<211> LENGTH: 124
<212> TYPE: PRT
<213> ORGANISM: Artificial Sequence
<220> FEATURE:
<223> OTHER INFORMATION: Synthetic Construct

<400> SEQUENCE: 371

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Ser Tyr Gly Ser Thr Asp Tyr Ala Ser Ser Val
50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Lys Asp Arg Gly Ala Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 372
<211> LENGTH: 124
<212> TYPE: PRT
<213> ORGANISM: Artificial Sequence
<220> FEATURE:
<223> OTHER INFORMATION: Synthetic Construct

<400> SEQUENCE: 372

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Ser Tyr
            20                  25                  30

Gly Ile Ser Trp Val Arg Gln Ala Pro Gly Lys Gly Leu Glu Trp Val
        35                  40                  45

Ser Tyr Ile Tyr Pro Ser Tyr Gly Ser Thr Asp Tyr Ala Asp Trp Val
50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Lys Asp Arg Gly Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 373
<211> LENGTH: 124
<212> TYPE: PRT
<213> ORGANISM: Artificial Sequence
<220> FEATURE:
<223> OTHER INFORMATION: Synthetic Construct

<400> SEQUENCE: 373

Glu Val Gln Leu Leu Glu Ser Gly Gly Gly Leu Val Gln Pro Gly Gly
1               5                   10                  15

Ser Leu Arg Leu Ser Cys Ala Ser Gly Ile Asp Phe Ser Ser Tyr
            20                  25                  30

Gly Ile Ser Trp Val Arg Gln Ala Pro Gly Lys Gly Leu Glu Trp Val
        35                  40                  45

Ser Tyr Ile Tyr Pro Ser Tyr Gly Ser Thr Asp Tyr Ala Ser Trp Val
50                      55                  60

Asn Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

-continued

Ala Lys Asp Arg Gly Val Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 374
<211> LENGTH: 124
<212> TYPE: PRT
<213> ORGANISM: Artificial Sequence
<220> FEATURE:
<223> OTHER INFORMATION: Synthetic Construct

<400> SEQUENCE: 374

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Thr Asp Tyr Ala Ser Trp Val
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Gly Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 375
<211> LENGTH: 124
<212> TYPE: PRT
<213> ORGANISM: Artificial Sequence
<220> FEATURE:
<223> OTHER INFORMATION: Synthetic Construct

<400> SEQUENCE: 375

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Gly Ile Ser Trp Val Arg Gln Ala Pro Gly Lys Gly Leu Glu Trp Val
        35                  40                  45

Ser Tyr Ile Tyr Pro Asn Tyr Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gln Tyr Tyr Ser Gly Ser Arg Gly Thr Arg Leu Asp
            100                 105                 110

Leu Trp Gly Gln Gly Thr Leu Val Thr Val Ser Ser
        115                 120

<210> SEQ ID NO 376
<211> LENGTH: 104
<212> TYPE: PRT

<213> ORGANISM: Artificial Sequence
<220> FEATURE:
<223> OTHER INFORMATION: Synthetic Construct

<400> SEQUENCE: 376

```
Ala Leu Thr Gln Pro Thr Ser Val Ser Ala Asn Leu Gly Gly Ser Val
1               5                   10                  15

Glu Ile Thr Cys Ser Gly Ser Asp Tyr Asp Tyr Gly Trp Tyr Gln Gln
            20                  25                  30

Lys Ala Pro Gly Ser Ala Pro Val Thr Val Ile Tyr Trp Asn Asp Lys
        35                  40                  45

Arg Pro Ser Asp Ile Pro Ser Arg Phe Ser Gly Ser Thr Ser Gly Ser
    50                  55                  60

Thr Ser Thr Leu Thr Ile Thr Gly Val Gln Ala Glu Asp Glu Ala Val
65                  70                  75                  80

Tyr Tyr Cys Gly Ala Tyr Asp Gly Ser Ala Gly Gly Ile Phe Gly
                85                  90                  95

Ala Gly Thr Thr Leu Thr Val Leu
            100
```

<210> SEQ ID NO 377
<211> LENGTH: 108
<212> TYPE: PRT
<213> ORGANISM: Homo sapiens

<400> SEQUENCE: 377

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105
```

<210> SEQ ID NO 378
<211> LENGTH: 105
<212> TYPE: PRT
<213> ORGANISM: Artificial Sequence
<220> FEATURE:
<223> OTHER INFORMATION: Synthetic Construct

<400> SEQUENCE: 378

```
Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asn
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
```

-continued

```
                65                  70                  75                  80
Asp Tyr Tyr Cys Gly Ala Tyr Asp Gly Ser Gly Gly His Gly Val Phe
                85                  90                  95

Gly Gly Gly Thr Lys Leu Thr Val Leu
            100                 105

<210> SEQ ID NO 379
<211> LENGTH: 105
<212> TYPE: PRT
<213> ORGANISM: Artificial Sequence
<220> FEATURE:
<223> OTHER INFORMATION: Synthetic Construct

<400> SEQUENCE: 379

Ser Ser Glu Leu Thr Gln Asp Pro Ala Val Ser Val Ala Leu Gly Gln
1               5                   10                  15

Thr Val Arg Ile Thr Cys Ser Gly Asp Asp Ser Tyr Tyr Gly Trp Tyr
            20                  25                  30

Gln Gln Lys Pro Gly Gln Ala Pro Val Thr Val Ile Tyr Gly Asn Asn
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Gly Ser Gly Gly His Gly Val Phe
                85                  90                  95

Gly Gly Gly Thr Lys Leu Thr Val Leu
            100                 105

<210> SEQ ID NO 380
<211> LENGTH: 105
<212> TYPE: PRT
<213> ORGANISM: Artificial Sequence
<220> FEATURE:
<223> OTHER INFORMATION: Synthetic Construct

<400> SEQUENCE: 380

Ser Ser Glu Leu Thr Gln Asp Pro Ala Val Ser Val Ala Leu Gly Gln
1               5                   10                  15

Thr Val Arg Ile Thr Cys Ser Gly Asp Asp Ser Tyr Tyr Gly Trp Tyr
            20                  25                  30

Gln Gln Lys Pro Gly Gln Ala Pro Val Thr Val Ile Tyr Gly Asn Asp
        35                  40                  45

Lys Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Gly Ser Gly Gly Gly Gly Val Phe
                85                  90                  95

Gly Gly Gly Thr Lys Leu Thr Val Leu
            100                 105

<210> SEQ ID NO 381
<211> LENGTH: 105
<212> TYPE: PRT
<213> ORGANISM: Artificial Sequence
<220> FEATURE:
<223> OTHER INFORMATION: Synthetic Construct

<400> SEQUENCE: 381
```

Ser Ser Glu Leu Thr Gln Asp Pro Ala Val Ser Val Ala Leu Gly His
1               5                   10                  15

Thr Val Arg Ile Thr Cys Ser Gly Asp Asp Ser Tyr Tyr Gly Trp Tyr
            20                  25                  30

Gln Gln Lys Pro Gly Gln Ala Pro Val Thr Val Ile Tyr Gly Asn Asp
        35                  40                  45

Lys Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Gly Ile Phe
                85                  90                  95

Gly Gly Gly Thr Lys Leu Thr Val Leu
            100                 105

<210> SEQ ID NO 382
<211> LENGTH: 105
<212> TYPE: PRT
<213> ORGANISM: Artificial Sequence
<220> FEATURE:
<223> OTHER INFORMATION: Synthetic Construct

<400> SEQUENCE: 382

Ser Ser Glu Leu Thr Gln Asp Pro Ala Val Ser Val Ala Leu Gly Gln
1               5                   10                  15

Thr Val Arg Leu Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asn
        35                  40                  45

Lys Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Gly Val Phe
                85                  90                  95

Gly Gly Gly Thr Lys Leu Thr Val Leu
            100                 105

<210> SEQ ID NO 383
<211> LENGTH: 105
<212> TYPE: PRT
<213> ORGANISM: Artificial Sequence
<220> FEATURE:
<223> OTHER INFORMATION: Synthetic Construct

<400> SEQUENCE: 383

Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asp
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Gly Ile Phe

Gly Gly Gly Thr Lys Leu Thr Val Leu
            100                 105

<210> SEQ ID NO 384
<211> LENGTH: 105
<212> TYPE: PRT
<213> ORGANISM: Artificial Sequence
<220> FEATURE:
<223> OTHER INFORMATION: Synthetic Construct

<400> SEQUENCE: 384

Ser Ser Glu Leu Thr Gln Asp Pro Ala Val Ser Val Ala Leu Gly Gln
1               5                   10                  15

Thr Val Arg Ile Thr Cys Gln Gly Asp Asp Ser Tyr Tyr Gly Trp Tyr
            20                  25                  30

Gln Gln Lys Pro Gly Gln Ala Pro Val Thr Val Ile Tyr Gly Asn Asp
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ala Tyr Asp Ser Ser Gly Gly Gly Ile Phe
                85                  90                  95

Gly Gly Gly Thr Lys Leu Thr Val Leu
            100                 105

<210> SEQ ID NO 385
<211> LENGTH: 105
<212> TYPE: PRT
<213> ORGANISM: Artificial Sequence
<220> FEATURE:
<223> OTHER INFORMATION: Synthetic Construct

<400> SEQUENCE: 385

Ser Ser Glu Leu Thr Gln Asp Pro Ala Val Ser Val Ala Leu Gly Gln
1               5                   10                  15

Thr Val Arg Ile Thr Cys Gln Gly Ser Asp Tyr Tyr Tyr Gly Trp Tyr
            20                  25                  30

Gln Gln Lys Pro Gly Gln Ala Pro Val Thr Val Ile Tyr Gly Asn Asp
        35                  40                  45

Asn Arg Pro Ser Gly Ile Pro Asp Arg Phe Ser Gly Ser Ser Ser Gly
    50                  55                  60

Asn Thr Ala Ser Leu Thr Ile Thr Gly Ala Gln Ala Glu Asp Glu Ala
65                  70                  75                  80

Asp Tyr Tyr Cys Gly Ser Tyr Asp Ser Ser Ala Gly His Gly Val Phe
                85                  90                  95

Gly Gly Gly Thr Lys Leu Thr Val Leu
            100                 105

<210> SEQ ID NO 386
<211> LENGTH: 127
<212> TYPE: PRT
<213> ORGANISM: Artificial Sequence
<220> FEATURE:
<223> OTHER INFORMATION: Synthetic Construct

<400> SEQUENCE: 386

Ala Val Thr Leu Asp Glu Ser Gly Gly Gly Leu Gln Thr Pro Gly Gly
1               5                   10                  15

-continued

```
Gly Leu Ser Leu Val Cys Lys Ala Ser Gly Phe Thr Leu Ser Ser Tyr
            20                  25                  30

Gln Met Met Trp Val Arg Gln Ala Pro Gly Lys Gly Leu Glu Trp Val
        35                  40                  45

Ala Gly Ile Thr Ser Arg Gly Gly Val Thr Gly Tyr Gly Ser Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly His Gly Thr Glu Val Ile Val Ser Ser
        115                 120                 125
```

<210> SEQ ID NO 387
<211> LENGTH: 112
<212> TYPE: PRT
<213> ORGANISM: Artificial Sequence
<220> FEATURE:
<223> OTHER INFORMATION: Synthetic Construct

<400> SEQUENCE: 387

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Asp Tyr Trp Gly Gln Gly Thr Leu Val Thr Val Ser Ser
            100                 105                 110
```

<210> SEQ ID NO 388
<211> LENGTH: 127
<212> TYPE: PRT
<213> ORGANISM: Artificial Sequence
<220> FEATURE:
<223> OTHER INFORMATION: Synthetic Construct

<400> SEQUENCE: 388

```
Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gln Met Met Trp Val Arg Gln Ala Pro Gly Lys Gly Leu Glu Trp Val
        35                  40                  45

Ala Gly Ile Thr Ser Arg Gly Gly Val Thr Gly Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Lys Pro Ala Leu Asp Ser Asp Gln Cys Gly Phe Pro Glu Ala Gly
                100                 105                 110
Cys Ile Asp Ala Trp Gly Gln Gly Thr Leu Val Thr Val Ser Ser
            115                 120                 125

<210> SEQ ID NO 389
<211> LENGTH: 127
<212> TYPE: PRT
<213> ORGANISM: Artificial Sequence
<220> FEATURE:
<223> OTHER INFORMATION: Synthetic Construct

<400> SEQUENCE: 389

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
                20                  25                  30

Gln Met Met Trp Val Arg Gln Ala Pro Gly Lys Gly Leu Glu Trp Val
            35                  40                  45

Ala Gly Ile Thr Ser Arg Gly Gly Val Thr Gly Tyr Ala Asp Ala Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ala Asp Gln Cys Gly Phe Pro Glu Ala Gly
                100                 105                 110

Cys Ile Asp Ala Trp Gly Gln Gly Thr Leu Val Thr Val Ser Ser
            115                 120                 125

<210> SEQ ID NO 390
<211> LENGTH: 127
<212> TYPE: PRT
<213> ORGANISM: Artificial Sequence
<220> FEATURE:
<223> OTHER INFORMATION: Synthetic Construct

<400> SEQUENCE: 390

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
                20                  25                  30

Gln Met Met Trp Val Arg Gln Ala Pro Gly Lys Gly Leu Glu Trp Val
            35                  40                  45

Ala Gly Ile Thr Ser Arg Gly Gly Val Thr Gly Tyr Gly Ser Ala Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
                100                 105                 110

Cys Ile Asp Ser Trp Gly Gln Gly Thr Leu Val Thr Val Ser Ser
            115                 120                 125

<210> SEQ ID NO 391
<211> LENGTH: 127
```

```
<212> TYPE: PRT
<213> ORGANISM: Artificial Sequence
<220> FEATURE:
<223> OTHER INFORMATION: Synthetic Construct

<400> SEQUENCE: 391

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gln Met Ser Trp Val Arg Gln Ala Pro Gly Lys Gly Leu Glu Trp Val
        35                  40                  45

Ala Gly Ile Thr Ser Arg Gly Val Thr Gly Tyr Gly Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Pro Ala Leu Asp Ala Asp Gln Cys Gly Phe Pro Glu Ala Gly
            100                 105                 110

Cys Ile Asp Ala Trp Gly Gln Gly Thr Leu Val Thr Val Ser Ser
            115                 120                 125

<210> SEQ ID NO 392
<211> LENGTH: 127
<212> TYPE: PRT
<213> ORGANISM: Artificial Sequence
<220> FEATURE:
<223> OTHER INFORMATION: Synthetic Construct

<400> SEQUENCE: 392

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gln Met Met Trp Val Arg Gln Ala Pro Gly Lys Gly Leu Glu Trp Val
            35                  40                  45

Ser Gly Ile Thr Ser Arg Gly Gly Val Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
            115                 120                 125

<210> SEQ ID NO 393
<211> LENGTH: 127
<212> TYPE: PRT
<213> ORGANISM: Artificial Sequence
<220> FEATURE:
<223> OTHER INFORMATION: Synthetic Construct

<400> SEQUENCE: 393

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Leu Ser Ser Tyr
```

```
                        20                  25                  30

Gln Met Met Trp Val Arg Gln Ala Pro Gly Lys Gly Leu Glu Trp Val
            35                  40                  45

Ala Gly Ile Thr Gly Arg Gly Val Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asp Ser Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 394
<211> LENGTH: 127
<212> TYPE: PRT
<213> ORGANISM: Artificial Sequence
<220> FEATURE:
<223> OTHER INFORMATION: Synthetic Construct

<400> SEQUENCE: 394

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gln Met Met Trp Val Arg Gln Ala Pro Gly Lys Gly Leu Glu Trp Val
            35                  40                  45

Ser Gly Ile Thr Ser Arg Gly Val Thr Gly Tyr Gly Ser Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ala Leu Asn Ser Asp Gln Cys Gly Phe Pro Glu Ala Gly
            100                 105                 110

Cys Ile Asp Ala Trp Gly Gln Gly Thr Leu Val Thr Val Ser Ser
        115                 120                 125

<210> SEQ ID NO 395
<211> LENGTH: 127
<212> TYPE: PRT
<213> ORGANISM: Artificial Sequence
<220> FEATURE:
<223> OTHER INFORMATION: Synthetic Construct

<400> SEQUENCE: 395

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Ser Ser Tyr
            20                  25                  30

Gln Met Ser Trp Val Arg Gln Ala Pro Gly Lys Gly Leu Glu Trp Val
            35                  40                  45

Ser Gly Ile Thr Gly Arg Gly Val Thr Gly Tyr Ala Asp Ala Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Pro Ala Leu Asp Ser Asp Gln Cys Gly Phe Pro Glu Met Gly
            100                 105                 110

Cys Ile Asp Ala Trp Gly Gln Gly Thr Leu Val Thr Val Ser Ser
        115                 120                 125
```

<210> SEQ ID NO 396
<211> LENGTH: 107
<212> TYPE: PRT
<213> ORGANISM: Artificial Sequence
<220> FEATURE:
<223> OTHER INFORMATION: Synthetic Construct

<400> SEQUENCE: 396

```
Asp Ile Gln Met Thr Gln Ser Pro Ser Ser Met Ser Val Ser Leu Gly
1               5                   10                  15

Asp Thr Ile Thr Ile Thr Cys Arg Ala Ser Gln Asp Val Gly Ile Tyr
            20                  25                  30

Val Asn Trp Phe Gln Gln Lys Pro Gly Lys Ser Pro Arg Arg Met Ile
        35                  40                  45

Tyr Arg Ala Thr Asn Leu Ala Asp Gly Val Pro Ser Arg Phe Ser Gly
    50                  55                  60

Ser Arg Ser Gly Ser Ile Tyr Ser Leu Thr Ile Ser Ser Leu Glu Ser
65                  70                  75                  80

Glu Asp Val Ala Asp Tyr His Cys Leu Glu Phe Asp Glu His Pro Leu
                85                  90                  95

Thr Phe Gly Ser Gly Thr Lys Val Glu Ile Lys
            100                 105
```

<210> SEQ ID NO 397
<211> LENGTH: 107
<212> TYPE: PRT
<213> ORGANISM: Artificial Sequence
<220> FEATURE:
<223> OTHER INFORMATION: Synthetic Construct

<400> SEQUENCE: 397

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 398
<211> LENGTH: 107
<212> TYPE: PRT
<213> ORGANISM: Artificial Sequence
<220> FEATURE:
<223> OTHER INFORMATION: Synthetic Construct

<400> SEQUENCE: 398

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Tyr
            20                  25                  30

Val Asn Trp Tyr Gln Gln Lys Pro Gly Lys Ala Pro Lys Leu Leu Ile
        35                  40                  45

Tyr Arg Ala Ser Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Phe Asp Glu His Pro Leu
                85                  90                  95

Thr Phe Gly Gly Gly Thr Lys Val Glu Ile Lys
            100                 105

<210> SEQ ID NO 399
<211> LENGTH: 107
<212> TYPE: PRT
<213> ORGANISM: Artificial Sequence
<220> FEATURE:
<223> OTHER INFORMATION: Synthetic Construct

<400> SEQUENCE: 399

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Tyr
            20                  25                  30

Val Asn Trp Tyr Gln Gln Lys Pro Gly Lys Ala Pro Lys Leu Leu Ile
        35                  40                  45

Tyr Arg Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Glu Phe Asp Glu His Pro Leu
                85                  90                  95

Thr Phe Gly Gly Gly Thr Lys Val Glu Ile Lys
            100                 105

<210> SEQ ID NO 400
<211> LENGTH: 107
<212> TYPE: PRT
<213> ORGANISM: Artificial Sequence
<220> FEATURE:
<223> OTHER INFORMATION: Synthetic Construct

<400> SEQUENCE: 400

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Tyr
            20                  25                  30

Val Asn Trp Tyr Gln Gln Lys Pro Gly Lys Ala Pro Lys Leu Leu Ile
        35                  40                  45

Tyr Arg Ala Ser Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Glu Phe Tyr Ser His Pro Leu
                85                  90                  95
Thr Phe Gly Gly Gly Thr Lys Val Glu Ile Lys
            100                 105

<210> SEQ ID NO 401
<211> LENGTH: 107
<212> TYPE: PRT
<213> ORGANISM: Artificial Sequence
<220> FEATURE:
<223> OTHER INFORMATION: Synthetic Construct

<400> SEQUENCE: 401

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Lys Leu Leu Ile
        35                  40                  45
Tyr Arg Ala Thr Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Glu Phe Asp Glu His Pro Leu
                85                  90                  95
Thr Phe Gly Gly Gly Thr Lys Val Glu Ile Lys
            100                 105

<210> SEQ ID NO 402
<211> LENGTH: 107
<212> TYPE: PRT
<213> ORGANISM: Artificial Sequence
<220> FEATURE:
<223> OTHER INFORMATION: Synthetic Construct

<400> SEQUENCE: 402

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Gly Ser Tyr
            20                  25                  30
Leu Asn Trp Tyr Gln Gln Lys Pro Gly Lys Ala Pro Lys Leu Leu Ile
        35                  40                  45
Tyr Arg Ala Ser Ser Leu Ala Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Glu Phe Asp Glu His Pro Leu
                85                  90                  95
Thr Phe Gly Gly Gly Thr Lys Val Glu Ile Lys
            100                 105

<210> SEQ ID NO 403
<211> LENGTH: 119
<212> TYPE: PRT
<213> ORGANISM: Artificial Sequence
<220> FEATURE:
<223> OTHER INFORMATION: Synthetic Construct

<400> SEQUENCE: 403

Glu Val Gln Leu Val Glu Ser Gly Gly Gly Leu Val Gln Pro Gly Arg

-continued

```
              1               5                  10                 15
            Ser Leu Lys Leu Ser Cys Val Val Ser Gly Phe Thr Phe Asn Asn Tyr
                            20                 25                 30

Trp Met Thr Trp Ile Arg Gln Thr Pro Gly Lys Gly Leu Glu Trp Val
                        35                 40                 45

Ala Ser Ile Asp Asn Ser Gly Asp Asn Thr Tyr Tyr Pro Asp Ser Val
                    50                 55                 60

Lys Asp Arg Phe Thr Ile Ser Arg Asp Asn Ala Lys Ser Thr Leu Tyr
             65                 70                 75                 80

Leu Gln Met Asn Ser Leu Arg Ser Glu Asp Thr Ala Thr Tyr Tyr Cys
                            85                 90                 95

Thr Arg Gly Gly Asp Ile Thr Thr Gly Phe Asp Tyr Trp Gly Gln Gly
                            100                105                110

Val Met Val Thr Val Ser Ser
                        115
```

<210> SEQ ID NO 404
<211> LENGTH: 111
<212> TYPE: PRT
<213> ORGANISM: Artificial Sequence
<220> FEATURE:
<223> OTHER INFORMATION: Synthetic Construct

<400> SEQUENCE: 404

```
            Glu Val Gln Leu Val Glu Ser Gly Gly Gly Leu Val Gln Pro Gly Gly
             1               5                  10                 15

Ser Leu Arg Leu Ser Cys Ala Ala Ser Gly Phe Thr Phe Ser Ser Tyr
                            20                 25                 30

Trp Met Ser Trp Val Arg Gln Ala Pro Gly Lys Gly Leu Glu Trp Val
                        35                 40                 45

Ala Asn Ile Lys Gln Asp Gly Ser Glu Lys Tyr Tyr Val Asp Ser Val
                    50                 55                 60

Lys Gly Arg Phe Thr Ile Ser Arg Asp Asn Ala Lys Asn Ser Leu Tyr
             65                 70                 75                 80

Leu Gln Met Asn Ser Leu Arg Ala Glu Asp Thr Ala Val Tyr Tyr Cys
                            85                 90                 95

Ala Arg Asp Tyr Trp Gly Gln Gly Thr Leu Val Thr Val Ser Ser
                            100                105                110
```

<210> SEQ ID NO 405
<211> LENGTH: 119
<212> TYPE: PRT
<213> ORGANISM: Artificial Sequence
<220> FEATURE:
<223> OTHER INFORMATION: Synthetic Construct

<400> SEQUENCE: 405

```
            Glu Val Gln Leu Val Glu Ser Gly Gly Gly Leu Val Gln Pro Gly Gly
             1               5                  10                 15

Ser Leu Arg Leu Ser Cys Ala Ala Ser Gly Phe Thr Phe Ser Asn Tyr
                            20                 25                 30

Trp Met Ser Trp Val Arg Gln Ala Pro Gly Lys Gly Leu Glu Trp Val
                        35                 40                 45

Ala Ser Ile Lys Asn Asp Gly Asp Asn Thr Tyr Tyr Val Asp Ser Val
                    50                 55                 60

Lys Asp Arg Phe Thr Ile Ser Arg Asp Asn Ala Lys Asn Ser Leu Tyr
             65                 70                 75                 80
```

Leu Gln Met Asn Ser Leu Arg Ala Glu Asp Thr Ala Val Tyr Tyr Cys
                85                  90                  95

Ala Arg Gly Gly Asp Ile Thr Thr Gly Leu Asp Tyr Trp Gly Gln Gly
            100                 105                 110

Thr Leu Val Thr Val Ser Ser
        115

<210> SEQ ID NO 406
<211> LENGTH: 119
<212> TYPE: PRT
<213> ORGANISM: Artificial Sequence
<220> FEATURE:
<223> OTHER INFORMATION: Synthetic Construct

<400> SEQUENCE: 406

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Ser Ile Asp Asn Ser Gly Ser Asn Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ile Thr Thr Gly Phe Asp Tyr Trp Gly Gln Gly
            100                 105                 110

Thr Leu Val Thr Val Ser Ser
        115

<210> SEQ ID NO 407
<211> LENGTH: 119
<212> TYPE: PRT
<213> ORGANISM: Artificial Sequence
<220> FEATURE:
<223> OTHER INFORMATION: Synthetic Construct

<400> SEQUENCE: 407

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Lys Asn Ser Gly Ser Glu Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ile Thr Thr Gly Phe Asp Tyr Trp Gly Gln Gly
            100                 105                 110

Thr Leu Val Thr Val Ser Ser
        115

<210> SEQ ID NO 408

```
<211> LENGTH: 119
<212> TYPE: PRT
<213> ORGANISM: Artificial Sequence
<220> FEATURE:
<223> OTHER INFORMATION: Synthetic Construct

<400> SEQUENCE: 408

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Asp Gln Asp Gly Ser Glu Lys Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ile Thr Thr Gly Leu Asp Tyr Trp Gly Gln Gly
            100                 105                 110

Thr Leu Val Thr Val Ser Ser
        115

<210> SEQ ID NO 409
<211> LENGTH: 119
<212> TYPE: PRT
<213> ORGANISM: Artificial Sequence
<220> FEATURE:
<223> OTHER INFORMATION: Synthetic Construct

<400> SEQUENCE: 409

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Ser Ile Asp Gln Asp Gly Ser Asn Lys Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ile Thr Thr Gly Leu Asp Tyr Trp Gly Gln Gly
            100                 105                 110

Thr Leu Val Thr Val Ser Ser
        115

<210> SEQ ID NO 410
<211> LENGTH: 11
<212> TYPE: PRT
<213> ORGANISM: Artificial Sequence
<220> FEATURE:
<223> OTHER INFORMATION: Synthetic Construct

<400> SEQUENCE: 410

Arg Ala Ser Gln Ser Ile Ser Ser Tyr Leu Asn
1               5                   10
```

```
<210> SEQ ID NO 411
<211> LENGTH: 7
<212> TYPE: PRT
<213> ORGANISM: Artificial Sequence
<220> FEATURE:
<223> OTHER INFORMATION: Synthetic Construct

<400> SEQUENCE: 411

Ala Ala Ser Ser Leu Gln Ser
1               5

<210> SEQ ID NO 412
<211> LENGTH: 7
<212> TYPE: PRT
<213> ORGANISM: Artificial Sequence
<220> FEATURE:
<223> OTHER INFORMATION: Synthetic Construct

<400> SEQUENCE: 412

Gln Gln Ser Tyr Ser Thr Pro
1               5

<210> SEQ ID NO 413
<211> LENGTH: 16
<212> TYPE: PRT
<213> ORGANISM: Artificial Sequence
<220> FEATURE:
<223> OTHER INFORMATION: Synthetic Construct

<400> SEQUENCE: 413

Lys Ser Ser Gln Ser Leu Leu His Ser Asp Gly Lys Thr Tyr Leu Tyr
1               5                   10                  15

<210> SEQ ID NO 414
<211> LENGTH: 7
<212> TYPE: PRT
<213> ORGANISM: Artificial Sequence
<220> FEATURE:
<223> OTHER INFORMATION: Synthetic Construct

<400> SEQUENCE: 414

Glu Val Ser Asn Arg Phe Ser
1               5

<210> SEQ ID NO 415
<211> LENGTH: 7
<212> TYPE: PRT
<213> ORGANISM: Artificial Sequence
<220> FEATURE:
<223> OTHER INFORMATION: Synthetic Construct

<400> SEQUENCE: 415

Met Gln Ser Ile Gln Leu Pro
1               5

<210> SEQ ID NO 416
<211> LENGTH: 16
<212> TYPE: PRT
<213> ORGANISM: Artificial Sequence
<220> FEATURE:
<223> OTHER INFORMATION: Synthetic Construct

<400> SEQUENCE: 416

Arg Ser Ser Gln Ser Leu Val Tyr Ser Asp Gly Asn Thr Tyr Leu Asn
1               5                   10                  15
```

-continued

```
<210> SEQ ID NO 417
<211> LENGTH: 7
<212> TYPE: PRT
<213> ORGANISM: Artificial Sequence
<220> FEATURE:
<223> OTHER INFORMATION: Synthetic Construct

<400> SEQUENCE: 417

Lys Val Ser Asn Arg Asp Ser
1               5

<210> SEQ ID NO 418
<211> LENGTH: 7
<212> TYPE: PRT
<213> ORGANISM: Artificial Sequence
<220> FEATURE:
<223> OTHER INFORMATION: Synthetic Construct

<400> SEQUENCE: 418

Met Gln Gly Thr His Trp Pro
1               5

<210> SEQ ID NO 419
<211> LENGTH: 17
<212> TYPE: PRT
<213> ORGANISM: Artificial Sequence
<220> FEATURE:
<223> OTHER INFORMATION: Synthetic Construct

<400> SEQUENCE: 419

Lys Ser Ser Gln Ser Val Leu Tyr Ser Ser Asn Asn Lys Asn Tyr Leu
1               5                   10                  15

Ala

<210> SEQ ID NO 420
<211> LENGTH: 7
<212> TYPE: PRT
<213> ORGANISM: Artificial Sequence
<220> FEATURE:
<223> OTHER INFORMATION: Synthetic Construct

<400> SEQUENCE: 420

Trp Ala Ser Thr Arg Glu Ser
1               5

<210> SEQ ID NO 421
<211> LENGTH: 7
<212> TYPE: PRT
<213> ORGANISM: Artificial Sequence
<220> FEATURE:
<223> OTHER INFORMATION: Synthetic Construct

<400> SEQUENCE: 421

Gln Gln Tyr Tyr Ser Thr Pro
1               5

<210> SEQ ID NO 422
<211> LENGTH: 11
<212> TYPE: PRT
<213> ORGANISM: Artificial Sequence
<220> FEATURE:
<223> OTHER INFORMATION: Synthetic Construct

<400> SEQUENCE: 422

Arg Ala Ser Gln Ser Ile Ser Ser Trp Leu Ala
1               5                   10
```

<210> SEQ ID NO 423
<211> LENGTH: 7
<212> TYPE: PRT
<213> ORGANISM: Artificial Sequence
<220> FEATURE:
<223> OTHER INFORMATION: Synthetic Construct

<400> SEQUENCE: 423

Asp Ala Ser Ser Leu Glu Ser
1               5

<210> SEQ ID NO 424
<211> LENGTH: 7
<212> TYPE: PRT
<213> ORGANISM: Artificial Sequence
<220> FEATURE:
<223> OTHER INFORMATION: Synthetic Construct

<400> SEQUENCE: 424

Gln Gln Tyr Asn Ser Tyr Ser
1               5

<210> SEQ ID NO 425
<211> LENGTH: 11
<212> TYPE: PRT
<213> ORGANISM: Artificial Sequence
<220> FEATURE:
<223> OTHER INFORMATION: Synthetic Construct

<400> SEQUENCE: 425

Gln Ala Ser Gln Asp Ile Ser Asn Tyr Leu Asn
1               5                   10

<210> SEQ ID NO 426
<211> LENGTH: 7
<212> TYPE: PRT
<213> ORGANISM: Artificial Sequence
<220> FEATURE:
<223> OTHER INFORMATION: Synthetic Construct

<400> SEQUENCE: 426

Asp Ala Ser Asn Leu Glu Thr
1               5

<210> SEQ ID NO 427
<211> LENGTH: 7
<212> TYPE: PRT
<213> ORGANISM: Artificial Sequence
<220> FEATURE:
<223> OTHER INFORMATION: Synthetic Construct

<400> SEQUENCE: 427

Gln Gln Tyr Asp Asn Leu Pro
1               5

<210> SEQ ID NO 428
<211> LENGTH: 11
<212> TYPE: PRT
<213> ORGANISM: Artificial Sequence
<220> FEATURE:
<223> OTHER INFORMATION: Synthetic Construct

<400> SEQUENCE: 428

Arg Ala Ser Gln Gly Ile Ser Ser Tyr Leu Ala
1               5                   10

```
<210> SEQ ID NO 429
<211> LENGTH: 7
<212> TYPE: PRT
<213> ORGANISM: Artificial Sequence
<220> FEATURE:
<223> OTHER INFORMATION: Synthetic Construct

<400> SEQUENCE: 429

Ala Ala Ser Thr Leu Gln Ser
1               5

<210> SEQ ID NO 430
<211> LENGTH: 7
<212> TYPE: PRT
<213> ORGANISM: Artificial Sequence
<220> FEATURE:
<223> OTHER INFORMATION: Synthetic Construct

<400> SEQUENCE: 430

Gln Gln Leu Asn Ser Tyr Pro
1               5

<210> SEQ ID NO 431
<211> LENGTH: 11
<212> TYPE: PRT
<213> ORGANISM: Artificial Sequence
<220> FEATURE:
<223> OTHER INFORMATION: Synthetic Construct

<400> SEQUENCE: 431

Arg Ala Ser Gln Ser Val Ser Ser Asn Leu Ala
1               5                   10

<210> SEQ ID NO 432
<211> LENGTH: 7
<212> TYPE: PRT
<213> ORGANISM: Artificial Sequence
<220> FEATURE:
<223> OTHER INFORMATION: Synthetic Construct

<400> SEQUENCE: 432

Gly Ala Ser Thr Arg Ala Thr
1               5

<210> SEQ ID NO 433
<211> LENGTH: 7
<212> TYPE: PRT
<213> ORGANISM: Artificial Sequence
<220> FEATURE:
<223> OTHER INFORMATION: Synthetic Construct

<400> SEQUENCE: 433

Gln Gln Tyr Asn Asn Trp Pro
1               5

<210> SEQ ID NO 434
<211> LENGTH: 11
<212> TYPE: PRT
<213> ORGANISM: Artificial Sequence
<220> FEATURE:
<223> OTHER INFORMATION: Synthetic Construct

<400> SEQUENCE: 434

Arg Ala Ser Gln Ser Val Ser Ser Tyr Leu Ala
1               5                   10

<210> SEQ ID NO 435
```

<211> LENGTH: 7
<212> TYPE: PRT
<213> ORGANISM: Artificial Sequence
<220> FEATURE:
<223> OTHER INFORMATION: Synthetic Construct

<400> SEQUENCE: 435

Asp Ala Ser Asn Arg Ala Thr
1               5

<210> SEQ ID NO 436
<211> LENGTH: 7
<212> TYPE: PRT
<213> ORGANISM: Artificial Sequence
<220> FEATURE:
<223> OTHER INFORMATION: Synthetic Construct

<400> SEQUENCE: 436

Gln Gln Arg Ser Asn Trp Pro
1               5

<210> SEQ ID NO 437
<211> LENGTH: 12
<212> TYPE: PRT
<213> ORGANISM: Artificial Sequence
<220> FEATURE:
<223> OTHER INFORMATION: Synthetic Construct

<400> SEQUENCE: 437

Arg Ala Ser Gln Ser Val Ser Ser Ser Tyr Leu Ala
1               5                   10

<210> SEQ ID NO 438
<211> LENGTH: 7
<212> TYPE: PRT
<213> ORGANISM: Artificial Sequence
<220> FEATURE:
<223> OTHER INFORMATION: Synthetic Construct

<400> SEQUENCE: 438

Gly Ala Ser Ser Arg Ala Thr
1               5

<210> SEQ ID NO 439
<211> LENGTH: 7
<212> TYPE: PRT
<213> ORGANISM: Artificial Sequence
<220> FEATURE:
<223> OTHER INFORMATION: Synthetic Construct

<400> SEQUENCE: 439

Gln Gln Tyr Gly Ser Ser Pro
1               5

<210> SEQ ID NO 440
<211> LENGTH: 16
<212> TYPE: PRT
<213> ORGANISM: Artificial Sequence
<220> FEATURE:
<223> OTHER INFORMATION: Synthetic Construct

<400> SEQUENCE: 440

Arg Ser Ser Gln Ser Leu Leu His Ser Asn Gly Tyr Asn Tyr Leu Asp
1               5                   10                  15

<210> SEQ ID NO 441
<211> LENGTH: 7

```
<212> TYPE: PRT
<213> ORGANISM: Artificial Sequence
<220> FEATURE:
<223> OTHER INFORMATION: Synthetic Construct

<400> SEQUENCE: 441

Leu Gly Ser Asn Arg Ala Ser
1               5

<210> SEQ ID NO 442
<211> LENGTH: 7
<212> TYPE: PRT
<213> ORGANISM: Artificial Sequence
<220> FEATURE:
<223> OTHER INFORMATION: Synthetic Construct

<400> SEQUENCE: 442

Met Gln Ala Leu Gln Thr Pro
1               5

<210> SEQ ID NO 443
<211> LENGTH: 11
<212> TYPE: PRT
<213> ORGANISM: Artificial Sequence
<220> FEATURE:
<223> OTHER INFORMATION: Synthetic Construct

<400> SEQUENCE: 443

Gln Gly Asp Ser Leu Arg Ser Tyr Tyr Ala Ser
1               5                   10

<210> SEQ ID NO 444
<211> LENGTH: 7
<212> TYPE: PRT
<213> ORGANISM: Artificial Sequence
<220> FEATURE:
<223> OTHER INFORMATION: Synthetic Construct

<400> SEQUENCE: 444

Gly Lys Asn Asn Arg Pro Ser
1               5

<210> SEQ ID NO 445
<211> LENGTH: 9
<212> TYPE: PRT
<213> ORGANISM: Artificial Sequence
<220> FEATURE:
<223> OTHER INFORMATION: Synthetic Construct

<400> SEQUENCE: 445

Asn Ser Arg Asp Ser Ser Gly Asn His
1               5

<210> SEQ ID NO 446
<211> LENGTH: 14
<212> TYPE: PRT
<213> ORGANISM: Artificial Sequence
<220> FEATURE:
<223> OTHER INFORMATION: Synthetic Construct

<400> SEQUENCE: 446

Thr Gly Ser Ser Ser Asn Ile Gly Ala Gly Tyr Asp Val His
1               5                   10

<210> SEQ ID NO 447
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 447

Gly Asn Ser Asn Arg Pro Ser
1               5

<210> SEQ ID NO 448
<211> LENGTH: 9
<212> TYPE: PRT
<213> ORGANISM: Artificial Sequence
<220> FEATURE:
<223> OTHER INFORMATION: Synthetic Construct

<400> SEQUENCE: 448

Gln Ser Tyr Asp Ser Ser Leu Ser Gly
1               5

<210> SEQ ID NO 449
<211> LENGTH: 13
<212> TYPE: PRT
<213> ORGANISM: Artificial Sequence
<220> FEATURE:
<223> OTHER INFORMATION: Synthetic Construct

<400> SEQUENCE: 449

Thr Arg Ser Ser Gly Ser Ile Ala Ser Asn Tyr Val Gln
1               5                   10

<210> SEQ ID NO 450
<211> LENGTH: 7
<212> TYPE: PRT
<213> ORGANISM: Artificial Sequence
<220> FEATURE:
<223> OTHER INFORMATION: Synthetic Construct

<400> SEQUENCE: 450

Glu Asp Asn Gln Arg Pro Ser
1               5

<210> SEQ ID NO 451
<211> LENGTH: 7
<212> TYPE: PRT
<213> ORGANISM: Artificial Sequence
<220> FEATURE:
<223> OTHER INFORMATION: Synthetic Construct

<400> SEQUENCE: 451

Gln Ser Tyr Asp Ser Ser Asn
1               5

<210> SEQ ID NO 452
<211> LENGTH: 12
<212> TYPE: PRT
<213> ORGANISM: Artificial Sequence
<220> FEATURE:
<223> OTHER INFORMATION: Synthetic Construct

<400> SEQUENCE: 452

Thr Gly Ser Ser Ser Gly Gly Ser Tyr Tyr Val Ser
1               5                   10

<210> SEQ ID NO 453
<211> LENGTH: 14
<212> TYPE: PRT
<213> ORGANISM: Artificial Sequence
```

<220> FEATURE:
<223> OTHER INFORMATION: Synthetic Construct

<400> SEQUENCE: 453

Thr Gly Ser Ser Ser Asp Val Gly Gly Ser Tyr Tyr Val Ser
1               5                   10

<210> SEQ ID NO 454
<211> LENGTH: 8
<212> TYPE: PRT
<213> ORGANISM: Artificial Sequence
<220> FEATURE:
<223> OTHER INFORMATION: Synthetic Construct

<400> SEQUENCE: 454

Glu Asn Asp Ser Asn Arg Pro Ser
1               5

<210> SEQ ID NO 455
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be S or D
<220> FEATURE:
<221> NAME/KEY: MISC_FEATURE
<222> LOCATION: (8)..(8)
<223> OTHER INFORMATION: Xaa can be Q or G

<400> SEQUENCE: 455

Glu Asp Ser Asn Arg Xaa Lys Xaa Gln Lys Pro Ser
1               5                   10

<210> SEQ ID NO 456
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or T

<400> SEQUENCE: 456

Gln Ser Trp Asp Ser Ser Ala Xaa
1               5

<210> SEQ ID NO 457
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or T
<220> FEATURE:
<221> NAME/KEY: MISC_FEATURE
<222> LOCATION: (10)..(10)
<223> OTHER INFORMATION: Xaa can be F or V
<220> FEATURE:
<221> NAME/KEY: MISC_FEATURE
<222> LOCATION: (11)..(11)
<223> OTHER INFORMATION: Xaa can be G or V

<400> SEQUENCE: 457

Gln Ser Trp Asp Ser Ser Ala Xaa Phe Xaa Xaa
1               5                   10

<210> SEQ ID NO 458
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa can be A or Y
<220> FEATURE:
<221> NAME/KEY: MISC_FEATURE
<222> LOCATION: (13)..(13)
<223> OTHER INFORMATION: Xaa can be N, H or S

<400> SEQUENCE: 458

Ser Gly Ser Ser Ser Asn Ile Gly Asn Asn Xaa Val Xaa
1               5                   10

<210> SEQ ID NO 459
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa can be A or Y
<220> FEATURE:
<221> NAME/KEY: MISC_FEATURE
<222> LOCATION: (14)..(14)
<223> OTHER INFORMATION: Xaa can be N, H or S

<400> SEQUENCE: 459

Ser Gly Ser Ser Ser Asn Ile Ile Gly Asn Asn Xaa Val Xaa
1               5                   10

<210> SEQ ID NO 460
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be K, N or Q

<400> SEQUENCE: 460

Gly Asn Asn Xaa Gln Arg Pro Ser
1               5

<210> SEQ ID NO 461
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or S

<400> SEQUENCE: 461

Ala Ala Trp Asp Asp Ser Leu Xaa Gly

<210> SEQ ID NO 462
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa can be A or V
<220> FEATURE:
<221> NAME/KEY: MISC_FEATURE
<222> LOCATION: (8)..(8)
<223> OTHER INFORMATION: Xaa can be K or S

<400> SEQUENCE: 462

Cys Ser Gly Asp Xaa Leu Gly Xaa Lys Tyr Ala His
1               5                   10

<210> SEQ ID NO 463
<211> LENGTH: 7
<212> TYPE: PRT
<213> ORGANISM: Artificial Sequence
<220> FEATURE:
<223> OTHER INFORMATION: Synthetic Construct

<400> SEQUENCE: 463

Lys Asp Ser Glu Arg Pro Ser
1               5

<210> SEQ ID NO 464
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N, D, T or A

<400> SEQUENCE: 464

Gln Ser Trp Asp Ser Ser Gly Xaa
1               5

<210> SEQ ID NO 465
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N, D, T or A

<400> SEQUENCE: 465

Gln Ser Trp Asp Ser Ser Gly Xaa His
1               5

<210> SEQ ID NO 466
<211> LENGTH: 17
<212> TYPE: PRT
<213> ORGANISM: Artificial Sequence
<220> FEATURE:
<223> OTHER INFORMATION: Synthetic Construct

<400> SEQUENCE: 466

```
Arg Ala Ser Gln Ser Leu Leu His Ser Asp Gly Ile Ser Ser Tyr Leu
1               5                   10                  15

Ala

<210> SEQ ID NO 467
<211> LENGTH: 11
<212> TYPE: PRT
<213> ORGANISM: Artificial Sequence
<220> FEATURE:
<223> OTHER INFORMATION: Synthetic Construct

<400> SEQUENCE: 467

Arg Ala Ser Gln Gly Ile Ser Ser Tyr Leu Ala
1               5                   10

<210> SEQ ID NO 468
<211> LENGTH: 7
<212> TYPE: PRT
<213> ORGANISM: Artificial Sequence
<220> FEATURE:
<223> OTHER INFORMATION: Synthetic Construct

<400> SEQUENCE: 468

Ala Ala Ser Ser Arg Ala Ser
1               5

<210> SEQ ID NO 469
<211> LENGTH: 7
<212> TYPE: PRT
<213> ORGANISM: Artificial Sequence
<220> FEATURE:
<223> OTHER INFORMATION: Synthetic Construct

<400> SEQUENCE: 469

Gln Gln Tyr Asn Ser Tyr Pro
1               5

<210> SEQ ID NO 470
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or S

<400> SEQUENCE: 470

Arg Ala Ser Gln Gly Ile Ser Xaa Tyr Leu Ala
1               5                   10

<210> SEQ ID NO 471
<211> LENGTH: 7
<212> TYPE: PRT
<213> ORGANISM: Artificial Sequence
<220> FEATURE:
<223> OTHER INFORMATION: Synthetic Construct

<400> SEQUENCE: 471

Ala Ala Ser Ser Leu Gln Ser
1               5

<210> SEQ ID NO 472
<211> LENGTH: 7
<212> TYPE: PRT
```

```
<213> ORGANISM: Artificial Sequence
<220> FEATURE:
<223> OTHER INFORMATION: Synthetic Construct

<400> SEQUENCE: 472

Gln Gln Tyr Asn Ser Tyr Pro
1               5

<210> SEQ ID NO 473
<211> LENGTH: 16
<212> TYPE: PRT
<213> ORGANISM: Artificial Sequence
<220> FEATURE:
<223> OTHER INFORMATION: Synthetic Construct

<400> SEQUENCE: 473

Arg Ser Ser Gln Ser Leu Leu His Ser Asp Gly Asn Thr Tyr Leu Asp
1               5                   10                  15

<210> SEQ ID NO 474
<211> LENGTH: 17
<212> TYPE: PRT
<213> ORGANISM: Artificial Sequence
<220> FEATURE:
<223> OTHER INFORMATION: Synthetic Construct

<400> SEQUENCE: 474

Arg Ser Ser Gln Ser Leu Leu His Ser Asp Asp Gly Asn Thr Tyr Leu
1               5                   10                  15

Asp

<210> SEQ ID NO 475
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be K or T
<220> FEATURE:
<221> NAME/KEY: MISC_FEATURE
<222> LOCATION: (2)..(2)
<223> OTHER INFORMATION: Xaa can be V or I
<220> FEATURE:
<221> NAME/KEY: MISC_FEATURE
<222> LOCATION: (6)..(6)
<223> OTHER INFORMATION: Xaa can be A or F

<400> SEQUENCE: 475

Xaa Xaa Ser Asn Arg Xaa Ser
1               5

<210> SEQ ID NO 476
<211> LENGTH: 7
<212> TYPE: PRT
<213> ORGANISM: Artificial Sequence
<220> FEATURE:
<223> OTHER INFORMATION: Synthetic Construct

<400> SEQUENCE: 476

Met Gln Ala Thr Gln Phe Pro
1               5

<210> SEQ ID NO 477
<211> LENGTH: 12
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be S or V
<220> FEATURE:
<221> NAME/KEY: MISC_FEATURE
<222> LOCATION: (7)..(7)
<223> OTHER INFORMATION: Xaa can be S or V

<400> SEQUENCE: 477

Arg Ala Ser Gln Ser Xaa Xaa Ser Ser Tyr Leu Ala
1               5                   10

<210> SEQ ID NO 478
<211> LENGTH: 7
<212> TYPE: PRT
<213> ORGANISM: Artificial Sequence
<220> FEATURE:
<223> OTHER INFORMATION: Synthetic Construct

<400> SEQUENCE: 478

Gly Ala Ser Thr Arg Ala Thr
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa can be S, N G or H

<400> SEQUENCE: 479

Gln Gln Tyr Xaa Asn Trp Pro
1               5

<210> SEQ ID NO 480
<211> LENGTH: 10
<212> TYPE: PRT
<213> ORGANISM: Artificial Sequence
<220> FEATURE:
<223> OTHER INFORMATION: Synthetic Construct

<400> SEQUENCE: 480

Gly Phe Thr Phe Ser Ser Tyr Trp Met Ser
1               5                   10

<210> SEQ ID NO 481
<211> LENGTH: 18
<212> TYPE: PRT
<213> ORGANISM: Artificial Sequence
<220> FEATURE:
<223> OTHER INFORMATION: Synthetic Construct

<400> SEQUENCE: 481

Ala Asn Ile Lys Gln Asp Gly Ser Glu Lys Tyr Tyr Val Asp Ser Val
1               5                   10                  15

Lys Gly

<210> SEQ ID NO 482
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 482

Gly Phe Thr Phe Ser Ser Tyr Ala Met Ser
1               5                   10

<210> SEQ ID NO 483
<211> LENGTH: 17
<212> TYPE: PRT
<213> ORGANISM: Artificial Sequence
<220> FEATURE:
<223> OTHER INFORMATION: Synthetic Construct

<400> SEQUENCE: 483

Ala Ile Ser Gly Ser Gly Gly Ser Thr Tyr Tyr Ala Asp Ser Val Lys
1               5                   10                  15

Gly

<210> SEQ ID NO 484
<211> LENGTH: 10
<212> TYPE: PRT
<213> ORGANISM: Artificial Sequence
<220> FEATURE:
<223> OTHER INFORMATION: Synthetic Construct

<400> SEQUENCE: 484

Gly Gly Ser Ile Ser Ser Tyr Tyr Trp Ser
1               5                   10

<210> SEQ ID NO 485
<211> LENGTH: 17
<212> TYPE: PRT
<213> ORGANISM: Artificial Sequence
<220> FEATURE:
<223> OTHER INFORMATION: Synthetic Construct

<400> SEQUENCE: 485

Gly Tyr Ile Tyr Tyr Ser Gly Ser Thr Asn Tyr Asn Pro Ser Leu Lys
1               5                   10                  15

Ser

<210> SEQ ID NO 486
<211> LENGTH: 10
<212> TYPE: PRT
<213> ORGANISM: Artificial Sequence
<220> FEATURE:
<223> OTHER INFORMATION: Synthetic Construct

<400> SEQUENCE: 486

Gly Tyr Thr Phe Thr Gly Tyr Tyr Met His
1               5                   10

<210> SEQ ID NO 487
<211> LENGTH: 18
<212> TYPE: PRT
<213> ORGANISM: Artificial Sequence
<220> FEATURE:
<223> OTHER INFORMATION: Synthetic Construct

<400> SEQUENCE: 487

Gly Trp Ile Asn Pro Asn Ser Gly Gly Thr Asn Tyr Ala Gln Lys Phe
1               5                   10                  15

Gln Gly
```

<210> SEQ ID NO 488
<211> LENGTH: 10
<212> TYPE: PRT
<213> ORGANISM: Artificial Sequence
<220> FEATURE:
<223> OTHER INFORMATION: Synthetic Construct

<400> SEQUENCE: 488

Gly Gly Thr Phe Ser Ser Tyr Ala Ile Ser
1               5                   10

<210> SEQ ID NO 489
<211> LENGTH: 18
<212> TYPE: PRT
<213> ORGANISM: Artificial Sequence
<220> FEATURE:
<223> OTHER INFORMATION: Synthetic Construct

<400> SEQUENCE: 489

Gly Gly Ile Ile Pro Ile Phe Gly Thr Ala Asn Tyr Ala Gln Lys Phe
1               5                   10                  15

Gln Gly

<210> SEQ ID NO 490
<211> LENGTH: 10
<212> TYPE: PRT
<213> ORGANISM: Artificial Sequence
<220> FEATURE:
<223> OTHER INFORMATION: Synthetic Construct

<400> SEQUENCE: 490

Gly Tyr Thr Gly Thr Ser Tyr Tyr Met His
1               5                   10

<210> SEQ ID NO 491
<211> LENGTH: 18
<212> TYPE: PRT
<213> ORGANISM: Artificial Sequence
<220> FEATURE:
<223> OTHER INFORMATION: Synthetic Construct

<400> SEQUENCE: 491

Gly Ile Ile Asn Pro Ser Gly Gly Ser Thr Ser Tyr Ala Gln Lys Phe
1               5                   10                  15

Gln Gly

<210> SEQ ID NO 492
<211> LENGTH: 10
<212> TYPE: PRT
<213> ORGANISM: Artificial Sequence
<220> FEATURE:
<223> OTHER INFORMATION: Synthetic Construct

<400> SEQUENCE: 492

Gly Phe Thr Phe Ser Ser Tyr Gly Met His
1               5                   10

<210> SEQ ID NO 493
<211> LENGTH: 18
<212> TYPE: PRT
<213> ORGANISM: Artificial Sequence
<220> FEATURE:
<223> OTHER INFORMATION: Synthetic Construct

<400> SEQUENCE: 493

```
Ala Val Ile Ser Tyr Asp Gly Ser Asn Lys Tyr Tyr Ala Asp Ser Val
1               5                   10                  15

Lys Gly

<210> SEQ ID NO 494
<211> LENGTH: 10
<212> TYPE: PRT
<213> ORGANISM: Artificial Sequence
<220> FEATURE:
<223> OTHER INFORMATION: Synthetic Construct

<400> SEQUENCE: 494

Gly Phe Thr Phe Ser Ser Tyr Ser Met Asn
1               5                   10

<210> SEQ ID NO 495
<211> LENGTH: 18
<212> TYPE: PRT
<213> ORGANISM: Artificial Sequence
<220> FEATURE:
<223> OTHER INFORMATION: Synthetic Construct

<400> SEQUENCE: 495

Ser Tyr Ile Ser Ser Ser Ser Thr Ile Tyr Tyr Ala Asp Ser Val
1               5                   10                  15

Lys Gly

<210> SEQ ID NO 496
<211> LENGTH: 10
<212> TYPE: PRT
<213> ORGANISM: Artificial Sequence
<220> FEATURE:
<223> OTHER INFORMATION: Synthetic Construct

<400> SEQUENCE: 496

Gly Phe Thr Phe Ser Asn Ala Trp Met Ser
1               5                   10

<210> SEQ ID NO 497
<211> LENGTH: 20
<212> TYPE: PRT
<213> ORGANISM: Artificial Sequence
<220> FEATURE:
<223> OTHER INFORMATION: Synthetic Construct

<400> SEQUENCE: 497

Gly Arg Ile Lys Ser Lys Thr Asp Gly Gly Thr Thr Asp Tyr Ala Ala
1               5                   10                  15

Pro Val Lys Gly
            20

<210> SEQ ID NO 498
<211> LENGTH: 12
<212> TYPE: PRT
<213> ORGANISM: Artificial Sequence
<220> FEATURE:
<223> OTHER INFORMATION: Synthetic Construct

<400> SEQUENCE: 498

Gly Gly Ser Ile Ser Ser Ser Ser Tyr Tyr Trp Gly
1               5                   10

<210> SEQ ID NO 499
<211> LENGTH: 17
```

```
<212> TYPE: PRT
<213> ORGANISM: Artificial Sequence
<220> FEATURE:
<223> OTHER INFORMATION: Synthetic Construct

<400> SEQUENCE: 499

Gly Ser Ile Tyr Tyr Ser Gly Ser Thr Tyr Tyr Asn Pro Ser Leu Lys
1               5                   10                  15

Ser

<210> SEQ ID NO 500
<211> LENGTH: 12
<212> TYPE: PRT
<213> ORGANISM: Artificial Sequence
<220> FEATURE:
<223> OTHER INFORMATION: Synthetic Construct

<400> SEQUENCE: 500

Gly Gly Ser Ile Ser Ser Gly Asp Tyr Tyr Trp Ser
1               5                   10

<210> SEQ ID NO 501
<211> LENGTH: 17
<212> TYPE: PRT
<213> ORGANISM: Artificial Sequence
<220> FEATURE:
<223> OTHER INFORMATION: Synthetic Construct

<400> SEQUENCE: 501

Gly Tyr Ile Tyr Tyr Ser Gly Ser Thr Tyr Tyr Asn Pro Ser Leu Lys
1               5                   10                  15

Ser

<210> SEQ ID NO 502
<211> LENGTH: 10
<212> TYPE: PRT
<213> ORGANISM: Artificial Sequence
<220> FEATURE:
<223> OTHER INFORMATION: Synthetic Construct

<400> SEQUENCE: 502

Gly Tyr Ser Phe Thr Ser Tyr Trp Ile Gly
1               5                   10

<210> SEQ ID NO 503
<211> LENGTH: 18
<212> TYPE: PRT
<213> ORGANISM: Artificial Sequence
<220> FEATURE:
<223> OTHER INFORMATION: Synthetic Construct

<400> SEQUENCE: 503

Gly Ile Ile Tyr Pro Gly Asp Ser Asp Thr Arg Tyr Ser Pro Ser Phe
1               5                   10                  15

Gln Gly

<210> SEQ ID NO 504
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be H or S
```

```
<400> SEQUENCE: 504

Gly Phe Thr Phe Ser Ser Tyr Ala Met Xaa
1               5                   10

<210> SEQ ID NO 505
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be H or S

<400> SEQUENCE: 505

Gly Phe Thr Phe Ser Ser Tyr Ala Met Xaa Trp Ser
1               5                   10

<210> SEQ ID NO 506
<211> LENGTH: 18
<212> TYPE: PRT
<213> ORGANISM: Artificial Sequence
<220> FEATURE:
<223> OTHER INFORMATION: Synthetic Construct

<400> SEQUENCE: 506

Gly Trp Ile Ser Pro Asn Gly Gly Ser Thr Tyr Tyr Ala Asp Ser Val
1               5                   10                  15

Lys Gly

<210> SEQ ID NO 507
<211> LENGTH: 20
<212> TYPE: PRT
<213> ORGANISM: Artificial Sequence
<220> FEATURE:
<223> OTHER INFORMATION: Synthetic Construct

<400> SEQUENCE: 507

Gly Trp Ile Ser Pro Lys Ala Asn Gly Gly Ser Thr Tyr Tyr Ala Asp
1               5                   10                  15

Ser Val Lys Gly
            20

<210> SEQ ID NO 508
<211> LENGTH: 10
<212> TYPE: PRT
<213> ORGANISM: Artificial Sequence
<220> FEATURE:
<223> OTHER INFORMATION: Synthetic Construct

<400> SEQUENCE: 508

Gly Phe Thr Phe Ser Ser Tyr Ala Met Ser
1               5                   10

<210> SEQ ID NO 509
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be G or S
```

<400> SEQUENCE: 509

Ser Val Ile Ser Ser Asp Gly Xaa Ser Thr Tyr Tyr Ala Asp Ser Val
1               5                   10                  15

Lys Gly

<210> SEQ ID NO 510
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be G or S

<400> SEQUENCE: 510

Ser Val Ile Ser Ser Lys Ala Asp Gly Xaa Ser Thr Tyr Tyr Ala Asp
1               5                   10                  15

Ser Val Lys Gly
            20

<210> SEQ ID NO 511
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa can be S, G or H

<400> SEQUENCE: 511

Gly Tyr Ser Phe Thr Ser Tyr Trp Ile Xaa
1               5                   10

<210> SEQ ID NO 512
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa can be R, I or S

<400> SEQUENCE: 512

Gly Xaa Ile Tyr Pro Gly Asp Ser Asp Thr Arg Tyr Ser Pro Ser Phe
1               5                   10                  15

Gln Gly

<210> SEQ ID NO 513
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be A or Y
<220> FEATURE:
<221> NAME/KEY: MISC_FEATURE
<222> LOCATION: (9)..(9)
<223> OTHER INFORMATION: Xaa can be I or M

<400> SEQUENCE: 513

Gly Tyr Thr Phe Thr Ser Tyr Xaa Xaa His
1               5                   10

<210> SEQ ID NO 514
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa can be G or Y

<400> SEQUENCE: 514

Gly Trp Ile Asn Pro Xaa Asn Gly Asn Thr Asn Tyr Ala Gln Lys Phe
1               5                   10                  15

Gln

<210> SEQ ID NO 515
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa can be N or Y

<400> SEQUENCE: 515

Gly Gly Ser Ile Ser Ser Gly Xaa Tyr Tyr Trp Ser
1               5                   10

<210> SEQ ID NO 516
<211> LENGTH: 17
<212> TYPE: PRT
<213> ORGANISM: Artificial Sequence
<220> FEATURE:
<223> OTHER INFORMATION: Synthetic Construct

<400> SEQUENCE: 516

Gly Tyr Ile Tyr Tyr Ser Gly Ser Thr Tyr Tyr Asn Pro Ser Leu Lys
1               5                   10                  15

Ser

<210> SEQ ID NO 517
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa can be S or D
<220> FEATURE:
<221> NAME/KEY: MISC_FEATURE
<222> LOCATION: (6)..(6)
<223> OTHER INFORMATION: Xaa can be I or V
<220> FEATURE:
<221> NAME/KEY: MISC_FEATURE
<222> LOCATION: (7)..(7)
<223> OTHER INFORMATION: Xaa can be S or G
<220> FEATURE:
<221> NAME/KEY: MISC_FEATURE
<222> LOCATION: (8)..(8)
<223> OTHER INFORMATION: Xaa can be S or I

```
<220> FEATURE:
<221> NAME/KEY: MISC_FEATURE
<222> LOCATION: (10)..(10)
<223> OTHER INFORMATION: Xaa can be L or V

<400> SEQUENCE: 517

Arg Ala Ser Gln Xaa Xaa Xaa Xaa Tyr Xaa Asn
1               5                   10

<210> SEQ ID NO 518
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa can be Q or R
<220> FEATURE:
<221> NAME/KEY: MISC_FEATURE
<222> LOCATION: (2)..(2)
<223> OTHER INFORMATION: Xaa can be G or A
<220> FEATURE:
<221> NAME/KEY: MISC_FEATURE
<222> LOCATION: (3)..(3)
<223> OTHER INFORMATION: Xaa can be D or S
<220> FEATURE:
<221> NAME/KEY: MISC_FEATURE
<222> LOCATION: (4)..(4)
<223> OTHER INFORMATION: Xaa can be S or Q
<220> FEATURE:
<221> NAME/KEY: MISC_FEATURE
<222> LOCATION: (5)..(5)
<223> OTHER INFORMATION: Xaa can be L or D
<220> FEATURE:
<221> NAME/KEY: MISC_FEATURE
<222> LOCATION: (6)..(6)
<223> OTHER INFORMATION: Xaa can be R or V
<220> FEATURE:
<221> NAME/KEY: MISC_FEATURE
<222> LOCATION: (7)..(7)
<223> OTHER INFORMATION: Xaa can be S or G
<220> FEATURE:
<221> NAME/KEY: MISC_FEATURE
<222> LOCATION: (8)..(8)
<223> OTHER INFORMATION: Xaa can be Y or I
<220> FEATURE:
<221> NAME/KEY: MISC_FEATURE
<222> LOCATION: (10)..(10)
<223> OTHER INFORMATION: Xaa can be A or V
<220> FEATURE:
<221> NAME/KEY: MISC_FEATURE
<222> LOCATION: (11)..(11)
<223> OTHER INFORMATION: Xaa can be S or N

<400> SEQUENCE: 518

Xaa Xaa Xaa Xaa Xaa Xaa Xaa Xaa Tyr Xaa Xaa
1               5                   10
```

HUMANIZED ANTIBODIES

CROSS-REFERENCE TO RELATED APPLICATIONS

This application claims the benefit of U.S. provisional application No. 62/162,905, filed May 18, 2016, which is incorporated by reference in its entirety for all purposes.

REFERENCE TO SEQUENCE LISTING

This application contains a Sequence Listing which has been submitted electronically in ASCII format and is hereby incorporated by reference in its entirety. Said ASCII copy, created on May 16, 2016, is named PC72222A_Seq_Listing_ST25.txt and is 367,747 bytes in size.

FIELD OF THE INVENTION

This invention relates to antibody humanization by introducing human germ-line residues in complementarity determining regions (CDRs).

BACKGROUND OF THE INVENTION

Monoclonal antibodies can rapidly be produced by the mouse immune system for biological studies. In a clinical setting, however, the use of these murine antibodies can result in a human anti-mouse antibody response (HAMA). Chimeric antibodies can reduce anti-IgG responses in human, but murine v-domains may still have provocative T-cell epitope content, necessitating "humanization" of their framework regions.

Classical humanization generally begins by transferring all six murine complementarity determining regions (CDRs) onto a human antibody framework (Jones et al., Nature 321, 522-525 (1986)). These CDR-grafted antibodies generally do not retain their original affinity for antigen binding, and in fact, affinity is often severely impaired. Besides the CDRs, certain non-human framework residues must also be incorporated into the variable domains to maintain proper CDR conformation (Chothia et al., Nature 342:877 (1989)). The incorporation of murine residues at key positions in the human frameworks to restore function is generally referred to as "back-mutations." Back-mutations can support structural conformation of the grafted CDRs and restore antigen binding and affinity. Many of the framework positions that are likely to affect affinity have been identified, thus structural modeling to select new residues in a stepwise fashion can generally lead to variants with restored antigen binding. Alternatively, phage antibody libraries targeted at these residues can also be used to enhance and speed up the affinity maturation process (Wu et al., J. Mol. Biol. 294: 151-162 (1999) and Wu, H., Methods in Mol. Biol. 207: 197-212 (2003)).

Current humanization techniques still suffer from flaws, such as high non-human amino acid content retention; grafting into poorly understood frameworks; requirement for homology modeling of the v-domains, which is often inaccurate; or a co-crystal structure with the target antigen. Therefore, there is a need to develop new humanization methods.

SUMMARY OF THE INVENTION

Disclosed herein are "ultra" humanized antibodies in which human germline residues are introduced to the complementarity determining regions (CDRs) of a non-human donor antibody. Also described herein are libraries and methods for screening for humanized antibodies.

Those skilled in the art will recognize, or be able to ascertain using no more than routine experimentation, many equivalents to the specific embodiments of the invention described herein. Such equivalents are intended to be encompassed by the following embodiments (E).

E1. A method of generating a library comprising a plurality of polypeptides, for selection of a humanized antibody that binds to a target antigen, comprising:
- (a) obtaining the sequence a non-human donor antibody that binds to said target antigen, and determining the donor CDR-L1, CDR-L2, CDR-L3, CDR-H1, and CDR-H2 sequences of said non-human antibody;
- (b) obtaining the sequences of a human germline VL and a human germline VH, and determining the germline framework and germline CDR-L1, CDR-L2, CDR-L3, CDR-H1, and CDR-H2 sequences of said human VL and VH;
- (c) aligning each of the non-human donor CDR-L1, CDR-L2, and CDR-L3 sequences with the corresponding germline CDR sequence from said human VL, and each of the non-human CDR-H1 and CDR-H2 sequences with corresponding germline CDR sequence from said human VH;
- (d) identifying positions in CDR-L1, CDR-L2, CDR-L3, CDR-H1, and CDR-H2 where human germline residue is the same as, or different from, the corresponding non-human donor residue;
- (e) generating a library of polypeptides, each polypeptide comprising an antibody variable domain, wherein said antibody variable domain comprises (1) a VH domain comprising: the framework sequence of the human germline VH from step (b), and CDR-H1, CDR-H2, and CDR-H3; and (2) a VL domain comprising: the framework sequence of the human germline VL from step (b), and CDR-L1, CDR-L2, and CDR-L3; wherein:
  - (i) for each individual position within CDR-L1, CDR-L2, CDR-L3, CDR-H1 and CDR-H2:
    if the human germline residue at said position is the same as the corresponding non-human donor residue, all polypeptides in the library comprise the human germline residue at said position;
    if the human germline residue at the position is different from the corresponding non-human donor residue, a portion of the polypeptides in the library comprise the human germline residue at said position, the remainder of the polypeptides comprise the corresponding non-human donor residue at said position;
  - (ii) for each individual position within CDR-H3, the residue is any one of the 20 natural amino acid residues;
  - (iii) less than 1% of the polypeptides in said library comprise the original non-human donor CDR-L1, CDR-L2, CDR-L3, CDR-H1, and CDR-H2 sequences; and
  - (iv) less than 1% of the polypeptides in said library comprise the original human VL germline CDR-L1, CDR-L2, and CDR-L3, and the original human VH germline CDR-H1 and CDR-H2 sequences.

E2. The method of embodiment 1, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 5% to about 95%, the remainder comprising the corresponding non-human donor residue at said position.

E3. The method of embodiment 1 or 2, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 10% to about 90%, the remainder comprising the corresponding non-human donor residue at said position.

E4. The method of any one of embodiments 1-3, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 15% to about 85%, the remainder comprising the corresponding non-human donor residue at said position.

E5. The method of any one of embodiments 1-4, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 20% to about 80%, the remainder comprising the corresponding non-human donor residue at said position.

E6. The method of any one of embodiments 1-5, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 25% to about 75%, the remainder comprising the corresponding non-human donor residue at said position.

E7. The method of any one of embodiments 1-6, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 30% to about 70%, the remainder comprising the corresponding non-human donor residue at said position.

E8. The method of any one of embodiments 1-7, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 35% to about 65%, the remainder comprising the corresponding non-human donor residue at said position.

E9. The method of any one of embodiments 1-8, wherein for each individual position within CDR-L1, CDR-L2, CDR-L3, CDR-H1, and CDR-H2, if the human germline residue and non-human donor residue are different according to step (d), the percentage of polypeptides comprising the human germline residue at said position is from about 40% to about 60%, the remainder comprising the corresponding non-human donor residue at said position.

E10. The method of any one of embodiments 1-9, wherein for each individual position within CDR-H3, each of the 20 natural amino acid residues is represented by at least about 0.1% of the polypeptides in the library.

E11. The method of any one of embodiments 1-10, wherein for each individual position within CDR-H3, each of the 20 natural amino acid residues is represented by at least about 1% of the polypeptides in the library.

E12. The method of any one of embodiments 1-11, wherein for each individual position within CDR-H3, each of the 20 natural amino acid residues is represented by at least about 2% of the polypeptides in the library.

E13. The method of any one of embodiments 1-12, wherein for each individual position within CDR-H3, each of the 20 natural amino acid residues is represented by from about 2% to about 8% of the polypeptides in the library.

E14. A method of humanizing a non-human donor antibody, wherein said non-human donor antibody binds to a target antigen, comprising:
(a) obtaining the sequence said non-human donor antibody, and determining the donor CDR-L1, CDR-L2, CDR-L3, CDR-H1, CDR-H2, and CDR-H3 sequences;
(b) obtaining the sequences of a human germline VL and a human germline VH, and determining the germline framework and germline CDR-L1, CDR-L2, CDR-L3, CDR-H1, and CDR-H2 sequences of said human VL and VH;
(c) aligning each of the non-human donor CDR-L1, CDR-L2, and CDR-L3 sequences with the corresponding germline CDR sequence from said human VL, and each of the non-human CDR-H1 and CDR-H2 sequences with corresponding germline CDR sequence from said human VH;
(d) identifying positions in CDR-L1, CDR-L2, CDR-L3, CDR-H1, and CDR-H2 where human germline residue is or different from the corresponding non-human donor residue;
(e) obtaining a humanized antibody by:
(i) grafting said non-human donor CDR-L1, CDR-L2, and CDR-L3 into said human VL germline framework, and said non-human donor CDR-H1, CDR-H2, CDR-H3 into said human VH germline framework; and
(ii) further introducing a mutation in at least one, but not all, of the positions identified in (d), wherein said mutation comprises replacing a non-human donor residue with the corresponding human germline residue;
(iii) introducing at least one random mutation in CDR-H3, wherein said mutation comprises replacing a non-human donor residue with a different amino acid residue;
(f) assessing the binding affinity of the humanized antibody obtained in (e) to the target antigen.

E15. The method of embodiment 14, comprising introducing mutations in at least three, but not all, of the positions identified in (d), wherein said mutations comprise replacing a non-human donor residue with the corresponding human germline residue.

E16. The method of embodiment 14 or 15, comprising introducing mutations in at least five, but not all, of the positions identified in (d), wherein said mutations comprise replacing a non-human donor residue with the corresponding human germline residue.

E17. The method of any one of embodiments 14-16, comprising introducing two or more random mutations in CDR-H3, wherein said mutations comprise replacing a non-human donor residue with a different amino acid residue.

E18. The method of any one of embodiments 1-17, wherein said human germline VH framework sequence comprises a VH3 framework sequence.

E19. The method of any one of embodiments 1-17, wherein said human germline VH framework sequence comprises a VH1 framework sequence.

E20. The method of any one of embodiments 1-17, wherein said human germline VH framework sequence comprises a VH5 framework sequence.

E21. The method of any one of embodiments 1-17, wherein said human germline VH framework sequence comprises the VH framework sequence of any one of the human germline sequences listed in Table 2.

E22. The method of any one of embodiments 1-17 and 21, wherein said human germline VH framework sequence comprises the VH framework sequence of human germline IGHV3-23 or IGHV1-69.

E23. The method of any one of embodiments 1-17 and 21, wherein said human germline VH framework sequence comprises the VH framework sequence of human germline IGHV3-7.

E24. The method of any one of embodiments 1-17, wherein said human germline VH framework sequence comprises a VH germline consensus framework sequence.

E25. The method of embodiment 24, wherein said human germline VH framework sequence comprises the VH framework sequence of any one of the consensus sequences listed in Table 5.

E26. The method of any one of embodiments 1-25, wherein said human germline VL framework sequence comprises a $V_K$ framework sequence.

E27. The method of any one of embodiments 1-26, wherein said human germline VL framework sequence comprises the VL framework sequence of any one of the human germline sequences listed in Table 3.

E28. The method of any one of embodiments 1-25 wherein said human germline VL framework sequence comprises a $V_\lambda$ framework sequence.

E29. The method of any one of embodiments 1-25 and 28, wherein said human germline VL framework sequence comprises the VL framework sequence of any one of the human germline sequences listed in Table 4.

E30. The method of any one of embodiments 1-25, wherein said human germline VL framework sequence comprises the VL framework sequence of human germline IGKV3-20.

E31. The method of any one of embodiments 1-25, wherein said human germline VL framework sequence comprises the VL framework sequence of human germline IGKV1-39.

E32. The method of any one of embodiments 1-25, wherein said human germline VL framework sequence comprises a VL germline consensus framework sequence.

E33. The method of any one of embodiments 1-25 and 32, wherein said human germline VL framework sequence comprises the VL framework sequence of any one of consensus sequences listed in Table 6.

E34. The method of any one of embodiments 1-33, wherein said non-human donor antibody is a non-human mammalian antibody.

E35. The method of any one of embodiments 1-34, wherein said non-human donor antibody is a murine antibody, a rat antibody, or a rabbit antibody.

E36. The method of any one of embodiments 1-35, wherein said non-human donor antibody is a murine antibody.

E37. The method of any one of embodiments 34-36, wherein said human germline VL framework comprises no more than 3 back-mutations or random mutations.

E38. The method of any one of embodiments 34-37, wherein said human germline VH framework comprises no more than 3 back-mutations or random mutations.

E39. The method of any one of embodiments 34-38, wherein said human germline VL framework and VH framework together comprise no more than 3 back-mutations or random mutations.

E40. The method of any one of embodiments 34-39, wherein at least one back-mutation or random mutation is located between heavy chain residues H71 to H80.

E41. The method of any one of embodiments 34-39, wherein said human germline VH framework and human germline VH framework do not comprise a back-mutation.

E42. The method of any one of embodiments 1-33, wherein said non-human donor antibody is an avian antibody.

E43. The method of embodiment 42, wherein said human germline VL framework comprises no more than 5 back-mutations or random mutations.

E44. The method of embodiment 42 or 43, wherein said human germline VH framework comprises no more than 5 back-mutations or random mutations.

E45. The method of any one of embodiments 42-44, wherein said human germline VL framework and VH framework together comprise no more than 5 back-mutations or random mutations.

E46. The method of any one of embodiments 42-45, wherein at least one back-mutation or random mutation is located between heavy chain residues H71 to H80.

E47. The method of any one of embodiments 42-45, wherein said human germline VL framework comprises a single back-mutation.

E48. The method of any one of embodiments 42-46, wherein said human germline VH framework comprises a single back-mutation.

E49. The method of any one of embodiments 42-47, wherein said non-human donor antibody is a chicken antibody.

E50. The method of any one of embodiments 42-45 and 47-49, wherein said human germline VL framework comprises a back-mutation at position 46 (such as Leu46Thr (L46T)).

E51. The method of any one of embodiments 1-13 and 18-50, wherein said library is a phage display library.

E52. The method of any one of embodiments 1-51, further comprising: obtaining the sequence of a human germline VH by: (i) aligning the framework sequence of said non-human donor antibody VH against a plurality of human germline VH framework sequences; and (ii) selecting a human germline VH framework that has the highest sequence identity according to step (i).

E53. The method of any one of embodiments 1-52, further comprising: obtaining the sequence of a human germline VL by: (i) aligning the framework sequence of said non-human donor antibody VL against a plurality of human germline VL framework sequences; and (ii) selecting a human germline VL framework that has the highest sequence identity according to step (i).

E54. A library for humanizing a non-human donor antibody that binds to a target antigen, wherein:
  (a) said library comprises a plurality of polypeptides, each polypeptide comprising an antibody variable domain;
  (b) said antibody variable domain comprises (i) a VH domain comprising: a human germline VH framework sequence, and CDR-H1, CDR-H2, and CDR-H3; and (ii) a VL domain comprising: a human germline VL framework sequence, and CDR-L1, CDR-L2, and CDR-L3;
  (c) for each individual position within said CDR-L1, CDR-L2, CDR-L3, CDR-H1, and CDR-H2,
    if the human germline residue at said position is the same as the corresponding non-human donor residue, all polypeptides in the library comprise the human germline residue at said position;

if the human germline residue at the position is different from the corresponding non-human donor residue, a portion of the polypeptides in the library comprise the human germline residue at said position, the remainder of the polypeptides comprise the corresponding non-human donor residue at said position;

(d) for each individual position within CDR-H3, the residue is any one of the natural amino acid residues;

(e) less than 1% of the polypeptides in said library comprise the original non-human donor CDR-L1, CDR-L2, CDR-L3, CDR-H1, and CDR-H2 sequences; and (f) less than 1% of the polypeptides in said library comprise the original human VL germline CDR-L1, CDR-L2, and CDR-L3, and the original human VH germline CDR-H1 and CDR-H2 sequences.

E55. The library of embodiment 54, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 5% to about 95%, the remainder comprising the corresponding non-human donor residue at said position.

E56. The library of embodiment 54 or 55, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 10% to about 90%, the remainder comprising the corresponding non-human donor residue at said position.

E57. The library of any one of embodiments 54-56, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 15% to about 85%, the remainder comprising the corresponding non-human donor residue at said position.

E58. The library of any one of embodiments 54-57, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 20% to about 80%, the remainder comprising the corresponding non-human donor residue at said position.

E59. The library of any one of embodiments 54-58, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 25% to about 75%, the remainder comprising the corresponding non-human donor residue at said position.

E60. The library of any one of embodiments 54-59, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 30% to about 70%, the remainder comprising the corresponding non-human donor residue at said position.

E61. The library of any one of embodiments 54-60, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 35% to about 65%, the remainder comprising the corresponding non-human donor residue at said position.

E62. The library of any one of embodiments 54-61, wherein for each individual position within CDR-L1, CDR-L2, CDR-L3, CDR-H1, and CDR-H2, if the human germline residue and non-human donor residue are different at said position, the percentage of polypeptides comprising the human germline residue at said position is from about 40% to about 60%, the remainder comprising the corresponding non-human donor residue at said position.

E63. The library of any one of embodiments 54-62, wherein for each individual position within CDR-H3, each of the 20 natural amino acid residues is represented by at least about 0.1% of the polypeptides in the library.

E64. The library of any one of embodiments 54-63, wherein for each individual position within CDR-H3, each of the 20 natural amino acid residues is represented by at least about 1% of the polypeptides in the library.

E65. The library of any one of embodiments 54-64, wherein for each individual position within CDR-H3, each of the 20 natural amino acid residues is represented by at least about 2% of the polypeptides in the library.

E66. The library of any one of embodiments 54-65, wherein for each individual position within CDR-H3, each of the 20 natural amino acid residues is represented by from about 2% to about 8% of the polypeptides in the library.

E67. The library of any one of embodiments 54-66, wherein said human germline VH framework sequence comprises a VH3 framework sequence.

E68. The library of any one of embodiments 54-66, wherein said human germline VH framework sequence comprises a VH1 framework sequence.

E69. The library of any one of embodiments 54-66, wherein said human germline VH framework sequence comprises a VH5 framework sequence.

E70. The library of any one of embodiments 54-66, wherein said human germline VH framework sequence comprises the VH framework sequence of any one of the human germline sequences listed in Table 2.

E71. The library of any one of embodiments 54-66 and 70, wherein said human germline VH framework sequence comprises the VH framework sequence of human germline IGHV3-23 or IGHV1-69.

E72. The library of any one of embodiments 54-66 and 70, wherein said human germline VH framework sequence comprises the VH framework sequence of human germline IGHV3-7.

E73. The library of any one of embodiments 54-66, wherein said human germline VH framework sequence comprises a VH germline consensus framework sequence.

E74. The library of embodiment 73, wherein said human germline VH framework sequence comprises the VH framework sequence of any one of the consensus sequences listed in Table 5.

E75. The library of any one of embodiments 54-74, wherein said human germline VL framework sequence comprises a $V_K$ framework sequence.

E76. The library of any one of embodiments 54-75, wherein said human germline VL framework sequence comprises the VL framework sequence of any one of the human germline sequences listed in Table 3.

E77. The library of any one of embodiments 54-74, wherein said human germline VL framework sequence comprises a $V_\lambda$ framework sequence.

E78. The library of any one of embodiments 54-74 and 77, wherein said human germline VL framework sequence comprises the VL framework sequence of any one of the human germline sequences listed in Table 4.

E79. The library of any one of embodiments 54-74, wherein said human germline VL framework sequence comprises the VL framework sequence of human germline IGKV3-20.

E80. The library of any one of embodiments 54-74, wherein said human germline VL framework sequence comprises the VL framework sequence of human germline IGKV1-39.

E81. The library of any one of embodiments 54-74, wherein said human germline VL framework sequence comprises a VL germline consensus framework sequence.

E82. The library of any one of embodiments 54-74 and 81, wherein said human germline VL framework sequence comprises the VL framework sequence of any one of consensus sequences listed in Table 6.

E83. The library of any one of embodiments 54-82, wherein said non-human donor antibody is a non-human mammalian antibody.

E84. The library of any one of embodiments 54-83, wherein said non-human donor antibody is a murine antibody, a rat antibody, or a rabbit antibody.

E85. The library of any one of embodiments 54-84, wherein said non-human donor antibody is a murine antibody.

E86. The library of any one of embodiments 83-85, wherein said human germline VL framework comprises no more than 3 back-mutations or random mutations.

E87. The library of any one of embodiments 83-86, wherein said human germline VH framework comprises no more than 3 back-mutations or random mutations.

E88. The library of any one of embodiments 83-87, wherein said human germline VL framework and VH framework together comprise no more than 3 back-mutations or random mutations.

E89. The library of any one of embodiments 83-88, wherein at least one back-mutation or random mutation is located between heavy chain residues H71 to H80.

E90. The library of any one of embodiments 83-88, wherein said human germline VH framework and human germline VH framework do not comprise a back-mutation.

E91. The library of any one of embodiments 54-82, wherein said non-human donor antibody is an avian antibody.

E92. The library of embodiment 91, wherein said human germline VL framework comprises no more than 5 back-mutations or random mutations.

E93. The library of embodiment 91 or 92, wherein said human germline VH framework comprises no more than 5 back-mutations or random mutations.

E94. The library of any one of embodiments 91-93, wherein said human germline VL framework and VH framework together comprise no more than 5 back-mutations or random mutations.

E95. The library of any one of embodiments 91-94, wherein at least one back-mutation or random mutation is located between heavy chain residues H71 to H80.

E96. The library of any one of embodiments 91-95, wherein said human germline VL framework comprises a single back-mutation.

E97. The library of any one of embodiments 91-96, wherein said human germline VH framework comprises a single back-mutation.

E98. The library of any one of embodiments 91-97, wherein said non-human donor antibody is a chicken antibody.

E99. The library of any one of embodiments 91-94 and 96-98, wherein said human germline VL framework comprises a back-mutation at position 46 (such as Leu46Thr (L46T).

E100. The library of any one of embodiments 54-99, wherein said library is a phage display library.

E101. A plurality of nucleic acid molecules encoding the library of any one of embodiments 54-100.

E102. The plurality of nucleic acid molecules of embodiment 101, wherein said nucleic acid molecules are phagemid vectors.

E103. A plurality of host cells comprising the nucleic acid molecules of embodiment 101 or 102.

E104. A method of identifying an antibody variable domain sequence that binds to a target antigen, comprising:
(a) obtaining the library of any one of embodiments 54-100;
(b) selecting a polypeptide that binds to said target antigen, with an affinity (Kd) value of $5 \times 10^{-5}$ M or less, and
(c) obtaining the sequence of the antibody variable domain of the polypeptide selected in step (b).

E105. The method of embodiment 104, wherein said an antibody variable domain binds to said target antigen with a binding affinity (Kd) value that is equal or less than that of said non-human donor antibody.

E106. The method of embodiment 104 or 105, further comprising producing a nucleic acid vector encoding a polypeptide comprising the antibody variable domain selected from step (c).

E107. The method of embodiment 106, further comprising introducing said vector into a host cell.

E108. The method of embodiment 106 or 107, wherein said vector is an expression vector.

E109. The method of embodiment 107 or 108, further comprising culturing said host cell in a medium under a suitable condition, such that said polypeptide is expressed.

E110. The method of embodiment 109, further comprising harvesting said polypeptide from the medium.

E111. The method of embodiment 110, further comprising purifying said polypeptide.

E112. A humanized antibody or antigen-binding fragment thereof that binds to a target antigen, wherein:
(a) said antibody or antigen-binding fragment thereof comprises (i) a VH domain comprising: a human germline VH framework sequence, and CDR-H1, CDR-H2, and CDR-H3; and (ii) a VL domain comprising: a human germline VL framework sequence, and CDR-L1, CDR-L2, and CDR-L3;
(b) said CDR-L1, CDR-L2, CDR-L3, CDR-H1, and CDR-H2 are derived from corresponding CDRs from a non-human donor antibody that binds to said target antigen;
(c) for each position within said CDR-L1, CDR-L2, CDR-L3, CDR-H1, and CDR-H2, the residue is either human germline residue from said human germline VL or VH, or corresponding residue from said non-human donor antibody;
(d) said CDR-L1, CDR-L2, CDR-L3, CDR-H1, and CDR-H2 each comprises at least one more human germline residue as compared to the corresponding non-human donor CDR,
(e) said CDR-L1, CDR-L2, CDR-L3, CDR-H1, and CDR-H2 each comprises at least one more non-human donor residue as compared to the corresponding human germline VH or VL CDR; and (f) for each position within CDR-H3, the residue is any one of the 20 natural amino acid residues.

E113. The antibody or antigen-binding fragment of embodiment 112, wherein said antibody or antigen-binding fragment binds to said target antigen with a binding affinity (Kd) value of $5\times10^{-5}$ M or less.

E114. The antibody or antigen-binding fragment of embodiment 112 or 113, wherein said antibody or antigen-binding fragment binds said target antigen with a binding affinity (Kd) value that is equal or less than the binding affinity (Kd) value of said non-human donor antibody.

E115. The antibody or antigen-binding fragment of any one of embodiments 112-114, wherein said human germline VH framework sequence comprises a VH3 framework sequence.

E116. The antibody or antigen-binding fragment of any one of embodiments 112-114, wherein said human germline VH framework sequence comprises a VH1 framework sequence.

E117. The antibody or antigen-binding fragment of any one of embodiments 112-114, wherein said human germline VH framework sequence comprises a VH5 framework sequence.

E118. The antibody or antigen-binding fragment of any one of embodiments 112-114, wherein said human germline VH framework sequence comprises the VH framework sequence of any one of the human germline sequences listed in Table 2.

E119. The antibody or antigen-binding fragment of any one of embodiments 112-114 and 118, wherein said human germline VH framework sequence comprises the VH framework sequence of human germline IGHV3-23 or IGHV1-69.

E120. The antibody or antigen-binding fragment of any one of embodiments 112-114 and 118, wherein said human germline VH framework sequence comprises the VH framework sequence of human germline IGHV3-7.

E121. The antibody or antigen-binding fragment thereof of any one of embodiments 112-114, wherein said human germline VH framework sequence comprises a VH germ line consensus framework sequence.

E122. The antibody or antigen-binding fragment thereof of embodiment 121, wherein said human germline VH framework sequence comprises the VH framework sequence of any one of the consensus sequences listed in Table 5.

E123. The antibody or antigen-binding fragment thereof of any one of embodiments 112-122, wherein said human germline VL framework sequence comprises a $V_K$-framework sequence.

E124. The antibody or antigen-binding fragment thereof of any one of embodiments 112-123, wherein said human germline VL framework sequence comprises the VL framework sequence of any one of the human germline sequences listed in Table 3.

E125. The antibody or antigen-binding fragment thereof of any one of embodiments 112-122 wherein said human germline VL framework sequence comprises a $V_\lambda$ framework sequence.

E126. The antibody or antigen-binding fragment thereof of any one of embodiments 112-122 and 125, wherein said human germline VL framework sequence comprises the VL framework sequence of any one of the human germline sequences listed in Table 4.

E127. The antibody or antigen-binding fragment thereof of any one of embodiments 112-122, wherein said human germline VL framework sequence comprises the VL framework sequence of human germline IGKV3-20.

E128. The antibody or antigen-binding fragment thereof of any one of embodiments 112-122, wherein said human germline VL framework sequence comprises the VL framework sequence of human germline IGKV1-39.

E129. The antibody or antigen-binding fragment thereof of any one of embodiments 112-122, wherein said human germline VL framework sequence comprises a VL germline consensus framework sequence.

E130. The antibody or antigen-binding fragment thereof of any one of embodiments 112-122 and 129, wherein said human germline VL framework sequence comprises the VL framework sequence of any one of consensus sequences listed in Table 6.

E131. The antibody or antigen-binding fragment thereof of any one of embodiments 112-130, wherein said non-human donor antibody is a non-human mammalian antibody.

E132. The antibody or antigen-binding fragment thereof of any one of embodiments 112-131, wherein said non-human donor antibody is a murine antibody, a rat antibody, or a rabbit antibody.

E133. The antibody or antigen-binding fragment thereof of any one of embodiments 112-132, wherein said non-human donor antibody is a murine antibody.

E134. The antibody or antigen-binding fragment thereof of any one of embodiments 112-133, wherein said human germline VL framework comprises no more than 3 back-mutations or random mutations.

E135. The antibody or antigen-binding fragment thereof of any one of embodiments 131-134, wherein said human germline VH framework comprises no more than 3 back-mutations or random mutations.

E136. The antibody or antigen-binding fragment thereof of any one of embodiments 131-135, wherein said human germline VL framework and VH framework together comprise no more than 3 back-mutations or random mutations.

E137. The antibody or antigen-binding fragment thereof of any one of embodiments 131-136, wherein at least one back-mutation or random mutation is located between heavy chain residues H71 to H80.

E138. The antibody or antigen-binding fragment thereof of any one of embodiments 131-136, wherein said human germline VH framework and human germline VH framework do not comprise a back-mutation.

E139. The antibody or antigen-binding fragment thereof of any one of embodiments 112-130, wherein said non-human donor antibody is an avian antibody.

E140. The antibody or antigen-binding fragment thereof of embodiment 139, wherein said human germline VL framework comprises no more than 5 back-mutations or random mutations.

E141. The antibody or antigen-binding fragment thereof of embodiment 139 or 140, wherein said human germline VH framework comprises no more than 5 back-mutations or random mutations.

E142. The antibody or antigen-binding fragment thereof of any one of embodiments 139-141, wherein said human germline VL framework and VH framework together comprise no more than 5 back-mutations or random mutations.

E143. The antibody or antigen-binding fragment thereof of any one of embodiments 139-142, wherein at least one back-mutation or random mutation is located between heavy chain residues H71 to H80.

E144. The antibody or antigen-binding fragment thereof of any one of embodiments 139-143, wherein said human germline VL framework comprises a single back-mutation.

E145. The antibody or antigen-binding fragment thereof of any one of embodiments 139-144, wherein said human germline VH framework comprises a single back-mutation.

E146. The antibody or antigen-binding fragment thereof of any one of embodiments 139-145, wherein said non-human donor antibody is a chicken antibody.

E147. The antibody or antigen-binding fragment thereof of any one of embodiments 139-142 and 144-146, wherein said human germline VL framework comprises a back-mutation at light chain position 46 (such as Leu46Thr (L46T)).

E148. The antibody or antigen-binding fragment of any one of embodiments 112-147, wherein position 24 of CDR-L1 comprises the corresponding human germline residue from said human VL germline.

E149. The antibody or antigen-binding fragment of any one of embodiments 112-148, wherein position 25 of CDR-L1 comprises the corresponding human germline residue from said human VL germline.

E150. The antibody or antigen-binding fragment of any one of embodiments 112-149, wherein position 26 of CDR-L1 comprises the corresponding human germline residue from said human VL germline.

E151. The antibody or antigen-binding fragment of any one of embodiments 112-150, wherein position 27 of CDR-L1 comprises the corresponding human germline residue from said human VL germline.

E152. The antibody or antigen-binding fragment of any one of embodiment 148-151, wherein said human germline VL is a VK germline.

E153. The antibody or antigen-binding fragment of any one of embodiments 112-152, wherein position 60 of CDR-H2 comprises the corresponding human germline residue from said human VH germline.

E154. The antibody or antigen-binding fragment of any one of embodiments 112-153, wherein position 61 of CDR-H2 comprises the corresponding human germline residue from said human VH germline.

E155. The antibody or antigen-binding fragment of any one of embodiments 112-154, wherein position 62 of CDR-H2 comprises the corresponding human germline residue from said human VH germline.

E156. The antibody or antigen-binding fragment of any one of embodiments 112-155, wherein position 63 of CDR-H2 comprises the corresponding human germline residue from said human VH germline.

E157. The antibody or antigen-binding fragment of any one of embodiments 112-156, wherein position 64 of CDR-H2 comprises the corresponding human germline residue from said human VH germline.

E158. The antibody or antigen-binding fragment of any one of embodiments 112-157, wherein position 65 of CDR-H2 comprises the corresponding human germline residue from said human VH germline.

E159. The antibody or antigen-binding fragment of any one of embodiment 153-158, wherein said human germline VH is a VH3 germline.

E160. The antibody or antigen-binding fragment of any one of embodiment 153-158, wherein said human germline VH is a VH1 germline.

E161. The antibody or antigen-binding fragment of any one of embodiment 153-158, wherein said human germline VH is a VH5 germline.

E162. The antibody or antigen-binding fragment of any one of embodiment 153-158, wherein said human germline VH is a VH4 germline.

E163. A nucleic acid molecule encoding the antibody or antigen-binding fragment thereof of any one of embodiments 112-162.

E164. A host cell comprising the nucleic acid molecule of embodiment 163.

E165. The host cell of embodiment 164, wherein said host cell is a CHO cell, a HEK cell, or an Sp2.0 cell.

E166. A method of making an antibody or antigen-binding fragment thereof, comprising culturing the host cell of embodiment 163 or 164 under a condition wherein said antibody or antigen-binding fragment is expressed by said host cell.

E167. An antibody or antigen-binding fragment thereof obtained by the method of any one of embodiments 1-53, 104-111, and 166.

E168. An antibody or antigen-binding fragment thereof obtained using the library of any one of embodiments 54-100.

E169. A kit comprising the library of any one of embodiments 54-100.

BRIEF DESCRIPTION OF THE DRAWINGS

FIGS. 2A-2C show the results of biophysical analyses for ABS-derived clones. DSC analysis of IgG thermal stability for anti-RAGE (A), anti-pTau (B) and anti-A33 (C) antibodies. FIGS. 2D-2F show the results of forced IgG aggregation analysis for anti-RAGE (D), anti-pTau (E) and anti-A33 (F) antibodies.

FIGS. 8A-8D show the results of IgG specificity testing.

FIG. 10A: VH; FIG. 10B: VK; FIG. 10A: Vλ.

DETAILED DESCRIPTION OF THE INVENTION

1. Overview

As disclosed herein, conventional antibody humanization "grafts" non-human (e.g., murine) CDRs into a human framework sequence. It is generally believed that CDRs are crucial for antigen binding; therefore, the original non-human CDR sequences are maintained, and back-mutations are introduced into human framework region to restore binding affinity of the grafted CDRs. However, such humanization techniques still retain high contents of non-human amino acids. For example, one or more of the non-human residues in the CDRs may still be immunogenic in human.

Surprisingly, the inventors recognized that the six CDRs can also be mutated in ways that could not be predicted a priori. In fact, due to redundancy of amino acid usage in the antibody paratope, a significant number of CDR residues could be substituted, for example, with human germline residues to further increase the human amino acid content. For example, structural analyses illustrated that only subsets of CDR residues actually make contact with antigen. Remarkably, many CDR residues do not contact a target antigen directly; instead, these CDR residues form redundant paratope space that can be used to bind a second, unrelated antigen (Bostrom et al. Science 1610-4, 2009). This finding challenges the traditional paradigm that describes antibody-antigen interaction as a lock and key (which suggests that each antibody surface can only accommodate one antigen). If not all CDR residues are required for binding of a single antigen, then a small number of "redundant" paratope residues may be further mutated without significantly affecting binding affinities.

Accordingly, as disclosed and exemplified herein, the inventors discovered that "redundant" paratope residues in CDRs can be replaced with human germline residues to create "ultra" humanized antibodies.

For example, as shown in the examples, the inventors created several phage display libraries to screen for "ultra" humanized antibodies (with increased number of human residues in CDRs as compared to the conventional CDR grafting methods). Each library was based on a starting non-human donor antibody (rat anti-RAGE, rabbit anti-A33, and chicken anti-pTau). As illustrated in FIG. 1A, in each case, five non-human donor CDRs (CDR-L1, CDR-L2, CDR-L3, CDR-H1, and CDR-H2) were aligned with their corresponding CDRs from a human germline sequence. If a donor residue is the same as the corresponding human germline residue, that residue remained unchanged, and incorporated into all clones of the library. If a donor residue is different from the corresponding human germline residue, both residues were incorporated combinatorially into library clones.

Figure 1:
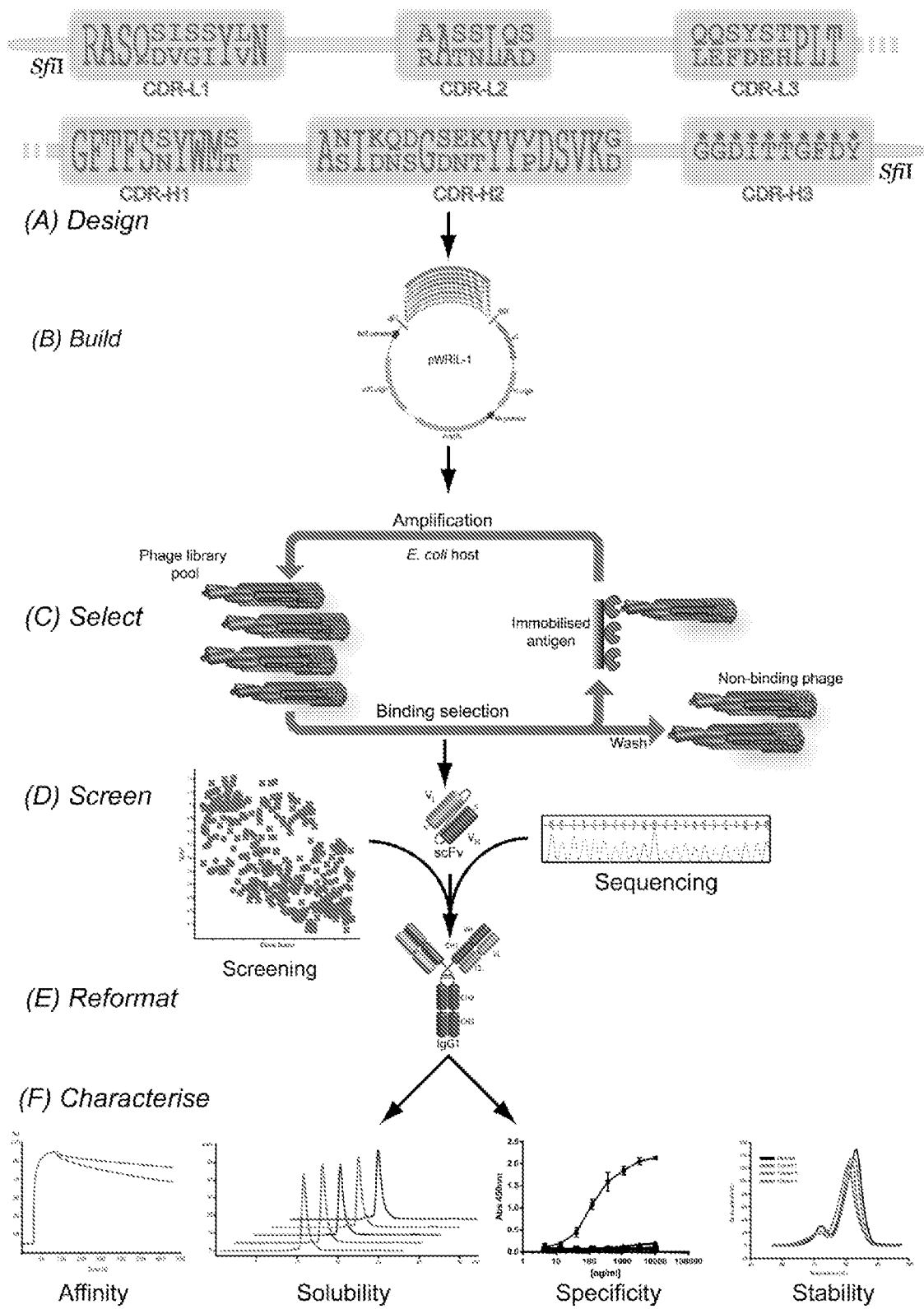
FIG. 1 is a schematic illustration of ABS library design, selection and screening principles. (A) Amino acid sequences are shown for the v-domains of Par-RAGE and destination germline (DPK9-DP54) scFvs in VL-VH format. At each position where the rat and human residues differed, both residues were encoded for in the ABS-RAGE library (human residue on top and rat residue at bottom). This principle was applied to all CDRs other than the CDR-H3, in a single combinatorial library. In the CDR-H3, point mutations were permitted at a frequency of 1±1 per clone. (B) Phage libraries were generated and (C) used in selections on cognate antigen. (D) Selection output clones were subsequently screened by ELISA, HTRF and DNA sequencing to identify hits with maintained target binding and epitope specificity. (E) Top clones were cloned as IgGs, expressed and purified, before (F) characterization of affinity by Biacore, solubility and aggregation analyses by SEC, in vitro specificity by ELISA and Biacore, and thermal stability analysis by DSC. Human and rat CDR-L1: SEQ ID NOs: 1 and 2, respectively; Human and rat CDR-L2: SEQ ID NOs: 3 and 4, respectively; Human and rat CDR-L3: SEQ ID NOs: 5 and 6, respectively; Human and rat CDR-H1: SEQ ID NOs: 7 and 8, respectively; Human and rat CDR-H2: SEQ ID NOs: 9 and 10, respectively; rat CDR-H3: SEQ ID NO: 11.

For example, as shown in FIG. 1, the alignment of the CDR-L1 of rat anti-RAGE antibody and human germline DPK9 is as follows:

TABLE 10

|  | Position | | | | | | | | | |
| --- | --- | --- | --- | --- | --- | --- | --- | --- | --- | --- |
|  | 24 | 25 | 26 | 27 | 28 | 29 | 30 | 31 | 32 | 33 | 34 |
| Human Germline DPK9 SEQ ID NO: 1 | R | A | S | Q | S | I | S | S | Y | L | N |
| Rat anti-RAGE antibody SEQ ID NO: 2 | R | A | S | Q | D | V | G | I | Y | V | N |

For positions 24, 25, 26, 27, 32, and 34 (in bold), the human residue and the corresponding rat residue are the same, therefore, all library clones incorporate the same residue (e.g., "R" at position 24) at the designated position. In certain embodiments, it may be preferable to use human germline codon to encode this residue. For positions 28, 29, 30, 31, and 33, the human residue and the corresponding rat residue are different. Therefore, only a portion of the library clones comprise the human germline residue (e.g., 60% of the library clones comprise the human residue "S" at position 28), the remainder of the library clones comprise the corresponding rat residue (e.g., 40% of the library clones comprise the rat residue D at position "28") at the designated position.

In certain embodiments, it may be desirable that for each position, about 50% of the clones have the human germline residue, and about 50% of the clones have the non-human donor residue; so that both residues are substantially equally represented in the library. However, as disclosed and exemplified herein, 50%:50% (human:non-human) distribution is not necessary. The libraries of the invention not only tolerate significant variations in human:non-human distribution, but in some circumstances, unequal distribution may be desired (e.g., to improve stability).

For CDR-H3, each position can be any one of the 20 natural amino acid residues. In certain embodiments, it may be desirable that for each position, each of the 20 natural amino acid residues are substantially equally represented in the library. Again, substantially equal distribution of the 20 natural amino acid residues is not necessary. For example, in some circumstances, the presence of certain residues may be reduced or avoided (e.g., residues that might cause stability problems).

This design principle is named "Augmented Binary Substitution" (ABS). "Binary" means that either human germline residue or non-human donor residue is used in CDR L1-L3 and H1-H2 to increase the human content of the antibody; and "augmented" refers to additional mutations introduced in CDR-H3 to further optimize the activities of the antibody.

Because both human and non-human residues are incorporated into the library clones combinatorially, it is theoretically possible that a very small number of library clones have only human germline residues in CDR-L1, CDR-L2, CDR-L3, CDR-H1 and CDR-H2 ("all human" clones). That is, each time the human and non-human donor residues differ, the human residue is incorporated, resulting in a clone that comprises the original human germline CDR-L1, CDR-L2, CDR-L3, CDR-H1 and CDR-H2 sequences. Conversely, it is also theoretically possible that a very small number of library clones have only non-human donor residues in CDR-L1, CDR-L2, CDR-L3, CDR-H1 and CDR-H2 ("all donor" clones). That is, each time human and non-human donor residues differ, the non-human donor residue is incorporated, resulting in a clone that comprises the original non-human donor CDR-L1, CDR-L2, CDR-L3, CDR-H1 and CDR-H2 sequences.

In general, all human and all donor clones should be less than 1%. Assuming that, for each antibody, there are at least seven positions (CDR-L1, CDR-L2, CDR-L3, CDR-H1 and CDR-H2 combined) where human and non-human donor residues differ, the number of "all human" library clones should be less than 1% (at least $1 \times 2^7$, or 128 individual clones; 1 out of 128 is less than 1 percent). Similarly, the number of "all non-human" library clones should be less than 1% as well. Accordingly, more than 99% of the clones in the library should comprise at least one more human germline residue in CDR-L1, CDR-L2, CDR-L3, CDR-H1 and CDR-H2 combined as compared to the original donor CDR donor sequences; and more than 99% of the clones in the library should comprise at least one non-human donor residue in CDR-L1, CDR-L2, CDR-L3, CDR-H1 and CDR-H2 combined, as compared to the original human germline CDR sequences.

In the CDR-H3, the library may or may not need to be "Augmented" by the addition of point mutations or random mutations. "Augmentation" may encourage the "fit" for this loop either into the human v-domains or in binding to target.

Based on ABS design principle, CDR repertoires (FIG. 1) were built into human germline frameworks (DP54 and DPK9 in the Examples), then screened to identify lead clones with epitope specificity and affinity equivalent to the parental clone. This proved to be a convenient and rapid method which retains the functionally-required CDR residues of the original non-human donor antibody, without the need for prior crystal-structure insight. Notably, this CDR redundancy-minimization approach generated highly stable and soluble human IgGs, from multiple key antibody discovery species. The resulting antibodies have significantly reduced non-human residue content, such as t-cell epitope content (which is a major risk factor for antibody immunogenicity in human) and reduced non-human germline surface amino acid exposure, which may lead to reduced B-cell epitope content.

2. Definitions

An antibody "variable domain" refers to the variable region of the antibody light chain (VL) or the variable region of the antibody heavy chain (VH), either alone or in combination. As known in the art, the variable regions of the heavy and light chains each consist of four framework regions (FR) connected by three complementarity determining regions (CDRs), and contribute to the formation of the antigen binding site of antibodies.

Residues in a variable domain are numbered according Kabat, which is a numbering system used for heavy chain variable domains or light chain variable domains of the compilation of antibodies. See, Kabat et al., Sequences of Proteins of Immunological Interest, 5th Ed. Public Health Service, National Institutes of Health, Bethesda, Md. (1991)). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

Various algorithms for assigning Kabat numbering are available. The algorithm implemented in the 2012 release of Abysis (www.abysis.org) is used herein to assign Kabat numbering to variable regions unless otherwise noted.

The term "Complementarity Determining Regions" (CDRs) are defined as follows (numbering according to Kabat; H: heavy chain; L: light chain):

CDR-HI: H26-H35B; CDR-H2: H49-H65; CDR-H3: H95-H102

CDR-LI: L24-L34; CDR-L2: L50-L56; CDR-L3: L89-L97

The boundaries of the CDRs defined herein are not identical to the CDRs originally defined by Kabat (1991), and the definition of instant disclosure controls.

"Framework" (FR) residues are antibody variable domain residues other than the CDR residues. A VH or VL domain framework comprises four framework sub-regions, FR1, FR2, FR3 and FR4, interspersed with CDRs in the following structure: FR1-CDR1-FR2-CDR2-FR3-CDR3-FR4. According to the definition provided herein, FR residues include the following (number according to Kabat; H: heavy chain; L: light chain):

TABLE 11

|  | FR1 | FR2 | FR3 | FR4 |
|---|---|---|---|---|
| Heavy Chain | H1-H25 | H36-H48 | H66-H94 | H103-H113 |
| Light Chain | L1-L23 | L35-L49 | L57-L88 | L98-L107 |

An "antigen-binding fragment" of an antibody refers to a fragment of a full-length antibody that retains the ability to specifically bind to an antigen (preferably with substantially the same binding affinity). Examples of an antigen-binding fragment includes (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR), disulfide-linked Fvs (dsFv), and anti-idiotypic (anti-Id) antibodies and intrabodies. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see e.g., Bird et. al. Science 242:423-426 (1988) and Huston et al. Proc. Natl. Acad. Sci. USA 85:5879-5883 (1988)). Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. Proc. Natl. Acad. Sci. USA 90:6444-6448 (1993); Poljak et al., 1994, Structure 2:1121-1123).

A "human antibody" is an antibody comprising an amino acid sequence that is derived from a human germline, such as an antibody expressed by a human B cell, or an antibody expressed by a transgenic animal that comprises a nucleic acid sequence encoding a human immunoglobulin. Also included herein is an antibody that comprises a consensus human antibody sequence. For example, the framework sequence of a human antibody can be a specific human germline framework sequence (e.g., Tables 2-4), or a consensus human germline framework sequence (e.g., Tables 5-6). This definition of a human antibody specifically excludes a humanized antibody comprising non-human CDR sequences.

A "non-human donor antibody" includes any antibody that is not a "human antibody" defined herein. A non-human donor antibody can be an antibody comprising an amino acid sequence that corresponds to an immunoglobulin produced by non-human species. The CDR residues (and a selected number of framework residues) of a non-human antibody can be used as "donor" residues during humanization process. Also included herein is a CDR-grafted antibody in which CDR sequences from a non-human species (such as murine) are grafted into a human framework. One aspect of the invention is to further humanize CDR-grafted, humanized antibody, by introducing additional human germline residues in the CDR region. Therefore, a CDR-grafted, humanized antibody can also serve as a "non-human donor" antibody.

"Corresponding" CDR or FR residues from different antibodies can be identified according to sequence alignment or structural alignment that is known in the art. For example, "corresponding" CDR or FR residues from different antibodies can be identified by alignment according to Kabat numbering, or any other numbering systems that are known in the art, such as AHo, IMGT, Chothia, or AbM. "Corresponding" CDR or FR residues share the same numbers under such a numbering system. Alternatively, alignments can be done by hand or by using well-known sequence alignment programs such as ClustalW2, or "BLAST 2 Sequences" using default parameters. For example, NCBI "IgBLAST" is specifically for antibodies.

In addition to sequence alignment, structural alignment may also be used to identify "corresponding" CDR or FR residues. Structural alignments use information about the secondary and tertiary structure to aid in aligning the sequences. These methods are used for two or more sequences and typically produce local alignments; however, because they depend on the availability of structural information, they can only be used for sequences whose corresponding structures are known (usually through X-ray crystallography or NMR spectroscopy). Sometimes, structural alignments can be more reliable between sequences that are very distantly related and that have diverged so extensively that sequence comparison cannot reliably detect their similarity. Where there is no available structural data on one of the proteins, a comparison can still be made if structural data is available on one or preferably more closely related proteins, such as immunoglobulins across species, and in particular antibody constant domains across species and subtype. A commonly used algorithm for structural alignments is TM-ALIGN (Zhang and Skolnick, Nucleic Acids Research, 33: 2302-2309 (2005)), which assigns increased weight to the most similar regions of the structure during superposition.

In certain embodiments, one or more "back-mutations" may be used during CDR grafting. A back-mutation refers to a mutation in antibody variable domain framework region where a human germline residue is replaced with the corresponding non-human donor residue to increase the antigen binding affinity of a humanized antibody. A "random mutation" refers to the substitution of an amino acid residue with a different amino acid residue.

Specific amino acid residue positions are also numbered according to Kabat. For example, for human VK1 germline IGKV1-39 used in the examples, "Leu46" (or L46) refers to position 46 according to Kabat numbering (which is a Leu). However, the "Leu46" (or L46) designation includes any residue from another antibody (e.g., an antibody from another human or non-human antibody) that corresponds to Leu46 of human VK1 germline IGKV1-39 (even though the actual position of that residue may or may not be 46, and the actual residue may or may not be Leu). For example, for human VK1D germline IGKV1D-16, position 46 (Kabat numbering) is Ser, and VK1D germline IGKV1 D-17, position 46 (Kabat numbering) is His. Therefore, for simplicity, Leu46 (or L46) is used to refer a residue that aligns with Leu46 of IGKV1-39, even if it is a Ser or His. Similarly, mutations are also identified according to Kabat numbering. For example, Leu46Thr (or "L46T") means that a residue from an antibody that corresponds to Leu46 of human germline IGKV1-39 (which may or may not be Leu) is mutated to Thr.

The binding affinity of an antibody can be expressed as Kd value, which refers to the dissociation rate of a particular antigen-antibody interaction. Kd is the ratio of the rate of dissociation, also called the "off-rate (koff)", to the association rate, or "on-rate (kon)". Thus, Kd equals koff/kon and is expressed as a molar concentration (M), and the smaller the Kd, the stronger the affinity of binding. Kd values for antibodies can be determined using methods well established in the art. One exemplary method for measuring Kd is surface plasmon resonance (SPR), typically using a biosensor system such as a BIACORE® system. BIAcore kinetic analysis comprises analyzing the binding and dissociation of an antigen from chips with immobilized molecules (e.g. molecules comprising epitope binding domains), on their surface. Another method for determining the Kd of an antibody is by using Bio-Layer Interferometry, typically using OCTET® technology (Octet QKe system, ForteBio). For example, a standard assay condition for surface plasmon resonance can be based on ligand immobilization of approximately 100 Response Units (RU) of IgG on the SPR chip. Purified target proteins are diluted in buffer to a range of final concentrations and injected at a requisite flow rate (e.g. 10-100 µl/min) to allow the calculation of $K_a$. Dissociation is allowed to proceed to establish off-rate ($K_d$), followed by a 5 sec pulse of 20 mM NaOH for regeneration of the chip surface. Sensorgrams are then analyzed using a kinetics evaluation software package.

The term "about", as used here, refers to +/−10% of a value.

3. Humanized Antibodies and Antibody Libraries

Provided herein are libraries for humanizing a non-human donor antibody that binds to a target antigen, wherein: (a) said library comprises a plurality of polypeptides, each polypeptide comprising an antibody variable domain; (b) said antibody variable domain comprises (i) a VH domain comprising: a human germline VH framework sequence, and CDR-H1, CDR-H2, and CDR-H3; and (ii) a VL domain comprising: a human germline VL framework sequence, and CDR-L1, CDR-L2, and CDR-L3; (c) for each individual position within said CDR-L1, CDR-L2, CDR-L3, CDR-H1, and CDR-H2: if the human germline residue at said position is the same as the corresponding non-human donor residue, all polypeptides in the library comprise the human germline residue at said position; if the human germline residue at the position is different from the corresponding non-human donor residue, a portion of the polypeptides in the library comprise the human germline residue at said position, the remainder of the polypeptides comprise the corresponding non-human donor residue at said position; (d) for each individual position within CDR-H3, the residue is any one of the 20 natural amino acid residues. In addition, less than 1% of the polypeptides in said library comprise the original non-human donor CDR-L1, CDR-L2, CDR-L3, CDR-H1, and CDR-H2 sequences; and less than 1% of the polypeptides in said library comprise the original human VL germline CDR-L1, CDR-L2, and CDR-L3, and the original human VH germline CDR-H1 and CDR-H2 sequences.

The libraries disclosed herein can be used to screen for "ultra" humanized antibodies, in particular antibodies where human germline residues are incorporated into non-human donor CDRs. Accordingly, also provided herein is humanized antibody or antigen-binding fragment thereof that binds to a target antigen, wherein: (a) said antibody or antigen-binding fragment thereof comprises (i) a VH domain comprising: a human germline VH framework sequence, and CDR-H1, CDR-H2, and CDR-H3; and (ii) a VL domain comprising: a human germline VL framework sequence, and CDR-L1, CDR-L2, and CDR-L3; (b) said CDR-L1, CDR-L2, CDR-L3, CDR-H1, and CDR-H2 are derived from corresponding CDRs from a non-human donor antibody that binds to said target antigen; (c) for each position within said CDR-L1, CDR-L2, CDR-L3, CDR-H1, and CDR-H2, the residue is either human germline residue from said human germline VL or VH, or corresponding residue from said non-human donor antibody; (d) said CDR-L1, CDR-L2, CDR-L3, CDR-H1, and CDR-H2 each comprises at least one more human germline residue as compared to the corresponding non-human donor CDR, (e) said CDR-L1, CDR-L2, CDR-L3, CDR-H1, and CDR-H2 each comprises at least one more non-human donor residue as compared to the corresponding human germline VH or VL CDR; and (f) for each position within CDR-H3, the residue is any one of the 20 natural amino acid residues.

A. Non-human Donor Antibodies

Humanization generally starts with obtaining CDR sequences from a non-human donor antibody that binds to a target antigen, and incorporating non-human donor residues into a human framework.

Non-human donor antibody binds to a target antigen and can be obtained, e.g., by conventional techniques (such as hybridoma technology, recombinant DNA technology). For example, the target antigen may be isolated from a natural source, or may be produced recombinantly or by in vitro synthesis. Alternatively, cells comprising native or recombinant antigen can be used. The antigen can be administered to a suitable non-human host to induce production of antibodies. Monoclonal antibodies can then be obtained by, for example, hybridoma technology.

Multiple non-human donor antibodies can be screened to select an antibody that has strong binding affinity for the target antigen. For example, the non-human donor antibody may bind the antigen of interest with a binding affinity (Kd) value of about $1 \times 10^{-5}$ M or less, such as about $1 \times 10^{-5}$ M or less, about $1 \times 10^{-6}$ M or less, about $1 \times 10^{-7}$ M or less, about $1 \times 10^{-8}$ M or less, about $1 \times 10^{-9}$ M or less, about $1 \times 10^{-10}$ M or less, about $1 \times 10^{-11}$ M or less, about $1 \times 10^{-12}$ M or less, about $1 \times 10^{-13}$ M or less, from about $1 \times 10^{-5}$ M to about 1×10$^{-13}$ M, from about 1×10$^{-6}$ M to about 1×10$^{-13}$ M, from about 1×10$^{-7}$ M to about 1×10$^{-13}$ M, from about 1×10$^{-8}$ M to about 1×10$^{-13}$ M, from about 1×10$^{-9}$ M to about 1×10$^{-13}$ M, from about 1×10$^{-5}$ M to about 1×10$^{-12}$ M, from about 1×10$^{-6}$ M to about 1×10$^{-12}$ M, from about 1×10$^{-7}$ M to about 1×10$^{-12}$ M, from about 1×10$^{-8}$ M to about 1×10$^{-12}$ M, from about 1×10$^{-9}$ M to about 1×10$^{-12}$ M, from about 1×10$^{-5}$ M to about 1×10$^{11}$ M, from about 1×10$^{-6}$ M to about 1×10$^{11}$ M, from about 1×10$^{-7}$ M to about 1×10$^{11}$ M, from about 1×10$^{-8}$ M to about 1×10$^{11}$ M, or from about 1×10$^{-9}$ M to about 1×10$^{11}$ M. Generally, the antibody will bind antigen with an affinity in the nanomolar or better range.

The sequence of the non-human donor antibody can be determined using standard sequencing techniques, or obtained from a sequence database or other literature resources. If desired, polynucleotide sequence(s) encoding the antibody may then be cloned into a vector for expression or propagation.

The CDR and framework sequences of the non-human donor antibody can be readily ascertained using standard antibody numbering systems, such as Kabat numbering.

Examples of antigens include: HER2, CD20, TNF ALPHA, C5, C5a, CD30, Blys, CTLA-4, IL1B, PD-1, PDL-1, IL12, IL23, IL17a, VEGF, EGFR, IL-6R, CD11a, APLHA-4-INTEGRIN, IgE, CD52, CD33, CD25, RSV, *B. anthracis* protective antigen, CD3, IL33, P-CADHERIN, NOTCH1, EPHA4, 5T4, IL4, IL13, MADCAM, IL6, 41BB, OX-40, TFPI, CXCR4, and FGF21.

Additional examples of antigens include: PDGFRα, PDGFRβ, PDGF, VEGF, VEGF-A, VEGF-B, VEGF-C, VEGF-D, VEGF-E, VEGF-F, VEGFR1, VEGFR2, VEGFR3, FGF, FGF2, HGF, KDR, fit-1, FLK-1, Ang-2, Ang-1, PLGF, CEA, CXCL13, Baff, IL-21, CCL21, TNF-α, CXCL12, SDF-I, bFGF, MAC-I, IL23pl9, FPR, IGFBP4, CXCR3, TLR4, CXCR2, EphA2, EphA4, EphrinB2, EGFR (ErbB1), HER2(ErbB2 or p185neu), HER3(ErbB3), HER4 ErbB4 or tyro2), SCI, LRP5, LRP6, RAGE, s100A8, s100A9, Navl.7, GLPI, RSV, RSV F protein, Influenza HA protein, Influenza NA protein, HMGBI, CD16, CD19, CD20, CD21, CD28, CD32, CD32b, CD64, CD79, CD22, ICAM-I, FGFRI, FGFR2, HDGF, EphB4, GITR, β-amyloid, hMPV, PIV-I, PIV-2, OX40L, IGFBP3, cMet, PD-I, PLGF, Neprolysin, CTD, IL-18, IL-6, CXCL-13, IL-IRI, IL-15, IL-4R, IgE, PAI-I, NGF, EphA2, uPARt, DLL-4, αvβ5, αvβ6, α5β1, α3β1, interferon receptor type I and type II, CD 19, ICOS, IL-17, Factor II, Hsp90, IGF, IGF-I, IGF-II, CD 19, GM-CSFR, PIV-3, CMV, IL-13, IL-9, and EBV.

Additional examples of antigens include: Tumor Necrosis Factor-α ("TNF-α"), Tumor Necrosis Factor-β ("TNF-β"), Lymphotoxin-α ("LT-α"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-I (also referred to as BlyS, BAFF or THANK), DR4, DR5 (also known as Apo-2, TRAIL-R2, TR6, Tango-63, hAPO8, TRICK2, or KILLER), DR6, DcRI, DcR2, DcR3 (also known as TR6 or M68), CARI, HVEM (also known as ATAR or TR2), GITR, ZTNFR-5, NTR-I, TNFLI, CD30, LTBr, 4-1BB receptor and TR9.

Additional examples of antigens include: 5T4, ABL, ABCB5, ABCFI, ACVRI, ACVRIB, ACVR2, ACVR2B, ACVRLI, ADORA2A, Aggrecan, AGR2, AICDA, AIFI, AIGI, AKAPI, AKAP2, AMH, AMHR2, angiogenin (ANG), ANGPTI, ANGPT2, ANGPTL3, ANGPTL4, Annexin A2, ANPEP, APC, APOCI, AR, aromatase, ATX, AXI, AZGPI (zinc-a-glycoprotein), B7.1, B7.2, B7-H1, BAD, BAFF, BAGI, BAII, BCR, BCL2, BCL6, BDNF, BLNK, BLRI (MDR15), BlyS, BMP1, BMP2, BMP3B (GDFIO), BMP4, BMP6, BMP7, BMP8, BMP9, BMP11, BMP12, BMPR1A, BMPR1B, BMPR2, BPAGI (plectin), BRCAI, C19orflO (IL27w), C3, C4A, C5, C5R1, CANTI, CASPI, CASP4, CAVI, CCBP2 (D6/JAB61), CCLI (1-309), CCLI 1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22(MDC/STC-I), CCL23 (MPIF-I), CCL24 (MPIF-2/eotaxin-2), CCL25 (TECK), CCL26(eotaxin-3), CCL27 (CTACK/ILC), CCL28, CCL3 (MIP-Ia), CCL4 (MIP-Ib), CCL5(RANTES), CCL7 (MCP-3), CCL8 (mcp-2), CCNAI, CCNA2, CCNDI, CCNEI, CCNE2, CCRI (CKRI/HM145), CCR2 (mcp-IRB/RA),CCR3 (CKR3/CM-KBR3), CCR4, CCR5(CMKBR5/ChemR13), CCR6 (CM-KBR6/CKR-L3/STRL22/DRY6), CCR7 (CKR7/EBI1), CCR8 (CMKBR8/TERI/CKR-LI), CCR9 (GPR-9-6), CCRLI (VSHKI), CCRL2 (L-CCR),CD164, CD19, CDIC, CD20, CD200, CD-22, CD24, CD28, CD3, CD33, CD35, CD37, CD38, CD3E, CD3G, CD3Z, CD4, CD40, CD40L, CD44, CD45RB, CD46, CD52, CD69, CD72, CD74, CD79A, CD79B, CD8, CD80, CD81, CD83, CD86, CD105, CD137, CDHI (E-cadherin), CDCP1CDH10, CDH12, CDH13, CDH18,CDH19, CDH20, CDH5, CDH7, CDH8, CDH9, CDK2, CDK3, CDK4, CDK5, CDK6, CDK7, CDK9, CDKNIA (p21Wapl/CipI), CDKNIB (p27KipI), CDKNIC, CDKN2A (pl61INK4a), CDKN2B, CDKN2C, CDKN3, CEBPB, CERI, CHGA, CHGB, Chitinase, CHSTIO, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLRI, CMKORI (RDCI), CNRI, COLI 8AI, COL1A1.COL4A3, COL6A1, CR2, Cripto, CRP, CSFI (M-CSF), CSF2 (GM-CSF), CSF3 (GCSF), CTLA4, CTL8, CTNNBI (b-catenin), CTSB (cathepsin B), CX3CL1 (SCYDI), CX3CR1 (V28), CXCLI (GROI), CXCLIO (IP-IO), CXCLII (I-TAC/IP-9), CXCL12 (SDFI), CXCL13, CXCL 14,CXCL 16, CXCL2 (GR02), CXCL3 (GR03), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, Cyr61, CYSLTRI, c-Met, DAB21P, DES, DKFZp451J0118, DNCLI, DPP4, E2F1, ECGFI5EDGI, EFNAI, EFNA3, EFNB2, EGF, ELAC2, ENG, endoglin, ENOI, EN02, EN03, EPHAI, EPHA2, EPHA3, EPHA4, EPHA5, EPHA6, EPHA7, EPHA8, EPHA9, EPHAIO, EPHBI, EPHB2, EPHB3, EPHB4, EPHB5, EPHB6, EPHRIN-AI, EPHRIN-A2, EPHRIN-A3, EPHRIN-A4, EPHRIN-A5, EPHRIN-A6, EPHRIN-BI, EPHRIN-B2, EPHRTN-B3, EPHB4,EPG, ERBB2 (Her-2), EREG, ERK8, Estrogen receptor, ESRI, ESR2, F3 (TF), FADD, farnesyltransferase, FasL, FASNf, FCER1A,FCER2, FCGR3A, FGF, FGFI (aFGF), FGFIO, FGFI 1, FGF12, FGF12B, FGF13, FGF14, FGF16, FGF17, FGF18, FGF19, FGF2 (bFGF), FGF20, FGF21 (such as mimAb1), FGF22, FGF23, FGF3 (int-2), FGF4 (HST), FGF5, FGF6 (HST-2), FGF7 (KGF), FGF8, FGF9, FGFR3, FIGF (VEGFD), FILI(EPSILON), FBLI (ZETA), FLJ12584, FLJ25530, FLRTI (fibronectin), FLTI, FLT-3, FOS, FOSLI(FRA-I), FY (DARC), GABRP (GABAa), GAGEBI, GAGECI, GALNAC4S-6ST, GATA3, GD2, GD3, GDF5, GDF8, GFII, GGTI, GM-CSF, GNASI, GNRHI, GPR2 (CCRIO), GPR31, GPR44, GPR81 (FKSG80), GRCCIO (CIO), gremlin, GRP, GSN (Gelsolin), GSTPI, HAVCR2, HDAC, HDAC4, HDACS5, HDAC7A, HDAC9, Hedgehog, HGF, HIFIA, HIPI, histamine and histamine receptors, HLA-A, HLA-DRA, HM74, HMOXI, HSP90, HUMCYT2A, ICEBERG, ICOSL, ID2, IFN-α, IFNAI, IFNA2, IFNA4,1FNA5, EFNA6, BFNA7, IFNBI, IFNgamma, IFNWI, IGBPI, IGFI, IGFIR, IGF2, IGFBP2, IGFBP3, IGFBP6, DL-I, ILIO, ILIORA, ILIORB, IL-1, ILIRI (CD121a), ILIR2(CD121b), IL-IRA, IL-2, IL2RA (CD25), IL2RB(CD122), IL2RG(CD132), IL-4, IL-4R (CD123), IL-5, IL5RA(CD125), IL3RB(CD131), IL-6, IL6RA (CD126), IR6RB(CD130), IL-7, IL7RA(CD127), IL-8, CXCRI (IL8RA), CXCR2 (IL8RB/CD128), IL-9, IL9R (CD129), IL-10, IL10RA(CD210), IL10RB (CDW210B), IL-11, IL1IRA, IL-12, IL-12A, IL-12B, IL-12RB1, IL-12RB2, IL-13, IL13RA1, IL13RA2, IL14, IL15, IL15RA, 1L16, IL17, IL17A, IL17B, IL17C, IL17R, IL18, IL18BP, IL18R1, IL18RAP, IL19, ILIA, ILIB, ILI-FIO, IL1F5, IL1F6, IL1F7, IL1F8, DL1F9, ILIHYI, ILIRI, IL1R2, ILIRAP, ILIRAPLI, IL1 RAPL2, ILIRLI, IL1RL2, ILIRN, IL2, IL20, IL20RA, IL21R, IL22, IL22R, IL22RA2, IL23,DL24, IL25, IL26, IL27, IL28A, IL28B, IL29, IL2RA, IL2RB, IL2RG, IL3, IL30, IL3RA, IL4,IL4R, IL6ST (glycoprotein 130), ILK, INHA, INHBA, INSL3, INSL4, IRAKI, IRAK2, ITGA1, ITGA2, ITGA3, ITGA6 (α 6 integrin), ITGAV, ITGB3, ITGB4 (β 4 integrin), JAKI, JAK3, JTB, JUN, K6HF, KAII, KDR, KIM-1, KITLG, KLF5 (GC Box BP), KLF6, KLKIO, KLK12, KLK13, KLK14, KLK15, KLK3, KLK4, KLK5, KLK6, KLK9, KRTI, KRT19 (Keratin 19), KRT2A, KRTHB6 (hair-specific type II keratin), LAMA5, LEP (leptin), Lingo-p75, Lingo-Troy, LPS, LRP5, LRP6, LTA (TNF-b), LTB, LTB4R (GPR16), LTB4R2, LTBR, MACMARCKS, MAG or Omgp, MAP2K7 (c-Jun), MCP-I, MDK, MIBI, midkine, MIF, MISRII, MJP-2, MK, MKI67 (Ki-67), MMP2, MMP9, MS4A1, MSMB, MT3 (metallothionectin-Ui), mTOR, MTSSI, MUCI (mucin), MYC, MYD88, NCK2, neurocan, neuregulin-1, neuropilin-1, NFKBI, NFKB2, NGFB (NGF), NGFR, NgR-Lingo, NgR-Nogo66 (Nogo), NgR-p75, NgR-Troy, NMEI (NM23A), NOTCH, NOTCHI, N0X5, NPPB, NROBI, NR0B2, NRIDI, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRPI, NRP2, NT5E, NTN4, OCT-1, ODZ1, OPN1, OPN2, OPRDI, P2RX7, PAP, PARTI, PATE, PAWR, PCA3, PCDGF, PCNA, PDGFA, PDGFB, PDGFRA, PDGFRB, PECAMI, pegasparaginase, PF4 (CXCL4), Plexin B2 (PLXNB2), PGF, PGR, phosphacan, PIAS2, PI3 Kinase, PIK3CG, PLAU (uPA), PLG5PLXDCI, PKC, PKC-β, PPBP (CXCL7), PPID, PRI, PRKCQ, PRKDI, PRL, PROC, PROK2, pro-NGF, prosaposin, PSAP, PSCA, PTAFR, PTEN, PTGS2 (COX-2), PTN, RAC2 (P21Rac2), RANK, RANK ligand, RARB, RGSI, RGS13, RGS3, RNFI10 (ZNF144), Ron, ROB02, RXR, selectin, S100A2, S100A8, S100A9, SCGB 1D2 (lipophilin B), SCGB2A1 (mammaglobin 2),SCGB2A2 (mammaglobin 1), SCYEI (endothelial Monocyte-activating cytokine), SDF2, SERPENA1, SERPINA3, SERPINB5 (maspin), SERPINEI (PAI-I), SERPINFI, SHIP-I, SHIP-2, SHBI, SHB2, SHBG, SfcAZ, SLC2A2, SLC33A1, SLC43A1, SLIT2, SPPI, SPRRIB (SprI), ST6GAL1, STABI, STAT6, STEAP, STEAP2, SULF-1, Sulf-2, TB4R2, TBX21, TCPIO, TDGFI, TEK, TGFA, TGFBI, TGFBIII, TGFB2,TGFB3, TGFBI, TGFBRI, TGFBR2, TGFBR3, THIL, THBSI (thrombospondin-1), THBS2/THBS4, THPO, TIE (Tie-1), TIMP3, tissue factor, TIKI2, TLR10, TLR2, TLR3, TLR4, TLR5, TLR6JLR7, TLR8, TLR9, TM4SF1, TNF, TNF-α, TNFAIP2 (B94), TNFAIP3, TNFRSFIIA, TNFRSFIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (AP03L), TNFSF13 (April), TNFSF13B, TNFSF14 (HVEM-L), TNFSF15 (VEGI), TNFSF 18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TLR2, TLR4, TLR9, TOP2A (topoisomerase lia), TP53, TPMI, TPM2,TRADD, TRAFI, TRAF2, TRAF3, TRAF4, TRAF5, TRAF6, TRKA, TREMI, TREM2, TRPC6, TROY, TSLP, TWEAK, Tyrosinase, uPAR, VEGF, VEGFB, VEGFC, versican, VHL C5, VLA-4, Wnt-1, XCLI (lymphotactin), XCL2 (SCM-Ib), XCRI (GPR5/CCXCRI), YYI, and ZFPM2.

Examples of non-human donor antibodies can be a non-human mammalian antibody (e.g., murine antibody, a rat antibody, a rabbit antibody, a llama antibody, an alpaca antibody), or an avian antibody (e.g., a chicken antibody or from any domesticated or non-domesticated bird). A camelid VHH single domain antibody (llama, alpaca or dromedary) may also be used. A CDR-grafted, humanized antibodies can also be used as a donor, to further humanize such antibodies by introducing additional human germline residues in the CDR region.

B. Human Frameworks

Sequences of human germline frameworks are available from various public databases, such as V-base, IMGT, NCBI, or Abysis. Exemplary human framework sequences are listed in Tables 2-6.

Suitable human framework can be the framework region from a particular human germline (Tables 2-4), or can be framework region of consensus germline sequences (Tables 5, 6).

Preferred human germline heavy chain frameworks are frameworks derived from VH1, VH3, or VH5 germlines. For example, VH frameworks from the following germlines may be used: IGHV3-23, IGHV3-7, or IGHV1-69 (germline names are based on IMGT germline definition).

Preferred human germline light chain frameworks are frameworks derived from $V_K$ or $V_\lambda$ germlines. For example, VL frameworks from the following germlines may be used: IGKV1-39 or IGKV3-20 (germline names are based on IMGT germline definition).

One exemplary method of selecting a suitable human framework is based sequence homology between non-human donor framework sequence and human framework sequences. For example, one can align the non-human donor framework sequence with various human framework sequences, and select the most homologous framework sequence. Alternatively, one may also select a framework on the basis of structural complimentarity (e.g., similarity in canonical CDR structure and therefore CDR presentation complimentarity).

As exemplified herein, in many cases, back-mutations in framework region (where a human germline residue is replaced with the corresponding non-human donor residue to restore binding affinity) is not required for the ABS method. For example, when the donor CDRs are from a mammalian species, high affinity humanized antibody were obtained without framework back-mutations (see Examples section). When the donor CDRs are from an avian species, only one back-mutation was made (see Examples section).

Accordingly, when the donor CDRs are from a mammalian species, in certain embodiment, the human germline VL framework comprises no more than 5 back-mutations or random mutations (such as 5, 4, 3, 2, or 1 back-mutation or random mutation); in certain embodiments, the human germline VH framework comprises no more than 5 back-mutations or random mutations (such as 5, 4, 3, 2, or 1 back-mutations or random mutation); in certain embodiments, the human germline VL framework and VH framework together comprise no more than 5 back-mutations or random mutations (such as 5, 4, 3, 2, or 1 back-mutation or random mutation); in certain embodiments, the human germline VL framework and VH framework together does not comprise a back-mutation or random mutation.

In particular, 1 or more back-mutations or random mutations can occur in heavy chain FR3, at positions H71-H80. Structural studies show that residues H71-H80 form a loop and play an auxiliary role for antigen binding in many natural antibodies. Some even refer to this region as "CDR4." The structure-based database indicates that this region can accommodate diversities comparable to those observed in the classical CDRs. Further, there appears to be no significant structural constraint on the diversity within the central portion of the loop. Accordingly, if desired, positions H71-H80 (in FR3) of heavy chain can be further mutated. In certain embodiment, positions H71-H80 (in FR3) of heavy chain are constructed in binary substitution form—each position is human germline residue or corresponding non-human donor residue, in a fashion similar to that of CDR-L1, CDR-L2, CDR-L3, CDR-H1, and CDR-H2. In certain embodiment, positions H71-H80 (in FR3) of heavy chain are randomized—each position within H71-H80 can be any one of the 20 natural amino acids, in a fashion similar to that of CDR-H3.

When the donor CDRs are from an avian species, in certain embodiment, the human germline VL framework comprises no more than 10 back-mutations or random mutations (such as 10, 9, 8, 7, 6, 5, 4, 3, 2, or 1 back-mutation or random mutation); in certain embodiments, the human germline VH framework comprises no more than 10 back-mutations or random mutations (such as 10, 9, 8, 7, 6, 5, 4, 3, 2, or 1 back-mutation or random mutation); in certain embodiments, the human germline VL framework and VH framework together comprise no more than 10 back-mutations or random mutations (such as 10, 9, 8, 7, 6, 5, 4, 3, 2, or 1 back-mutation or random); in certain embodiments, the human germline VL framework and VH framework together comprise a single back-mutation or random mutation.

In an exemplary embodiment, the human germline VL framework comprises a back-mutation at position 46.

In an exemplary embodiment, the non-human CDRs are from a chicken antibody, and the back-mutation is at Leu46Thr (L46T).

As described above, 1 or more back-mutations or random mutations can occur in heavy chain FR3, at positions H71-H80.

C. Humanization of Donor CDRs

The ABS method disclosed herein modifies the donor CDR residues to increase the human content of donor CDRs.

As illustrated in FIG. 1A, five non-human donor CDRs (CDR-L1, CDR-L2, CDR-L3, CDR-H1, and CDR-H2) are aligned with their corresponding CDRs from a human germline sequence. If a donor residue is the same as the corresponding human germline residue, that residue remained unchanged, and all library clones incorporate this residue at the designated position. If a donor residue is different from the corresponding human germline residue, both residues are incorporated combinatorially into library clones (i.e., a portion of the polypeptides in the library comprise the human germline residue at the designated position, the remainder of the polypeptides comprise the corresponding non-human donor residue at the designated position.

In certain embodiments, it may be desirable that for each position, about 50% of the clones had the human germline residue, and about 50% of the clones have the non-human donor residue; so that both residues are substantially equally represented in the library. However, it should be understood that even if the synthesis scheme is carried out to achieve the goal of 50%/50% for human/non-human distribution, certain synthesis biases may exist, and substantially equal distribution may not be achieved. For example, experimental and/or mechanical error in the synthesis methods used to generate DNA libraries may lead to the imprecise incorporation of individual nucleotides or codons such that 50:50 distribution of human to non-human is not achieved. In fact, in many cases, substantially equal distribution of human/non-human residues is also not necessary.

Accordingly, in certain embodiments, for each position within CDR-L1, CDR-L2, CDR-L3, CDR-H1, and CDR-H2, the percentage of polypeptides in the library comprising the human germline residue can be from about 1% to about 99%, such as from about 5% to about 95%, from about 10% to about 95%, from about 15% to about 95%, from about 20% to about 95%, from about 25% to about 95%, from about 30% to about 95%, from about 35% to about 95%, from about 40% to about 95%, from about 5% to about 90%, from about 10% to about 90%, from about 15% to about 90%, from about 20% to about 90%, from about 25% to about 90%, from about 30% to about 90%, from about 35% to about 90%, from about 40% to about 90%, from about 5% to about 85%, from about 10% to about 85%, from about 15% to about 85%, from about 20% to about 85%, from about 25% to about 85%, from about 30% to about 85%, from about 35% to about 85%, from about 40% to about 85%, from about 5% to about 80%, from about 10% to about 80%, from about 15% to about 80%, from about 20% to about 80%, from about 25% to about 80%, from about 30% to about 80%, from about 35% to about 80%, from about 40% to about 80%, from about 5% to about 75%, from about 10% to about 75%, from about 15% to about 75%, from about 20% to about 75%, from about 25% to about 75%, from about 30% to about 75%, from about 35% to about 75%, from about 40% to about 75%, from about 5% to about 70%, from about 10% to about 70%, from about 15% to about 70%, from about 20% to about 70%, from about 25% to about 70%, from about 30% to about 70%, from about 35% to about 70%, from about 40% to about 70%, from about 5% to about 65%, from about 10% to about 65%, from about 15% to about 65%, from about 20% to about 65%, from about 25% to about 65%, from about 30% to about 65%, from about 35% to about 65%, from about 40% to about 65%, from about 5% to about 60%, from about 10% to about 60%, from about 15% to about 60%, from about 20% to about 60%, from about 25% to about 60%, from about 30% to about 60%, from about 35% to about 60%, from about 40% to about 60%, or about 50%, the remainder comprising the corresponding non-human donor residue at the designated position.

In certain embodiments, it may be preferable to reduce the content of certain amino acids that impart chemical instability or heterogeneity problems, such as methionine, aspartic acid, tryptophan, asparagine, cysteine, tryptophan. Often, these residues are involved in post-transcriptional modifications, such as glycosylation, methylation, acetylation, oxidation, acid hydrolysis and deamination. Certain types of post-transcriptional modifications may be undesirable.

For example, as shown in FIG. 1, the human residue at position 53 of CDR-L2 is S, and the rat residue is N. If desired, the percentage of library clones incorporating N may be reduced to significantly below 50% to minimize the risk of generating daughter clones with deamidation or glycosylation motifs. For example, synthesis may be carried out such that only about 1-2% of the clones have N, and 98-99% of the clones have S. Other circumstances where one may not wish to achieve a 50:50 distribution of human: non-human amino acids at given positions could be to avoid the generation of structural motifs that affect protein drug development such as surface charge patches, and/or hydrophobicity patches.

For CDR-H3, each position can be any one of the 20 natural amino acid residues. In certain embodiments, it may be desirable that for each position, each of the 20 natural amino acid residues are substantially equally represented in the library (i.e., about 5% the library clones incorporate one particular amino acid). Again, because synthesis biases, substantially equal distribution of the 20 residues may not be achieve, and in many cases, is not necessary. Accordingly, in certain embodiments, for each position within CDR-H3, each of the 20 amino acid residues is represented by at least about 0.1% (e.g., at least about 0.1%, at least about 0.2%, at least about 0.5%, at least about 0.8%, at least about 1%, at least about 1.5%, at least about 2%, at least about 2.5%, at least about 3%, at least about 3.5%, at least about 4%, or at least about 4.5%) of the polypeptides in the library. In certain embodiments, for each position within CDR-H3, each of the 20 amino acid residues is represented by from about 0.1% to about 20% (e.g., from about 0.1% to about 20%, from about 0.1% to about 15%, from about 0.1% to about 10%, from about 0.2% to about 20%, from about 0.2% to about 15%, from about 0.2% to about 10%, from about 0.5% to about 20%, from about 0.5% to about 15%, from about 0.5% to about 10%, from about 0.8% to about 20%, from about 0.8% to about 15%, from about 0.8% to about 10%, from about 1% to about 20%, from about 1% to about 15%, from about 1% to about 10%, from about 2% to about 20%, from about 2% to about 15%, from about 2% to about 10%, from about 3% to about 20%, from about 3% to about 15%, from about 3% to about 10%, from about 4% to about 20%, from about 4% to about 15%, from about 4% to about 10%, from about 0.1% to about 9%, from about 0.2% to about 9%, from about 0.5% to about 9%, from about 0.8% to about 9%, from about 1% to about 9%, from about 2% to about 9%, from about 3% to about 9%, from about 4% to about 9%, from about 0.1% to about 8%, from about 0.2% to about 8%, from about 0.5% to about 8%, from about 0.8% to about 8%,from about 1% to about 8%, from about 2% to about 8%, from about 3% to about 8%, from about 4% to about 8%, from about 0.1% to about 7%, from about 0.2% to about 7%, from about 0.5% to about 7%, from about 0.8% to about 7%, from about 1% to about 7%, from about 2% to about 7%, from about 3% to about 7%, from about 4% to about 7%, from about 0.1% to about 6%, from about 0.2% to about 6%, from about 0.5% to about 6%, from about 0.8% to about 6%, from about 0.1% to about 6%, from about 0.2% to about 6%, from about 0.5% to about 6%, from about 0.8% to about 6%, from about 1% to about 6%, from about 2% to about 6%, from about 3% to about 6%, or from about 4% to about 6%) of the polypeptides in the library.

In certain embodiments, it may be preferable to reduce the content of certain amino acids in CDR-H3 that impart chemical instability or heterogeneity problems such as methionine, aspartic acid, tryptophan, asparagine, cysteine, tryptophan, as described above.

Often it is not necessary for the library to incorporate all 20 natural amino acids at each position within CDR-H3. Since conservative substitutions are generally well tolerated, certain residues may be omitted from the library. For example, since Gln is a conservative substitution of Asn, the library can omit Asn in CDR-H3, and use Gln instead. Sometimes it may be desirable to increase the percentage of Gln if Asn is replaced with Gln in CDR-H3. Other conservative substitutions can be similarly used to omit certain residues.

TABLE 12

| Residue | Conservative substitution | Residue | Conservative substitution |
|---|---|---|---|
| Ala | Ser | Leu | Ile, Val |
| Arg | Lys | Lys | Arg, Gln |
| Asn | Gln; His | Met | Leu, Ile |
| Asp | Glu | Phe | Met, Leu, Tyr |
| Cys | Ser | Ser | Thr; Gly |
| Gln | Asn | Thr | Ser, Val |
| Glu | Asp | Trp | Tyr |
| Gly | Pro | Tyr | Trp, Phe |
| His | Asn, Gln | Val | Ile, Leu |
| Ile | Leu, Val | Pro | — |

Methods of incorporating both human and non-human residues (CDR-L1, CDR-L2, CDR-L3, CDR-H1, and CDR-H3) and 20 natural amino acid residues (CDR-H3) into a combinatorial library are generally known, for example, by amplifying VH sequence by PCR, and/or performing random mutagenesis in CDR3.

The libraries disclosed herein can be used to screen for "ultra" humanized antibodies, in particular antibodies where human germline residues are incorporated into non-human donor CDRs. Accordingly, also provided herein is humanized antibody or antigen-binding fragment thereof that binds to a target antigen, wherein human germline residues are incorporated into CDRs.

In certain embodiments, the human germline VL framework is the framework of DPK9 (IMGT name: IGKV1-39), and for each position within CDR-L1, CDR-L2, and CDR-L3, the residue is either the respective human residue shown below, or its corresponding residue from the non-human donor antibody:

TABLE 13

| SEQ ID NO. | | Light Chain |
|---|---|---|
| 410 | CDR-L1 | RASQSISSYLN |
| 411 | CDR-L2 | AASSLQS |
| 412 | CDR-L3 | QQSYSTP |

In certain embodiments, the human germline VL framework is the framework of DPK12 (IMGT name: IGKV2D-29), and for each position within CDR-L1, CDR-L2, and CDR-L3, the residue is either the respective human residue shown below, or its corresponding residue from the non-human donor antibody:

TABLE 14

| SEQ ID NO. | | Light Chain |
|---|---|---|
| 413 | CDR-L1 | KSSQSLLHSDGKTYLY |
| 414 | CDR-L2 | EVSNRFS |
| 415 | CDR-L3 | MQSIQLP |

In certain embodiments, the human germline VL framework is the framework of DPK18 (IMGT name: IGKV2-30), and for each position within CDR-L1, CDR-L2, and CDR-L3, the residue is either the respective human residue shown below, or its corresponding residue from the non-human donor antibody:

TABLE 15

| SEQ ID NO. | | Light Chain |
|---|---|---|
| 416 | CDR-L1 | RSSQSLVYSDGNTYLN |
| 417 | CDR-L2 | KVSNRDS |
| 418 | CDR-L3 | MQGTHWP |

In certain embodiments, the human germline VL framework is the framework of DPK24 (IMGT name: IGKV4-1), and for each position within CDR-L1, CDR-L2, and CDR-L3, the residue is either the respective human residue shown below, or its corresponding residue from the non-human donor antibody:

TABLE 16

| SEQ ID NO. | | Light Chain |
|---|---|---|
| 419 | CDR-L1 | KSSQSVLYSSNNKNYLA |
| 420 | CDR-L2 | WASTRES |
| 421 | CDR-L3 | QQYYSTP |

In certain embodiments, the human germline VL framework is the framework of HK102_V1 (IMGT name: IGKV1-5), and for each position within CDR-L1, CDR-L2, and CDR-L3, the residue is either the respective human residue shown below, or its corresponding residue from the non-human donor antibody:

TABLE 17

| SEQ ID NO. | | Light Chain |
|---|---|---|
| 422 | CDR-L1 | RASQSISSWLA |
| 423 | CDR-L2 | DASSLES |
| 424 | CDR-L3 | QQYNSYS |

In certain embodiments, the human germline VL framework is the framework of DPK1 (IMGT name: IGKV1-33), and for each position within CDR-L1, CDR-L2, and CDR-L3, the residue is either the respective human residue shown below, or its corresponding residue from the non-human donor antibody:

TABLE 18

| SEQ ID NO. | | Light Chain |
|---|---|---|
| 425 | CDR-L1 | QASQDISNYLN |
| 426 | CDR-L2 | DASNLET |
| 427 | CDR-L3 | QQYDNLP |

In certain embodiments, the human germline VL framework is the framework of DPK8 (IMGT name: IGKV1-9), and for each position within CDR-L1, CDR-L2, and CDR-L3, the residue is either the respective human residue shown below, or its corresponding residue from the non-human donor antibody:

TABLE 19

| SEQ ID NO. | | Light Chain |
|---|---|---|
| 428 | CDR-L1 | RASQGISSYLA |
| 429 | CDR-L2 | AASTLQS |
| 430 | CDR-L3 | QQLNSYP |

In certain embodiments, the human germline VL framework is the framework of DPK21 (IMGT name: IGKV3-15), and for each position within CDR-L1, CDR-L2, and CDR-L3, the residue is either the respective human residue shown below, or its corresponding residue from the non-human donor antibody:

TABLE 20

| SEQ ID NO. | | Light Chain |
|---|---|---|
| 431 | CDR-L1 | RASQSVSSNLA |
| 432 | CDR-L2 | GASTRAT |
| 433 | CDR-L3 | QQYNNWP |

In certain embodiments, the human germline VL framework is the framework of Vg_38K (IMGT name: IGKV3-11), and for each position within CDR-L1, CDR-L2, and CDR-L3, the residue is either the respective human residue shown below, or its corresponding residue from the non-human donor antibody:

TABLE 21

| SEQ ID NO. | | Light Chain |
|---|---|---|
| 434 | CDR-L1 | RASQSVSSYLA |
| 435 | CDR-L2 | DASNRAT |
| 436 | CDR-L3 | QQRSNWP |

In certain embodiments, the human germline VL framework is the framework of DPK22 (IMGT name: IGKV3-20), and for each position within CDR-L1, CDR-L2, and CDR-L3, the residue is either the respective human residue shown below, or its corresponding residue from the non-human donor antibody:

TABLE 22

| SEQ ID NO. | | Light Chain |
|---|---|---|
| 437 | CDR-L1 | RASQSVSSSYLA |
| 438 | CDR-L2 | GASSRAT |
| 439 | CDR-L3 | QQYGSSP |

In certain embodiments, the human germline VL framework is the framework of DPK15 (IMGT name: IGKV2-28), and for each position within CDR-L1, CDR-L2, and CDR-L3, the residue is either the respective human residue shown below, or its corresponding residue from the non-human donor antibody:

TABLE 23

| SEQ ID NO. | | Light Chain |
|---|---|---|
| 440 | CDR-L1 | RSSQSLLHSNGYNYLD |
| 441 | CDR-L2 | LGSNRAS |
| 442 | CDR-L3 | MQALQTP |

In certain embodiments, the human germline VL framework is the framework of DPL16 (IMGT name: IGLV3-19), and for each position within CDR-L1, CDR-L2, and CDR-L3, the residue is either the respective human residue shown below, or its corresponding residue from the non-human donor antibody:

TABLE 24

| SEQ ID NO. | | Light Chain |
|---|---|---|
| 443 | CDR-L1 | QGDSLRSYYAS |
| 444 | CDR-L2 | GKNNRPS |
| 445 | CDR-L3 | NSRDSSGNH |

In certain embodiments, the human germline VL framework is the framework of DPL8 (IMGT name: IGLV1-40), and for each position within CDR-L1, CDR-L2, and CDR-L3, the residue is either the respective human residue shown below, or its corresponding residue from the non-human donor antibody:

TABLE 25

| SEQ ID NO. | | Light Chain |
|---|---|---|
| 446 | CDR-L1 | TGSSSNIGAGYDVH |
| 447 | CDR-L2 | GNSNRPS |
| 448 | CDR-L3 | QSYDSSLSG |

In certain embodiments, the human germline VL framework is the framework of V1-22 (IMGT name: IGLV6-57), and for each position within CDR-L1, CDR-L2, and CDR-L3, the residue is either the respective human residue shown below, or its corresponding residue from the non-human donor antibody:

TABLE 26

| SEQ ID NO. | | Light Chain |
|---|---|---|
| 449 | CDR-L1 | TRSSGSIASNYVQ |
| 450 | CDR-L2 | EDNQRPS |
| 451 | CDR-L3 | QSYDSSN |

In certain embodiments, the human germline VL framework is the framework of human Vλ consensus sequence, and for each position within CDR-L1, CDR-L2, and CDR-L3, the residue is either the respective human residue shown below, or its corresponding residue from the non-human donor antibody. Alternative sequences are provided for the consensus sequence with and without gaps. At positions where there is no consensus, residues in ( ) are those that are tied for the most frequent residues.

TABLE 27

| SEQ ID NO. | | Light Chain |
|---|---|---|
| 452 | CDR-L1 | TGSSSGGSYYVS or |
| 453 | | TGSSSDVGGSYYVS |
| 454 | CDR-L2 | ENDSNRPS or |
| 455 | | EDSNR(S/D)K(Q/G)QKPS |
| 456 | CDR-L3 | QSWDSSA(N/T) or |
| 457 | | QSWDSSA(N/T)F(F/V)(G/V) |

In certain embodiment, the human germline VL framework is the framework of human Vλ1 consensus sequence, and for each position within CDR-L1, CDR-L2, and CDR-L3, the residue is either the respective human residue shown below, or its corresponding residue from the non-human donor antibody. Alternative sequences are provided for the consensus sequence with and without gaps. At positions where there is no consensus, residues in ( ) are those that are tied for the most frequent residues.

TABLE 28

| SEQ ID NO. | | Light Chain |
|---|---|---|
| 458 | CDR-L1 | SGSSSNIGNN(A/Y)V(N/H/S) or |
| 459 | | SGSSSNIIGNN(A/Y)V(N/H/S) |
| 460 | CDR-L2 | GNN(K/N/Q)RPS |
| 461 | CDR-L3 | AAWDDSL(N/S)G |

In certain embodiment, the human germline VL framework is the framework of human Vλ3 consensus sequence, and for each position within CDR-L1, CDR-L2, and CDR-L3, the residue is either the respective human residue shown below, or its corresponding residue from the non-human donor antibody. Alternative sequences are provided for the consensus sequence with and without gaps. At positions where there is no consensus, residues in ( ) are those that are tied for the most frequent residues.

TABLE 29

| SEQ ID NO. | | Light Chain |
|---|---|---|
| 462 | CDR-L1 | CSGD(A/V)LG(K/S)KYAH |
| 463 | CDR-L2 | KDSERPS |
| 464 | CDR-L3 | QSWDSSG(N/D/T/A) or |
| 465 | | QSWDSSG(N/D/T/A)H |

In certain embodiment, the human germline VL framework is the framework of human VK consensus sequence, and for each position within CDR-L1, CDR-L2, and CDR-L3, the residue is either the respective human residue shown below, or its corresponding residue from the non-human donor antibody. Alternative sequences are provided for the consensus sequence with and without gaps.

TABLE 30

| SEQ ID NO. | | Light Chain |
|---|---|---|
| 466 | CDR-L1 | RASQSLLHSDGISSYLA or |
| 467 | | RASQGISSYLA |
| 468 | CDR-L2 | AASSRAS |
| 469 | CDR-L3 | QQYNSYP |

In certain embodiment, the human germline VL framework is the framework of human VK1 consensus sequence, and for each position within CDR-L1, CDR-L2, and CDR-L3, the residue is either the respective human residue shown below, or its corresponding residue from the non-human donor antibody. At positions where there is no consensus, residues in ( ) are those that are tied for the most frequent residues.

TABLE 31

| SEQ ID NO. | | Light Chain |
|---|---|---|
| 470 | CDR-L1 | RASQGIS(N/S)YLA |
| 471 | CDR-L2 | AASSLQS |
| 472 | CDR-L3 | QQYNSYP |

In certain embodiment, the human germline VL framework is the framework of human VK2 consensus sequence, and for each position within CDR-L1, CDR-L2, and CDR-L3, the residue is either the respective human residue shown below, or its corresponding residue from the non-human donor antibody. Alternative sequences are provided for the consensus sequence with and without gaps. At positions where there is no consensus, residues in ( ) are those that are tied for the most frequent residues.

TABLE 32

| SEQ ID NO. | | Light Chain |
|---|---|---|
| 473 | CDR-L1 | RSSQSLLHSDGNTYLD or |
| 474 | | RSSQSLLHSDDGNTYLD |
| 475 | CDR-L2 | (K/T)(V/I)SNR(A/F)S |
| 476 | CDR-L3 | MQATQFP |

In certain embodiment, the human germline VL framework is the framework of human VK3 consensus sequence, and for each position within CDR-L1, CDR-L2, and CDR-L3, the residue is either the respective human residue shown below, or its corresponding residue from the non-human donor antibody. At positions where there is no consensus, residues in ( ) are those that are tied for the most frequent residues.

TABLE 33

| SEQ ID NO. | | Light Chain |
|---|---|---|
| 477 | CDR-L1 | RASQS(S/V)(S/V)SSYLA |
| 478 | CDR-L2 | GASTRAT |
| 479 | CDR-L3 | QQY(S/N/G/H)NWP |

In certain embodiments, the human germline VH framework is the framework of DP54 or IGHV3-7, and for each position within CDR-H1, and CDR-H2, the residue is either the respective human residue shown below, or its corresponding residue from the non-human donor antibody:

TABLE 34

| SEQ ID NO. | | Heavy Chain |
|---|---|---|
| 480 | CDR-H1 | GFTFSSYWMS |
| 481 | CDR-H2 | ANIKQDGSEKYYVDSVKG |

In certain embodiments, the human germline VH framework is the framework of DP47 or IGHV3-23 and for each position within CDR-H1, and CDR-H2, the residue is either the respective human residue shown below, or its corresponding residue from the non-human donor antibody:

TABLE 35

| SEQ ID NO. | | Heavy Chain |
|---|---|---|
| 482 | CDR-H1 | GFTFSSYAMS |
| 483 | CDR-H2 | AISGSGGSTYYADSVKG |

In certain embodiments, the human germline VH framework is the framework of DP71 or IGHV4-59 and for each position within CDR-H1, and CDR-H2, the residue is either the respective human residue shown below, or its corresponding residue from the non-human donor antibody:

TABLE 36

| SEQ ID NO. | | Heavy Chain |
|---|---|---|
| 484 | CDR-H1 | GGSISSYYWS |
| 485 | CDR-H2 | GYIYYSGSTNYNPSLKS |

In certain embodiments, the human germline VH framework is the framework of DP75 or IGHV1-2_02 and for each position within CDR-H1, and CDR-H2, the residue is either the respective human residue shown below, or its corresponding residue from the non-human donor antibody:

TABLE 37

| SEQ ID NO. | | Heavy Chain |
|---|---|---|
| 486 | CDR-H1 | GYTFTGYYMH |
| 487 | CDR-H2 | GWINPNSGGTNYAQKFQG |

In certain embodiments, the human germline VH framework is the framework of DP10 or IGHV1-69 and for each position within CDR-H1, and CDR-H2, the residue is either the respective human residue shown below, or its corresponding residue from the non-human donor antibody:

TABLE 38

| SEQ ID NO. | | Heavy Chain |
|---|---|---|
| 488 | CDR-H1 | GGTFSSYAIS |
| 489 | CDR-H2 | GGIIPIFGTANYAQKFQG |

In certain embodiments, the human germline VH framework is the framework of DP7 or IGHV1-46, and for each position within CDR-H1, and CDR-H2, the residue is either the respective human residue shown below, or its corresponding residue from the non-human donor antibody:

TABLE 39

| SEQ ID NO. | | Heavy Chain |
|---|---|---|
| 490 | CDR-H1 | GYTGTSYYMH |
| 491 | CDR-H2 | GIINPSGGSTSYAQKFQG |

In certain embodiments, the human germline VH framework is the framework of DP49 or IGHV3-30, and for each position within CDR-H1, and CDR-H2, the residue is either the respective human residue shown below, or its corresponding residue from the non-human donor antibody:

TABLE 40

| SEQ ID NO. | | Heavy Chain |
|---|---|---|
| 492 | CDR-H1 | GFTFSSYGMH |
| 493 | CDR-H2 | AVISYDGSNKYYADSVKG |

In certain embodiments, the human germline VH framework is the framework of DP51 or IGHV3-48, and for each position within CDR-H1, and CDR-H2, the residue is either the respective human residue shown below, or its corresponding residue from the non-human donor antibody:

TABLE 41

| SEQ ID NO. | | Heavy Chain |
|---|---|---|
| 494 | CDR-H1 | GFTFSSYSMN |
| 495 | CDR-H2 | SYISSSSSTIYYADSVKG |

In certain embodiments, the human germline VH framework is the framework of DP38 or IGHV3-15, and for each position within CDR-H1, and CDR-H2, the residue is either the respective human residue shown below, or its corresponding residue from the non-human donor antibody:

TABLE 42

| SEQ ID NO. | | Heavy Chain |
|---|---|---|
| 496 | CDR-H1 | GFTFSNAWMS |
| 497 | CDR-H2 | GRIKSKTDGGTTDYAAPVKG |

In certain embodiments, the human germline VH framework is the framework of DP79 or IGHV4-39, and for each position within CDR-H1, and CDR-H2, the residue is either the respective human residue shown below, or its corresponding residue from the non-human donor antibody:

TABLE 43

| SEQ ID NO. | | Heavy Chain |
|---|---|---|
| 498 | CDR-H1 | GGSISSSSYYWG |
| 499 | CDR-H2 | GSIYYSGSTYYNPSLKS |

In certain embodiments, the human germline VH framework is the framework of DP78 or IGHV4-30-4, and for each position within CDR-H1, and CDR-H2, the residue is either the respective human residue shown below, or its corresponding residue from the non-human donor antibody:

TABLE 44

| SEQ ID NO. | | Heavy Chain |
|---|---|---|
| 500 | CDR-H1 | GGSISSGDYYWS |
| 501 | CDR-H2 | GYIYYSGSTYYNPSLKS |

In certain embodiments, the human germline VH framework is the framework of DP73 or IGHV5-51, and for each position within CDR-H1, and CDR-H2, the residue is either the respective human residue shown below, or its corresponding residue from the non-human donor antibody:

TABLE 45

| SEQ ID NO. | | Heavy Chain |
|---|---|---|
| 502 | CDR-H1 | GYSFTSYWIG |
| 503 | CDR-H2 | GIIYPGDSDTRYSPSFQG |

In certain embodiments, the human germline VH framework is the framework of human VH germline consensus sequence and for each position within CDR-H1, and CDR-H2, the residue is either the respective human residue shown below, or its corresponding residue from the non-human donor antibody. Alternative sequences are provided for the consensus sequence with and without gaps. At positions where there is no consensus, residues in ( ) are those that are tied for the most frequent residues.

TABLE 46

| SEQ ID NO. | | Heavy Chain |
|---|---|---|
| 504 | CDR-H1 | GFTFSSYAM(H/S) or |
| 505 | | GFTFSSYAM(H/S)WS |
| 506 | CDR-H2 | GWISPNGGSTYYADSVKG or |
| 507 | | GWISPKANGGSTYYADSVKG |

In certain embodiments, the human germline VH framework is the framework of human VH3 germline consensus sequence, and for each position within CDR-H1, and CDR-H2, the residue is either the respective human residue shown below, or its corresponding residue from the non-human donor antibody. Alternative sequences are provided for the consensus sequence with and without gaps. At positions where there is no consensus, residues in ( ) are those that are tied for the most frequent residues.

TABLE 47

| SEQ ID NO. | | Heavy Chain |
|---|---|---|
| 508 | CDR-H1 | GFTFSSYAMS |
| 509 | CDR-H2 | SVISSDG(G/S)STYYADSVKG or |
| 510 | | SVISSKADG(G/S)STYYADSVKG |

In certain embodiments, the human germline VH framework is the framework of human VH5 germline consensus sequence, and for each position within CDR-H1, and CDR-H2, the residue is either the respective human residue shown below, or its corresponding residue from the non-human donor antibody. At positions where there is no consensus, residues in ( ) are those that are tied for the most frequent residues.

TABLE 48

| SEQ ID NO. | | Heavy Chain |
|---|---|---|
| 511 | CDR-H1 | GYSFTSYWI(S/G/H) |
| 512 | CDR-H2 | G(R/I/S)IYPGDSDTRYSPSFQG |

In certain embodiments, the human germline VH framework is the framework of human VH1 germline consensus sequence, and for each position within CDR-H1, and CDR-H2, the residue is either the respective human residue shown below, or its corresponding residue from the non-human donor antibody. At positions where there is no consensus, residues in ( ) are those that are tied for the most.

TABLE 49

| SEQ ID NO. | | Heavy Chain |
|---|---|---|
| 513 | CDR-H1 | GYTFTSY(A/Y)(I/M)H |
| 514 | CDR-H2 | GWINP(G/Y)NGNTNYAQKFQ |

In certain embodiments, the human germline VH framework is the framework of human VH4 germline consensus sequence, and for each position within CDR-H1, and CDR-H2, the residue is either the respective human residue shown below, or its corresponding residue from the non-human donor antibody. At positions where there is no consensus, residues in ( ) are those that are tied for the most frequent residues.

TABLE 50

| SEQ ID NO. | | Heavy Chain |
|---|---|---|
| 515 | CDR-H1 | GGSISSG(N/Y)YYWS |
| 516 | CDR-H2 | GYIYYSGSTYYNPSLKS |

For example, if the framework sequence of human germline DPK9 is used as an acceptor for humanization, and the non-human donor CDR-L1 sequence is RASQDVGIYVN (SEQ ID NO: 2), then the CDR-L1 of the resulting humanized antibody or antigen-binding fragment should be: RASQ(S/D)(IN)(S/G)(S/I)Y(L/V)N(SEQ ID NO:518). If the framework sequence of human germline DPL16 is used as an acceptor for humanization, and the non-human donor CDR-L1 sequence is RASQDVGIYVN (SEQ ID NO: 2), then the CDR-L1 of the resulting humanized antibody or antigen-binding fragment should be: (Q/R)(G/A)(D/S)(S/Q)(L/D)(RN)(S/G)(Y/I)Y(AN)(S/N) (SEQ ID NO:518). Under this design rationale, once a specific human germline sequence is selected as an acceptor, then five of the six CDR can be readily designed, as each individual position generally only has two choices—the germline residue from the same human germline, or the corresponding donor residue.

Figure 10A:
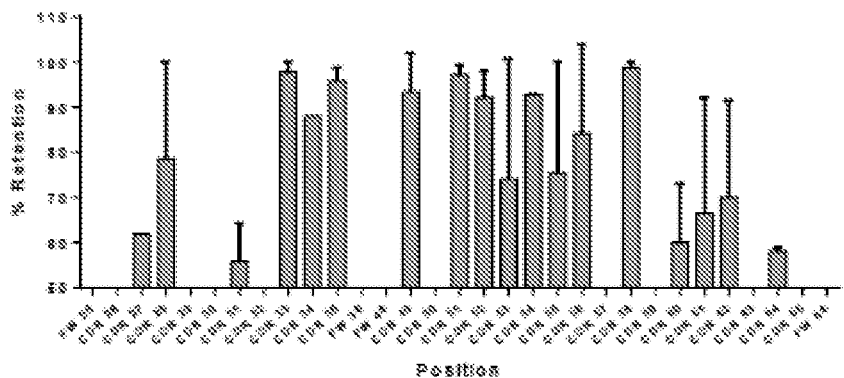
FIGS. 10A-10C are retention frequency plots for all positions across 5 CDR-humanized antibodies (A33, pTau, BDNF, IL33, and FN14) using the ABS methods described herein.
Figure 10B:
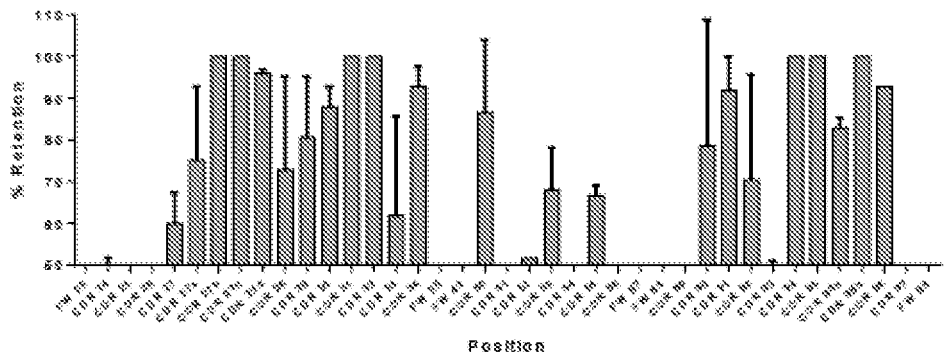
Figure 10C:
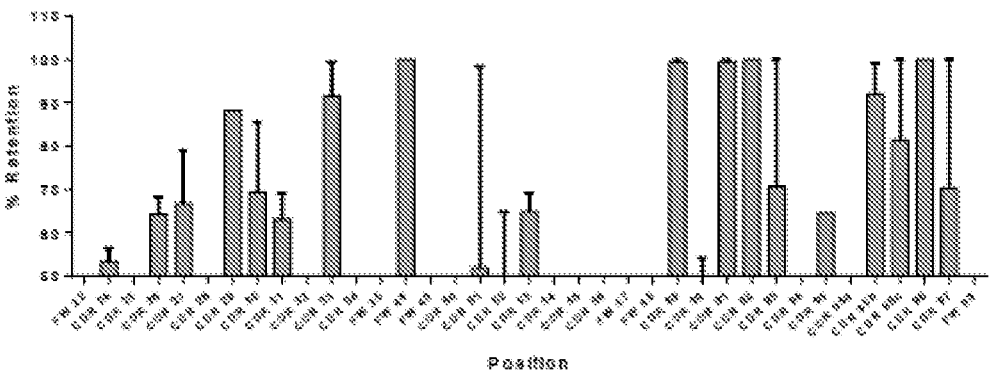

As shown in the Examples, certain positions in CDRs prefer non-human donor residues, whereas certain positions in CDRs tolerate human germline residues well. Positions that generally tolerate human germline residues well are candidates for CDR humanization. For example, as shown in FIG. 10, the n-terminal 4 residues of the VK CDR1, and last 6 residues of the VH CDR2 showed low retention rate of non-human donor residues. This indicates that these residues are candidates for CDR humanization.

Accordingly, provided herein are humanized antibodies or antigen-binding fragment thereof (such as an antibody variable domain), and libraries comprising such antibodies or antigen-binding fragment thereof (such as an antibody variable domain), wherein one or more of the n-terminal 4 residues of CDR-L1 (residues 24, 25, 26, and 27 respectively, based on Kabat numbering) comprise the corresponding human germline residues. In certain embodiments, the light chain framework sequence is from a human VK germline.

Also provided herein are humanized antibodies or antigen-binding fragment thereof (such as an antibody variable domain), and libraries comprising such antibodies or antigen-binding fragment thereof (such as an antibody variable domain), wherein one or more of the last 6 residues of CDR-H2 (residues 60, 61, 62, 63, 64, 65 respectively, based on Kabat numbering) comprise the corresponding human germline residues. In certain embodiments, the heavy chain framework sequence is from a human VH3 germline, VH1 germline, VH5 germline, or VH4 germline.

D. Antibody Display

The antibody libraries described herein are generally screened to identify specific clones that show desired antigen-binding affinities, or other properties (e.g., potency). For screening, a variety of techniques may be used to display these antibody variable domains.

Commonly used display libraries include, e.g., phage display, yeast display, mammalian cell surface display, bacterial display, viral display, mRNA display, ribosome display or DNA display library.

One exemplary display library is a phage display library. Phage display is a technique by which variant polypeptides are displayed as fusion proteins to a coat protein on the surface of phage, e.g., filamentous phage, particles. One advantage of phage display library is that large libraries of randomized protein variants can be rapidly and efficiently sorted for those sequences that bind to a target molecule with high affinity. Polyvalent phage display methods have been used for displaying small random peptides and small proteins through fusions to either gene III or gene VIII of filamentous phage. Wells and Lowman, Curr Opin Struct Biol, 3:355-362 (1992). In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, Methods: A companion to Methods in Enzymology, 3:205-0216 (1991).

A phagemid is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. Phagemids may contain a phage coat protein gene or fragment thereof linked to a heterologous polypeptide gene as a gene fusion such that the heterologous polypeptide is displayed on the surface of the phage particle.

A phage vector is a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, phage 21, phi80, phi81, 82, 424, 434, or a derivative thereof.

A phage vector may also encode a tag, for example, a polyhistidine tag, to facilitate the detection or identification of antibody variable domains that bind to a specific antigen.

4. Screening and Selection of Antibodies

The displayed antibody variable domains can then be screened for, e.g., the ability to bind the target antigen. For example, the target antigen can be attached with a detectable moiety, such as biotin. Polypeptides that bind to the target antigen can be separated from unbound ones by a molecule that binds to the detectable moiety, such as streptavidin-coated beads where biotin is the detectable moiety. Affinity of binders (polypeptide that binds to target) can be determined based on concentration of the target molecule used, using formulas and based on criteria known in the art.

The target antigen may also be attached to a suitable matrix such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. After attachment of the target antigen to the matrix, the immobilized target is contacted with the antibody library. Polypeptides bound to the immobilized antigen can then be separated from those that do not bind to the target by washing.

The binders can be isolated and then re-amplified or expressed in a host cell, and subjected to additional rounds of selection for binding of target molecules. Any number of rounds of selection or sorting can be utilized.

In certain embodiments, the library is screened to select a polypeptide that binds to the target antigen, with an affinity (Kd) value of no more than about $1\times10^{-3}$ M, such as no more than about $1\times10^{-3}$ M, no more than about $9\times10^{-4}$ M, no more than about $8\times10^{-4}$ M, no more than about $7\times10^{-4}$ M, no more than about $6\times10^{-4}$ M, no more than about $5\times10^{-4}$ M, no more than about $4\times10^{-4}$ M, no more than about $3\times10^{-4}$ M, no more than about $2\times10^{-4}$ M, no more than about $1\times10^{-4}$ M, no more than about $9\times10^{-5}$ M, no more than about $8\times10^{-5}$ M, no more than about $7\times10^{-5}$ M, no more than about $6\times10^{-5}$ M, no more than about $5\times10^{-5}$ M, no more than about $4\times10^{-5}$ M, no more than about $3\times10^{-5}$ M, no more than about $2\times10^{-5}$ M, no more than about $1\times10^{-5}$ M, no more than about $9\times10^{-6}$ M, no more than about $8\times10^{-6}$ M, no more than about $7\times10^{-6}$ M, no more than about $6\times10^{-6}$ M, no more than about $5\times10^{-6}$ M, no more than about $4\times10^{-6}$ M, no more than about $3\times10^{-6}$ M, no more than about $2\times10^{-6}$ M, no more than about $1\times10^{-6}$ M, no more than about $9\times10^{-7}$ M, no more than about $8\times10^{-7}$ M, no more than about $7\times10^{-7}$ M, no more than about $6\times10^{-7}$ M, no more than about $5\times10^{-7}$ M, no more than about $4\times10^{-7}$ M, no more than about $3\times10^{-7}$ M, no more than about $2\times10^{-7}$ M, no more than about $1\times10^{-7}$ M, no more than about $9\times10^{-8}$ M, no more than about $8\times10^{-8}$ M, no more than about $7\times10^{-8}$ M, no more than about $6\times10^{-8}$ M, no more than about $5\times10^{-8}$ M, no more than about $4\times10^{-8}$ M, no more than about $3\times10^{-8}$ M, no more than about $2\times10^{-8}$ M, no more than about $1\times10^{-8}$ M, no more than about $9\times10^{-9}$ M, no more than about $8\times10^{-9}$ M, no more than about $7\times10^{-9}$ M, no more than about $6\times10^{-9}$ M, no more than about $5\times10^{-9}$ M, no more than about $4\times10^{-9}$ M, no more than about $3\times10^{-9}$ M, no more than about $2\times10^{-9}$ M, no more than about $1\times10^{-9}$ M, from about $1\times10^{-3}$ M to about $1\times10^{-13}$ M, $1\times10^{-4}$ M to about $1\times10^{-13}$ M, $1\times10^{-5}$ M to about $1\times10^{-13}$ M, from about $1\times10^{-6}$ M to about $1\times10^{-13}$ M, from about $1\times10^{-7}$ M to about $1\times10^{-13}$ M, from about $1\times10^{-8}$ M to about $1\times10^{-13}$ M, from about $1\times10^{-9}$ M to about $1\times10^{-13}$ M, $1\times10^{-3}$ M to about $1\times10^{-12}$ M, $1\times10^{-4}$ M to about $1\times10^{-12}$ M, from about $1\times10^{-5}$ M to about $1\times10^{-12}$ M, from about $1\times10^{-6}$ M to about $1\times10^{-12}$ M, from about $1\times10^{-7}$ M to about $1\times10^{-12}$ M, from about $1\times10^{-8}$ M to about $1\times10^{-12}$ M, from about $1\times10^{-9}$ M to about $1\times10^{-12}$ M, $1\times10^{-3}$ M to about $1\times10^{11}$ M, $1\times10^{-4}$ M to about $1\times10^{11}$ M, from about $1\times10^{-5}$ M to about $1\times10^{11}$ M, from about $1\times10^{-6}$ M to about $1\times10^{-11}$ M, from about $1\times10^{-7}$ M to about $1\times10^{-11}$ M, from about $1\times10^{-8}$ M to about $1\times10^{11}$ M, from about $1\times10^{-9}$ M to about $1\times10^{-11}$ M, $1\times10^{-3}$ M to about $1\times10^{-10}$ M, $1\times10^{-4}$ M to about $1\times10^{-10}$ M, from about $1\times10^{-5}$ M to about $1\times10^{-10}$ M, from about $1\times10^{-6}$ M to about $1\times10^{-10}$ M, from about $1\times10^{-7}$ M to about $1\times10^{-10}$ M, from about $1\times10^{-8}$ M to about $1\times10^{10}$ M, or from about $1\times10^{-9}$ M to about $1\times10^{10}$ M.

In certain embodiments, a polypeptide that binds to the target antigen with a binding affinity (Kd) value that is equal or less than the binding affinity (Kd) value of the original non-human donor antibody.

Although in general, Kd at nanomolar range is desired, in certain embodiments, low affinity antibodies may be preferred, for example, for targeting highly expressed receptors in compartments and avoiding off-target binding. Further, some therapeutic applications may benefit from an antibody with lower binding affinity to facilitate antibody recycling.

In certain embodiments, the selected antibody variable domains may also be further screened by other biological activity assays, e.g., in order to evaluate its potency, pharmacological activity, and potential efficacy as a therapeutic agent. Such assays are known in the art and depend on the target antigen and intended use for the antibody. Examples include e.g., tumor cell growth inhibition assays; antibody-dependent cellular cytotoxicity (ADCC) and complement-mediated cytotoxicity (CDC) assays; agonistic activity or antagonist activity assays.

Once a desired clone is selected, the sequence of the antibody variable domain, and nucleic acid encoding such antibody variable domain, can be determined using standard sequencing techniques. Nucleic acid sequence encoding a desired antibody variable domain may be inserted into other vectors (such as cloning and expression vectors) for recombinant production and characterization.

Suitable cloning and expression vectors can include a variety of components, such as promoter, enhancer, and other transcriptional regulatory sequences. The vector may also be constructed to allow for movement of antibody variable domain between different vectors.

Selected antibody (or antigen-binding fragment thereof) may be made recombinantly produced using a suitable host cell. Nucleic acid encoding the antibody or antigen-binding fragment thereof can be cloned into an expression vector, which can then be into a host cell, such as E. coli cell, a yeast cell, an insect cell, a simian COS cell, a Chinese hamster ovary (CHO) cell, or a myeloma cell that do not otherwise produce immunoglobulin protein, to obtain the synthesis of monoclonal antibodies in the recombinant host cells.

Antibody fragments can be produced by proteolytic or other degradation of the antibodies, by recombinant methods, or by chemical synthesis. Polypeptides of the antibodies, especially shorter polypeptides up to about 50 amino acids, are conveniently made by chemical synthesis. Methods of chemical synthesis are known in the art and are commercially available.

The selected antibody or antigen-binding fragment thereof may be affinity-matured. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al., 1992, J. Mol. Biol., 226:889-896; and WO2004/058184).

5. Formulations and Uses

Antibodies or antigen-binding fragments identified from the library described herein can be formulated as pharmaceutical formulations. The pharmaceutical formulation may further comprise pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The antibodies or antigen-binding fragments identified from the library described herein can be used for therapeutic, diagnostic, or non-therapeutic purposes. For example, the antibody or antigen-binding fragment thereof may be used as an affinity purification agents (e.g., for in vitro purification), as a diagnostic agent (e.g., for detecting expression of an antigen of interest in specific cells, tissues, or serum)

For therapeutic applications, antibodies or antigen-binding fragments identified from the library described herein can be administered to a mammal, especially a human by conventional techniques, such as intravenously (as a bolus or by continuous infusion over a period of time), intramuscularly, intraperitoneally, intra-cerebrospinally, subcutaneously, intra-articularly, intrasynovially, intrathecally, orally, topically, or by inhalation. The antibodies or antigen-binding fragments also are suitably administered by intra-tumoral, peri-tumoral, intra-lesional, or peri-lesional routes. The antibodies or antigen-binding fragments can be used in prophylactic treatment or therapeutic treatment.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Current evidence suggests that the main risk factors for antibody immunogenicity in man are human t-cell epitope content and, to a lesser extent, t-cell independent b-cell responses. B-cell epitopes are challenging to predict and b-cell-only responses to biotherapeutics appear to be driven by protein aggregates. Important factors in reducing antibody immunogenicity risk in the clinic are low t-cell epitope content, minimized non-human germline content and low aggregation potential.

Examples provided herein describe the "Augmented Binary Substitution" design principle that generates stable, soluble, ultra-humanized antibodies via single-step CDR redundancy minimization. For three antibodies from three separate key immune host species, binary substitution CDR cassettes were inserted into preferred human frameworks to form libraries in which only the donor (non-human) residue or human germline destination residue was encoded at each position. The CDR-H3 in each case was also augmented with 1±1 random substitution per clone. Each library was then screened for clones with restored antigen binding capacity. Lead ultra-humanized clones demonstrated high stability, with affinity and specificity equivalent to, or better than, the parental immunoglobulin. Significantly, this was mainly achieved on germline frameworks by simultaneously subtracting up to 19 redundant non-human residues in the CDRs. This significantly lowered non-human sequence content, minimized t and b-cell epitope risk in the final molecules and provided a heat map for desired non-human CDR residue content of each antibody.

Example 1: Library Design, Build and Characterization

Figure 5A:
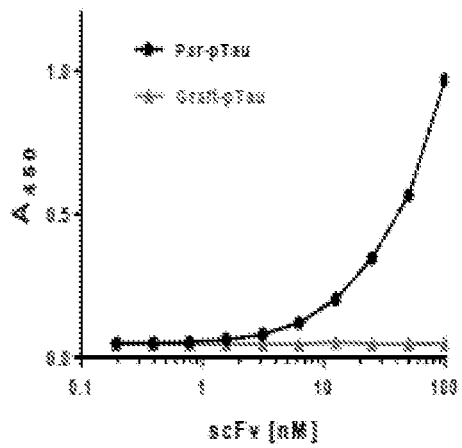
FIGS. 5A-5C show ELISA analyses of scFv function after expression in *E. coli* from phagemid vector pWRIL-1. Binding signals in titration ELISA against: (A) pT231_pS235 peptide for purified $V_L$-$V_H$ scFv forms of Par-pTau and Graft-pTau. (B) hRAGE and mRAGE for periprep $V_L$-$V_H$ scFv forms of CL-Hum-pTau and Graft-RAGE. (C) Human A33 ectodomain protein for purified $V_L$-$V_H$ scFv forms of Par-A33 and Graft-A33. In all cases (A-C), the grafted scFvs show significantly impaired binding activity.
Figure 5B:
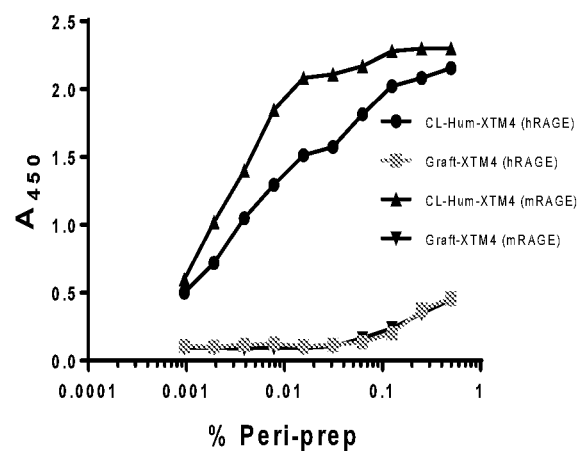
Figure 5C:
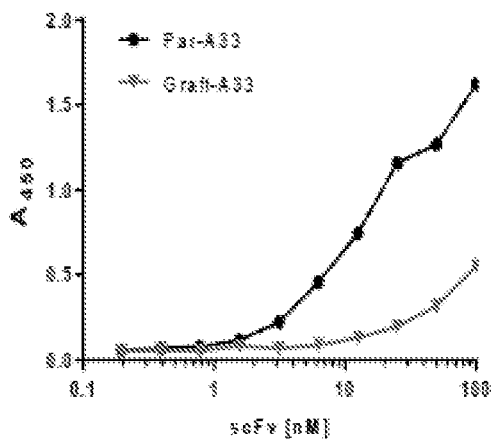

Rat anti-RAGE XT-M4, rabbit anti-A33, and chicken anti-pTau pT231/pS235_1 IgGs were generated on the human IgG1 backbone with either parental (Par-RAGE, Par-A33 or Par-pTau), grafted (Graft-RAGE, Graft-A33 or Graft-pTau), or classically humanized (CL-Hum-RAGE, CL-Hum-A33) v-domains. In scFv format, the parental form of each of these antibodies retained antigen binding, while the human FW-grafted versions demonstrated little to no binding (FIGS. 5A-5C). ABS ultra-humanization libraries (ABS-RAGE, ABS-A33, ABS-pTau) were constructed (FIG. 1) to generate $1.8 \times 10^9$ independent clones for ABS-RAGE, $1.1 \times 10^{10}$ for ABS-A33 and $4.9 \times 10^9$ for ABS-pTau (theoretical binary diversity for ABS-RAGE is $2^{27}$ positions=$1.34 \times 10^8$, for ABS-A33 232=$4.29 \times 10^9$ and for ABS-pTau $2^{33}$=$8.59 \times 10^9$).

The quality of pTau library build was verified by sequence analyses of ≥96 clones/library. After library transformation, the full scFv insert sequences were obtained for 96 clones, via sanger sequencing. Positions mutated in the CDRs show the expected (approximately 50:50) variability at all positions expected to be sampled by binary substitutions and low-level mutagenesis in the CDR-H3, confirming the integrity of the sampled library. <1% of clones contained out of frame or truncated inserts. Libraries were rescued using helper phage M13 and selections performed on their cognate targets.

Example 2: Identification and Analysis of Ultra-Humanized Clones

Clone selection in ABS library screening (pTau example) was conducted. Periprep ELISA was conducted to screen for single clones picked from multiple rounds of phage display selections of the ABS-pTau library. One hundred and eighty-eight clones were prioritized on the basis of retention of binding to the pT231_pS253 phosphopeptide, with A450 readings above the negative control (Anti-RAGE scFv), and equivalent to or above that of Par-pTau scFv. Periprep HTRF was conducted to screen these 188 single clones for epitope competition with wild-type IgG. Clones were prioritized on the basis of neutralisation of Par-pTau IgG binding to the pT231_pS253 phosphopeptide, with % ΔF readings lower than the negative control (Anti-RAGE scFv) and equivalent to or better that of Par-pTau scFv.

Post-selection screening revealed the presence of numerous scFv clones with significantly increased human content within the CDRs. In the ABS-RAGE and ABS-A33 leads, the FW sequences remained fully germline. In the ABS-pTau leads, all selected clones retained the T46 back-mutation, illustrating that this VL-FW2 residue is desired to humanize chicken antibodies (FIGS. 6A-6B). Human germline amino acid content was quantified within the CDRs of parental antibodies and ABS leads and expressed as a percentage (Table 1). Human content had raised 17-29% in each case. From top to bottom, CDRL1: SEQ ID NOs. 278-290; CDRL2: SEQ ID NOs. 291-303; CDRL3: SEQ ID NOs. 304-316; CDRH1: SEQ ID NOs. 317-329; CDRH2: SEQ ID NOs. 330-342; CDRH3: SEQ ID NOs. 343-352.

Example 3: Lead IgG Affinity, Stability and Specificity Characteristics

Figure 7A:
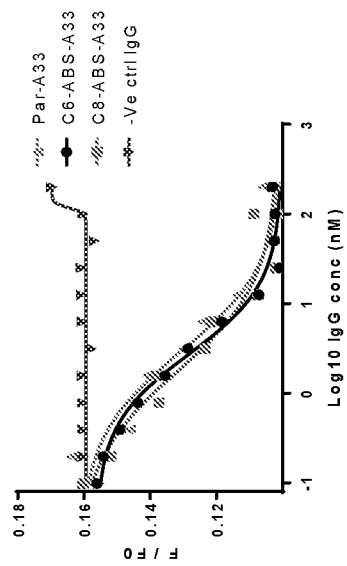
FIGS. 7A-7C show the IgG titration HTRF data for representative lead ABS-derived clones prioritized on the basis of: % reduction in parental residue CDR content and neutralisation of parental IgG binding to antigen, with the change in fluorescence intensity relative to baseline (F/F0) $IC_{50}$ values approximately equivalent to or better than parental IgG. (A) Anti-pTau clones, (B) Anti-RAGE clones, (C) Anti-A33 clones (-ve control non-A33-specific IgG added instead of graft due to graft expression problems).
Figure 7B:
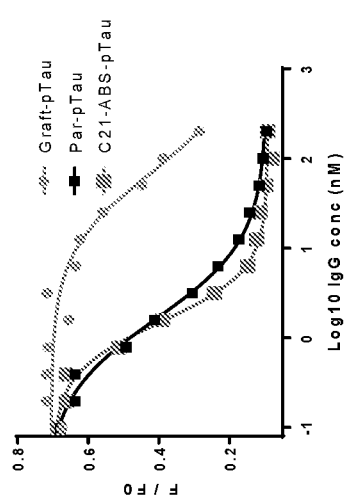
Figure 7C:
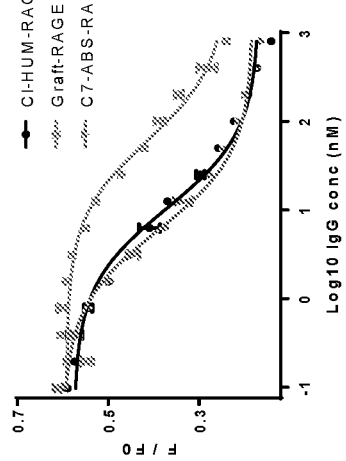

ABS leads in human IgG1 format were analyzed for specificity and stability. HTRF data (FIGS. 7A-7C), showed that the lead ABS-derived IgGs had successfully maintained full epitope competition with their respective parental clones (Table 1). Biacore analyses showed approximately 2-fold affinity improvements for C7-ABS-RAGE and C21-ABS-pTau over Par-RAGE and Par-pTau, respectively, while C2-ABS-A33 maintained equivalent affinity to Par-A33 (Table 1).

A baculovirus ELISA assay (FIG. 8A) has been reported in antibody polyreactivity screening as a risk indicator for poor pK in vivo. In this assay, no reactivity was observed for any of the RAGE, A33 or pTau clones in comparison to an internal positive control antibody. For the anti-RAGE and anti-A33 antibodies, a high-sensitivity Biacore assay was also established, to examine the possibility that v-gene engineering might lead to low affinity interactions with multiple classes of proteins. A panel of 18 fully-purified, recombinant, non-target proteins was examined. This method showed that C7-ABS-RAGE and C2-ABS-A33 both maintained highly specific binding to their respective antigens (FIGS. 8B and 8C). For the anti-pTau antibodies, specificity for pT231/pS235 was confirmed using Biacore assays (FIG. 8D). All ABS-derived leads in this study were, therefore, absent of the 'charge asymmetry', lipophilicity, off-target protein binding or other problems that can arise during v-gene engineering.

DSC analysis of IgG thermal stabilities demonstrated that C7-ABS-RAGE, C2-ABS-A33 and C21-ABS-pTau were highly stable. C7-ABS-RAGE was particularly thermostable with a Fab Tm of 85° C.; similar to Graft-RAGE, but almost 8° C. higher than that of the CL-Hum-RAGE (FIG. 2A, Table 1). This is a finding of note, as it highlighted that the presence of back-mutations in CL-Hum-RAGE had significantly decreased the stability of the v-domains in comparison to the highly stable graft. C21-ABS-pTau exhibited a Fab Tm of 70° C., 4° C. higher than Graft-pTau (FIG. 2B). In forced aggregation analyses C7-ABS-RAGE, C21-ABS-pTau and C2-ABS-A33 all showed <1% aggregation at 60° C. (FIG. 2D, E, F, Table 1). Graft-pTau, in contrast, exhibited >90% aggregation at 60° C. Importantly, analysis of pH shock tolerance (which mimics virus-killing pH hold in mAb manufacturing) also showed each of the IgGs to be highly stable, with <3% loss observed.

Example 4: Human t and b-Cell Epitope Minimization in ABS Leads

Figure 3B:
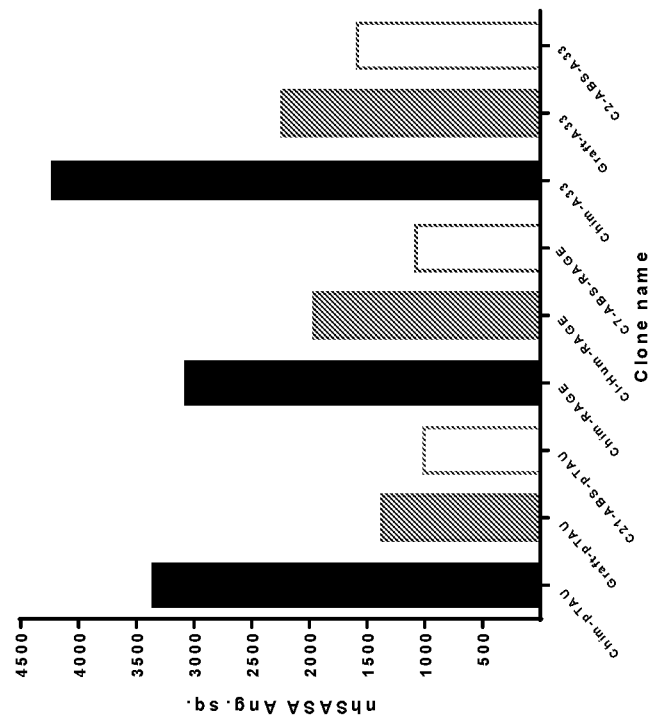
FIGS. 3A-3C show the assessment of potential immunogenicity and level of human identity in the v-domains of ABS-derived leads. (A) EpiMatrix was used to estimate the potential for T-cell epitope driven immunogenicity in the v-domains of C21-ABS-pTau, C2-ABS-A33 and C7-ABS-RAGE in comparison to 31 FDA-approved therapeutic antibodies that are rodent, humanized or "fully human" in sequence. Lower score suggests lower predicted immunogenicity. (B) Comparison of non-human solvent-accessible surface area (nhSASA, in $Å^2$) that contributed to the v-domains of parental (black), grafted (grey) and ABS (white) clones for pTau, A33 and RAGE. While CDR grafting dramatically lowers the nhSASA score in all cases, the ABS lead clones all exhibit minimized exposure of non-human amino acid motifs that might constitute b-cell epitopes. (C) Publically available, online tools which estimate levels of v-gene sequence identity to the human v-domain repertoire were used to calculate T20, Z and G scores for 31 approved therapeutic antibodies that are rodent, humanized or "fully human" in origin, plus the parental, graft (triangles) and ABS leads for pTau (black squares), RAGE (stars) and A33 (diamonds).
Figure 3A:
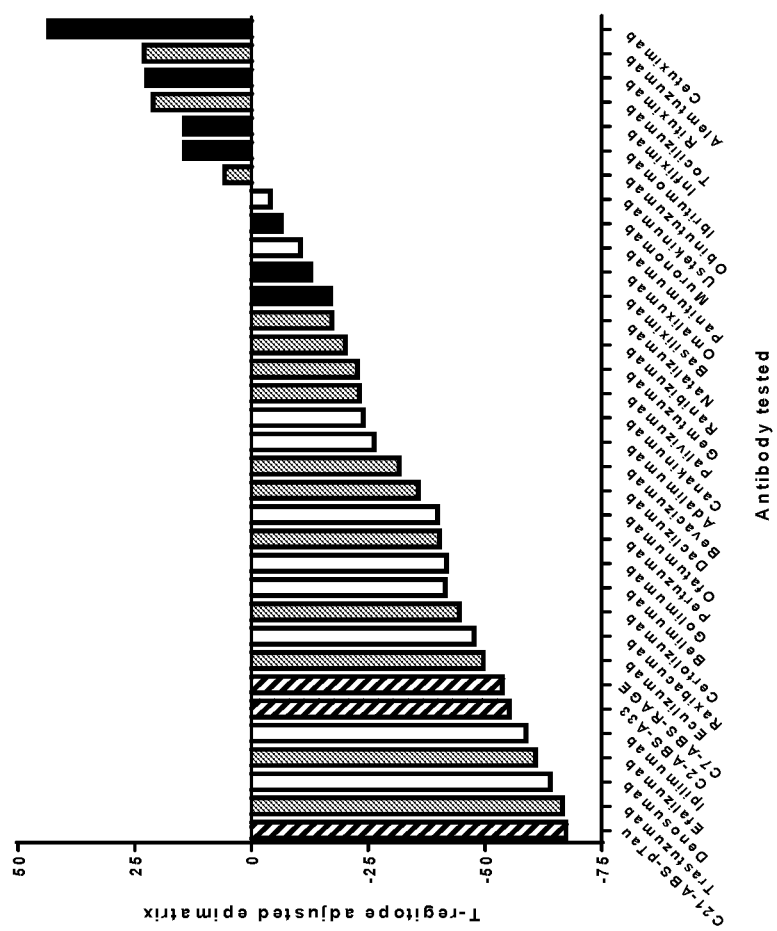

ABS leads and associated precursors were examined for potential t-cell epitope content using the EpiMatrix software, generating a t-regitope adjusted score for each clone (FIG. 3A), as suggested in the recent draft FDA immunogenicity assessment guidelines. C7-ABS-RAGE, C2-ABS-A33 and C21-ABS-pTau showed scores of −53.72, −55.22 and −67.33 points, respectively. This lowered the projected immunogenicity of all clones into the same range as antibodies such as trastuzumab, which has been well tolerated in the clinic, and lower than 'fully human' antibodies such as adalimumab (FIG. 3A).

Figure 9:
FIG. 9 shows in silico predictions for T-cell epitopes within the full $V_H$ and $V_L$ regions of lead clones were performed with EpiMatrix (Epivax, RI) (from top to bottom, SEQ ID NOs. 30-49, 45, 50-52, 30, 53-55). Possible epitopes are defined as 9-mer sequences with four or more hits and are shown based on potential epitopes different to human germ-line, potential epitopes in germ-line sequence to which most patients should exhibit self-tolerance, and epitopes in germ-line sequence reported to be potential t-regulatory cell stimulating sequences. Where potential epitopes overlap the coloring of the C-terminal epitope is used. C7-ABS-RAGE has the lowest immunogenicity potential of the anti-RAGE clones as it contains 2 potential t-cell epitopes and 13 potential t-regitopes, in comparison to 9 potential t-cell epitopes and only one t-regitope in Par-RAGE and 2 potential t-cell epitopes with 10 potential t-regitopes in CL-Hum-RAGE. Notably, the ABS germlining of the c-terminal end of the CDR-H2 (VKD>VKG) reinstates a potential germline t-regitope, as does the germlining of the $V_L$ FW2. Similarly, C21-ABS-pTau has the lowest immunogenicity potential of the anti-pTau clones as it contains only 1 potential t-cell epitope and 9 potential t-regitopes, in comparison to 5 potential t-cell epitopes and only one t-regitope in Par-pTau and 2 potential t-cell epitopes with 9 potential t-regitopes in Graft-pTau.

Analysis at the individual peptide level predicted that t-cell epitope content was clearly reduced for C7-ABS-RAGE and C21-ABS-pTau in comparison to their respective parental forms (FIG. 9). T-regitope content was also increased. Notably, the ratio of t-cell epitopes to t-regitopes was improved in C7-ABS-RAGE in comparison to CL-Hum-RAGE. Indeed, the removal of the back mutation found in the VL FW2 of CL-Hum-RAGE not only aided stabilization of the v-domains (FIG. 2A), but also removes a t-cell epitope and converts it into a germline t-regitope (FIG. 9). Analysis of the sequence of C21-ABS-pTau showed that the ABS-derived germlining at key positions in the CDR-H2 had ablated a foreign t-cell epitope at the N-terminus of the loop that had been introduced by CDR-grafting. Some potential epitopes of foreign sequence were still present however, even after ultra-humanization (FIG. 9). This reflects the need to retain certain key contact residues in the paratope and balance target recognition with t-cell epitopes and overall "humanness". The L46T back mutation in C21-ABS-pTau was not predicted to introduce a t-cell epitope and this clone retained only a single predicted foreign t-cell epitope (in comparison to 5 in Par-pTau), driven by Q33 in the $V_H$.

As a surrogate for b-cell epitope availability, non-human solvent-accessible surface area (nhSASA, measured in $Å^2$) was calculated for the parental, graft and ABS lead clones. Clones C7-ABS-RAGE, C2-ABS-A33 and C21-ABS-pTau demonstrated minimized non-human surface area (FIG. 3B). C7-ABS-RAGE exhibited a reduction in nhSASA to 1077.6 $Å^2$, in comparison to the Par-RAGE and Graft-RAGE at 3084.8 and 1957.6, respectively. This represents a 45% reduction even in comparison to the Graft-RAGE. C21-ABS-pTau demonstrated a reduction to 1009.0 $Å^2$, in comparison to the Par-pTau and Graft-pTau at 3365.3 and 1372.1, respectively. C2-ABS-A33 showed a reduction to 1583.9 $Å^2$, in comparison to the Par-pTau and Graft-pTau at 4260.7 and 2240.2, respectively (FIG. 3B).

Figure 3C:
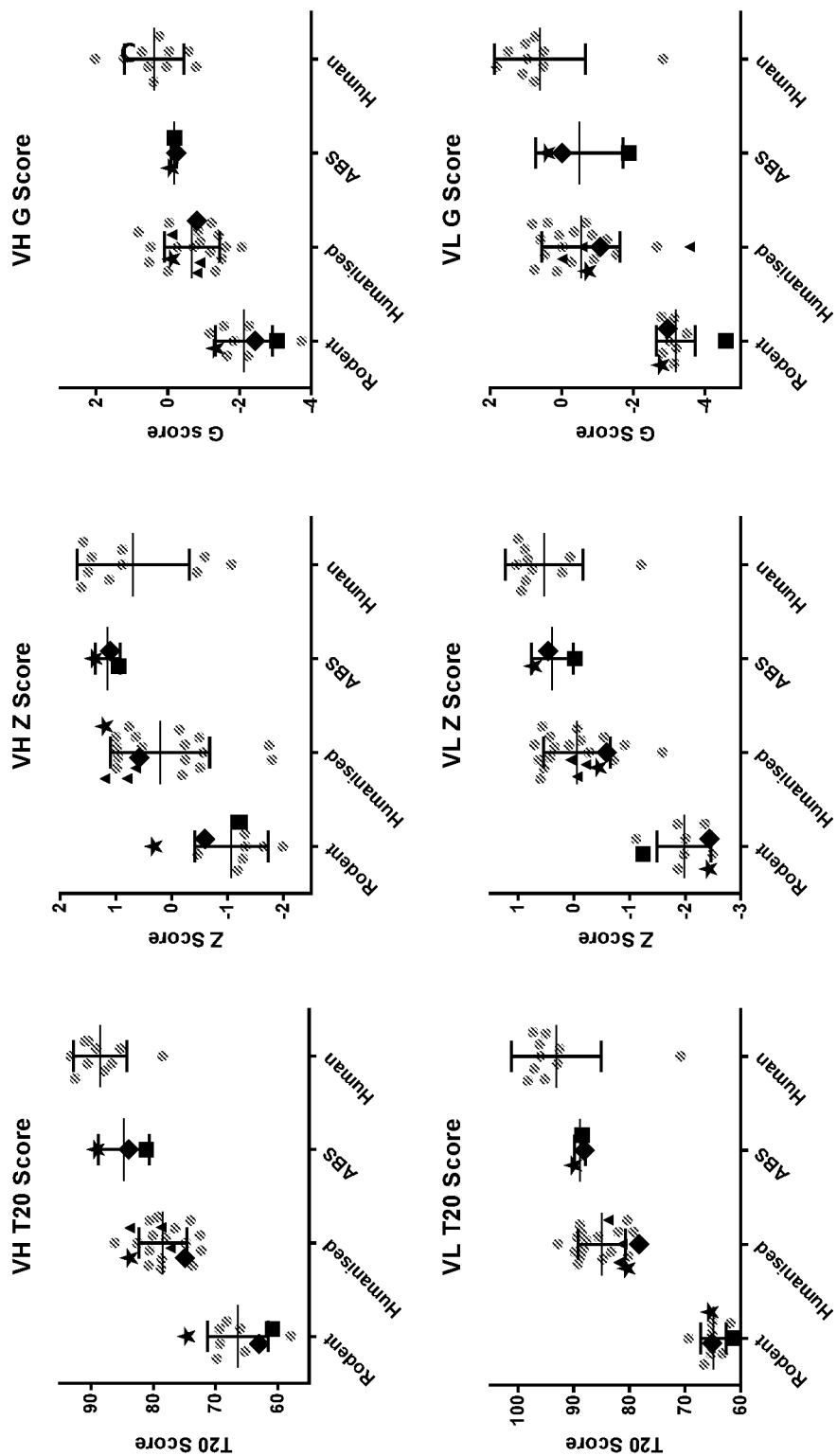

Further analyses were performed using publically available software, to numerically define the overall levels of human repertoire identity of the parental and ABS-derived leads, in comparison with 33 antibodies currently approved as therapeutics with murine, humanized or "fully human" v-domains. These analyses showed that the ABS clones had distinctly improved T20, G and Z scores over parental clones. Indeed, the C7-ABS-RAGE clone had scores placing it in the range of values found for the 'fully human' antibody group, with the C2-ABS-A33 and C21-ABS-pTau clones close behind (FIG. 3C).

Figure 4A:
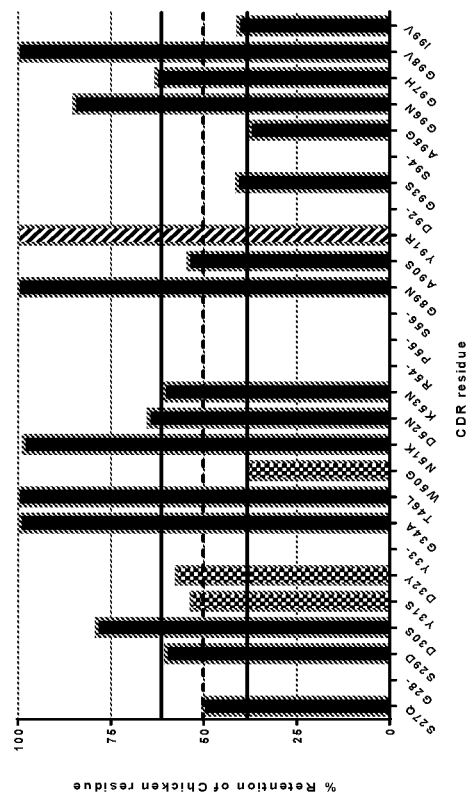
FIGS. 4A-4B show CDR redundancy analyses in anti-pTau via mutational tolerance analysis. A plot of chicken amino acid retention frequencies in the CDRs of the ELISA-positive population of 188 unique clones from ABS-pTau library screening is shown for (A) $V_H$ and (B) $V_L$ domains, respectively. Only those residues targeted for binary human/chicken substitution are plotted. CDR residues noted on the X-axis whose values are set at 0 were identical human-chicken and not sampled in the library, but are included in the figure for clarity (e.g G26-). In both plots the mean human-chicken frequency (~50%) in sequenced clones from the starting library is plotted as a dashed line, with standard deviations as solid bold lines. Residues predicted to be making antigen contacts in a co-crystal structural analysis that were also retained at >80% (i.e. where mutational tolerance was low) are highlighted with striped bars. Predicted contact residues not found to be retained are highlighted in checked bars.
Figure 4B:
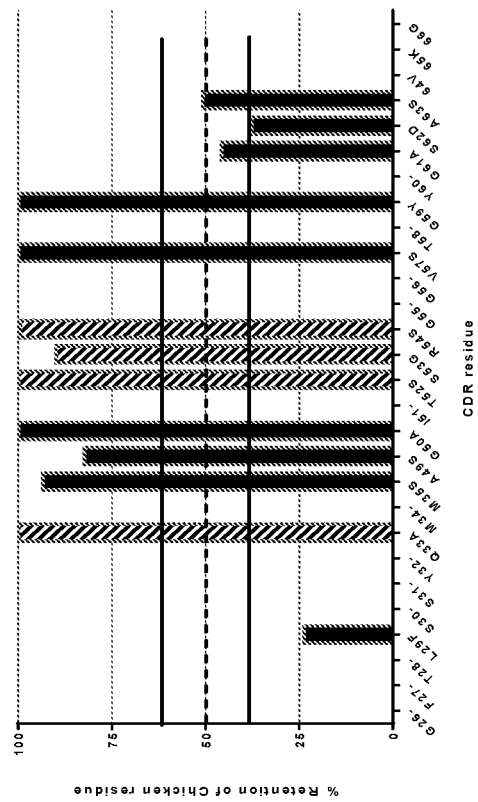

Example 5: Strongly Maintained Non-Human CDR Content Via Mutational Tolerance and Structural Analyses The screening of output clones from the ABS-pTau library identified 188 sequence-unique hits with binding signals ≥the parental scFv (data not shown). For residues targeted in the library for binary substitution, positional amino acid usage frequencies were calculated for these hits and expressed as a percentage (FIGS. 4A-4B). Amino acid positions with parental residue usage frequencies of >75% were labeled "strongly maintained" (SM), i.e. with the chicken residue being positively selected. Those with frequencies below 25% were labeled "strongly deleted" (SD), i.e. the human germline residue being preferred.

Heatmaps of non-human residue content in the anti-pTau binding site for Par-pTau, Graft-pTau and C8-ABS-pTau were also generated (data not shown). The heatmaps show that the ABS process better defines residues that may be important for antigen-binding function.

Figure 6:
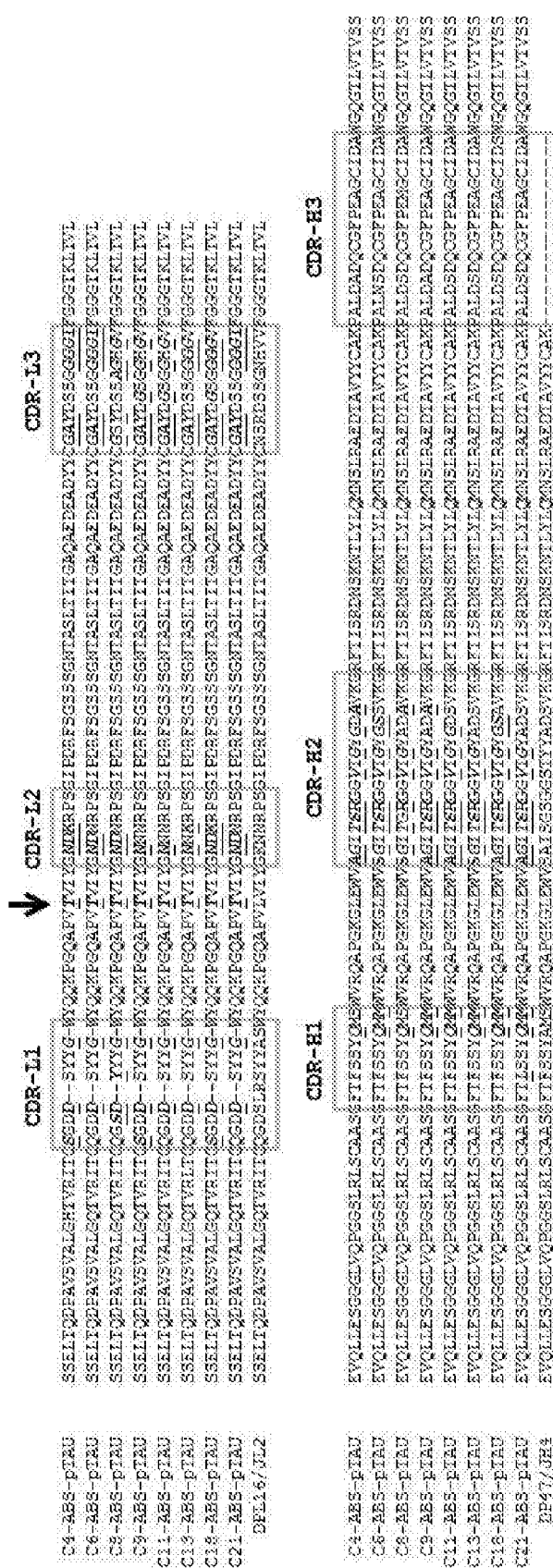
FIG. 6 shows sequence alignments for $V_L$ and $V_H$ domains of 8 prioritized lead clones from the ABS-pTau library (from top to bottom, SEQ ID NOs. 12-29). CDR regions are boxed in grey. Amino acids differing from the human DPL16/JL2 and DP47/JH4 germlines are underlined. Black arrow indicates the position of the L46T mutation positively selected in the FW2 of all clones showing functional binding to target.

When the SM residues were compared with those previously predicted to be key contacts via a co-crystal structure, the two populations were found to clearly overlap. Across both chains, however, SM positions were found to be only 29.6% (17/55) of the total CDR residues outside the CDR-H3. In the $V_H$ domain, Q33, T52, S53, R54 were all predicted contact residues and all were SM, with retention frequencies >90%. G55 and G56 were also predicted to be key contacts but were not sampled in the library, as they were fully conserved human to chicken. Interestingly, the S53G substitution, while not heavily favored in the selected population, could clearly be functional, as seen in the C21-ABS-pTau clone, so long as T52, R54, G55 and G56 were maintained (FIG. 6). Other SM residues in the $V_H$ were found to be contact-proximal and/or desirable for appropriate presentation of the contact residues, such as M35, A49, G50, V57 and G59.

Of 4 predicted contact residues in the $V_L$, only Y91 was found to be SM and was retained at 100%. Other SM residues were predominantly found in stem-loop positions of CDR-L3 (G89, G96, G98) and CDR-L1 (G34), which may be influential on loop structure. Additionally, the SM N51 site forms structurally supportive hydrogen bonds between the CDR-L1 and $V_L$ FW2.

Out of 33 residues sampled by binary substitution, only a single SD residue ($V_H$L29) was identified, suggesting that all 16 other non-SM residues were interchangeable. On the basis of these analyses, we interpreted the "strongly non-human CDR content", meaning those parental residues that are unlikely be germlined, even if compensated by the mutation of a residue elsewhere in the paratope (FIGS. 4A-4B). This also informed the minimization of chicken residue content by making a combination clone, Combo-ABS-pTau. This clone contains the most "human" variant of each CDR that had been observed in the top ABS-pTau hits (FIG. 6, Table 1). This reduced non-human content by another 6 residues versus C21-ABS-pTau, pushing the Combo-ABS-pTau to 76% human in the CDRs, but adding one more predicted t-cell epitope than C21-ABS-pTau (FIG. 9). The retained non-human residues in Combo-ABS-pTau closely matched to the SM set of residues described above (FIGS. 4A-4B). Combo-ABS-pTau was found to be soluble, stable and maintained the binding affinity and specificity of Par-pTau (Table 1, FIG. 2A).

Example 6: Additional CDR-Humanized Antibodies

The sequences of additional CDR-humanized antibodies are shown in Tables 7-12. CDR sequences are in bold. Donor v-genes (murine, rat, rabbit, or chicken) and human germline DP/J designations are included. CDR residues from the parent clone that differ from human germline are underlined.

Summary

Despite considerable investigation, current antibody humanization methods often create therapeutic molecules with significant risk factors for the failure of a lead drug due to potential immunogenicity and/or poor pK in the clinic, or because the molecule cannot be manufactured and delivered in a cost-effective manner. These risks are potentially exacerbated if the lead is derived from hosts such as rats, rabbits or chickens, rather than the heavily characterized antibody repertoires of mice and humans.

Antibodies from alternative immune species can provide excellent IgGs with unique functional characteristics against problematic targets (e.g. highly conserved across species), but their antibodies are also known to exhibit unique sequence/structural features. These antibodies therefore require maximal humanization and development validation if they are to gain broad acceptance as potential clinical leads. Indeed, despite their therapeutic potential, there are currently no chicken antibodies and only one known humanized rabbit antibody in the clinic. In establishing the ABS technology we have shown that it is possible to minimize clinical and manufacturing concerns, by making antibodies from all 3 sources stable, soluble and of low immunogenicity risk. When analyzed in silico, human identity and t-cell epitope risk appeared to be indivisible between C7-ABS-RAGE and currently marketed 'fully human' antibodies, with C21-ABS-pTau and C2-ABS-A33 comparable to the best of the humanized mouse antibodies currently approved for clinical use.

Other humanization methods do not factor in the CDRs themselves as mediators of stability and solubility, in addition to the frameworks. Antibodies from species with limited starting framework diversity in both the $V_H$ and $V_L$ genes fit the ABS technology particularly well. Indeed, chickens and rabbits use $V_H$ repertoires that are highly homologous to human $V_H3$ domain. For murine antibodies, FW diversity in the functional repertoire is much higher than for chickens or rabbits. Prior estimations of v-domain homology, pairing angle and $V_H$-$V_L$ packing are therefore prudent, to aid the prediction of whether preferred germlines.

Previous methods that maintain the animal CDR-H3 (+/−CDR-L3), then sample human repertoire diversity to return binding affinity, may suffer from an inability to recapitulate the critical structural characteristics found outside the CDR-H3s of non-murine antibodies, as exemplified by our anti-pTau mAb. These methods also frequently leave, or generate, significant numbers of framework mutations away from germline which can lower the stability of v-domains. Indeed, the C7-ABS-RAGE clone illustrated that the CDRs from XT-M4 could be heavily germlined and the back mutations from classical humanization fully removed, greatly improving stability in the final molecule.

This study illustrates that 3 separate antibodies from 3 species, targeting 3 different epitopes, all have high levels of sequence redundancy in their paratopes that can be exploited for v-domain risk reduction engineering without the need for prior structural analyses. The retention of SM residues in the CDRs of selected clones after ABS strongly correlated with the prediction of key contact residues in the co-crystal structure of anti-pTau with its target antigen. Residues were also found to be SM if they were likely to be desirable for the correct presentation of CDR loops. In only one case was a framework back mutation necessary to include during humanization ($V_L$ L46T, anti-pTau). This suggests that many of the back mutations required during classical humanization of anti-RAGE and anti-A33 were likely necessitated by the retention of non-human CDR residues that clash with human framework residue side chains, but are functionally redundant in antigen binding. ABS intrinsically minimized redundant animal-derived CDR content by selecting for the retention of essential non-human residues and allowing the rest of the CDR to be converted to the sequence of the destination v-gene. This approach thereby simultaneously optimized all functional parameters of these three potential therapeutic antibodies, which were derived from species often used in monoclonal antibody generation against challenging therapeutic targets.

Materials and Methods for Examples 1-6

ScFv-based library designs. Parental and CDR-grafted forms of rat Anti-RAGE, rabbit anti-A33 and chicken anti-pTau antibodies, plus a classically humanized (CL-Hum) version of XT-M4 were synthesized (Geneart™) in $V_L$-$V_H$ scFv format, ligated into the phagemid pWRIL-1 and cloned into E. coli TG1 cells. Soluble periplasmic E. coli expression was confirmed by SDS-PAGE and western blot. Function of each construct was assessed via direct binding ELISA (as purified scFv or periprep). Based on these scFv constructs, Augmented Binary Substitution libraries were designed in silico (FIG. 1) and synthesized as finished dsDNA scFv fragments (Geneart™). Anti-pTau is a Type 1 chicken IgG with critical secondary structural characteristics in CDR H2 and H3, and a recent structural study of a humanized chicken antibody suggested that a back mutation at $V_λ$ FW2 position 46 (L46T) is critical to the correct packing of the $V_λ$ against the CDR-H3 stem-loopTo examine whether or not this was still true when random point mutations are also being simultaneously sampled in the CDR-H3, a binary substitution (L/T) was allowed at VA position 46 in the ABS-pTau library.

Construction, Selection and Screening of scFv Libraries.

The ABS scFv libraries were constructed rescued and selected. Solution phase selection on biotinylated target antigen with streptavidin beads was employed throughout. Post-selection ELISA and HTRF screening, epitope competition analyses and reformatting were performed. For details, see Finlay, W. J. et al. *J Mol Biol* 388, 541-558 (2009).

IgG Expression and Biophysical Analyses.

IgGs were transiently expressed in HEK-293f cells after transfection with IgG expression plasmids and lipofectamine 2000 (Invitrogen), according to manufacturer's protocols. Automated purification was carried out using ProPlus resin tips on the MEA system (Phynexus). Differential Scanning Calorimetry, Forced Aggregation and pH stability analyses were performed according to King, A. C. et al. *Protein Sci* 20, 1546-1557 (2011).

Biacore Analysis of Binding Kinetics.

Biacore analysis was performed using the T-200 biosensor, series S CM5 chips, an amine-coupling kit, 10 mM sodium acetate immobilization buffer at pH 5.0, 10×HBS-P running buffer and NaOH for regeneration (GE Healthcare). Kinetic assay conditions were established to minimize the influence of mass transfer, avidity and rebinding events. A predefined ligand immobilization program was set up to immobilize approximately 100 Response Units (RU) of IgG on the chip. Purified target proteins were diluted in HBS-P running buffer to a range of final concentrations and injected at 50 μl/min for 3 mins. Dissociation was allowed to proceed for 10 min followed by a 5 sec pulse of 20 mM NaOH for regeneration of the chip surface. All sensorgrams were analyzed using the Biacore T-200 evaluation software.

Binding Specificity Analyses.

Anti-RAGE, pTau and A33 antibodies were tested for polyreactivity by ELISA and Biacore analyses. ELISAs were performed against single stranded DNA, double stranded DNA, insulin and lipopolysaccharide, and against Baculovirus particles All polyreactivity analyses used parental antibodies and Pfizer in-house positive and negative control antibodies.

Biacore specificity analyses were performed using the T-200 biosensor, series S CM5 chips, an amine-coupling kit, 10 mM sodium acetate immobilization buffer at pH 5.0, 10×HBS-P running buffer and NaOH for regeneration (GE Healthcare). A predefined ligand (IgG) immobilization program was set up to immobilize approximately 300 Response Units (RU) on the flow cell for each IgG to be tested. For Anti-RAGE and anti-A33, a panel of fully-purified recombinant target and non-target antigens were diluted in HBS-P running buffer to a final concentration of 500 nM. Four groups of antigens were examined, including: cell membrane proteins (mTRKB, hTRKB, mEGFR, hEGFR, hFceR1, hIL-21R, mICAM1, mICAM2, hICAM1, hCD33, hLAMP-1, hLOX-1, and), soluble signaling molecules (mTNFa, hVEGF, hCXCL13) and albumins (BSA, HSA and MSA). These proteins were injected at 50 μl/min for 3 min, followed by a 5 sec pulse of 20 mM NaOH for regeneration of the chip surface. For pTau, a series of pTau-derived phosphorylated and non-phosphorylated peptides were flowed, as in Shih et al.[3]. All sensorgrams were analyzed using the Biacore T-200 evaluation software.

Modeling Analyses.

Variable domain structural models were generated for the parental, humanized and ABS humanized variants of the anti-pTAU and the anti-RAGE antibodies. The Protein Databank (PDB) crystal structure 4GLR of the anti-pTau antibody was used for the parental pTau model. For the humanized and ABS humanized pTau antibodies, we generated homology models using Modeller version 9.12 with the PDB structures of 4GLR and 3G6A as templates. For all three XTM4 structures, homology models were also generated using Modeller with template structure 1fvd, 1dql, 3hns, 1mhp, 1bbj, 1bog, 1aif, 1arl and 1rmf for the parental; 1fvd, 1dql, 1mhp, 3hns, 1bbj, 1bog, 1aif, 1arl and 1 rmf for the humanized; and 1mhp, 3hns, 2cmr, 1gig, 2ghw, 1aif and 1rmf for the ABS humanized. The non-human solvent accessible surface area (nhSASA) was calculated using the "Solvent Accessibility" calculator in the molecular modeling software suite Discovery Studio Client 4.0 (Accelrys Inc). The nhSASA was defined as the sum of the side-chain SASA of residues that were not identical to germline.

In Silico t-Cel Epitope Assessment.

Sequences of antibody $V_H$ and $V_L$ regions were analyzed by EpiMatrix (Epivax, RI) Briefly, each domain was parsed into overlapping 9-mer peptides with each peptide overlapping the last by eight amino acids. Each peptide was then scored for predicted binding to each of eight HLA Class II alleles (DRB1*0101, DRB1*0301, DRB1*0401, DRB1*0701, DRB1*0801, DRB1*1101, DRB1*1301, and DRB1*1501) which represent HLA supertypes covering 97% of human populations worldwide. Any peptide scoring above 1.64 on the EpiMatrix "Z" scale (approximately the top 5% of the random peptide set) was classed as a "hit" for binding to the MHC molecule for which it was predicted. Peptides scoring four or more hits from the eight alleles predicted are considered as possible epitopes. Some germline sequences have been suggested to induce t regulatory cells. A previous study with a therapeutic protein demonstrated a correlation between an immunologically active peptide, i.e. t-cell epitope, and the EpiMatrix prediction (Koren, E. et al. *Clin Immunol* 124, 26-32 (2007)).

The various features and embodiments of the present invention, referred to in individual sections above apply, as appropriate, to other sections, mutatis mutandis. Consequently features specified in one section may be combined with features specified in other sections, as appropriate.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

TABLE 1

CDR sequence, affinity and stability characteristics of parental, grafted and ABS-derived lead clones.

| | CDRL1* | CDRL2 | CDRL3 | CDRH1 | CDRH2 | CDRH3 | % germline in CDRs | # FW mutations |
|---|---|---|---|---|---|---|---|---|
| DPK9/DP54 germlines | RASQSISSYLN | AASSLQS | QQSYSTPLT | GFTFSSYWMS | ANIKQDGSEKYYVDSVKG | n/a | 100 | n/a |
| CL-Hum-RAGE | RASQDVGIYVN | RATNLAD | LEFDEHPLT | GFTFSNYWMT | ASIDNSGDNTYYPDSVKD | GGDITTGFDY | 45 | 5 |
| Graft-RAGE | RASQDVGIYVN | RATNLAD | LEFDEHPLT | GFTFSNYWMT | ASIDNSGDNTYYPDSVKD | GGDITTGFDY | 45 | 0 |
| C7-ABS-RAGE | RASQSIGSYLN | RASSLAS | LEFDEHPLT | GFTFSSYWMS | ASIDQDGSNKYYPDSVKG | GGDITTGLDY | 74 | 0 |
| DPK9/DP47 germlines | RASQSISSYLN | AASSLQS | QQSYS--TPLT | GFTFSSYAMS | SAISGSGGSTYYADSVKG | n/a | 100 | n/a |
| Chim-A33 | LASEFLFNGVS | GASNLES | LGGYSGSSGLT | GIDFSHYGIS | AYIYPNYGSVDYASWVNG | DRGYYSGSRGTRLDL | 39 | n/a |
| Graft-A33 | LASEFLFNGVS | GASNLES | LGGYSGSSGLT | GIDFSHYGIS | SYIYPNYGSVDYASWVNG | DRGYYSGSRGTRLDL | 39 | 0 |
| C6-ABS-A33 | RASQFLFNGVS | AASNLES | QGGYSGSTGLT | GFTFSHYGIS | SYIYPSYGSTDYASSVKG | DRGYYSGSRGTRLDL | 56 | 0 |
| DPL16/DP47 germlines | QGDSLRSYYAS | GKNNRPS | NSRDSSGNHVV | GFTFSSYAMS | SAISGSGGSTYYADSVKG | n/a | 100 | n/a |
| Chim-pTau | SGSD--YDYG- | WNDKRPS | GAYDGSAGGGI | GFTLSSYQMM | AGITSRGGVTGYGSAVKG | PALDSDQCGFPEA-GCIDA | 41 | n/a |
| Graft-ABS-pTau | SGSD--YDYG- | WNDKRPS | GAYDGSAGGGI | GFTLSSYQMM | AGITSRGGVTGYGSAVKG | PALDSDQCGFPEA-GCIDA | 41 | 0 |
| C21-ABS-pTau | QGDD--SYYG- | GNDNRPS | GAYDSSGGGGI | GFTLSSYQMM | AGITGRGGVTGYADSVKG | PALDSDQCGFPEA-GCIDA | 65 | 1 |
| Com-ABS-pTau | QGDD--SYYG- | GNNNRPS | GSYDSSGGHGV | GFTFSSYQMS | SGITGRGGVTGYADSVKG | PALDSDQCGFPEM-GCIDA | 76 | 1 |
| From top to bottom: | SEQ ID NOs: 278-290 | SEQ ID NOs: 291-303 | SEQ ID NOs: 304-316 | SEQ ID NOs: 317-329 | SEQ ID NOs: 330-342 | SEQ ID NOs: 343-352 | | |

| | IC50 (nM) HTRF | kD (nM) SPR | % Agg 60° C. | Tm (° C.) | % Agg pH shock |
|---|---|---|---|---|---|
| DPK9/DP54 germlines | n/a | n/a | n/a | n/a | n/a |
| CL-Hum-RAGE | 10.3 | 31.0 | 14 | 77 | 3.2 |

TABLE 1-continued

CDR sequence, affinity and stability characteristics of parental, grafted and ABS-derived lead clones.

| | | | | | |
|---|---|---|---|---|---|
| Graft-RAGE | >61.9 | ND | 0 | 84 | 1.8 |
| C7-ABS-RAGE | 5.8 | 17.0 | 0 | 85 | 2.1 |
| DPK9/DP47 germlines | n/a | n/a | n/a | n/a | n/a |
| Chim-A33 | 2.9 | 2.1 | 0 | 74 | 1.5 |
| Graft-A33 | ND | ND | ND | ND | ND |
| C6-ABS-A33 | 2.7 | 2.1 | 0 | 74 | 0.4 |
| DPL16/DP47 germlines | n/a | n/a | n/a | n/a | n/a |
| Chim-pTau | 1.6 | 0.41 | 17 | 70 | 1.2 |
| Graft-ABS-pTau | >64.7 | NB | 90 | 66 | 0.8 |
| C21-ABS-pTau | 2.1 | 0.25 | 3 | 70 | 1.2 |
| Com-ABS-pTau | ND | 0.50 | 2 | 71 | 1.4 |

*The pTau CDR-L1 is shorter than its DPL16 counterpart by 3 amino acids. Sequence dashes in this CDR are added to show the spacing of sampled residues.
Residues differing from human germline are underlined.

TABLE 2

Exemplary Human V$_H$ germline sequences

Human VH1 germline sequence (from top to bottom, SEQ ID NOs. 56-69).

| VH1 | FW1 | CDR1 | FW2 | CDR2 | FW3 |
|---|---|---|---|---|---|
| IGHV1-2 | QVQLVQSGAEVKKPGASVKVSCKAS | GYTFTGYYMH.. | WVRQAPGQGLEWM | GRINP..NSGGTNYAQKFQG | RVTSTRDTSISTAYMELS RLRSDDTVVYYCAR. |
| IGHV1-3 | QVQLVQSGAEVKKPGASVKVSCKAS | GYTFTSYAMH.. | WVRQAPGQRLEWM | GWINA..GNGNTKYSQKFQG | RVTITRDTSASTAYMELS SLRSEDIAVYYCAR. |
| IGHV1-8 | QVQLVQSGAEVKKPGASVKVSCKAS | GYTFTSYDIN.. | WVRQATGQGLEWM | GWMNP..NSGNTGYAQKFQG | RVTMTRNTSTAYMELS SLRSEDTAVYYCAR. |
| IGHV1-18 | QVQLVQSGAEVKKPGASVKVSCKAS | GYTFTSYGIS.. | WVRQAPGQGLEWM | GWISA..YNGNTNYAQKLQG | RVTMTTDTSTSTAYMELR SLRSDDTAVYYCAR. |
| IGHV1-24 | QVQLVQSGAEVKKPGASVKVSCKVS | GYTLTELSMH.. | WVRQAPGKGLEWM | GGFDP..EDGETIYAQKFQG | RVTMTEDTSTDTAYMELS SLRSEDTAVYYCAT. |
| IGHV1-38-4 | QVQLVQSWAEVRKSGASVKVSCSFS | GFTITSYGIH.. | WVQQSPGQGLEWM | GWINP..GNGSPSYAKKFQG | RFTMTRDMSTITAYTDLS SLTSEDMAVYYYAR. |
| IGHV1-45 | QMQLVQSGAEVKKTGSSVKVSCKAS | GYTFTYRYLH.. | WVRQAPGQALEWM | GWITP..FNGNTNYAQKFQD | RVTITRDRSMSTAYMELS SLRSEDTAMYYCAR. |
| IGHV1-46 | QVQLVQSGAEVKKPGASVKVSCKAS | GYTFTSYYMH.. | WVRQAPGQALEWM | GIINP..SGGSTSYAQKFQG | RVTMTRDISTSTVYMELS SLRSEDTAVYYCAR. |
| IGHV1-58 | QMQLVQSGPEVKKPGTSVKVSCKAS | GFTFTSSAVQ.. | WVRQARGQRLEWI | GWIVV..GSGNTNYAQKFQE | RVTITRDMSTSTAYMELS SLRSEDTAVYYCAA. |
| IGHV1-68 | QVQLGQSEAEVKKPGASVKVSCKAS | GYTFTCCSLH.. | WLQQAPGQGLERM | RWITL..YNGNTNYAKKFQG | RVTITRDMSLRTAYIELS SLRSEDSAVYYWAR. |
| IGHV1-68-2 | EVQLVQSGAEVKKPGATVKISCKVS | GYTFTDYYMH.. | WVQQAPGKGLEWM | GLVDP..EDGETIYAEKFQG | RVTITADTSTDTAYMELS SLRSEDTAVYYCAT. |
| IGHV1-69 | QVQLVQSGAEVKKPGSSVKVSCKAS | GGTFSSYAIS.. | WVRQAPGQGLEWM | GGIIP..IFGTANYAQKFQG | RVTITADESTSTAYMELS SLRSEDTAVYYCAR. |

TABLE 2-continued

Exemplary Human V<sub>H</sub> germline sequences

| IGHV1-69D | QVQLVQSGAEVKKPGSSVKVSCKAS | GGTFSSYAIS.. | WVRQAPGQGLEWMGGIIP...IFGTANYAQKFQG | RVTITADESTSTAYMELS SLRSEDTAVYYCAR. |
|---|---|---|---|---|
| IGHV1-NL1 | QVQLLQPGVQVKKPGSSVKVSC*AS | RYTFTKYFTR.. | WV*QSPGQGHXWMG*INP...YNDNTHYAQTFWG | RVTITSDRSMSTAYMELS XLRSEDMVVYYCVR. |

Human VH2 germline sequence (from top to bottom, SEQ ID NOs. 70-73).

| VH2 | FW1 | CDR1 | FW2 | CDR2 | FW3 |
|---|---|---|---|---|---|
| IGHV2-5 | QITLKESGPTLVKPTQTLTLTCTFS | GFSLSTSGVGVG | WIRQPPGKALEWLALIY...WNDDKRYSPSLKS | | RLTITKDISKNQVVLTMT NMDFVDTATYYCAHR |
| IGHV2-10 | QVTLKESGPALVKPTQTLMLTCTFS | GFSLSTSGMGVG | *ICQPSAKALEWLAHIY....*NDNKYYSPSLKS | | RLIISKDTSKNEVVLTVI NMDIVDTATHYCARR |
| IGHV2-26 | QVTLKESGPVLVKPTETLTLTCTVS | GFSLSNARMGVG | WIRQPPGKALEWLAHIF...SNDEKSYSTSLKS | | RLTISKDTSKSQVVLTMT NMDPVDTATYYCARI |
| IGHV2-70 | QVTLRESGPALVKPTQTLTLTCTFS | GFSLSTSGMCVS | WIRQPPGKALEWLALID...WDDSKYYSTSLKT | | RLTISKDTSKNQVVLTMT NMDPVDTATYYCARI |

Human VH3 germline sequence (from top to bottom, SEQ ID NOs: 74-114):

| VH3 | FW1 | CDR1 | FW2 | CDR2 | FW3 |
|---|---|---|---|---|---|
| IGHV3-7 | EVQLVESGGGLVQPGGSLRLSCAAS | GFTFSSYWMS.. | WVRQAPGKGLEWVANIKQ..DGSEKYYVDSVKG | | RFTISRDNAKNSLYLQMN SLRAEDTAVYYCAR. |
| IGHV3-9 | EVQLVESGGGLVQPGRSLRLSCAAS | GFTFDDYAMH.. | WVRQAPGKGLEWVSGISN..NSGSIGYADSVKG | | RFTISRDNAKNSLYLQMN SLRAEDTALYYCAKD |
| IGHV3-11 | QVQLVESGGGLVKPGGSLRLSCAAS | GFTFSDYYMS.. | WIRQAPGKGLEWVSYISS..SGSTIYYADSVKG | | RFTISRDNAKNSLYLQMN SLRAEDTAVYYCAR. |
| IGHV3-13 | EVQLVESGGGLVQPGGSLRLSCAAS | GFTFSSYDMH.. | WVRQAIGKGLEWVSAIG...TAGDTYYPGSVKG | | RFTISRENAKNSLYLQMN SLRAGDTAVYYCAR. |
| IGHV3-15 | EVQLVESGGGLVKPGGSLRLSCAAS | GFTFSNAWMS.. | WVRQAPGKGLEWVGRIKSKTDGGTTDYAAPVKG | | RFTISRDDSKNTLYLQMN SLKTEDTAVYYCTT. |
| IGHV3-16 | EVQLVESGGGLVQPGGSLRLSCAAS | GFTFSNSDMN.. | WARKAPGKGLEWVSGVSW..NGSRTHYVDSVKR | | RFTISRDNSRNSLYLQKN RRRAEDMAVYYCVR. |
| IGHV3-19 | TVQLVESGGGLVEPGGSLRLSCAAS | GFTFSNSDMN.. | WVRQAPGKGLEWVSGVSW..NGSRTHYADSVKG | | RFTISRDNSRNFYLQQMN SLRPEDMAVYYCVR. |
| IGHV3-20 | EVQLVESGGGLVRPGGSLRLSCAAS | GFTFDDYGMS.. | WVRQAPGKGLEWVSGINW..NGGSTGYADSVKG | | RFTISRDNAKNSLYLQMN SLRAEDTALYHCAR. |
| IGHV3-21 | EVQLVESGGGLVKPGGSLRLSCAAS | GFTFSSYSMN.. | WVRQAPGKGLEWVSSISS..SSSYIYYADSVKG | | RFTISRDNAKNSLYLQMN SLRAEDTAVYYCAR. |
| IGHV3-22 | EVHLVESGGALVQPGGSLRLSCAAS | GFTFSYYYMS.. | GVRQAPGKGLEWVGFIRNKANGGTTE*TTSVKG | | RFTISRDDSKSITYLQMK SLKTEDTAVYYCAR. |
| IGHV3-23 | EVQLLESGGGLVQPGGSLRLSCAAS | GFTFSSYAMS.. | WVRQAPGKGLEWVSAISG..SGGSTYYADSVKG | | RFTISRDNSKNTLYLQMN SLRAEDTAVYYCAK. |
| IGHV3-23D | EVQLLESGGGLVQPGGSLRLSCAAS | GFTFSSYAMS.. | WVRQAPGKGLEWVSAISG..SGGSTYYADSVKG | | RFTISRDNSKNTLYLQMN SLRAEDTAVYYCAK. |
| IGHV3-25 | EMQLVESGGGLQKPAWSPRLSCAAS | QFTFSSYYMN.. | CVRQAPGNGLELV*QVNP..NGGSTYLIDSGKD | | RFNTSRDNARNTLHLQMN SLKTEDTALY*CTR. |
| IGHV3-29 | EVELIEPTEDLRQPGKFLRLSCVAS | RFAFSSF*MS.. | PVHQSAGKGLE*VIDIKD..DGSQIHHADSVKG | | RFSISKDNAKNSLYLQMN SQRTEDMAVYGCT*G |
| IGHV3-30-2 | EVQLVESGEDPRQPGGSLRLSCADS | GLTFSSY*RN.. | SVSQAPGKGLE*VVDIQC..DGSQICYA*SLKS | | KFTISKENAKNSLYLLMN SLRAAGTAVCYCM*G |
| IGHV3-30-3 | QVQLVESGGGVVQPGRSLRLSCAAS | GFTFSSYAMH.. | WVRQAPGKGLEWVAVISY..DGSNKYYADSVKG | | RFTISRDNSKNTLYLQMN SLRAEDTAVYYCAR. |
| IGHV3-30 | QVQLVESGGGVVQPGRSLRLSCAAS | GFTFSSYAMH.. | WVRQAPGKGLEWVAVISY..DGSNKYYADSVKG | | RFTISRDNSKNTLYLQMN SLRAEDTAVYYCAR. |

TABLE 2-continued

Exemplary Human V_H germline sequences

| | | | | | |
|---|---|---|---|---|---|
| IGHV3-32 | EVELIESIEDLRQPGKFLRLSCVAS | RFAFSSF*MS.. | RVHQSPGKGLE*V IDIKD..DGSQIHHADSVKG | RFSISKDNAKNSLYLMN TQRAEDVAVYGYT*G |
| IGHV3-33-2 | EVQLVESGEDPRQPGGSLRLSCADS | GLTFSSY*MS.. | SVSQAPGKGLE*V VDIQC..DGSQICYAQSVKG | KFTISKENAKNSLYLQMN SLRAEGTAVCYCM*G |
| IGHV3-33 | QVQLVESGGGVVQPGRSLRLSCAAS | GFTFSSYGMH.. | WVRQAPGKGLEWV AVIWY..DGSNKYYADSVKG | RFTISRDNSKNTLYLQMN SLRAEDTAVYYCAR. |
| IGHV3-35 | EVQLVESGGGLVQPGGSLRLSCAAS | GFTFSNSDMN.. | WVHQAPGKGLEWV SGVSW..NGSRTHYADSVKG | RFTISRDNSRNTLYLQTN SLRAEDTAVYYCVR. |
| IGHV3-38-3 | EVQLVESRGVLVQPGGSLRLSCAAS | GFTVSSNEMS.. | WVRQAPGKGLEWV SSIS....GGSTYYADSRKG | RFTISRDNSKNTLHLQMN SLRAEDTAVYYCKK. |
| IGHV3-38 | EVQLVESGGGLVQPRGSLRLSCAAS | GFTVSSNEMS.. | WIRQAPGKGLEWV SSIS....GGSTYYADSRKG | RFTISRDNSKNTLYLQMN NLRAEGTAAYYCARY |
| IGHV3-43 | EVQLVESGGVVVQPGGSLRLSCAAS | GFTFDDYTMH.. | WVRQAPGKGLEWV SLISW..DGGSTYYADSVKG | RFTISRDNSKNSLYLQMN SLRTEDTALYYCAKD |
| IGHV3-43D | EVQLVESGGVVVQPGGSLRLSCAAS | GFTFDDYAMH.. | WVRQAPGKGLEWV SLISW..DGGSTYYADSVKG | RFTISRDNSKNSLYLQMN SLRAEDTALYYCAKD |
| IGHV3-47 | EVQLVESGGGLVQPGGSLRPSCAAS | GFAFSSYALH.. | WVRRAPGKGLEWV SAIG...TGGDTYYADSVMG | RFTISRDNAKKSLYLHMN SLIAEDMAVYYCAR. |
| IGHV3-48 | EVQLVESGGGLVQPGGSLRLSCAAS | GFTFSSYSMN.. | WVRQAPGKGLEWV SYISS...SSTIYYADSVKG | RFTISRDNAKNSLYLQMN SLRAEDTAVYYCAR. |
| IGHV3-49 | EVQLVESGGGLVQPGGSLRLSCTAS | GFTFGDYAMS.. | WFRQAPGKGLEWV GFIRSKAYGGTTEYTASVKG | RFTISRDGSKSIAYLQMN SLKTEDTAVYYCTR. |
| IGHV3-52 | EVQLVESG*GLVQPGGSLRLSCAAS | GFTFSSSWMH.. | WVCQAPEKGLEWV ADIKC..DGSEKYYVDSVKG | RLTISRDNAKNSLYLQVN SLRAEDMTVYYCVR. |
| IGHV3-53 | EVQLVESGGGLIQPGGSLRLSCAAS | GFTVSSNYMS.. | WVRQAPGKGLEWV SVIY...SGGSTYYADSVKG | RFTISRDNSKNTLYLQMN SLRAEDTAVYYCAR. |
| IGHV3-54 | EVQLVESERNQRQLGGSLRLSCADS | GLTFSSY*MS.. | SDSQAPGKGLE*V VDI**..DRSQLCYAQSVKS | RFTISKENAKNSLCLQMN SLRAEGTAVYYCM*. |
| IGHV3-62 | EVQLVESGEGLVQPGGSLRLSCAAS | GFTFSSSAMH.. | WVRQAPRKGL*WV SVIST..SGDTVLYTDSVKG | RFTISRDNAQNSLSLQMN SLRAEGTVVYYCVK. |
| IGHV3-63 | EVELIESIEGLRQLGKFLRLSCVAS | GFTFSSY*MS.. | WVNETLGKGLEGV IDVKY..DGSQIYHADSVKG | RFTISKDNAKNSPYLQVN SLRAEDMTMHGCT*G |
| IGHV3-64 | EVQLVESGGGLVQPGGSLRLSCAAS | GFTFSSYAMH.. | WVRQAPGKGLEYV SAISS..NGGSTYYANSVKG | RFTISRDNSKNTLYLQMG SLRAEDMAVYYCAR. |
| IGHV3-65 | EVQLVESGGGLVQPGGSLRLSCAAS | GFTVSSNYMS.. | WVRQAPGKGLEWV SVIY...SGGSTYYADSVKG | RFTISRDNSKNTLYLQMN SLRAEDTAVYYCAR. |
| IGHV3-69-1 | EVQLVESGGGLVKPGGSLRLSCAAS | GFTFSDYYMN.. | WVRQAPGKGLEWV SSIS...SSTIYYADSVKG | RFTISRDNAKNSLYLQMN SLRAEDTAVYYCAR. |
| IGHV3-71 | EVQLVESGGGLVQPGGSLRLSCAAS | GFTFSDYYMS.. | WVRQAPGKGLEWV GFIRNKANGGTTE*TTSVKG | RFTISRDDSKSITYLQMN SLRAEDTAVYYCAR. |
| IGHV3-72 | EVQLVESGGGLVQPGGSLRLSCAAS | GFTFSDHYMD.. | WVRQAPGKGLEWV GRIRNKANSYTTEYAASVKG | RFTISRDDSKNSLYLQMN SLKTEDTAVYYCAR. |
| IGHV3-73 | EVQLVESGGGLVQPGGSLKLSCAAS | GFTFSGSAMH.. | WVRQASGKGLEWV GRIRSKANSYATAYAASVKG | RFTISRDDSKNTAYLQMN SLKTEDTAVYYCTR. |
| IGHV3-74 | EVQLVESGGGLVQPGGSLRLSCAAS | GFTFSSYWMH.. | WVRQAPGKGLVWV SRINS..DGSSTSYADSVKG | RFTISRDNAKNTLYLQMN SLRAEDTAVYYCAR. |
| IGHV3-NL1 | QVQLVESGGGVVQPGGSLRLSCAAS | GFTFSSYGMH.. | WVRQAPGKGLEWV EVIYS..GGSTYYADSVKG | RFTISRDNSKNTLYLQMN SLRAEDTAVYYCAK. |

Human VH4 germline sequence (from top to bottom, SEQ ID NOs. 115-125):

| VH4 | FW1 | CDR1 | FW2 | CDR2 | FW3 |
|---|---|---|---|---|---|
| IGHV4-4 | QVQLQESGPGLVKPPGTLSLTCAVS | GGSISSSNWWS. | WVRQPPGKGLEWI | GEIY...HSGSTNYNPSLKS | RVTISVDKSKNQFSLKLS SVTAADTAVYCCAR. |

TABLE 2-continued

Exemplary Human V_H germline sequences

| | FW1 | CDR1 | FW2 | CDR2 | FW3 |
|---|---|---|---|---|---|
| IGHV4-28 | QVQLQESGPGLVKPPDTLSLTCAVS | GYSISSSNWWG. | WIRQPPGKGLEWI | GYIY...YSGSTYYNPSLKS | RVTMSVDTSKNQFSLKLS SVTAVDTAVYYCAR. |
| IGHV4-30-2 | QLQLQESGSGLVKPSQTLSLTCAVS | GGSISSGGYSWS | WIRQPPGKGLEWI | GYIY...HSGSTYYNPSLKS | RVTISVDRSKNQFSLKLS SVTAADTAVYYCAR. |
| IGHV4-30-4 | QVQLQESGPGLVKPSQTLSLTCTVS | GGSISSGDYYWS | WIRQPPGKGLEWI | GYIY...YSGSTYYNPSLKS | RVTISVDTSKNQFSLKLS SVTAADTAVYYCAR. |
| IGHV4-31 | QVQLQESGPGLVKPSQTLSLTCTVS | GGSISSGGYYWS | WIRQHPGKGLEWI | GYIY...YSGSTYYNPSLKS | LVTISVDTSKNQFSLKLS SVTAADTAVYYCAR. |
| IGHV4-34 | QVQLQQWGAGLLKPSETLSLTCAVY | GGSFSGYYWS.. | WIRQPPGKGLEWI | GEIN...HSGSTNYNPSLKS | RVTISVDTSKNQFSLKLS SVTAADTAVYYCAR. |
| IGHV4-38-2 | QVQLQESGPGLVKPSETLSLTCAVS | GYSISSGYYWG. | WIRQPPGKGLEWI | GSIY...HSGSTYYNPSLKS | RVTISVDTSKNQFSLKLS SVTAADTAVYYCAR. |
| IGHV4-39 | QLQLQESGPGLVKPSETLSLTCTVS | GGSISSSSYYWG | WIRQPPGKGLEWI | GSIY...YSGSTYYNPSLKS | RVTISVDTSKNQFSLKLS SVTAADTAVYYCAR. |
| IGHV4-55 | QVQLQESGPGLVKPSETLSLTCAVS | GDSISSGNW*I. | WVRQPPGKGLEWI | GEIH...HSGSTYYNPSLKS | RITMSVDTSKNQFYLKLS SVTAADTAVYYCAR. |
| IGHV4-59 | QVQLQESGPGLVKPSETLSLTCTVS | GGSISSYYWS.. | WIRQPPGKGLEWI | GYIY...YSGSTNYNPSLKS | RVTISVDTSKNQFSLKLS SVTAADTAVYYCAR. |
| IGHV4-61 | QVQLQESGPGLVKPSETLSLTCTVS | GGSVSSGSYYWS | WIRQPPGKGLEWI | GYIY...YSGSTNYNPSLKS | RVTISVDTSKNQFSLKLS SVTAADTAVYYCAR. |

Human VH5 germline sequence (from top to bottom, SEQ ID NOs. 126-128):

| VH5 | FW1 | CDR1 | FW2 | CDR2 | FW3 |
|---|---|---|---|---|---|
| IGHV5-10-1 | EVQLVQSGAEVKKPGESLRISCKGS | GYSFTSYWIS.. | WVRQMPGKGLEWM | GRIDP..SDSYTNYSPSFQG | HVTISADKSISTAYLQWS SLKASDTAMYYCAR. |
| IGHV5-51 | EVQLVQSGAEVKKPGESLKISCKGS | GYSFTSYWIG.. | WVRQMPGKGLEWM | GIIYP..GDSDTRYSPSFQG | QVTISADKSISTAYLQWS SLKASDTAMYYCAR. |
| IGHV5-78 | EVQLLQSAAEVKRPGESLRISCKIS | GYSFTSYWIH.. | WVRQMPGKGKEWM | GSIYP..GNSDTRYSPSFQG | HVTISADSSSSTAYLQWS SLKASDAAMYYCVR. |

Human VH6 germline sequence (SEQ ID NO: 129)

| VH6 | FW1 | CDR1 | FW2 | CDR2 | FW3 |
|---|---|---|---|---|---|
| IGHV6-1 | QVQLQQSGPGLVKPSQTLSLTCAIS | GDSVSSNSAAWN | WIRQSPSRGLEWL | GRIYY.RSKWYNDYAVSVKS | RITINPDTSKNQFSLQLN SVTPEDTAVYYCAR. |

Human VH7 germline sequence (from top to bottom, SEQ ID NOs. 130-132):

| VH7 | FW1 | CDR1 | FW2 | CDR2 | FW3 |
|---|---|---|---|---|---|
| IGHV7-4-1 | QVQLVQSGSELKKPGASVKVSCKAS | GYTFTSYAMN.. | WVRQAPGQGLEWM | GWINT..NTGNPTYAQGFTG | RFVFSLDTSVSTAYLQIC SLKAEDTAVYYCAR. |
| IGHV7-34-1 | -LQLVQSGPEVKKPGASVKVSYKSS | GYTFIIYGMN.. | WV**IPGQGFEWM | *WIIT...YTGNPTYTHGFTG | WFVFSMDTSVSTACLQIS SLKAEDTAEYYCAR. |
| IGHV7-81 | QVQLVQSGHEVKQPGASVKVSCKAS | GYSFTTYGMN.. | WVPQAPGQGLEWM | GWFNT..YTGNPTYAQGFTG | RFVFSMDTSASTAYLQIS SLKAEDMAMYYCAR. |

TABLE 3

Exemplary Human Vκ germline sequences

Human VK1 germline sequence (from top to bottom, SEQ ID NOs. 133-145):

| VK1 | FW1 | CDR1 | FW2 | CDR2 | FW3 | CDR3 |
|---|---|---|---|---|---|---|
| IGKV1-5 | DIQMTQSPSTLSASVGDRVTITC | RASQ......SISSWLA | WYQQKPGKAPKLLIY | DASSLES | GVPSRFSGSGSGTEF TLTISSLQPDDFATYYC | QQYNSYS |

TABLE 3-continued

Exemplary Human Vκ germline sequences

| | | | | | | |
|---|---|---|---|---|---|---|
| IGKV1-6 | AIQMTQSPSSLSASVGDRVTITC | RASQ......GIRNDLG | WYQQKPGKAPKLLIY | AASSLQS | GVPSRFSGSGSGTDF TLTISSLQPEDFATYYC | LQDYNYP |
| IGKV1-8 | AIRMTQSPSSFSASTGDRVTITC | RASQ......GISSYLA | WYQQKPGKAPKLLIY | AASTLQS | GVPSRFSGSGSGTEF ILTISCLQSEDFATYYC | QQYYSYP |
| IGKV1-9 | DIQLTQSPSFLSASVGDRVTITC | RASQ......GISSYLA | WYQQKPGKAPKLLIY | AASTLQS | GVPSRFSGSGSGTEF TLTISSLQPEDFATYYC | QQLNSYP |
| IGKV1-12 | DIQMTQSPSSVSASVGDRVTITC | RASQ......GISSWLA | WYQQKPGKAPKLLIY | AASSLQS | GVPSRFSGSGSGTD FTLTISSLQPEDFATYYC | QQANSFP |
| IGKV1-13 | AIQLIQSPSSLSASVGDRVTITC | RASQ......GISSALA | *YQQKPGKAPKLLIY | DASSLES | GVPSRFSGSGSGTDF ILTISSLQPEDFATYYC | QQFNNYP |
| IGKV1-16 | DIQMTQSPSSLSASVGDRVTITC | RASQ......GISNYLA | WFQQKPGKAPKSLIY | AASSLQS | GVPSRFSGSGSGTDF TLTISSLQPEDFATYYC | QQYNSYP |
| IGKV1-17 | DIQMTQSPSSLSASVGDRVTITC | RASQ......GIRNDLG | WYQQKPGKAPKRLIY | AASSLQS | GVPSRFSGSGSGTEF TLTISSLQPEDFATYYC | LQHNSYP |
| IGKV1-27 | DIQMTQSPSSLSASVGDRVTITC | RASQ......GISNYLA | WYQQKPGKVPKLLIY | AASTLQS | GVPSRFSGSGSGTDF TLTISSLQPEDVATYYC | QKYNSAP |
| IGKV1-33 | DIQMTQSPSSLSASVGDRVTITC | QASQ......DISNYLN | WYQQKPGKAPKLLIY | DASNLET | GVPSRFSGSGSGTDF TFTISSLQPEDIATYYC | QQYDNLP |
| IGKV1-37 | DIQLTQSPSSLSASVGDRVTITC | RVSQ......GISSYLN | WYRQKPGKVPKLLIY | SASNLQS | GVPSRFSGSGSGTDF TLTISSLQPEDVATYYG | QRTYNAP |
| IGKV1-39 | DIQMTQSPSSLSASVGDRVTITC | RASQ......SISSYLN | WYQQKPGKAPKLLIY | AASSLQS | GVPSRFSGSGSGTDF TLTISSLQPEDFATYYC | QQSYSTP |
| IGKV1-NL1 | DIQMTQSPSSLSASVGDRVTITC | RASQ......GISNSLA | WYQQKPGKAPKLLLY | AASRLES | GVPSRFSGSGSGTD YTLTISSLQPEDFATYYC | QQYYSTP |

Human VK1D germline sequence (from top to bottom, SEQ ID NOs. 146-155):

| VK1D | FW1 | CDR1 | FW2 | CDR2 | FW3 | CDR3 |
|---|---|---|---|---|---|---|
| IGKV1D-8 | VIWMTQSPSLLSASTGDRVTISC | RMSQ......GISSYLA | WYQQKPGKAPELLIY | AASTLQS | GVPSRFSGSGSGTD FTLTISCLQSEDFATYYC | QQYYSFP |
| IGKV1D-12 | DIQMTQSPSSVSASVGDRVTITC | RASQ......GISSWLA | WYQQKPGKAPKLLIY | AASSLQS | GVPSRFSGSGSGTD FTLTISSLQPEDFATYYC | QQANSFP |
| IGKV1D-13 | AIQLTQSPSSLSASVGDRVTITC | RASQ......GISSALA | WYQQKPGKAPKLLIY | DASSLES | GVPSRFSGSGSGTD FTLTISSLQPEDFATYYC | QQFNNYP |
| IGKV1D-16 | DIQMTQSPSSLSASVGDRVTITC | RASQ......GISSWLA | WYQQKPEKAPKSLIY | AASSLQS | GVPSRFSGSGSGTD FTLTISSLQPEDFATYYC | QQYNSYP |
| IGKV1D-17 | NIQMTQSPSAMSASVGDRVTITC | RARQ......GISNYLA | WFQQKPGKVPKHLIY | AASSLQS | GVPSRFSGSGSGTE FTLTISSLQPEDFATYYC | LQHNSYP |
| IGKV1D-33 | DIQMTQSPSSLSASVGDRVTITC | QASQ......DISNYLN | WYQQKPGKAPKLLIY | DASNLET | GVPSRFSGSGSGTD FTFTISSLQPEDIATYYC | QQYDNLP |
| IGKV1D-37 | DIQLTQSPSSLSASVGDRVTITC | RVSQ......GISSYLN | WYRQKPGKVPKLLIY | SASNLQS | GVPSRFSGSGSGTD FTLTISSLQPEDVATYYG | QRTYNAP |
| IGKV1D-39 | DIQMTQSPSSLSASVGDRVTITC | RASQ......SISSYLN | WYQQKPGKAPKLLIY | AASSLQS | GVPSRFSGSGSGTD FTLTISSLQPEDFATYYC | QQSYSTP |
| IGKV1D-42 | DIQMIQSPSFLSASVGDRVSIIC | WASE......GISSNLA | WYLQKPGKSPKLFLY | DAKDLHP | GVSSRFSGRGSGTDF TLTIISSLKPEDFAAYYC | KQDFSYP |
| IGKV1D-43 | AIRMTQSPFSLSASVGDRVTITC | WASQ......GISSYLA | WYQQKPAKAPKLFIY | YASSLQS | GVPSRFSGSGSGTD YTLTISSLQPEDFATYYC | QQYYSTP |

Human VK2 germline sequence (from top to bottom, SEQ ID NOs. 156-162):

| VK2 | FW1 | CDR1 | FW2 | CDR2 | FW3 | CDR3 |
|---|---|---|---|---|---|---|
| IGKV2-4 | DIVMTQHLLSLPIPLGEPASISC | RSSQSLLHS.DGNTYLD | WYLQKPGQSPQLLIY | TISNKFY | GVPNKFSGSRSGTGF TLKFSKVEAEDVGVYCC | EQGLQGP |

TABLE 3-continued

Exemplary Human Vκ germline sequences

| | FW1 | CDR1 | FW2 | CDR2 | FW3 | CDR3 |
|---|---|---|---|---|---|---|
| IGKV2-18 | DIVMTQTPPSLPVNPGEPASISC | RSSQSLLHS.NGYTYLH | WYLQKPGQSPQLLIY | RVSNHLS | GVPDRFSGSGSGSDF TLKISWVEAEDVGVYYC | MQATQFP |
| IGKV2-24 | DIVMTQTPLSSPVTLGQPASISC | RSSQSLVHS.DGNTYLS | WLQQRPGQPPRLLIV | KISNRFS | GVPDRFSGSGAGTDF TLKISRVEAEDVGVYYC | MQATQFP |
| IGKV2-28 | DIVMTQSPLSLPVTPGEPASISC | RSSQSLLHS.NGYNYLD | WYLQKPGQSPQLLIY | LGSNRAS | GVPDRFSGSGSGTDF TLKISRVEAEDVGVYYC | MQALQTP |
| IGKV2-29 | DIVMTQSPLSLSVTPGQPASISC | RSSQSLLHS.DGKTYLY | WYLQKPGQSPQLLIY | EVSSRFS | GVPDRFSGSGSGTDF TLKISRVEAEDVGVYY* | MQGIHLP |
| IGKV2-30 | DVVMTQSPLSLPVTLGQPASISC | RSSQSLVYS.DGNTYLN | WFQQRPGQSPRRLIY | KVSNRDS | GVPDRFSGSGSGTD FTLKISRVEAEDVGVYYC | MQGTHWP |
| IGKV2-40 | DIVMTQTPLSLPVTPGEPASISC | RSSQSLLDSDDGNTYLD | WYLQKPGQSPQLLIY | TLSYRAS | GVPDRFSGSGSGTDF TLKISRVEAEDVGVYYC | MQRIEEP |

Human VK2D germline sequence (from top to bottom, SEQ ID NOs. 163-169):

| VK2D | FW1 | CDR1 | FW2 | CDR2 | FW3 | CDR3 |
|---|---|---|---|---|---|---|
| IGKV2D-18 | DIVMTQTPPSLPVNPGEPASISC | RSSQSLLHS.NGYTYLH | WYPQKPGQSPQLLIY | RVSSRFS | GVPDRFSGSGSGSDF TLKISWVEAEDVGVYYC | MQATQFP |
| IGKV2D-24 | DIVMTQTPLSSPVTLGQPASISF | RSSQSLVHS.DGNTYLS | WLQQRPGQPPRLLIY | KVSNRFS | GVPDRFSGSGAGTDFT LKISRVEAEDVGVYYC | TQATQFP |
| IGKV2D-26 | EIVMTQTPLSLSITPGEQASISC | RSSQSLLHS.DGYTYLY | WFLQKARPVSTLLIY | EVSNRFS | GVPDRFSGSGSGTDFTL KISRVEAEDFGVYYC | MQDAQDP |
| IGKV2D-28 | DIVMTQSPLSLSVTPGEPASISC | RSSQSLLHS.NGYNYLD | WYLQKPGQSPQLLIY | LGSNRAS | GVPDRFSGSGSGTD FTLKISRVEAEDVGVYYC | MQALQTP |
| IGKV2D-29 | DIVMTQSPLSLSVTPGQPASISC | KSSQSLLHS.DGKTYLY | WYLQKPGQPPQLLIY | EVSNRFS | GVPDRFSGSGSGTD FTLKISRVEAEDVGVYYC | MQSIQLP |
| IGKV2D-30 | DVVMTQSPLSLPVTLGQPASISC | RSSQSLVYS.DGNTYLN | WFQQRPGQSPRRLIY | KVSNWDS | GVPDRFSGSGSGTD FTLKISRVEAEDVGVYYC | MQGTHWP |
| IGKV2D-40 | DIVMTQTPLSLPVTPGEPASISC | RSSQSLLDSDDGNTYLD | WYLQKPGQSPQLLIY | TLSYRAS | GVPDRFSGSGSGTDF TLKISRVEAEDVGVYYC | MQRIEEP |

Human VK3 germline sequence (from top to bottom, SEQ ID NOs. 170-178):

| VK3 | FW1 | CDR1 | FW2 | CDR2 | FW3 | CDR3 |
|---|---|---|---|---|---|---|
| IGKV3-7 | EIVMTQSPPTLSLSPGERVTLSC | RASQS.....VSSSYLT | WYQQKPGQAPRLLIY | GASTRAT | SIPARFSGSGSGTDF TLTISSLQPEDFAVYYC | QQDHNLP |
| IGKV3-11 | EIVLTQSPATLSLSPGERATLSC | RASQ......SVSSYLA | WYQQKPGQAPRLLIY | DASNRAT | GIPARFSGSGSGTDF TLTISSLEPEDFAVYYC | QQRSNWP |
| IGKV3-15 | EIVMTQSPATLSLSPGERATLSC | RASQ......SVSSNLA | WYQQKPGQAPRLLIY | GASTRAT | GIPARFSGSGSGTEF TLTISSLQSEDFAVYYC | QQYNNWP |
| IGKV3-20 | EIVLTQSPATLSLSPGERATLSC | RASQ......VSSSYLA | WYQQKPGQAPRLLIY | GASSRAT | GIPDRFSGSGSGTDF TLTISRLEPEDFAVYYC | QQYGSSP |
| IGKV3-NL1 | EIVLTQSPATLSLSPGERATLSC | RASQ......SVSSYLA | WYQQKPGQAPRLLIY | GASTRAT | GIPARFSGSGSGTEF TLTISSLQSEDFAVYYC | Q...... |
| IGKV3-NL2 | EIVLTQSPATLSLSPGERATLSC | RASQ......GVSSYLA | WYQQKPGQAPRLLIY | DASSRAT | GIPARFSGSGSGTDF TLTISSLEPEDFAVYYC | Q...... |
| IGKV3-NL3 | EIVLTQSPGTLSLSPGERATLSC | RASQS.....VSSSYLA | WYQQKPGLAPRLLIY | GASTRAT | GIPARFSGSGSGTEF TLTISRLESEDFAVYYC | Q...... |
| IGKV3-NL4 | EIVLTQSPATLSLSPGERATLSC | RASQ......GVSSNLA | WYQQKPGQAPRLLIY | DASNRAT | GIPARFSGSGSGTDF TLTISSLEPEDFAVYYC | QQRSNWH |
| IGKV3-NL5 | EIVLTQSPATLSLSPGERATLSC | RASQS.....VSSSYLA | WYQQKPGQAPRLLIY | DASSRAT | GIPDRFSGSGSGTDF TLTISRLEPEDFAVYYC | QQRSNWH |

TABLE 3-continued

Exemplary Human Vκ germline sequences

Human VK3D germline sequence (from top to bottom, SEQ ID NOs. 179-182):

| VK3D | FW1 | CDR1 | FW2 | CDR2 | FW3 | CDR3 |
|---|---|---|---|---|---|---|
| IGKV3D-7 | EIVMTQSPATLSLSPGERATLSC | RASQS.....VSSSYLS | WYQQKPGQAPRLLIY | GASTRAT | GIPARFSGSGSGTDF TLTISSLQPEDFAVYYC | QQDYNLP |
| IGKV3D-11 | EIVLTQSPATLSLSPGERATLSC | RASQ.....GVSSYLA | WYQQKPGQAPRLLIY | DASNRAT | GIPARFSGSPGTDF TLTISSLEPEDFAVYYC | QQRSNWH |
| IGKV3D-15 | EIVMTQSPATLSVSPGERATLSC | RASQ.....SVSSNLA | WYQQKPGQAPRLLIY | GASTRAT | GIPARFSGSGSGTDF TLTISSLQSEDFAVYYC | QQYNNWP |
| IGKV3D-20 | EIVLTQSPATLSLSPGERATLSC | GASQS.....VSSSYLA | WYQQKPGLAPRLLIY | DASSRAT | GIPDRFSGSGSGTDF TLTISSLEPEDFAVYYC | QQYGSSP |

Human VK4 germline sequence (SEQ ID NO: 183)

| VK4 | FW1 | CDR1 | FW2 | CDR2 | FW3 | CDR3 |
|---|---|---|---|---|---|---|
| IGKV4-1 | DIVMIQSPDSLAVSLGERATINC | KSSQSVLYSSNNKNYLA | WYQQKPGQPPKLLIY | WASTRES | GVPDRFSGSGSGTDF TLTISSLQAEDVAVYYC | QQYYSTP |

Human VK5 germline sequence (SEQ ID NO: 184)

| VK5 | FW1 | CDR1 | FW2 | CDR2 | FW3 | CDR3 |
|---|---|---|---|---|---|---|
| IGKV5-2 | ETTLTQSPAFMSATPGDKVNISC | KASQ......DIDDDMN | WYQQKPGEAAIFIIQ | EATTLVP | GIPPRFSGSGYGTDF TLTINNIESEDAAYYFC | LQHDNFP |

Human VK6 germline sequence (SEQ ID NO: 185)

| VK6 | FW1 | CDR1 | FW2 | CDR2 | FW3 | CDR3 |
|---|---|---|---|---|---|---|
| IGKV6-21 | EIVLIQSPDFQSVTPKEKVTIIC | RASQ......SIGSSLH | WYQQKPDQSPKLLIK | YASQSFS | GVPSRFSGSGSGTDF TLTINSLEAEDAATYYC | HQSSSLP |

Human VK6D germline sequence (from top to bottom, SEQ ID NOs. 186-187):

| VK6D | FW1 | CDR1 | FW2 | CDR2 | FW3 | CDR3 |
|---|---|---|---|---|---|---|
| IGKV6D-21 | EIVLTQSPDFQSVTPKEKVTITC | RASQ......SIGSSLH | WYQQKPDQSPKLLIK | YASQSFS | GVPSRFSGSGSGTDF TLTINSLEAEDAATYYC | HQSSSLP |
| IGKV6D-41 | DVVMIQSPAFLSVTPGEKVTITC | QASE......GIGNYLY | WYQQKPDQAPKLLIK | YASQSIS | GVPSRFSGSGSGTDFTF TISSLEAEDAATYYC | QQGNKHP |

Human VK7 germline sequence (SEQ ID NO: 188)

| VK7 | FW1 | CDR1 | FW2 | CDR2 | FW3 | CDR3 |
|---|---|---|---|---|---|---|
| IGKV7-3 | DIVLTQSPASLAVSPGQRATITC | RASESVSF..LGINLIH | WYQQKPGQPPKLLIY | QASNKDT | GVPARFSGSGSGTDF TLTINPVEANDTANYYC | LQSKNFP |

TABLE 4

Exemplary Human Vλ germline sequences

Human Vλ1 germline sequences (from top to bottom, SEQ ID NOs. 189-196):

| Vλ1 | FW1 | CDR1 | FW2 | CDR2 | FW3 | CDR3 |
|---|---|---|---|---|---|---|
| IGLV1-36 | QSVLTQPPSVS EAPRQRVTISC | SGSSSN..IGNNAVN | WYQQLPGKAPKLLIY | YDDLL.....PS | GVSDRFSGSK..SGTSAS LAISGLQSEDEADYYC | AAWDDSLNG... |
| IGLV1-40 | QSVLTQPPSVS GAPGQRVTISC | TGSSSNI.GAGYDVH | WYQQLPGTAPKLLIY | GNSNR.....PS | GVPDRFSGSK..SGTSAS LAITGLQAEDEADYYC | QSYDSSLSG... |
| IGLV1-41 | QSVLTQPPSVS AAPGQKVTISC | SGSSSD..MGNYAVS | WYQQLPGTAPKLLIY | ENNKR.....PS | GIPDRFSGSK..SGTSAT LGITGLWPEDEADYYC | LAWDTSPRA... |
| IGLV1-44 | QSVLTQPPSAS GTPGQRVTISC | SGSSSN..IGSNTVN | WYQQLPGTAPKLLIY | SNNQR.....PS | GVPDRFSGSK..SGTSAS LAISGLQSEDEADYYC | AAWDDSLNG... |

TABLE 4-continued

Exemplary Human V<sub>λ</sub> germline sequences

| | | | | | | |
|---|---|---|---|---|---|---|
| IGLV1-47 | QSVLTQPPSAS GTPGQRVTISC | SGSSSN..IGSNYVY | WYQQLPGTAPKLLIY | RNNQR.....PS | GVPDRFSGSK..SGTSAS | AAWDDSLSG... LAISGLRSEDEADYYC |
| IGLV1-50 | QSVLTQPPSVS GAPGQRVTISC | TGSSSNI.GAGYVVH | WYQQLPGTAPKLLIY | GNSNR.....PS | GVPDQFSGSK..SGTSAS | KAWDNSLNA... LAITGLQSEDEADYYC |
| IGLV1-51 | QSVLTQPPSVS AAPGQKVTISC | SGSSSN..IGNNYVS | WYQQLPGTAPKLLIY | DNNKR.....PS | GIPDRFSGSK..SGTSAT | GTWDSSLSA... LGTTGLQTGDEADYYC |
| IGLV1-52 | QSVLTQPPSVS WATRQRLTVSC | TGSSSNTGTGYNVNC | WQ*LPRTDPKLLPH | GDKNW.....PS | WVSDQFSGSK..SGSLAS | QSRDIC*VL... LGTTGIWAEDKTDYHC |

Human Vλ2 germline sequences (from top to bottom, SEQ ID NOs. 197-205):

| Vλ2 | FW1 | CDR1 | FW2 | CDR2 | FW3 | CDR3 |
|---|---|---|---|---|---|---|
| IGLV2-5 | QSALTQPPSVS GSPGQSVTISC | TGTSSDV.GSYDYVS | WYQQHPGTVPKPMIY | NVNTQ.....PS | GVPDRFSGSK..SGNTAS | CSYTSSAT*... MTISGLQAEDEADY*C |
| IGLV2-8 | QSALTQPPSAS GSPGQSVTISC | TGTSSDV.GGYNYVS | WYQQHPGKAPKLMIY | EVSKR.....PS | GVPDRFSGSK..SGNTAS | SSYAGSNNF... LTVSGLQAEDEADYYC |
| IGLV2-11 | QSALTQPRSVS GSPGQSVTISC | TGTSSDV.GGYNYVS | WYQQHPGKAPKLMIY | DVSKR.....PS | GVPDRFSGSK..SGNTAS | CSYAGSYTF... LTISGLQAEDEADYYC |
| IGLV2-14 | QSALTQPASVS GSPGQSITISC | TGTSSDV.GGYNYVS | WYQQHPGKAPKLMIY | EVSNR.....PS | GVSNRFSGSK..SGNTAS | SSYTSSSTL... LTISGLQAEDEADYYC |
| IGLV2-18 | QSALTQPPSVS GSPGQSVTISC | TGTSSDV.GSYNRVS | WYQQPPGTAPKLMIY | EVSNR.....PS | GVPDRFSGSK..SGNTAS | SLYTSSSTF... LTISGLQAEDEADYYC |
| IGLV2-23 | QSALTQPASVS GSPGQSITISC | TGTSSDV.GSYNLVS | WYQQHPGKAPKLMIY | EGSKR.....PS | GVSNRFSGSK..SGNTAS | CSYAGSSTL... LTISGLQAEDEADYYC |
| IGLV2-33 | QSALTQPPFVS GAPGQSVTISC | TGTSSDV.GDYDHVF | WYQKRLSTTSRLLIY | NVNTR.....PS | GISDLFSGSK..SGIMAS | SLYSSSYTF... LTISGLKSEVEANYHC |
| IGLV2-34 | QSVLTQPRSVS RSPGQ*VTIFC | TGTSSDI.GGYDLVS | WOQ*HPGKAPKLMIY | DVANW.....PS | GAPGCFSGSK..SGNTAS | SSYAGSYNF... LTISGLQAEDEADYYC |
| IGLV2-NL1 | QSVLTQPRSVS RSPGQ*VTIFC | TGTSSDI.GGYDLVS | WOQ*HPGKAPKLMIY | DVGNW.....PS | GAPGCFSGSK..SGNTAS | SSYAGSYNF... LTISGLQAEDEADYYC |

Human Vλ3 germline sequences (from top to bottom, SEQ ID NOs. 206-218):

| Vλ3 | FW1 | CDR1 | FW2 | CDR2 | FW3 | CDR3 |
|---|---|---|---|---|---|---|
| IGLV3-1 | SYELTQPPSVS VSPGQTASITC | SGDK....LGDKYAC | WYQQKPGQSPVLVTY | QDSKR.....PS | GIPERFSGSN..SGNTAT | QAWDSSTA..... LTISGTQAMDEADYYC |
| IGLV3-9 | SYELTQPLSVS VALGQTARITC | GGNN....IGSKNVH | WYQQKPGQAPVLVTY | PDSNR.....PS | GIPERFSGSN..SGNTAT | QVWDSSTA..... LTISRAQAGDEADYYC |
| IGLV3-10 | SYELTQPPSVS VSPGQTARITC | SGDA....LPKKYAY | WYQQKSGQAPVLVTY | EDSKR.....PS | GIPERFSGSS..SGTMAT | YSTDSSGNH... LTISGAQVEDEADYYC |
| IGLV3-12 | SYELTQPHSVS VATAQMARITC | GGNN....IGSYAVH | WYQQKPGQDPVLVTY | SDSNR.....PS | GIPERFSGSN..PGNTTT | QVWDSSSDH... LTISRTEAGDEADYYC |
| IGLV3-13 | SYELTQPPAVS VSPGQTARISC | SGDV....LRDNYAD | WYPQKPGQAPVLVTY | KDGER.....PS | GIPERFSGST..SGNTTA | FSGD*NN...... LTISRVLTKGGADYYC |
| IGLV3-15 | SYELTQPPSVS VSLGQMARITC | SGEA....LPKKYAY | WYQQKPGQFPVLVTY | KDSER.....PS | GIPERFSGSS..SGTIVT | LSADSSGTY... LTISGVQAEDEADYYC |
| IGLV3-19 | SSELTQDPAVS VALGQTVRITC | QGDS....LRSYYAS | WYQQKPGQAPVLVTY | GKNNR.....PS | GIPDRFSGSS..SGNTAS | NPRDSSGNH... LTITGAQAEDEADYYC |
| IGLV3-21 | SYVLTQPPSVS VAPGKTARITC | GGNN....IGSKSVH | WYQQKPGQAPVLVTY | YDSDR.....PS | GIPERFSGSN..SGNTAT | QVWDSSSDH... LTISRVEAGDEADYYC |
| IGLV3-22 | SYELTQLPSVS VSPGQTARITC | SGDV....LGENYAD | WYQQKPGQAPELVTY | EDSER.....YP | GIPERFSGST..SGNTTT | LSGDEDN...... LTISRVLTEDEADYYC |
| IGLV3-25 | SYELNQPPSVS VSPGQTARITC | SGDA....LPKQYAY | WYQQKPGQAPVLVTY | KDSER.....PS | GIPERFSGSS..SGTTVT | QSADSSGTY... LTISGVQAEDEADYYC |

TABLE 4-continued

Exemplary Human Vλ germline sequences

| IGLV3-27 | SYELTQPSSVS VSPGQTARITC | SGDV....LAKEYAR | WFQQKPGQAPVLVTY | KDSER.....PS | GIPERFSGSS..SGTTVT LTISGAQVEDEADYYC | YSAADNN..... |
|---|---|---|---|---|---|---|
| IGLV3-31 | SSELSQEPAVS VALG*TARITC | QGDS....IEDSVVN | WYKQKPSQAPGLVT* | INSVQ.....SS | GIPKKFSGSS..SGNMAT LTITGTQVEDKADYYC | QSWDSSRTH... |
| IGLV3-32 | SSGPTQVPAVS VALGQMARITC | QGDS....MEGSYEH | WYQQKPGQAPVLVTY | DSSDR.....PS | GIPERFSGSE..SGNTTT LTITGAQAEDEADYYT | QLIDNHA..... |

Human Vλ4 germline sequences (from top to bottom, SEQ ID NOs. 219-221):

| Vλ4 | FW1 | CDR1 | FW2 | CDR2 | FW3 | CDR3 |
|---|---|---|---|---|---|---|
| IGLV4-3 | LPVLTQPPSAS ALLGASIKLTC | TLSSE...HSTYTIE | WYQQRPGRSPQYIMK | VKSDGSHSK.GD | GIPDRFMGSS..SGADRY LTFSNLQSDDEAEYHC | GESHTTDGQVG* |
| IGLV4-50 | QPVLTQSSSAS ASLGSSVKLTC | TLSSG...HSSYIIA | WHQQQPGKAPRYLMK | LEGSGSYNK.GS | GVPDRFSGSS..SGADRY LTISNLQLEDEADYYC | ETWDSNT..... |
| IGLV4-59 | QPVLTQSPSAS ASLGASVKLTC | TLSSG...HSSYAIA | WHQQQPEKGPRYLMK | LNSDGSHSK.GS | GIPDRFSGSS..SGAERY LTISSLQSEDEADYYC | QTWGTGI..... |

Human Vλ5 germline sequences (from top to bottom, SEQ ID NOs. 222-2261):

| Vλ5 | FW1 | CDR1 | FW2 | CDR2 | FW3 | CDR3 |
|---|---|---|---|---|---|---|
| IGLV5-37 | QPVLTQPPSSSA SPGESARLTC | TLPSDIN.VGSYNIY | WYQQKPGSPPRYLLY | YYSDSDKGQ.GS | GVPSRFSGSKDASANTGI LLISGLQSEDERDYYC | MIWPSNAS.... |
| IGLV5-39 | QPVLTQPTSLSA SPGASARFTC | TLRSDIN.VGTYRIY | WYQQKPGSLPRYLLR | YKSDSDKQQ.GS | GVPSRFSGSKDASTNAG LLLISGLQSEDEADYYC | AIWYSSTS.... |
| IGLV5-45 | QAVLTQPASLSA SPGASASLTC | TLRSGIN.VGTYRIY | WYQQKPGSPPQYLLR | YKSDSDKQQ.GS | GVPSRFSGSKDASANAGI LLISGLQSEDEADYYC | MIWHSSAS.... |
| IGLV5-48 | QPVLTQPTSLSA SPGASARLTC | TLRSGIN.LGSYRIF | WYQQKPESPPRYLLS | YYSDSSKRQ.GS | GVPSRFSGSKDASSNAGI LVISGLQSEDEADYYC | MIWHSSAS.... |
| IGLV5-52 | QPVLTQPSSHSA SSGASVRLTC | MLSSGFS.VGDFWIR | WYQQKPGNPPRYLLY | YHSDSNKGQ.GS | GVPSRFSGSNDASANAGI LRISGLQPEDEADYYC | GTWHSNSKT... |

Human Vλ6 germline sequences (SEQ ID NOs. 227)

| Vλ6 | FW1 | CDR1 | FW2 | CDR2 | FW3 | CDR3 |
|---|---|---|---|---|---|---|
| IGLV6-57 | NFMLTQPHSVSE SPGKTVTISC | TPSSGS...IASNYVQ | WYQQROGSSOTTVIY | EDNQR.....PS | GVPDRFSGSIDSSSNSAS LTISGLKTEDEADYYC | QSYESSN..... |

Human Vλ7 germline sequence (from top to bottom, SEQ ID NOs. 228-229):

| Vλ7 | FW1 | CDR1 | FW2 | CDR2 | FW3 | CDR3 |
|---|---|---|---|---|---|---|
| IGLV7-43 | QTVVTQEPSLTV SPGGTVTLTC | ASSTGAV.TSGYYPN | WFQQKPGQAPRALIY | STSNK.....HS | WTPARFSGSL..LGGKAA LTLSGVQPEDEAYYC | LLYYGGAQ.... |
| IGLV7-45 | QAVVTQEPSLTV SPGGTVTLTC | GSSTGAV.TSGHYPY | WFQQKPGQAPRTLIY | DTSNK.....HS | WTPARFSGSL..LGGKAA LTLSGAQPEDEAEYYC | LLSYSGAR.... |

Human Vλ8 germline sequence (SEQ ID NO: 230)

| VλD | FW1 | CDR1 | FW2 | CDR2 | FW3 | CDR3 |
|---|---|---|---|---|---|---|
| IGLV8-61 | QTVVTQEPSFSV SPGGTVTLTC | GLSSGSV.STSYYPS | WFQQTPGQAPRTLIY | STNTR.....SS | GVPDRFSGSI..LGNKAA LTITGAQADDESDYYC | VLYMGSGI.... |

Human Vλ9 germline sequence (SEQ ID NO: 231)

| Vλ9 | FW1 | CDR1 | FW2 | CDR2 | FW3 | CDR3 |
|---|---|---|---|---|---|---|
| IGLV9-49 | QPVLTQPPSASA SLGASVTLTC | TLSSG...YSNYKVD | WQQQRPGKGPRFMVR | VGTGGIVGSKGD | GIPDRFSVLG..SGLNRY LTIKNIQEEDESDYHC | GADHGSGSNFV* |

TABLE 4-continued

Exemplary Human Vλ germline sequences

Human Vλ10 germline sequence (SEQ ID NO: 232)

| Vλ10 | FW1 | CDR1 | FW2 | CDR2 | FW3 | CDR3 |
|---|---|---|---|---|---|---|
| IGLV10-54 | QAGLTQPPSVSK GLRQTATLTC | TGNSNN..VGNQGAA | WLQQHQGHPPKLLSY | RNNNR.....PS | GISERLSASR..SGNTAS LTITGLQPEDEADYYC | SAWDSSLSA... |

Human Vλ11 germline sequence (SEQ ID NO: 233)

| Vλ11 | FW1 | CDR1 | FW2 | CDR2 | FW3 | CDR3 |
|---|---|---|---|---|---|---|
| IGLV11-55 | RPVLTQPPSLSA SPGATARLPC | TLSSDLS.VGGKNMF | WYQQKPGSSPRLFLY | HYSDSDKQL.GP | GVPSRVSGSKETSSNTAF LLISGLQPEDEADYYC | QVYESSAN.... |

TABLE 5

Exemplary Human Germline Heavy Chain Consensus Sequence

| Consensus VH | FW1 | CDR1 | FW2 | CDR2 | FW3 | CDR3 |
|---|---|---|---|---|---|---|
| All-VH | EVQLVESGGGLVKP GGSLRLSCAAS | GFTFSSYAMX-- | WVRQAPGKGLEWV | GWISP--NGGSTYYADSVKG | RFTISRDNSKNTLYLQMN SLRAEDTAVYYCAR- | |
| All-VH+ | EVQLVESGGGLVKP GGSLRLSCAAS | GFTFSSYAMXWS | WVRQAPGKGLEWV | GWISPKANGGSTYYADSVKG | RFTISRDNSKNTLYLQMN SLRAEDTAVYYCARX | |
| VH1 | QVQLVQSGAEVKKP GASVKVSCKAS | GYTFTSYXXM-- | WVRQAPGQGLEWV | GWINP--XNGNTNYAQKEQG | RVTITRDTSTSTAYMELS SLRSEDTAVYYCAR- | |
| VH2 | QVTLKESGPALVKP TQTLTLTCTFS | GFSLSTSGMGVX | WIRQPPGKALEAL | AXIY---WNDDKYYSXSLES | RLTISKDTSKNQVVLTMT NMDPVDTATYYCARX | |
| VH3 | EVQLVESGGGLVQP GGSLRLSCAAS | GFTFSSYAMS-- | WVRQAPGQGLEWV | SVISS--DGXSTYYADSVKG | RFTISRDNSKNSLYLQMN SLRAEDTAVYYCARX | |
| VH3+ | EVQLVESGGGLVQP GGSLRLSCAAS | GFTFSSYAMS-- | WVRQAPGKGLEWV | SVISSKADGXSTYYADSVKG | RFTISRDNSKNSLYLQMN SLRAEDTAVYYCARX | |
| VH4 | QVQLQESGPGLVKP SETLSLTCAVS | GGSISSGXYYS- | WIRQPPGKGLEWI | GYIY--YSGSTYYNPSLKS | RVTISVDTSKNQESLKLS SVTAADTAVYYCAR- | |
| VH4+ | QVQLQESGPGLVKP SETLSLTCVAS | GGSISSGXYYWS | WIRQPPGKGLEWI | GYIY--YSGSTYYNPSLKS | RVTISVDTSKNQESLKLS SVTAADTAVYYCAR- | |
| VH5 | EVQLVQSGAEVKKP GESLRISCKGS | GYSFTSYWIX-- | WVRQMPGKGLEWS | GXIYP--GDSDTRYSPSEQG | HVTISADKSISTAYLQNS SLKASDTAMYYCAR- | |
| VH6 | QVQLQQSGPGLVKP SQTLSLTCAIS | GDSVSSNSAAWN | WIRQSPSRGLEWL | GRTYYR-SKWYNDYAVSVKS | RITINPDTSKNQESLQIN SVTPEDTAVYYCAR- | |
| VH7 | QVQLVQSGXEXRXP GASVKVSCKAS | GYXFTXYXMN-- | WVXQAPGQGLEWS | GWXNT--XTGNPTYAQGETG | REVESXDTSXSTAYLQIX SLKAEDXAXYYCAR- | |

+Consensus sequence where consensus gaps are replaced with most common amino acid From top to bottom: SEQ ID NOs. 234-244.

TABLE 6

Exemplary Human Germline Light Chain Consensus Sequence

Vλ germline consensus sequences

| Consensus Vλ | FW1 | CDR1 | FW2 | CDR2 | FW3 | CDR3 |
|---|---|---|---|---|---|---|
| All-VL | QSVLTQPPSV SVSPGQSVTITC | TGSSS--GGSYYVS | WYQQKPGQAPKLLIY | EDSNR-----PS | GVPDRFSGSK--SGNTAS LTISGLQAEDEADYYC | QSWDSSAXF--- |
| All-VL+ | QSVLTQPPSV SVSPGQSVTITC | TGSSSDVGGSYYVS | WYQQKPGQAPKLLIY | EDSNRXRXQKPS | GVPDRFSGSKDASGNTAS LTISGLQAEDEADYYC | QSWDSSAXFXXX |
| VL1 | QSVLTQPPSV SGAPGQRVTISC | SGSSSN-INGNNXVX | WYQQLPGTAPKLLIY | GNNXR-----PS | GVPDRFSGSK--SGTSAS LAIIGLQSEDEADYYC | AAWDDSLXG--- |

TABLE 6-continued

| | FW1 | CDR1 | FW2 | CDR2 | FW3 | CDR3 |
|---|---|---|---|---|---|---|
| VL1+ | QSVLTQPPSV SGAPGQRVTISC | SGSSSNIIGNNXVX | WYQQLPGTAPKLLIY | GNNXR-----PS | GVPDRFSGSK--SGTSAS LAIIGLQSEDEADYYC | AAWDDSLXG--- |
| VL2 | QSALTQPPSV SGSPGQSVTISC | TGTSSDVGGYNYVS | WYQQHPGKAPKIMIY | EVSNR-----PS | GVPDRFSGSK--SGNTAS LTISGLQAEDEADYYC | SSYAGSYTF--- |
| VL3 | SYELTQPPSV SVSPGQTARITC | SGDX---LGXKYAH | WYQQKPGQAPVLVIY | KDSER-----PS | GIPERFSGSS--SGNTAT LTISGXQAEDEADYYC | QSWDSSG----- |
| VL3+ | SYELTQPPSV SVSPGQTARITC | SGDX---LGXKYAH | WYQQKPGQAPVLVIY | KDSER-----PS | GIPERFSGSS--SGNTAT LTISGXQAEDEADYYC | QSWDSSGXH--- |
| VL4 | QPVLTQSPSA SASLGASVRLTC | TLSSG--HSSYXIA | WHQQQPGKXPRYLMK | LXSDGSHSK-GD | GIPDRFSGSS--SGADRY LTISNLQSEDEADYYC | XIWXTXX----- |
| VL4+ | QPVLTQSPSA SASLGASVRLTC | TLSSG--HSSYXIA | WHQQQPGKXPRYLMK | LXSDGSHSK-GD | GIPDRFSGSS--SGADRY LTISNLQSEDEADYYC | XIWXTXXGQVG- |
| VL5 | QPVLTQPTSL SASPGASARLTC | TLRSGINVGXYRIY | WYQQKPGSPPRYLLX | YXSDSDKXQ-GS | GVPSRFSGSKDASANAGI LLISGLQSEDEADYYC | MIWHSSAS---- |
| VL5+ | QPVLTQPTSL SASPGASARLTC | TLRSGINVGXYRIY | WYQQKPGSPPRYLLX | YXSDSDKXQ-GS | GVPSRFSGSKDASANAGI LLISGLQSEDEADYYC | MIWHSSASI--- |
| VL6 | NFMLTQPKSV SESPGRTVTISC | TRSSGS-IASNYVQ | WYQQRPGSSPTTVIY | EDNQR-----PS | GVPDRFSGSIDSSSNSAS LTISGLKTEDEADYYC | QSYDSSN----- |
| VL7 | QXVVTQEPSL IVSPGGTVTLTC | XSSTGAVTSGXYPX | WFQQKPGQAPRXLIY | NISNK-----HS | WIPARFSGSL--LGGKAA LTISGXQPEDEAEYYC | LLXYXGAX---- |
| VL8 | QTVVTQEPSF SVSPGGTVTLTC | GLSSGSVSTSYYPS | WYQQTPGQAPRTLIY | STNTR-----SS | GVPDRFSGSI--LGNKAA LTITGAQADDESDYYC | VLYXGSGI---- |
| VL9 | QPVLTQPPSA SASLGASVTLTC | TLSSG--YSNYRVD | WYQQRPGKGPRFVMR | VGTGGTVGSRGD | GIPDRFSVLG--SGLNRY LTIKNIQEEDESDYHC | GADHGSGSNFV- |
| VL10 | QAGLTQPPSV SKGLRQTATLTC | TGNSNN-VGNQAA | WLQQHQGHPPKLLSY | RNDDNR-----PS | GISERLSASR--SGNTAS LTITGLQPEDEADYYC | SAWDSSLSA--- |
| VL11 | RPVLTQPPSL SASPGATARLPC | TLSSDLSVGGKNMF | WYQQKPGSSPRLFLY | HYSDSDKQL-GP | GVPSRVSGSKETSSNTAF LLISGLQPEDEADYYC | QVYESSAN---- |

+Consensus sequence where consensus gaps are replaced with most common amino acid
From top to bottom: SEQ ID NOs. 245-261.

VK germline consensus sequences

| Consensus VK | FW1 | CDR1 | FW2 | CDR2 | FW3 | CDR3 |
|---|---|---|---|---|---|---|
| All-VK | DIVMTQSPSS LSASPGERATISC | RASQ------GISSYLA | WYQQKPGQAPKLLIY | AASSRAS | GVPSRFSGSGSGTDFTLT ISSLQPEDFAVYYC | QQYNSYP |
| All-VK+ | DIVMTQSPSS LSASPGERATISC | RASQSLLHSDGISSYLA | WYQQKPGQAPKLLIY | AASSRAS | GVPSRFSGSGSGTDFTLT ISSLQPEDFAVYYC | QQYNSYP |
| VK1 | DIQMTQSPSS LSASVGDRVTITC | RASQ------GISXYLA | WYQQKPGKAPKLLIY | AASSLQS | GVPSRFSGSGSGTDFTLT ISSLQPEDFATYYC | QQYNSYP |
| VK1D | DIQMTQSPSS LSASVGDRVTITC | RASQ------GISSYLA | WYQQKPGKAPKLLIY | AASSLQS | GVPSRFSGSGSGTDFTLT ISSLQPEDFATYYC | QQYNSYP |
| VK2 | DIVMTQTPLS LPVTXGEPASISC | RSSQSLLHSD-GNTYLD | WYLQKPGQSPQLLIY | XXSNRXS | GVPDRFSGSGSGTDFTLK ISRVEAEDVGVYYC | MQATQFP |
| VK2+ | DIVMTQTPLS LPVTXGEPASISC | RSSQSLLHSDDGNTYLD | WYLQKPGQSPQLLIY | XXSNRXS | GVPDRFSGSGSGTDFTLK ISRVEAEDVGVYYC | MQATQFP |
| VK2D | DIVMTQTPLS LPVTPGEPASISC | RSSQSLLHS-DGXTYLX | WYLQKPGQSPQLLIY | XVSNRFS | GVPDRFSGSGSGTDFTLK ISRVEAEDVGVYYC | MQATQFP |
| VK2D+ | DIVMTQTPLS LPVTPGEPASISC | RSSQSLLHSDDGXTYLX | WYLQKPGQSPQLLIY | XVSNRFS | GVPDRFSGSGSGTDFTLK ISRVEAEDVGVYYC | MQATQFP |
| VK3 | EIVLTQSPAT LSLSPGERATLSC | RASQS-----VVSSYLA | WYQQKPGQAPRLLIY | GASTRAT | GIPARFSGSGSGTDFTLT ISSLEPEDFAVYYC | QQRSNWP |
| VK3D | EIVXTQSPAT LSLSPGERATLSC | RASQS-----VXSSYLA | AWQQKPGQAPRLLIY | XASTRAT | GIPARFSGSGSGTDFTLT ISSLXPEDFAVYYC | QQYXNWP |

TABLE 6-continued

| | | | | |
|---|---|---|---|---|
| VK4 | DIVMTQSPDS LAVSLGERATINC | RSSQSVLYSSNNKNYLA | WYQQKPGQPPKLLIY | RASTRES | GVPDRFSGSGSGTDFTLT ISSLQAEDVAVYYV QQYYSTP |
| VK5 | XIVLTQSPXF XSVTPXEKVTITC | RASX------SIGXSLH | WYQQKPDQSPKLLIK | YASQSFS | GVPSRFSGSGSGTDFTLT INSLEAEDAATYYC HQSSSLP |
| VK5+ | XIVLTQSPXF XSVTPXEKVTITC | RASXSVSF--SIGXSLH | WYQQKPDQSPKLLIK | YASQSFS | GVPSRFSGSGSGTDFTLT INSLEAEDAATYYC HQSSSLP |
| VK5 | EIVLTQSPDF QSVTPKEKVTITC | RASQ------SIGSSLH | WYQQKPDQSPKLLIK | YASQSFS | GVPSRFSGSGSGTDFTLT INSLEAEDAATYYC HQSSSLP |
| VK5D | XXVXTQSPXF XSVTPXEKVTITC | XASX------XIGXXLX | WYQQKPDQXPKLLIK | YASQSXS | GVPSRFSGSGSGTDFTXT IXSLEAEDAATYYC XQXXXXP |
| VK7 | DIVLTQSPAS LAVSPGQRATITC | RASESVS--FLGINLIH | WYQQKPGQPPKLLIY | QASNRDT | GVPARFSGSGSGTDFTLT INPVEANDTANYYC LQSKNFP |

+Consensus sequence where consensus gaps are replaced with most common amino acid
From top to bottom: SEQ ID NOs. 262-277.

TABLE 7

Sequence alignment of CDR-humanized anti-A33 antibodies

A33 Rabbit ELVMTQTPPSLSASVGETVRIRCLASEFLFNGVSWYQQKPGKPPKFLISGASNLESGVPP
RFSGSGSGTDYTLTIGGVQAEDVATYYCLGGYSGSSGLTFGAGTNVEIK DPK9/JK4 DIQMTQSPSSLSASVGDRVTITCRASQSISSYLNWYQQKPGKAPKLLIYAASSLQSGVPS
RFSGSGSGTDFTLTISSLQPEDFATYYCQQSYS TPLTFGGGTKVEIK ABS-A33-1 DIQMTQSPSSLSASVGDRVTITCRASQSISSY<u>V</u>SWYQQKPGKAPKLLIYGASNLQSGVPS
RFSGSGSGTDFTLTISSLQPEDFATYYCLGGYSGS<u>T</u>GLTFGGGTKVEIK ABS-A33-2 DIQMTQSPSSLSASVGDRVTITCRAS<u>EFLFNGVS</u>WYQQKPGKAPKLLIYGASSLESGVPS
RFSGSGSGTDFTLTISSLQPEDFATYYC<u>Q</u>GGYSGSSGLTFGGGTKVEIK ABS-A33-3 DIQMTQSPSSLSASVGDRVTITCRAS<u>ESLSSYL</u>SWYQQKPGKAPKLLIYGASNLQSGVPS
RFSGSGSGTDFTLTISSLQPEDFATYYCLGGYSGSSGLTFGGGTKVEIK ABS-A33-4 DIQMTQSPSSLSASVGDRVTITCRAS<u>QFLFNGL</u>SWYQQKPGKAPKLLIYGASNLQSGVPS
RFSGSGSGTDFTLTISSLQPEDFATYYC<u>Q</u>GGYSGS<u>T</u>GLTFGGGTKVEIK ABS-A33-6 DIQMTQSPSSLSASVGDRVTITCRAS<u>QFLFNGV</u>SWYQQKPGKAPKLLIYAASNLESGVPS
RFSGSGSGTDFTLTISSLQPEDFATYYC<u>Q</u>GGYSGS<u>T</u>GLTFGGGTKVEIK ABS-A33-7 DIQMTQSPSSLSASVGDRVTITCRAS<u>EFLFNGV</u>SWYQQKPGKAPKLLIYAASSLQSGVPS
RFSGSGSGTDFTLTISSLQPEDFATYYC<u>Q</u>GGYSGSSGLTFGGGTKVEIK ABS-A33-8 DIQMTQSPSSLSASVGDRVTITCRAS<u>QFLFNGV</u>SWYQQKPGKAPKLLIYAASNLQSGVPS
RFSGSGSGTDFTLTISSLQPEDFATYYC<u>Q</u>GGYSGSSGLTFGGGTKVEIK ABS-A33-9 DIQMTQSPSSLSASVGDRVTITCRAS<u>QFLFNVLV</u>WYQQKPGKAPKLLIYAASNLESGVPS
RFSGSGSGTDFTLTISSLQPEDFATYYC<u>Q</u>GGYSGS<u>T</u>GLTFGGGTKVEIK ABS-A33-10 DIQMTQSPSSLSASVGDRVTITCRAS<u>EFLFNGV</u>SWYQQKPGKAPKLLIYGASSLESGVPS
RFSGSGSGTDFTLTISSLQPEDFATYYC<u>Q</u>GGYSGSSGLTFGGGTKVEIK ABS-A33-11 DIQMTQSPSSLSASVGDRVTITCRAS<u>EFLFNGV</u>SWYQQKPGKAPKLLIYGASSLESGVPS
RFSGSGSGTDFTLTISSLQPEDFATYYC<u>Q</u>GGYSGSSGLTFGGGTKVEIK A33 Rabbit QEQLMESGGGLVTLGGSLKLSCKASGIDFSHYGISWVRQAPGKGLEWIAYIYPNYGSVDYASWVNG
RFTISLDNAQNTVFLQMISLTAADTATYFCARDRGYYSGSRGTRLDLWGQGTLVTISS DP47/JH4 EVQLLESGGGLVQPGGSLRLSCAASGFTFSSYAMSWVRQAPGKGLEWVSAISGSGGSTYYADSVKG
RFTISRDNSKNTLYLQMNSLRAEDTAVYYCAK WGQGTLVTVSS ABS-A33-1 EVQLLESGGGLVQPGGSLRLSCAASG<u>F</u>DFSSYAMSWVRQAPGKGLEWVSAIS<u>PN</u>GGSVYYADSV<u>N</u>G
RFTISRDNSKNTLYLQMNSLRAEDTAVYYCAKDRGY<u>Y</u>TGSRGTRLALWGQGTLVTVSS ABS-A33-2 EVQLLESGGGLVQPGGSLRLSCAASGFTFSHYGISWVRQAPGKGLEWVSYIYPNYGSTDYADSVKG
RFTISRDNSKNTLYLQMNSLRAEDTAVYYCAKDR<u>Q</u>YYSGSRGTRLDLWGQGTLVTVSS ABS-A33-3 EVQLLESGGGLVQPGGSLRLSCAASGFTFSSYAISWVRQAPGKGLEWVSYIY<u>GN</u>GGSVDYASWVNG
RFTISRDNSKNTLYLQMNSLRAEDTAVYYCAKDR<u>V</u>YYSVSRGTRLDLWGQGTLVTVSS ABS-A33-4 EVQLLESGGGLVQPGGSLRLSCAASG<u>F</u>DFSHYGISWVRQAPGKGLEWVSYIYP<u>SY</u>GSTDYADSVKG
RFTISRDNSKNTLYLQMNSLRAEDTAVYYCAKDRGYYSGSRGTRLDLWGQGTLVTVSS TABLE 7-continued Sequence alignment of CDR-humanized anti-A33 antibodies ABS-A33-6   EVQLLESGGGLVQPGGSLRLSCAASGFTFSHYGISWVRQAPGKGLEWVSYIYPSYGSTDYASSVKG
            RFTISRDNSKNTLYLQMNSLRAEDTAVYYCAKDRGAYSGSRGTRLDLWGQGTLVTVSS ABS-A33-7   EVQLLESGGGLVQPGGSLRLSCAASGIDFSSYGISWVRQAPGKGLEWVSYIYPSYGSTDYADWVKG
            RFTISRDNSKNTLYLQMNSLRAEDTAVYYCAKDRGYYSGSRGTRLDLWGQGTLVTVSS ABS-A33-8   EVQLLESGGGLVQPGGSLRLSCAASGIDFSSYGISWVRQAPGKGLEWVSYIYPSYGSTDYASWVNG
            RFTISRDNSKNTLYLQMNSLRAEDTAVYYCAKDRGVYSGSRGTRLDLWGQGTLVTVSS ABS-A33-9   EVQLLESGGGLVQPGGSLRLSCAASGIDFSHYGISWVRQAPGKGLEWVSYIYPNYGSTDYASWVNG
            RFTISRDNSKNTLYLQMNSLRAEDTAVYYCAKDKGYYSGSRGTRLDLWGQGTLVTVSS ABS-A33-10  EVQLLESGGGLVQPGGSLRLSCAASGFTFSHYGISWVRQAPGKGLEWVSYIYPNYGSTDYADSVKG
            RFTISRDNSKNTLYLQMNSLRAEDTAVYYCAKDRQYYSGSRGTRLDLWGQGTLVTVSS A33 Rabbit = rabbit anti-A33 v-gene sequences.
CDRs in bold.
From Top to Bottom: SEQ ID NOs. 353-375.

TABLE 8

Sequence alignment of CDR-humanized antib-pTau antibodies pT231 pTau   ALTQPTSVSANLGGSVEITCSGSD--YDYG-WYQQKAPGSAPVTVIYWNDKRPSDIPS
             RFSGSTSGSTSTLTITGVQAEDEAVYYCGAYDGSAGGGIFGAGTTLTVL DPL16/Jλ2    SSELTQDPAVSVALGQTVRITCQGDSLRSYYASWYQQK-PGQAPVLVIYGKNNRPSGIPD
             RFSGSSSGNTASLTITGAQAEDEADYYCNSRDSSGNHVVFGGGTKLTVL C11-ABS-pTAU SSELTQDPAVSVALGQTVRITCQGDD--SYYG-WYQQK-PGQAPVTVIYGNNNRPSGIPD
             RFSGSSSGNTASLTITGAQAEDEADYYCGAYDGSGGHGVFGGGTKLTVL C9-ABS-pTAU  SSELTQDPAVSVALGQTVRITCSGDD--SYYG-WYQQK-PGQAPVTVIYGNNNRPSGIPD
             RFSGSSSGNTASLTITGAQAEDEADYYCGAYDGSGGHGVFGGGTKLTVL C18-ABS-pTAU SSELTQDPAVSVALGQTVRITCQGDD--SYYG-WYQQK-PGQAPVTVIYGNDKRPSGIPD
             RFSGSSSGNTASLTITGAQAEDEADYYCGAYDGSGGGGVFGGGTKLTVL C4-ABS-pTAU  SSELTQDPAVSVALGHTVRITCSGDD--SYYG-WYQQK-PGQAPVTVIYGNNNRPSGIPD
             RFSGSSSGNTASLTITGAQAEDEADYYCGAYDSSGGGGIFGGGTKLTVL C13-ABS-pTAU SSELTQDPAVSVALGQTVRITCQGDD--SYYG-WYQQK-PGQAPVTVIYGNNKRPSGIPD
             RFSGSSSGNTASLTITGAQAEDEADYYCGAYDSSGGGGVFGGGTKLTVL C21-ABS-pTAU SSELTQDPAVSVALGQTVRITCQGDD--SYYG-WYQQK-PGQAPVTVIYGNDNRPSGIPD
             RFSGSSSGNTASLTITGAQAEDEADYYCGAYDSSGGGGIFGGGTKLTVL C6-ABS-pTAU  SSELTQDPAVSVALGQTVRITCQGDD--SYYG-WYQQK-PGQAPVTVIYGNDNRPSGIPD
             RFSGSSSGNTASLTITGAQAEDEADYYCGAYDSSGGGGIFGGGTKLTVL C8-ABS-pTAU  SSELTQDPAVSVALGQTVRITCQGSD--YYYG-WYQQK-PGQAPVTVIYGNDNRPSGIPD
             RFSGSSSGNTASLTITGAQAEDEADYYCGSYDSSAGHGVFGGGTKLTVL pT231 pTau   AVTLDESGGGLQTPGGGLSLVCKASGFTLSSYQMMWVRQAPGKGLEWVAGITSRGGVTGYGSAVKG
             RATISRDNGQSTVRLQLNNLRAEDTGTYYCAKPALDSDQCGFPEAGCIDAWGHGTEVIVSS DP47/JH4     EVQLLESGGGLVQPGGSLRLSCAASGFTFSSYAMSWVRQAPGKGLEWVSAISGSGGSTYYADSVKG
             RFTISRDNSKNTLYLQMNSLRAEDTAVYYCAK                FDYWGQGTLVTVSS C11-ABS-pTAU EVQLLESGGGLVQPGGSLRLSCKASGFTFSSYQMMWVRQAPGKGLEWVAGITSRGGVTGYGDSVKG
             RFTISRDNSKNTLYLQMNSLRAEDTAVYYCAKPALDSDQCGFPEAGCIDAWGQGTLVTVSS C09-ABS-pTAU EVQLLESGGGLVQPGGSLRLSCKASGFTFSSYQMMWVRQAPGKGLEWVAGITSRGGVTGYADAVKG
             RFTISRDNSKNTLYLQMNSLRAEDTAVYYCAKPALDADQCGFPEAGCIDAWGQGTLVTVSS C18-ABS-pTAU EVQLLESGGGLVQPGGSLRLSCKASGFTFSSYQMMWVRQAPGKGLEWVAGITSRGGVTGYGSAVKG
             RFTISRDNSKNTLYLQMNSLRAEDTAVYYCAKPALDSDQCGFPEAGCIDSWGQGTLVTVSS C04-ABS-pTAU EVQLLESGGGLVQPGGSLRLSCKASGFTFSSYQMSWVRQAPGKGLEWVAGITSRGGVTGYGDAVKG
             RFTISRDNSKNTLYLQMNSLRAEDTAVYYCAKPALDADQCGFPEAGCIDAWGQGTLVTVSS C13-ABS-pTAU EVQLLESGGGLVQPGGSLRLSCKASGFTFSSYQMMWVRQAPGKGLEWVSGITSRGGVTGYADSVKG
             RFTISRDNSKNTLYLQMNSLRAEDTAVYYCAKPALDSDQCGFPEAGCIDAWGQGTLVTVSS C21-ABS-pTAU EVQLLESGGGLVQPGGSLRLSCKASGFTLSSYQMMWVRQAPGKGLEWVAGITSRGGVTGYGDSVKG
             RFTISRDNSKNTLYLQMNSLRAEDTAVYYCAKPALDSDQCGFPEAGCIDAWGQGTLVTVSS

TABLE 8-continued

Sequence alignment of CDR-humanized antib-pTau antibodies

C06-ABS-pTAU  EVQLLESGGGLVQPGGSLRLSCKASGFTFSSYQMMWVRQAPGKGLEWVSGITSRGGVTGYGSSVKG
              RFTISRDNSKNTLYLQMNSLRAEDTAVYYCAKPALNSDQCGFPEAGCIDAWGQGTLVTVSS

C08-ABS-pTAU  EVQLLESGGGLVQPGGSLRLSCKASGFTFSSYQMSWVRQAPGKGLEWVSGITRGGVTGYADAVKG
              RFTISRDNSKNTLYLQMNSLRAEDTAVYYCAKPALDSDQCGFPEAGCIDAWGQGTLVTVSS

From Top to Bottom: SEQ ID NOs. 376-395.

TABLE 9

Sequence alignment of CDR-humanized anti-RAGE antibodies

XTM4 RAGE     DIQMTQSPSSMSVSLGDTITITCRASQDVGIYVNWFQQKPGKSPRRMIYRATNLADGVPSRFSGSRSGSIYS
              LTISSLESEDVADYHCLEFDEHPLTFGSGTKVEIK

DPK9/JK4      DIQMTQSPSSLSASVGDRVTITCRASQSISSYLNWYQQKPGKAPKLLIYAASSLQSGYPSRFSGSGSGTDFTL
              TISSLQPEDFATYYCQQSYSTPLTFGGGTKVEIK

C4-ABS-RAGE   DIQMTQSPSSLSASVGDRVTITCRASQSVGSYVNWYQQKPGKAPKLLIYRASSLADGVPSRFSGSGSGT
              DFTLTISSLQPEDFATYYCLEFDEHPLTFGGGTKVEIK

C11-ABS-RAGE  DIQMTQSPSSLSASVGDRVTITCRASQSVGSYVNWYQQKPGKAPKLLIYRASNLQSGVPSRFSGSGSG
              TDFTLTISSLQPEDFATYYCLEFDEHPLTFGGGTKVEIK

C10-ABS-RAGE  DIQMTQSPSSLSASVGDRVTITCRASQDVGSYVNWYQQKPGKAPKLLIYRASNLADGVPSRFSGSGSG
              TDFTLTISSLQPEDFATYYCQEFYSHPLTFGGGTKVEIK

C3-ABS-RAGE   DIQMTQSPSSLSASVGDRVTITCRASQSISSYLNWYQQKPGKAPKLLIYRATNLQSGVPSRFSGSGSGTDF
              TLTISSLQPEDFATYYCLEFDEHPLTFGGGTKVEIK

C7-ABS-RAGE   DIQMTQSPSSLSASVGDRVTITCRASQSIGSYLNWYQQKPGKAPKLLIYRASSLASGVPSRFSGSGSGTD
              FTLTISSLQPEDFATYYCLEFDEHPLTFGGGTKVEIK

XTM4 RAGE     EVQLVESGGGLVQPGRSLKLSCVVSGFTFNNYWMTWIRQTPGKGLEWVASIDNSGDNTYYPDSVKDRFTIS
              RDNAKSTLYLQMNSLRSEDTATYYCTRGGDITTGFDYWGQGVMVTVSS

DP54/JH4      EVQLVESGGGLVQPGGSLRLSCAASGFTFSSYWMSWVRQAPGKGLEWVANIKQDGSEKYYVDSVKGRFTISR
              DNAKNSLYLQMNSLRAEDTAVYYCAR            DYWGQGTLVTVSS

C4-ABS-RAGE   EVQLVESGGGLVQPGGSLRLSCAASGFTFSNYWMSWVRQAPGKGLEWVASIKNDGDNTYYVDSVKDRFT
              ISRDNAKNSLYLQMNSLRAEDTAVYYCARGGDITTGLDYWGQGTLVTVSS

C11-ABS-RAGE  EVQLVESGGGLVQPGGSLRLSCAAS GFTFSNYWMSWVRQAPGKGLEWVATSIDNSGSNKYYVDSVKGRFT
              ISRDNAKNSLYLQMNSLRAEDTAVYYCARGGDITTGFDYWGQGTLVTVSS

C10-ABS-RAGE  EVQLVESGGGLVQPGGSLRLSCAASGFTFSSYWMSWVRQAPGKGLEWVASIKNSGSETYYPDSVKGRFT
              ISRDNAKNSLYLQMNSLRAEDTAVYYCARGGDITTGFDYWGQGTLVTVSS

C3-ABS-RAGE   EVQLVESGGGLVQPGGSLRLSCAASGFTFSSYWMSWVRQAPGKGLEWVASIDQDGSEKYYPDSVKGRFT
              ISRDNAKNSLYLQMNSLRAEDTAVYYCARGGDITTGLDYWGQGTLVTVSS

C7-ABS-RAGE   EVQLVESGGGLVQPGGSLRLSCAASGFTFSSYWMSWVRQAPGKGLEWVASIDQDGSNKYYPDSVKGRFT
              ISRDNAKNSLYLQMNSLRAEDTAVYYCARGGDITTGLDYWGQGTLVTVSS

XTM4 RAGE = rat anti-RAGE v-gene sequences.
From Top to Bottom: SEQ ID NOs. 396-409.

---

What is claimed is:

1. An isolated humanized monoclonal antibody or antigen-binding fragment thereof that binds to a target antigen prepared by a method comprising,
   (1) obtaining the sequence of a non-human donor antibody that binds to said target antigen, and determining the donor CDR-L1, CDR-L2, CDR-L3, CDR-H1, and CDR-H2 sequences of said non-human donor antibody;
   (2) obtaining the sequences of a human germline VL and a human germline VH, and determining the germline framework and germline CDR-L1, CDR-L2, CDR-L3, CDR-H1, and CDR-H2 sequences of said human VL and VH;
   (3) aligning each of the non-human donor CDR-L1, CDR-L2, and CDR-L3 sequences with the corresponding germline CDR sequence from said human VL, and each of the non-human CDR-H1 and CDR-H2 sequences with corresponding germline CDR sequence from said human VH;
   (4) identifying positions in CDR-L1, CDR-L2, CDR-L3, CDR-H1, and CDR-H2 where human germline residue is the same as, or different from, the corresponding non-human donor residue; and
   (5) generating the isolated humanized monoclonal antibody or antigen-binding fragment thereof by changing a non-human donor residue of the donor CDR-L1, CDR-L2, CDR-L3, CDR-H1, and CDR-H2 to the corresponding human germline residue if the human germline residue at the position is different from the corresponding non-human residue, wherein:
(a) said isolated humanized monoclonal antibody or antigen-binding fragment thereof comprises (i) a VH domain comprising a human germline VH framework sequence from step (2) and a VL domain comprising a human germline VL framework sequence from step (2); and (ii) a CDR-L1, CDR-L2, CDR-L3, CDR-H1 and CDR-H2 from step (5); and (iii) a CDR-H3;
(b) for each position within said CDR-L1, CDR-L2, CDR-L3, CDR-H1, and CDR-H2, the residue is either human germline residue from said human germline VL or VH, or corresponding residue from said non-human donor antibody;
(c) said CDR-L1, CDR-L2, CDR-L3, CDR-H1, and CDR-H2 each comprises at least one more human germline residue as compared to the corresponding non-human donor CDR,
(d) said CDR-L1, CDR-L2, CDR-L3, CDR-H1, and CDR-H2 each comprises at least one more non-human donor residue as compared to the corresponding human germline VH or VL CDR; and
(e) for each position within CDR-H3, the residue is any one of the 20 natural amino acid residues.

2. The antibody or antigen-binding fragment thereof of claim 1, wherein said human germline VH framework sequence comprises a VH3, VH1, or VH5 framework sequence.

3. The antibody or antigen-binding fragment thereof of claim 1, wherein said human germline VH framework sequence comprises a VH germline consensus framework sequence.

4. The antibody or antigen-binding fragment thereof of claim 1, wherein said human germline VH framework sequence comprises the VH framework sequence of any one of the consensus sequences listed in Table 2 and Table 5.

5. The antibody or antigen-binding fragment thereof of claim 1, wherein said human germline VL framework sequence comprises a VK or V?, framework sequence.

6. The antibody or antigen-binding fragment thereof of claim 1, wherein said human germline VL framework sequence comprises a VL germline consensus framework sequence.

7. The antibody or antigen-binding fragment thereof of claim 1, wherein said human germline VL framework sequence comprises the VL framework sequence of any one of the human germline sequences listed in Table 3, Table 4 and Table 6.

8. The antibody or antigen-binding fragment thereof of claim 1, wherein said human germline VH framework sequence is derived from the VH framework sequence of human germline DP54.

9. The antibody or antigen-binding fragment thereof of claim 1, wherein said human germline VH framework sequence is derived from the VH framework sequence of SEQ ID NO:74.

10. The antibody or antigen-binding fragment thereof of claim 1, wherein said human germline VL framework sequence is derived from a VK framework sequence.

11. The antibody or antigen-binding fragment thereof of claim 1, wherein said human germline VL framework sequence is derived from the VL framework sequence of human germline DPK9.

12. The antibody or antigen-binding fragment thereof of claim 1, wherein said human germline VL framework sequence is derived from the VL framework sequence of SEQ ID NO:144.

13. The antibody or antigen-binding fragment thereof of claim 1, wherein the antibody or antigen-binding fragment binds said target antigen with a binding affinity (Kd) value that is equal or less than the binding affinity (Kd) value of said non-human donor antibody.

14. The antibody or antigen-binding fragment thereof of claim 1, wherein the antibody or antigen-binding fragment maintains highly specific binding to said target antigen as compared to binding of said non-human donor antibody to said target antigen.

* * * * *